(12) United States Patent
Andersen et al.

(10) Patent No.: US 8,142,797 B2
(45) Date of Patent: Mar. 27, 2012

(54) THERAPEUTIC TB VACCINE

(75) Inventors: Peter Andersen, Brønshøj (DK); Ida Rosenkrands, Vaerløse (DK); Anette Stryhn, Virum (DK)

(73) Assignee: Statens Serum Institut, Copenhagen S (DK)

( * ) Notice: Subject to any disclaimer, the term of this patent is extended or adjusted under 35 U.S.C. 154(b) by 0 days.

(21) Appl. No.: 12/785,053

(22) Filed: May 21, 2010

(65) Prior Publication Data

US 2011/0020384 A1    Jan. 27, 2011

Related U.S. Application Data

(63) Continuation of application No. 10/617,038, filed on Jul. 11, 2003, now abandoned.

(60) Provisional application No. 60/401,725, filed on Aug. 7, 2002.

(30) Foreign Application Priority Data

Jul. 13, 2002 (DK) .......................... PA 2002 01098

(51) Int. Cl.
*A61K 39/04* (2006.01)
*A61K 39/02* (2006.01)
*A61K 39/00* (2006.01)

(52) U.S. Cl. ............... 424/248.1; 424/184.1; 424/185.1; 424/190.1; 424/192.1; 424/234.1; 530/300; 530/350

(58) Field of Classification Search ............... 424/184.1, 424/185.1, 190.1, 192.1, 234.1, 248.1; 530/300, 530/350
See application file for complete search history.

(56) References Cited

U.S. PATENT DOCUMENTS

| | | | |
|---|---|---|---|
| 6,641,814 | B1 | 11/2003 | Andersen et al. |
| 6,649,170 | B1 | 11/2003 | Lindblad et al. |
| 7,749,520 | B2 | 7/2010 | Davidsen et al. |
| 7,838,018 | B2 | 11/2010 | Lindblad et al. |
| 2003/0036638 | A1 | 2/2003 | Joergensen et al. |
| 2008/0008724 | A1 | 1/2008 | Aagaard et al. |
| 2009/0186048 | A1 | 7/2009 | Aagaard et al. |
| 2010/0015171 | A1 | 1/2010 | Dietrich et al. |
| 2010/0160421 | A1 | 6/2010 | Fomsgaard et al. |

FOREIGN PATENT DOCUMENTS

| | | |
|---|---|---|
| DK | PA 2000 00666 | 4/2000 |
| WO | WO 01/79274 | 10/2001 |

OTHER PUBLICATIONS

Sambrook et al, molecular cloning, A laboratory manual, Cold Spring Harbor Laboratories, NY, (1989) XP-002091112.
Anon. Global Tuberculosis Control, WHO Report (2001).
Brandt et al, ESAT-6 Subunit Vaccination against Mycobacterium Tuberculosis, Infection and Immunity, vol. 68, No. 2, pp. 791-795 (Feb. 2000).
Boon et al, Journal of Bacteriology, vol. 183, No. 8 pp. 2672-2676, (Apr. 2001).
Doherty et al, Immune Responses to the Mycobacterium Tuberculosis-Specific Antigen ESAT-6 Signal Subclinical Infection among Contacts of Tuberculosis Patients, Journal of Clinical Microbiology, vol. 40, No. 2, pp. 704-706, (Feb. 2002).
Florczyk et al, Identification and Characterization of Mycobacterial Proteins Differentially Expressed under Standing and Shaking Culture Conditions, Including Rv2623 from a Novel Class of Putative ATP-Binding Proteins, Infection and Immunity, vol. 69, No. 9, pp. 5777-5785, (Sep. 2001).
Harboe et al, B-Cell Epitopes and Quantification of the ESAT-6 Protein of Mycobacterium Tuberculosis, Infection and Immunity, vol. 66, No. 2, pp. 717-723, (Feb. 1998).
Manganelli et al, The Mycobacterium Tuberculosis ECF Sigma Factor δ: Role in Global Gene Expression and Survival in Macrophages, Molecular Microbiology, vol. 41, No. 2, pp. 423-437, (May 2001).
Monahan et al, Differential Expression of Mycobacterial Proteins Following Phagocytosis by Macrophages, Microbiology, 147, pp. 459-471, (2001).
Raven et al, Human T Cell Responses to the ESAT-6 Antigen from Mycobacterium Tuberculosis, The Journal of Infectious Diseases, 179, pp. 637-645, (1999).
Rosenkrands et al, Identification an Characterization of a 29-Kilodalton Protein from Mycobacterium Tuberculosis Culture Filtrate Recognized By Mouse Memory Effector Cells, Infection and Immunity, vol. 66, No. 6, pp. 2728-2735, (Jun. 1998).
Rosenkrands et al, Hypoxie Response of Mycobacterium Tuberculosis Studied by Metabolic Labeling and Proteome Analysis of Cellular and Extracellular Proteins, Journal of Bacteriology, vol. 184, No. 13, pp. 3485-3491, (Jul. 2002).
Sherman et al, Regulation of the Mycobacterium Tuberculosis Hypoxic Response Gene Encoding αCrystallin, PNAS, vol. 98, No. 13, pp. 7534-7539, (Jun. 19, 2001).
Skjøt et al, Comparative Evaluation of Low-Molecular-Mass Proteins form Mycobacterium Tuberculosis Identifies Members of the ESAT-6 Family as Immmodominant T-Cell Antigens, Infections and Immunity, vol. 68, No. 1, pp. 214-220, (Jan. 2000).
Vordermeier et al, Correlation of ESAAT-6-Specific Gamma Interferon Production with Pathology in Cattle Following Mycobacterium Bovis BCG Vaccination against Experimental Bovine Tuberculosis, Infections and Immunity, vol. 70, No. 6, pp. 3026-3032, (Jun. 2002).
Merrifield, Solid Phase Peptide Synthesis, I. The Synthesis of a Tetrapeptide, J. Am. Chem. Soc., 85:2149, (Jul. 20, 1963).
Pearson et al, Improved Tools for Biological Sequence Comparison, Proc. Natl. Acad. Sci., vol. 85, pp. 2444-2448, (Apr. 1988).
Rolph et al, Recombinant Viruses as Vaccines and Immunological Tools, Curr. Opin. Immunol. 9:517-24, (1997).
Ulmer et al, Polynucleotide Vaccines, Curr. Opin. Invest. Drugs, 2(9):983-989 (1993).
Cote-Sierra et al, A New Membrane-bound OprI lipoprotein Expression Vector High Production of Heterologous Fusion Proteins in Gram (−) Bacteria and the Implications for Oral Vaccination, Gene 221 pp. 25-34, (Aug. 10, 1998).

(Continued)

Primary Examiner — Rodney P. Swartz
(74) Attorney, Agent, or Firm — Howson & Howson LLP

(57) ABSTRACT

Therapeutic vaccines comprising polypeptides expressed during the latent stage of mycobacteria infection are provided, as are multiphase vaccines, and methods for treating and preventing *tuberculosis*.

15 Claims, 7 Drawing Sheets

OTHER PUBLICATIONS

Gosselin et al, Enhanced Antigen Presentation Using Human FcγReceptor (Monocyte/Macrophage)-Specific Immunogens, The Journal of Immunolgy, vol. 149, No. 11, pp. 3477-3481 (Dec. 1, 1992).

Höner Zu Bentrup et al, Mycobacterial Persistence: Adaptation to a Changing Environment, Trends in Microbiology, vol. 9, No. 12, pp. 597-605, (Dec. 2001).

Kilgus et al, Analysis of the Permissive Association of a Malaria T Cell Epitope with DR Molecules, The Journal of Immunology, vol. 146, No. 1, pp. 307-315, (Jan. 1, 1991).

Kohler et al, Continuous Cultures of Fused Cells Secreting Antibody of Predefined Specificity, Nature, vol. 256 (5517):pp. 495-497, (Aug. 7, 1975).

Lowrie et al, Therapy of Tuberculosis in Mice By DNA Vaccination, Nature, vol. 400, pp. 269-271, (Jul. 15, 1999).

Lustig et al, Humoral and Cellular Responses to Native Antigen Following Oral and Parenteral Immunization with Lipid-Conjugated Bovine Serum Albumin, Cellular Immunology, 24, pp. 164-172, (Jun. 1, 1976).

McCafferty et al, Phage Antobodies: Filamentous Phage Displaying Antibody Variable Domains, Nature vol. 348, pp. 552-554, (Dec. 6, 1990).

Mowat et al, Immune-Stimulating Complexes Containing Quil A and Protein Antigen Prime Class I MHC-restricted T Lymphocytes In Vivo and are Immunogenic by the Oral Route, Immumology, 72, (3), pp. 317-322, (Mar. 1991).

Nagai et al, Isolation and Partial Characterization of Major Protein Antigens in the Culture Fluid of Mycobacterium Tuberculosis, Infection and Immunity, vol. 59, No. 1, pp. 372-382, (Jan 1991).

Stryhn et al, Peptide Binding Specificity of Major Histocompatibility Complex Class I Resolved into and Array of Apparently Independent Subspecificities: Quantitation by Peptide Libraries and Improves Prediction of Binding, Eur. J. Immunol. 26, pp. 1911-1918, (Aug. 1996).

Rolph et al, Recombinant Viruses as Vaccines and Immunological Tools, Curr. Opin. Immunol. 9,4, pp. 453-455, (Aug. 1997).

Olsen et al, Efficient Protection Against Mycobacterium Tuberculosis by Vaccination with a Single Subdominant Epitope from the ESAT-6 Antigen, 30, 6, pp. 1724-1732, (Jun. 2000).

Thompson et al, Clustal W: Improving the Sensitivity of Progressive Multiple Sequence Alignment Through Sequence Weighting, Position-Specific Gap Penalties and Weight Matrix Choice, Nucleic Acids research, vol. 22, No. 22, pp. 4673-4680, (Nov. 11, 1994).

Van Pinxteren et al, Control of Latent Mycobacterium Tuberculosis Infections is Dependent on CD8 T Cells, Eur. J. Immunol. 30, 12, pp. 3689-3698, (Dec. 2000).

Sinigaglia et al, "A Malaria T-Cell Epitope Recognized in Association with Most Mouse and Human MHC Class II Molecules", Nature, vol. 336, 6201, pp. 778-780, (Dec. 22-29, 1988).

Turner et al., "Effective preexposure tuberculosis vaccines fail to protect when they are given in an immunotherapeutic mode", Infect Immun. Mar. 2000; 68(3):1709-9.

Oct. 26, 2005 Office Action and Notice of References in parent U.S. Appl. No. 10/617,038.

Response to Oct. 26, 2005 Office Action in parent U.S. Appl. No. 10/617,038, 2005.

Apr. 12, 2006 Office Action in parent U.S. Appl. No. 10/617,038.

Response to Apr. 12, 2006 Office Action in parent U.S. Appl. No. 10/617,038, 2006.

Jan. 17, 2007 Office Action in parent U.S. Appl. No. 10/617,038.

Response to Jan. 17, 2007 Office Action in parent U.S. Appl. No. 10/617,038, 2007.

Oct. 30, 2007 Office Action in parent U.S. Appl. No. 10/617,038.

Response to Oct. 30, 2007 Office Action in parent U.S. Appl. No. 10/617,038, 2008.

May 19, 2008 Office Action and Notice of References in parent U.S. Appl. No. 10/617,038, 2008.

Response to May 19, 2008 Office Action in parent U.S. Appl. No. 10/617,038, 2008.

Dec. 8, 2008 Office Action in parent U.S. Appl. No. 10/617,038.

Response and 1.132 Declaration responsive to Dec. 8, 2008 Office Action in parent U.S. Appl. No. 10/617,038, 2009.

Mar. 9, 2009 Office Action in parent U.S. Appl. No. 10/617,038.

Response to Mar. 9, 2009 Office Action in parent U.S. Appl. No. 10/617,038, 2009.

Aug. 5, 2009 Office Action in parent U.S. Appl. No. 10/617,038.

Response to Aug. 5, 2009 Office Action in parent U.S. Appl. No. 10/617,038, 2009.

Feb. 22, 2010 Office Action in parent U.S. Appl. No. 10/617,038.

Fig. 1A. Infection model for prophylactic vaccination
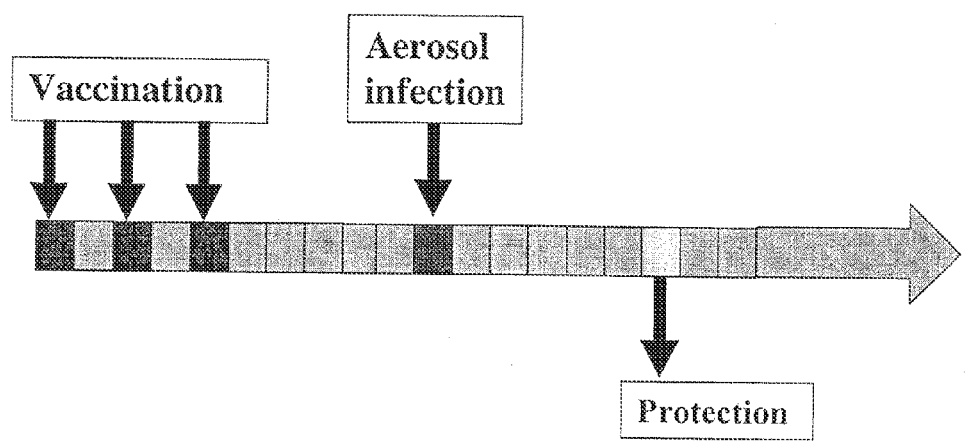
Fig. 1B. Latency model for therapeutic vaccination
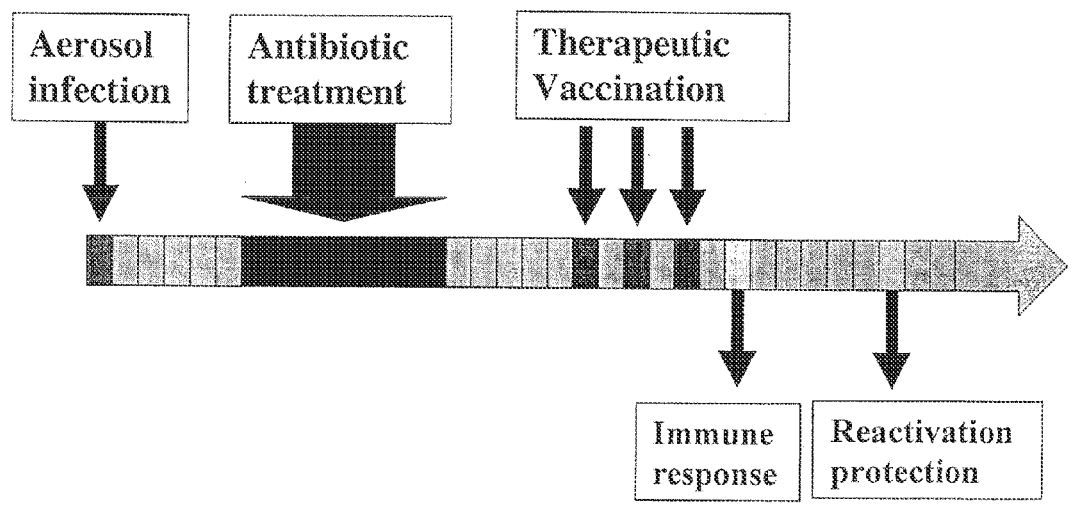

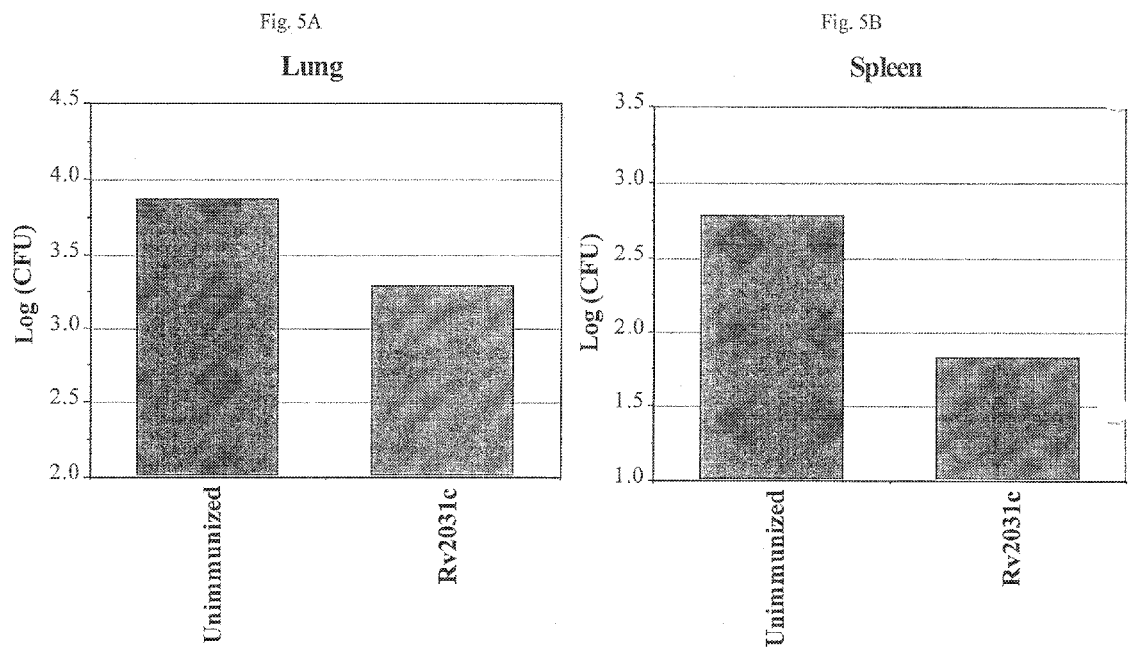

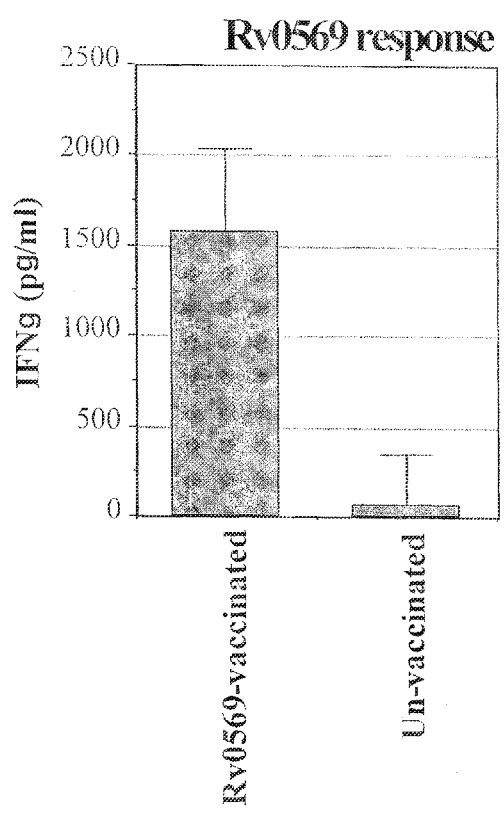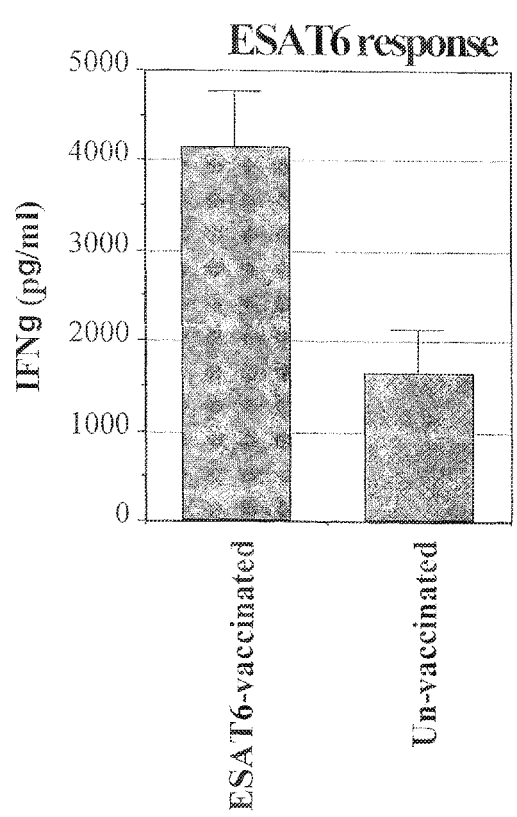
Fig. 6A                    Fig. 6B

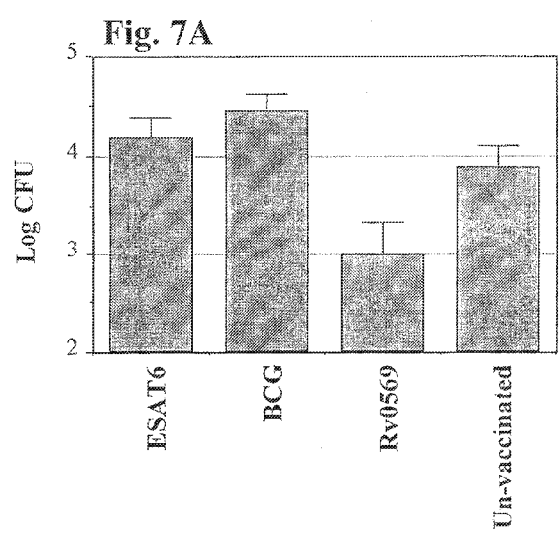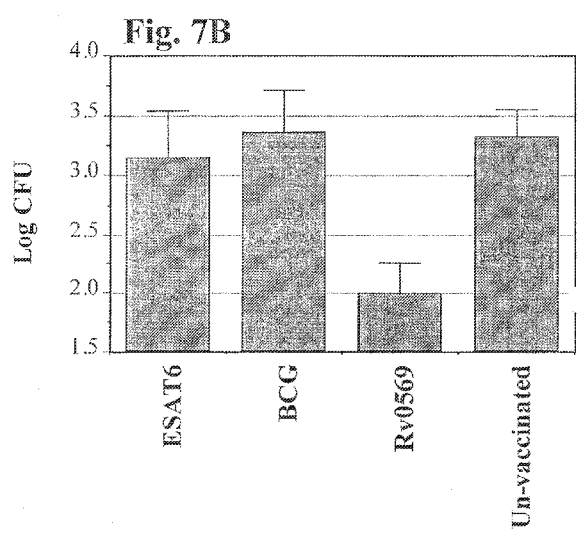

THERAPEUTIC TB VACCINE

CROSS-REFERENCE TO RELATED APPLICATIONS

This application is a continuation of U.S. patent application Ser. No. 10/617,038, filed Jul. 11, 2003, now abandoned, which claims the benefit of the priority of U.S. Provisional Patent Application No. 60/401,725, filed Aug. 7, 2002, now expired, and the priority of Danish Patent Application No. PA 2002 01098, filed Jul. 13, 2002, which applications are incorporated herein by reference.

BACKGROUND OF THE INVENTION

The present invention discloses a therapeutic vaccine against latent or active *tuberculosis* infection caused by the *tuberculosis* complex microorganisms (*Mycobacterium tuberculosis, M. bovis, M. africanum*). The invention furthermore discloses a multi-phase vaccine that can be administered either prophylactically or therapeutically as well as a diagnostic reagent for the detection of latent stages of *tuberculosis*.

Human *tuberculosis* caused by *Mycobacterium tuberculosis* (*M. tuberculosis*) is a severe global health problem, responsible for approx. 3 million deaths annually, according to the WHO. The worldwide incidence of new *tuberculosis* (TB) cases had been falling during the 1960s and 1970s but during recent decades this trend has markedly changed in part due to the advent of AIDS and the appearance of multidrug resistant strains of *M. tuberculosis*.

Organisms of the *tuberculosis* complex can cause a variety of diseases, but the commonest route of invasion is by inhalation of bacteria. This initiates an infection in the lung, which can ultimately spread to other parts of the body. Normally, this infection is restricted in growth by the immune system, so that the majority of infected individuals show few signs apart from cough and fever, which eventually abates. Approximately 30% of individuals are unable to contain the infection and they will develop primary disease, which in many cases will eventually prove fatal. However, it is believed that even those individuals who apparently control the infection remain infected, probably for the rest of their life. Certainly, individuals who have been healthy for years or even decades can suddenly develop *tuberculosis*, which has proven to be caused by the same organism they were infected with many years previously. *M. tuberculosis* and other organisms of the TB complex are unique in that the mycobacteria can evade the immune response and survive for long periods in a refractory non-replicating or slowly-replicating stage. This is referred to as latent TB and is at present a very significant global health problem that is estimated to affect approximately ⅓ of the world's population (Anon., 2001).

The course of a *M. tuberculosis* infection runs essentially through 3 phases, as illustrated in FIG. 1. During the acute phase, the bacteria proliferate in the organs, until the immune response increases to the point at which it can control the infection, whereupon the bacterial load peaks and starts declining. After this, a latent phase is established where the bacterial load is kept stable at a low level. In this phase *M. tuberculosis* goes from active multiplication to dormancy, essentially becoming non-replicating and remaining inside the granuloma. In some cases, the infection goes to the reactivation phase, where the dormant bacteria start replicating again. The full nature of the immune response that controls latent infection and the factors that lead to reactivation are largely unknown. However, there is some evidence for a shift in the dominant cell types responsible. While CD4 T cells are essential and sufficient for control of infection during the acute phase, studies suggest that CD8 T cell responses are more important in the latent phase. It is also likely that changes in the antigen-specificity of the response occur, as the bacterium modulates gene expression during its transition from active replication to dormancy.

The only vaccine presently available for clinical use is BCG, a vaccine whose efficacy remains a matter of controversy. Although BCG consistently performs well in animal models of primary infection, it has clearly failed to control the TB epidemic. Consistent with that, BCG vaccination appears to provide protection against pediatric TB (which is due to primary infection), while offering little or no protection against adult disease (which is often reactivation of latent infection acquired in childhood). It has also been shown that vaccination of individuals who are currently sensitized to mycobacteria or latently infected is ineffective. Thus, current vaccination strategies, while effective against primary disease, fail to activate immune responses that efficiently control surviving dormant bacteria.

At this point no vaccine has been developed that confers protection against reactivation whether given as a prophylactic vaccine prior to infection or as a therapeutic vaccine given to already latently infected individuals.

This makes the development of a new and improved vaccine against TB an urgent matter, which has been given a very high priority by the WHO. Many attempts to define protective mycobacterial substances have been made, and different investigators have reported increased resistance after experimental vaccination. However, these efforts have almost exclusively focused on the development of prophylactic vaccines for the prevention of disease (Doherty, 2002), and such vaccines have not been demonstrated to work if given in an immunotherapeutic fashion (J. Turner et al., *Infect and Immunity*, 2000, pp. 1706-1709).

It has been suggested that the transition of *M. tuberculosis* from primary infection to latency is accompanied by changes in gene expression (see, for example, Honer zu Bentrup, 2001, which is incorporated herein by reference). In vitro hypoxic culture conditions, which mimic the conditions of low oxygen tension and restricted nutrients found in the granuloma (the location of the latent infection), have been used to analyze changes in gene expression and a number of antigens have been found that are induced or markedly upregulated under these conditions e.g. the 16 kDa antigen α-crystalline (Boon, 2001, Monahan, 2001, Florczyk 2001, Sherman 2001, Manganelli, 2001, all of which are incorporated herein by reference) and Rv0569 as described in Rosenkrands, 2002, and which is described in WO0179274.

As noted in the references cited above, it is already known that some genes are upregulated under conditions that mimic latency. However, these are a limited subset of the total gene expression during latent infection. Moreover, as one skilled in the art will readily appreciate, expression of a gene is not sufficient to make it a good vaccine candidate. The only way to determine if a protein is recognized by the immune system during latent infection with *M. tuberculosis* is to produce the given protein and test it in an appropriate assay as described herein. Of the more than 200 hundred antigens known to be expressed during primary infection, and tested as vaccines, less than a half dozen have demonstrated significant potential. So far only one antigen has been shown to have any potential as a therapeutic vaccine (Lowrie, 1999). However this vaccine only worked if given as a DNA vaccine, an experimental technique so far not approved for use in humans. Moreover, the technique has proved controversial, with other groups claiming that vaccination using this protocol induces either non-specific protection or even worsens disease (J. Turner et al., *Infect and Immunity,* 2000, pp. 1706-1709).

What are needed are therapeutic vaccines that treat latent TB infection.

SUMMARY OF THE INVENTION

The present invention provides therapeutic vaccines based on molecules that are induced or upregulated under the conditions of low oxygen transmission and restricted nutrients found in the granuloma (i.e., the location of latent TB infection). These vaccines are therapeutic and contrast with prior art vaccines which are designed to elicit protective immune responses prior to infection (prophylactic vaccination) that are only effective against primary infection. The immune responses elicited are powerless against the latent stage of the disease, because the bacteria have changed the antigens that they produce so that in essence they have altered their appearance and the immune system can no longer recognize them. However, latency is a dynamic process, maintained by the immune response, as indicated by the dramatic increase in the risk of reactivation of TB after HIV infection or other events that compromise immunity. Therefore, an effective vaccination strategy to protect infected individuals (therapeutic vaccination) is possible, but only if it is directed against those antigens expressed in the latent stage.

Further, the present invention provides a multiphase vaccine that combines components with prophylactic and therapeutic activity. In contrast, existing TB vaccines do not result in sterilizing immunity but rather control the infection at a subclinical level (thereby resulting in the subsequent establishment of latent infection. After conventional prophylactic vaccination, the evasion of the primary immune response and the subsequent development of latent disease are probably at least in part due to the change in the antigenic profile of the invading bacteria. Thus, vaccinating with antigens associated with latent TB prevents or reduces the establishment of latent infection and therefore, a vaccine incorporating antigens expressed by the bacteria both in the first logarithmic growth phase and during latent disease improve long-term immunity when used as a prophylactic vaccine. A multiphase vaccine of the invention will also be efficient as a therapeutic vaccine thereby addressing the problem that the majority of the population in the third world who would receive a future TB vaccine could be already latently infected.

For a number of years, a major effort has been put into the identification of protective antigens for the development of novel prophylactic vaccines against TB and today a few antigens with demonstrated protective activity in prophylactic vaccines have been identified (e.g. ESAT-6, the 38 kDa antigen, Ag85A and Ag85B). Such molecules are useful components, which in combination with latency associated antigens such as α-crystalline, form a multiphase vaccine of the invention. Advantageously and in contrast to antigens in the art, the antigens described in the invention are incorporated in vaccines through the use of well-recognized vaccination technology, as demonstrated in provided examples.

Finally, the immunodominant antigens identified in this invention may be used as diagnostic reagents. Our group has abundantly demonstrated that antigens expressed by mycobacteria during the early stages of the infection, such as ESAT-6 (Early Secretory Antigen Target-6) are recognized in individuals who are in the process of developing primary TB, even though they are healthy at the time of diagnosis (Doherty 2002). However, the large numbers of contacts who are exposed, and almost certainly infected, remain negative to this antigen (Doherty 2002). Since those individuals latently infected remain healthy by making an immune response against the latent bacteria, they must be making an immune response to those antigens expressed by the latent bacteria. Thus, the antigens of the invention may also be used to diagnose latent infection and differentiate it from primary acute TB.

Other aspects and advantages of the invention will be readily apparent to one of skill in the art.

BRIEF DESCRIPTION OF THE DRAWINGS

FIGS. 1A and 1B illustrate the results of testing in TB vaccination models. A schematic time schedule of the models for FIG. 1A, prophylactic vaccination and FIG. 1B, therapeutic vaccination. Each square on the time axis represents one week. Three prophylactic vaccinations two weeks apart are given 6 weeks prior to an aerosol infection. The protective effect of the vaccines is measured 6 weeks after infection, in the acute phase of the infection. For analysis of therapeutic vaccinations a reactivation model is established, where aerosol infected mice are treated with anti-*M tuberculosis* drugs for 8 weeks from the peak of infection (6 weeks after infection). This induces a latent infection phase with a low bacterial load. Four to five weeks into the latency phase three therapeutic vaccinations are given two weeks apart and the protective effect of the vaccines is measured as bacterial load in the reactivation phase, seven weeks after the last immunization.

In FIG. 2A, the immunization was given as a prophylactic vaccine 6 weeks before the mice were given a *M. tuberculosis* infection (approx. 250 bacilli) through the aerosol route with. Bacterial numbers in the lung was enumerated 6 weeks post infection. In FIG. 2B, the immunization was given as a therapeutic vaccine after a latent infection had been established. Bacterial numbers in the lung was enumerated 8 weeks after the last immunization. The data represents the mean of 5 individual mice.

In FIG. 4A, the peptides were analyzed in pools of 3-4 peptides. PBMCs ($2\times10^5$) were incubated for 72 h with the peptide pools at 5 μg/ml per peptide. Supernatant was harvested and secreted IFN-γ was quantitated by ELISA. In FIG. 4B, individual peptides of positive pools were reanalyzed. PBMCs (2×10⁵) were incubated for 72 h with 1 µg/ml of each peptide. Secreted IFN-γ in the supernatant was quantitated.

FIGS. 5A and 5B illustrate protection against reactivation conferred by therapeutic vaccine given during latent infection. Latent infected C57Bl/6j mice were immunized 3 times with or without rRv2031c. Bacterial numbers in lung (FIG. 5A) and spleen (FIG. 5B) was enumerated 8 weeks after the last immunization. The data represents the mean of 8 individual mice.

FIGS. 6A and 6B illustrate Rv0569 specific IFN-γ responses. Latent infected C57Bl/6j mice were vaccinated with 3 µg of either recombinant Rv0569 or recombinant ESAT6 in a DDA/MPL adjuvant. The vaccines were given as 3 s.c. injections with a two-week interval and the induced immune response were evaluated 7 weeks after the last vaccination. Isolated splenocytes (2×10⁵) were incubated for 72 h with antigen at 1 µg/ml. Supernatant was harvested and secreted IFN-γ was quantitated by ELISA using paired anti-murine IFN-γ antibodies (PharMingen) and recombinant IFN-γ (PharMingen) as standard. In FIG. 6A, Rv0569 specific response is measured in Rv0569-vaccinated and un-vaccinated latently infected mice; in FIG. 6B, the ESAT6 specific response is measured in ESAT6-vaccinated and un-vaccinated latently infected mice FIGS. 7A and 7B illustrate therapeutic vaccine induced protection against reactivation. Latently infected C57Bl/6j mice were vaccinated once with BCG or 3 times with a 2-week interval with either recombinant Rv0569 or recombinant ESAT6. Seven weeks after the last vaccination the bacterial numbers was enumerated in FIG. 7A, the lung and in FIG. 7B, the spleen of vaccinated and un-vaccinated mice. The data represents the mean of Log CFU per organ of 6-8 individual mice.

DETAILED DESCRIPTION OF THE INVENTION

Figures 2A, 2B:
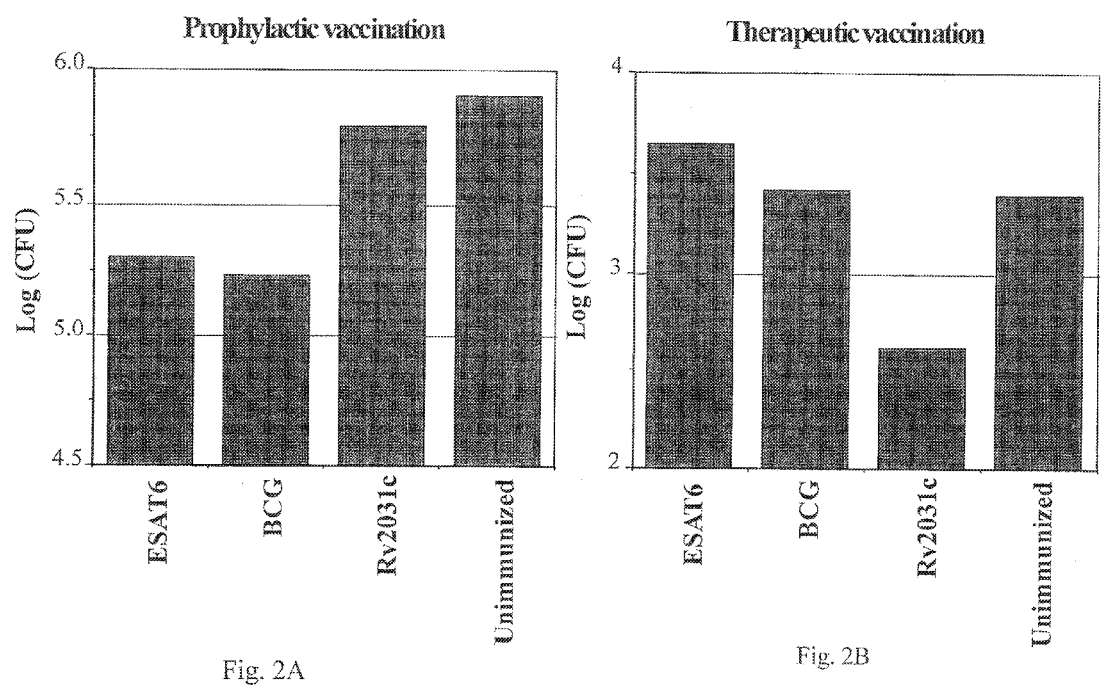
FIGS. 2A and 2B illustrate prophylactic and therapeutic vaccine induced protection. C57Bl/6j mice were immunized 3 times with a 2-week interval with recombinant ESAT6, BCG or recombinant Rv2031c.

The invention is related to preventing, treating and detecting infections caused by species of the *tuberculosis* complex (*Mycobacterium tuberculosis, M. bovis, M. africanum*) by the use of a polypeptide comprising a *M. tuberculosis* antigen or an immunogenic portion or other variant thereof, or by the use of a DNA sequence encoding a *M. tuberculosis* antigen or an immunogenic portion or other variant thereof. The invention discloses a new therapeutic vaccine against *tuberculosis* comprising antigens induced during the latent stage of TB-infection. It also discloses a multiphase vaccine incorporating a combination of prophylactic and therapeutic antigens as well as diagnostic reagents for the detection of the latent stage of *M. tuberculosis* infection.

The present invention discloses the use of one or more polypeptides, nucleic acids encoding these polypeptides or fragments hereof, which polypeptides are expressed during the latent stage of the mycobacteria infection, which stage is characterized by low-oxygen tension in the microenvironment of the mycobacteria, for a therapeutic vaccine against *tuberculosis.*

The polypeptides comprises one or more amino acid sequences selected from (a) The sequences presented in Table 1.

(b) an immunogenic portion, e.g. a T-cell epitope, of any one of the sequences in (a); and/or (c) an amino acid sequence analogue having at least 70% sequence identity to any one of the sequences in (a) or (b) and at the same time being immunogenic.

TABLE 1

Amino acid sequences of selected low oxygen induced antigens

| Rv no. | SEQ ID NO: | Sequence |
|---|---|---|
| Rv0569 | 91 | MKAKVGDWLVIKGATIDQPDHRGLIIEVRSSDGSPPYVVRWLETDHVATV IPGPDAVVVTAEEQNAADERAQHRFGAVQSAILHARGT |
| Rv0079 | 1 | VEPKRSRLVVCAPEPSHAREFPDVAVFSGGRANASQAERLARAVGRVLAD RGVTGGARVRLTMANCADGPTLVQINLQVGDTPLRAQAATAGIDDLRPAL IRLDRQIVRASAQWCPRPWPDRPRRRLTTPAEALVTRRKPVVLRRATPLQ AIAAMDAMDYDVHLFTDAETGEDAVVYRAGPSGLRLARQHHVFPPGWSRC RAPAGPPVPLIVNSRPTPVLTEAAAVDRAREHGLPFLFFTDQATGRGQLL YSRYDGNLGLITPTGDGVADGLA |
| Rv0080 | 2 | MSPGSRRASPQSAREVVELDRDEAMRLLASVDHGRVVFTRAALPAIRPVN HLVVDGRVIGRTRLTAKVSVAVRSSADAGVVVAYEADDLDPRRRTGWSVV VTGLATEVSDPEQVARYQRLLHPWVNMAMDTVVAIEPEIVTGIRIVADSR TP |
| Rv0081 | 3 | VESEPLYKLKAEFFKTLAHPARIRILELLVERDRSVGELLSSDVGLESSN LSQQLGVLRRAGVVAARRDGNAMIYSIAAPDIAELLAVARKVLARVLSDR VAVLEDLRAGGSAT |
| Rv0363c | 4 | MPIATPEVYAEMLGQAKQNSYAFPAINCTSSETVNAAIKGFADAGSDGII QFSTGGAEFGSGLGVKDMVTGAVALAEFTHVIAAKYPVNVALHTDHCPKD KLDSYVRPLLAISAQRVSKGGNPLFQSHMWDGSAVPIDENLAIAQELLKA AAAAKIILEIEIGVVGGEEDGVANEINEKLYTSPEDFEKTIEALGAGEHG KYLLAATFGNVHGVYKPGNVKLRPDILAQGQQVAAAKLGLPADAKPFDFV FHGGSGSLKSEIEEALRYGVVKMNVDTDTQYAFTRPIAGHMFTNYDGVLK VDGEVGVKKVYDPRSYLKKAEASMSQRVVQACNDLHCAGKSLTH |
| Rv0572c | 5 | MGEHAIKRHMRQRKPTKHPLAQKRGARILVFTDDPRRSVLIVPGCHLDSM RREKNAYYFQDGNALVGMVVSGGTVEYDADDRTYVVQLTDGRHTTESSFE HSSPSRSPQSDDL |
| Rv0574c | 6 | VAGNPDVVTVLLGGDVMLGRGVDQILPHPGKPQLRERYMRDATGYVRLAE RVNGRIPLPVDWRWPWGEALAVLENTATDVCLINLETTITADGEFADRKP |

TABLE 1-continued Amino acid sequences of selected low oxygen induced antigens

| Rv no. | SEQ ID NO: | Sequence |
|---|---|---|
| | | VCYRMHPDNVPALTALRPHVCALANNHILDFGYQGLTDTVAALAGAGIQS VGAGADLLAARRSALVTVGHERRVIVGSVAAESSGVPESWAARRDRPGVW LIRDPAQRDVADDVAAQVLADKRPGDIAIVSMHWGSNWGYATAPGDVAFA HRLIDAGIDMVHGHSSHHPRPIEIYRGKPILYGCGDVVDDYEGIGGHESF RSELRLLYLTVTDPASGNLISLQMLPLRVSRMRLQRASQTDTEWLRNTIE RISRRFGIRVVTRPDNLLEVVPAANLTSKE |
| Rv1264 | 7 | VTDHVREADDANIDDLLGDLGGTARAERAKLVEWLLEQGITPDEIRATNP PLLLATRHLVGDDGTYVSAREISENYGVDLELLQRVQRAVGLARVDDPDA VVHMRADGEAAARAQRFVELGLNPDQVVLVVRVLAEGLSHAAEAMRYTAL EAIMRPGATELDIAKGSQALVSQIVPLLGPMIQDMLFMQLRHMMETEAVN AGERAAGKPLPGARQVTVAFADLVGFTQLGEVVSAEELGHLAGRLAGLAR DLTAPPVWFIKTIGDAVMLVCPDPAPLLDTVLKLVEVVDTDNNFPRLRAG VASGMAVSRAGDWFGSPVNVASRVTGVARPGAVLVADSVREALGDAPEAD GFQWSFAGPRRLRGIRGDVRLFRVRRGATRTGSGGAAQDDDLAGSSP |
| Rv1592c | 8 | MVEPGNLAGATGAEWIGRPPHEELQRKVRPLLPSDDPFYFPPAGYQHAVP GTVLRSRDVELAFMGLIPQPVTATQLLYRTTNMYGNPEATVTTVIVPAEL APGQTCPLLSYQCAIDAMSSRCFPSYALRRRAKALGSLTQMELLMISAAL AEGWAVSVPDHEGPKGLWGSPYEPGYRVLDGIRAALNSERVGLSPATPIG LWGYSGGGLASAWAAEACGEYAPDLDIVGAVLGSPVGDLGHTFRRLNGTL LAGLPALVVAALQHSYPGLARVIKEHANDEGRQLLEQLTEMTTVDAVIRM AGRDMGDFLDEPLEDILSTPEISHVFGDTKLGSAVPTPPVLIVQAVHDYL IDVSDIDALADSYTAGGANVTYHRDLFSEHVSLHPLSAPMTLRWLTDRFA GKPLTDHRVRTTWPTIFNPMTYAGMARLAVIAAKVITGRKLSRRPL |
| Rv1733c | 9 | MIATTRDREGATMITFRLRLPCRTILRVFSRNPLVRGTDRLEAVVMLLAV TVSLLTIPFAAAAGTAVQDSRSHVYAHQAQTRHPATATVIDHEGVIDSNT TATSAPPRTKITVPARWVVNGIERSGEVNAKPGTKSGDRVGIWVDSAGQL VDEPAPPARAIADAALAALGLWLSVAAVAGALLALTRAILIRVRNASWQH DIDSLFCTQR |
| Rv1734c | 10 | MTNVGDQGVDAVFGVIYPPQVALVSFGKPAQRVCAVDGAIHVMTTVLATL PADHGCSDDHRGALFFLSINELTRCAAVTG |
| Rv1736c | 11 | VTVTPRTGSRIEELLARSGRFFIPGEISADLRTVTRRGGRDGDVFYRDRW SHDKVVRSTHGVNCTGSCSWKIYVKDDIITWETQETDYPSVGPDRPEYEP RGCPRGAAFSWYTYSPTRVRHPYARGVLVEMYREAKARLGDPVAAWADIQ ADPRRRRRYQRARGKGGLVRVSWAEATEMIAAAHVHTISTYGPDRVAGFS PIPAMSMVSHAAGSRFVELIGGVMTSFYDWYADLPVASPQVFGDQTDVPE SGDWWDVVWQCASVLLTYPNSRQLGTAEELLAHIDGPAADLLGRTVSELR RADPLTAATRYVDTFDLRGRATLYLTYWTAGDTRNRGREMLAFAQTYRST DVAPPRGETPDFLPVVLEFAATVDPEAGRRLLSGYRVPIAALCNALTEAA LPYAHTVAAVCRTGDMMGELFWTVVPYVTMTIAVGSWWRYRYDKFGWTT RSSQLYESRLLRIASPMFHFGILVVIVGHGIGLVIPQSWTQAAGLSEGAY HVQAVVLGSIAGITTLAGVTLLIYRRRTRGPVFMATTVNDKVMYLVLVAA IVAGLGATALGSGVVGEAYNYRETVSVWFRSVWVLQPRGDLMAEAPLYYQ IHVLIGLALFALWPFTRLVHAFSAPIGYLFRPYIIYRSREELVLTRPRRR GW |
| Rv1737c | 12 | MRGQAANLVLATWISVVNFWAWNLIGPLSTSYARDMSLSSAEASLLVATP ILVGALGRIVTGPLTDRFGGRAMLIAVTLASILPVLAVGVAATMGSYALL VFFGLFLGVAGTIFAVGIPFANNWYQPARRGFSTGVFGMGMVGTALSAFF TPRFVRWFGLFTTHAIVAAALASTAVVAMVVLRDAPYFRPNADPVLPRLK AAARLPVTWEMSFLYAIVFGGFVAFSNYLPTYITTIYGFSTVDAGARTAG FALAAVLARPVGGWLSDRIAPRHVVLASLAGTALLAFAAALQPPPEVWSA ATFITLAVCLGVGTGGVFAWVARRAPAASVGSVTGIVAAAGGLGGYFPPL VMGATYDPVDNDYTVGLLLLVATALVACTYTALHAREPVSEEASR |
| Rv1738c | 13 | MCGDQSDHVLQHWTVDISIDEHEGLTRAKARLRWREKELVGVGLARLNPA DRNVPEIGDELSVARALSDLGKRMLKVSTHDIEAVTHQPARLLY |
| Rv1739c | 14 | MIPTMTSAGWAPGVVQFREYQRRWLRGDVLAGLTVAAYLIPQAMAYATVA GLPPAAGLWASIAPLAIYALLGSSRQLSIGPESATALMTAAVLAPMAAGD LRRYAVLAATLGLLVGLICLLAGTARLGFLASLRSRPVLVGYMAGIALVM ISSQLGTITGTSVEGNEFFSEVHSFATSVTRVHWPTFVLAMSVLALLTML TRWAPRAPGPIIAVLAATMLVAVMSLDAKGIAIVGRIPSGLPTPGVPPVS VEDLRALIIPAAGIAIVTFTDGVLTARAFAARRGQEVNANAELRAVGACN IAAGLTHGFPVSSSSSRTALADVVGGRTQLYSLIALGLVVIVMVFASGLL AMFPIAALGALVVYAALRLIDLSEFRRLARFRRSELMLALATTAAVLGLG VFYGVLAAVALSILELLRRVAHPDSVLGFVPGIAGMHDIDDYPQAKRVP GLVVYRYDAPLCFANAEDFRRRALTVVDQDPGQVEWFVLNAESNVEVDLT ALDALDQLRTELLRRGIVFAMARVKQDLRESLRAASLLDKIGEDHIFMTL PTAVQAFRRR |

TABLE 1-continued

Amino acid sequences of selected low oxygen induced antigens

| Rv no. | SEQ ID NO: | Sequence |
|---|---|---|
| Rv1813c | 15 | MITNLRRRTAMAAAGLGAALGLGILLVPTVDAHLANGSMSEVMMSE IAGLPIPPIIHYGAIAYAPSGASGKAWHQRTPARAEQVALEKCGDK TCKVVSRFTRCGAVAYNGSKYQGGTGLTRRAAEDDAVNRLEGGRIV NWACN |
| Rv1997c | 16 | LSASVSATTAHHGLPAHEVVLLLESDPYHGLSDGEAAQRLERFGPNTLAV VTRASLLARILRQFHHPLIYVLLVAGTITAGLKEFVDAAVIFGVVINAI VGFIQESKAEAALQGLRSMVHTHAKVVREGHEHTMPSEELVPGDLVLLAA GDKVPADLRLVRQTGLSVNESALTGESTPVHKDEVALPEGTPVADRRNIA YSGTLVTAGHGAGIVVATGAETELGEIHRLVGAAEVVATPLTAKLAWFSK FLTIAILGLAALTFGVGLLRRQDAVETFTAAIALAVGAIPEGLPTAVTIT LAIGMARMAKRRAVIRRLPAVETLGSTTVICADKTGTLTENQMTVQSIWT PHGEIRATGTGYAPDVLLCDTDDAPVPVNANAALRWSLLAGACSNDAALV RDGTRWQIVGDPTEGAMLVVAAKAGFNPERLATTLPQVAAIPFSSERQYM ATLHRDGTDHVVLAKGAVERMLDLCGTEMGADGALRPLDRATVLRATEML TSRGLRVLATGMGAGAGTPDDFDENVIPGSLALTGLQAMSDPPRAAAASA VAACHSAGIAVKMITGDHAGTATAIATEVGLLDNTEPAAGSVLTGAELAA LSADQYPEAVDTASVFARVSPEQKLRLVQALQARGHVVAMTGDGVNDAPA LRQANIGVAMGRGGTEVAKDAADMVLTDDDFATIEAAVEEGRGVFDNLTK FITWTLPTNLGEGLVILAAIAVGVALPILPTQILWINMTTAIALGLMLAF EPKEAGIMTRPPRDPDQPLLTGWLVRRTLLVSTLLVASAWWLFAWELDNG AGLHEARTAALNLFVVVEAFYLFSCRSLTRSAWRLGMFANRWIILGVSAQ AIAQFAITYLPAMNMVFDTAPIDIGVWVRIFAVATAITIVVATDTLLPRI RAQPP |
| Rv1998c | 17 | MSFHDLHHQGVPFVLPNAWDVPSALAYLAEGFTAIGTTSFGVSSSGGHPD GHRATRGANIALAAALAPLQCYVSVDIEDGYSDEPDAIADYVAQLSTAGI NIEDSSAEKLIDPALAAAKIVAIKQRNPEVFVNARVDTYWLRQHADTTSTT IQRALRYVDAGADGVFVPLANDPDELAELTRNIPCPVNTLPVPGLTIADL GELGVARVSTGSVPYSAGLYAAAHAARAVSDGEQLPRSVPYAELQARLVD YENRTSTT |
| RV2003c | 18 | VVKRSRATRLSPSIWSGWESPQCRSIRARLLLPRGRSRPPNADCCWNQLA VTPDTRMPASSAAGRDAAAYDAWYDSPTGRPILATEVAALRPLIEVFAQP RLEIGVGTGRFADLLGVRFGLDPSRDALMFARRRGVLVANAVGEAVPFVS RHFGAVLMAFTLCFVTDPAAIFRETRRLLADGGGLVIGFLPRGTPWADLY ALRAARGQPGYRDARFYTAAELEQLLADSGFRVIARRCTLHQPPGLARYD IEAAHDGIQAGAGFVAISAVDQAHEPKDDHPLESE |
| RV2005c | 19 | MSKPRKQHGVVVGVDGSLESDAAACWGATDAAMRNIPLTVVHVVNADVAT WPPMPYPETWGVWQEDEGRQIVANAVKLAKEAVGADRKLSVKSELVFSTP VPTMVEISNEAEMVVLGSSGRGALARGLLGSVSSSLVRRAGCPVAVIHSD DAVIPDPQHAPVLVGIDGSPVSELATAVAFDEASRRGVELIAVHAWSDVE VVELPGLDFSAVQQEAELSLAERLAGWQERYPDVPVSRVVVCDRPARKLV QKSASAQLVVVGSHGRGGLTGMLLGSVSNAVLHAARVPVIVARQS |
| Rv2007c | 20 | VTYVIGSECVDVMDKSCVQECPVDCIYEGARMLYINPDECVDCGACKPAC RVEAIYWEGDLPDDQHQHLGDNAAFFHQVLPGRVAPLGSPGGAAAVGPIG VDTPLVAAIPVECP |
| Rv2028c | 21 | MNQSHKPPSIVVGIDGSKPAVQAALWAVDEAASRDIPLRLLYAIEPDDPG YAAHGAAARKLAAAENAVRYAFTAVEAADRPVKVEVEITQERPVTSLIRA SAAAALVCVGAIGVHHFRPERVGSTAAALALSAQCPVAIVRPHRVPIGRD AAWIVVEADGSSDIGVLLGAVMAEARLRDSPVRVVTCRQSGVGDTGDDVR ASLDRWLARWQPRYPDVRVQSAAVHGELLDYLAGLGRSVHMVVLSASDQE HVEQLVGAPGNAVLQEAGCTLLVVGQQYL |
| Rv2029c | 22 | MTEPAAWDEGKPRIITLTMNPALDITTSVDVVRPTEKMRCGAPRYDPGGG GINVARIVHVLGGCSTALFPAGGSTGSLLMALLGDAGVPFRVIPIAASTR ESFTVNESRTAKQYRFVLPGPSLTVAEQEQCLDELRGAAASAAFVVASGS LPPGVAADYYQRVADICRRSSTPLILDTSGGGLQHISSGVFLLKASVREL RECVGSELLTEPEQLAAAHELIDRGRAEVVVVSLGSQGALLATRHASHRE SSIPMTAVSGVGAGDAMVAAITVGLSRGWSLIKSVRLGNAAGAAMLLTPG TAACNRDDVERFFELAAEPTEVGQDQYVWHPIVNPEASP |
| Rv2030c | 23 | VLMTAAADVTRRSPRRVFRDRREAGRVLAELLAAYRDQPDVIVLGLARGG LPVAWEVAAALHAPLDAFVVRKLGAPGHDEFAVGALASGGRVVVNDDVVR GLRITPQQLRDIAEREGRELLRRESAYRGERPPTDITGKTVIVVDDGLAT GASMFAAVQALRDAQPAQIVIAVPAAPESTCREFAGLVDDVVCATMPTPF LAVGESFWDFRQVTDEEVRRLLATPTAGPSLRRPAASTAADVLRRVAIDA PGGVPTHEVLAELVGDARIVLIGESSHGTHEFYQARAAMTQWLIEEKGFG AVAAEADWPDAYRVNRYVRGLGEDTNADEALSGFERPPAWMWRNTVVRDF VEWLRTRNQRYESGALRQAGFYGLDLYSLHRSIQEVISYLDKVDPRAAAR ARARYACFDHACADDGQAYGFAAAFGAGPSCEREAVEQLVDVQRNALAYA RQDGLLAEDELFYAQQNAQTVRDAEVYYRAMFSGRVTSWNLRDQHMAQTL |

TABLE 1-continued

Amino acid sequences of selected low oxygen induced antigens

| Rv no. | SEQ ID NO: | Sequence |
|---|---|---|
| | | GSLLTHLDRHLDAPPARIVVWAHNSHVGDARATEVWADGQLTLGQIVRER<br>YGDESRSIGFSTYTGTVTAASEWGGIAQRKAVRPALHGSVEELFHQTADS<br>FLVSARLSRDAEAPLDVVRLGRAIGVVYLPATERQSHYLHVRPADQFDAM<br>IHIDQTRALEPLEVTSRWIAGENPETYPTGL |
| Rv2031c | 24 | MATTLPVQRHPRSLFPEFSELFAAFPSFAGLRPTFDTRLMRLEDEMKEGR<br>YEVRAELPGVDPDKDVDIMVRDGQLTIKAERTEQKDFDGRSEFAYGSPVR<br>TVSLPVGADEDDIKATYDKGILTVSVAVSEGKPTEKHIQIRSTN |
| Rv2032 | 25 | MPDTMVTTDVIKSAVQLACRAPSLHNSQPWRWIAEDHTVALFLDKDRVLY<br>ATDHSGREALLGCGAVLDHFRVAMAAAGTTANVERFPNPNDPLHLASIDF<br>SPADFVTEGHRLRADAILLRRTDRLPFAEPPDWDLVESQLRTTVTADTVR<br>IDVIADDMRPELAAASKLTESLRLYDSSYHAELFWWTGAFETSEGIPHSS<br>LVSAAESDRVTFGRDFPVVANTDRRPEFGHDRSKVLVLSTYDNERASLLR<br>CGEMLSAVLLDATMAGLATCTLTHITELHASRDLVAALIGQPATPQALVR<br>VGLAPEMEEPPPATPRRPIDEVFHVRAKDHR |
| Rv2428 | 26 | MPLLTIGDQFPAYQLTALIGGDLSKVDAKQPGDYFTTITSDEHPGKWRVV<br>FFWPKDFTFVCPTEIAAFSKLNDEFEDRDAQILGVSIDSEFAHFQWRAQH<br>NDLKTLPFPMLSDIKRELSQAAGVLNADGVADRVTFIVDPNNEIQFVSAT<br>AGSVGRNVDEVLRVLDALQSDELCACNWRKGDPTLDAGELLKASA |
| Rv2624c | 27 | MSGRGEPTMKTIIVGIDGSHAAITAALWGVDEAISRAVPLRLVSVIKPTH<br>PSPDDYDRDLAHAERSLREAQSAVEAAGKLVKIETDIPRGPAGPVLVEAS<br>RDAEMICVGSVGIGRYASSILGSTATELAEKAHCPVAVMRSKVDQPASDI<br>NWIVVRMTDAPDNEAVLEYAAREAKLRQAPILALGGRPEELREIPDGEFE<br>RRVQDWHHRHPDVRVYPITTHTGIARFLADHDERVQLAVIGGGEAGQLAR<br>LVGPSGHPVFRHAECSVLVVRR |
| Rv2625c | 28 | MRDAIPLGRIAGFVVNVHWSVLVILWLFTWSLATMLPGTVGGYPAVVYWL<br>LGAGGAVMLLASLLAHELAHAVVARRAGVSVESVTLWLFGGVTALGGEAK<br>TPKAAFRIAFAGPATSLALSATFGALAITLAGVRTPAIVISVAWWLATVN<br>LLLGLFNLLPGAPLDGGRLVRAYLWRRHGDSVRAGIGAARAGRVVALVLI<br>ALGLAEFVAGGLVGGVWLAFIGWFIFAAAREEETRISTQQLFAGVRVADA<br>MTAQPHTAPGWINVEDFIQRYVLGERHSAYPVADRDGSITGLVALRQLRD<br>VAPSRRSTTSVGDIALPLHSVPTARPQEPLTALLERMAPLGPRSRALVTE<br>GSAVVGIVTPSDVARLIDVYRLAQPEPTFTTSPQDADRFSDAG |
| Rv2727c | 29 | MASSASDGTHERSAFRLSPPVLSGAMGPFMHTGLYVAQSWRDYLGQQPDK<br>LPIARPTIALAAQAFRDEIVLLGLKARRPVSNHRVFERISQEVAAGLEFY<br>GNRRWLEKPSGFFAQPPPLTEVAVRKVKDRRRSFYRIFFDSGFTPHPGEP<br>GSQRWLSYTANNREYALLLRHPEPRPWLVCVHGTEMGRAPLDLAVFRAWK<br>LHDELGLNIVMPVLPMHGPRGQGLPKGAVFPGEDVLDDVHGTAQAVWDIR<br>RLLSWIRSQEEESLIGLNGLSLGGYIASLVASLEEGLACAILGVPVADLI<br>ELLGRHCGLRHKDPRRHTVKMAEPIGRMISPLSLTPLVPMPGRFIYAGIA<br>DRLVHPREQVTRLWEHWGKPEIVWYPGGHTGFFQSRPVRRFVQAALEQSG<br>LLDAPRTQRDRSA |
| Rv2628 | 30 | MSTQRPRHSGIRAVGPYAWAGRCGRIGRWGVHQEAMMNLAIWHPRKVQSA<br>TIYQVTDRSHDGRTARVPGDEITSTVSGWLSELGTQSPLADELARAVRIG<br>DWPAAYAIGEHLSVEIAVAV |
| Rv2629 | 31 | MRSERLRWLVAAEGPFASVYFDDSHDTLDAVERREATWRDVRKHLESRDA<br>KQELIDSLEEAVRDSRPAVGQRGRALIATGEQVLVNEHLIGPPPATVIRL<br>SDYPYVVPLIDLEMRRPTYVFAAVDHTGADVKLYQGATISSTKIDGVGYP<br>VHKPVTAGWNGYGDFQHTTEEAIRMNCRAVADHLTRLVDAADPEVVFVSG<br>EVRSRTDLLSTLPQRVAVRVSQLHAGPRKSALDEEEIWDLTSAEFTRRRY<br>AEITNVAQQFEAEIGRGSGLAAQGLAEVCAALRDGDVDTLIVGELGEATV<br>VTGKARTTVARDADMLSELGEPVDRVARADEALPFAAIAVGAALVRDDNR<br>IAPLDGVGALLRYAATNRLGSHRS |
| Rv2630 | 32 | MLHRDDHINPPRPRGLDVPCARLRATNPLRALARCVQAGKPGTSSGHRSV<br>PHTADLRIEAWAPTRDGCIRQAVLGTVESFLDLESAHAVHTRLRRLTADR<br>DDDLLVAVLEEVIYLLDTVGETPVDLRLRDVDGGVDVTFATTDASTLVQV<br>GAVPKAVSLNELRFSQGRHGWRCAVTLDV |
| Rv2659c | 33 | VTQTGKRQRRKFGRIRQFNSGRWQASYTGPDGRVYIAPKTFNAKIDAEAW<br>LTDRRREIDRQLWSPASGQEDRPGAPFGEYAEGWLKQRGIKDRTRAHYRK<br>LLDDNHILATFADTDLRDITPAAVRRWYATTAVGTPTMRAHSYSLLRAIMQ<br>TALADDLIDSNPCRISGASTARRVHKIRPATLDELETITKAMPDPYQAFV<br>LMAAWLAMRYGELTELRRKDIDLHGEVARVRRAVVRVGEGFKVTTPKSDA<br>GVRDISIPPHLIPAIEDHLHKHVNPGRESLLFPSVNDPNRHLAPSALYRM<br>FYKARKAAGRPDLRVHDLRHSGAVLAASTGATLAELMQRLGHSTAGAALR<br>YQHAAKGRDREIAALLSKLAENQEM |

TABLE 1-continued

Amino acid sequences of selected low oxygen induced antigens

| Rv no. | SEQ ID NO: | Sequence |
|---|---|---|
| Rv2780 | 34 | MRVGIPTETKNNEFRVAITPAGVAELTRRGHEVLIQAGAGEGSAITDADF KAAGAQLVGTADQVWADADLLLKVKEPIAAEYGRLRHGQILFTFLHLAAS RACTDALLDSGTTSIAYETVQTADGALPLLAPMSEVAGRLAAQVGAYHLM RTQGGRGVLMGGVPGVEPADVVVIGAGTAGYNAARIANGMGATVTVLDIN IDKLRQLDAEFCGRIHTRYSSAYELEGAVKRADLVIGAVLVPGAKAPKLV SNSLVAHMKPGAVLVDIAIDQGGCFEGSRPTTYDHPTFAVHDTLFYCVAN MPASVPKTSTYALTNATMPYVLELADHGWRAACRSNPALAKGLSTHEGAL LSERVATDLGVPFTEPASVLA |
| Rv3126c | 35 | MVIRFDQIGSLVLSMKSLASLSFQRCLRENSSLVAALDRLDAAVDELSAL SFDALTTPERDRARRDRDHHPWSRSRSQLSPRMAHGAVHQCQWPKAVWAV IDNP |
| Rv3127 | 36 | VLKNAVLLACRAPSVHNSQPWRWVAESGSEHTTVHLFVNRHRTVPATDHS GRQAIISCGAVLDHLRIAMTAAHWQANITRFPQPNQPDQLATVEFSPIDH VTAGQRNRAQAILQRRTDRLPFDSPMYWHLFEPALRDAVDKDVAMLDVVS DDQRTRLVVASQLSEVLRRDDPYYHAELEWWTSPFVLAHGVPPDTLASDA ERLRVDLGRDFPVRSYQNRRAELADDRSKVLVLSTPSDTRADALRCGEVL STILLECTMAGMATCTLTHLIESSDSRDIVRGLTRQRGEPQALIRVGIAP PLAAVPAPTPRRPLDSVLQIRQTPEKGRNASDRNARETGWFSPP |
| Rv3128c | 37 | VWSASGGQCGKYLAASMVLQLDGLERHGVLEFGRDRYGPEVREELLAMSA ASIDRYLKTAKAKDQISGVSTTKPSPLLRNSIKVRRAGDEVEAEPGFFEG DTVAHCGPTLKGEFAHTLNLTDVHIGWVFTRTVRNNARTHILAGLKASVT EIPHGITGLDFDNGTVFLNKPVISWAGDNGIYFTRFRPYKKNH*ATIESK NNHLVRKYAFYYRYDTAEERAVLNRMWKLVNDRLNYLTPTIKPIGYASSA DGRRRRLYDAPQTPLDRPLAARVLSAAQQADLITYRDSLNPAQIGRKIAD LQNRLLILAKEKTEQLYLANIPTALPDIHKGILIKAG |
| Rv3129 | 38 | VVQGRTVLFRTAEGAKLFSAVAKCAVAFEADDHNVAEGWSVIVKVRAQVL TTDAGVREAERAQLLPWTATLKRHCVRVIPWEITGRHFRFGPEPDRSQTF ACEASSHNQR |
| Rv3130c | 39 | MNHLTTLDAGFLKAEDVDRHVSLAIGALAVIEGPAPDQEAFLSSLAQRLR PCTRFGQRLRLRPFDLGAPKWVDDPDFDLGRHVWRIALPRPGNEDQLFEL IADLMARRLDRGRPLWEVWVIEGLADSKWAILTKLHHCMADGIAATHLLA GLSDESMSDSFASNIHTTMQSQSASVRRGGFRVNPSEALTASTAVMAGIV RAAKGASEIAAGVLSPAASSLNGPISDLRRYSAAKVPLADVEQVCRKFDV TINDVALAAITESYRNVLIQRGERPRFDSLRTLVPVSTRSNSALSKTDNR VSLMLPNLPVDQENPLQRLRIVHSRLTRAKAGGQRQFGNTLMAIANRLPF PMTAWAVGLLMRLPQRGVVTVATNVPGPRRPLQIMGRRVLDLYPVSPIAM QLRTSVAMLSYADDLYFGILADYDVVADAGQLARGIEDAVARLVAISKRR KVTRRRGALSLVV |
| Rv3131 | 40 | MNTHFPDAETVRTVLTLAVRAPSIHNTQPWRWRVCPTSLELFSRPDMQLR STDPDGRELILSCGVALHHCVVALASLGWQAKVNRFPDPKDRCHLATIGV QPLVPDQADVALAAAIPRRRTDRRAYSCWPVPGGDIALMAARAARGGVML RQVSALDRMKAIVAQAVLDHVTDEEYLRELTIWSGRYGSVAGVPARNEPP SDPSAPIPGRLFAGPGLSQPSDVLPADDGAAILALGTETDDRLARLRAGE AASIVLLTATAMGLACCPITEPLEIAKTRDAVRAEVFGAGGYPQMLLRVG WAPINADPLPPTPRRELSQVVEWPEELLRQRC |
| Rv3132 | 41 | MTTGGLVDENDGAAMRPLRHTLSQLRLHELLVEVQDRVEQIVEGRDRLDG LVEAMLVVTAGLDLEATLRAIVHSATSLVDARYGAMEVHDRQHRVLHFVY EGIDEETVRRIGHLPKGLGVIGLLIEDPKPLRLDDVSAHPASIGFPPYHP PMRTFLGVPVRVRDESFGTLYLTDKTNGQPFSDDDEVLVQALAAAAGIAV ANARLYQQAKARQSWIEATRDIATELLSGTEPATVFRLVAAEEALKLTAAD AALVAVPVDEDMPAADVGELLVIETVGSAVASIVGRTIPVAGAVLREVFV NGIPRRVDRVDLEGLDELADAGPALLLPLRARGTVAGVVVVLSQGGPGAF TDEQLEMMAAFADQAALAWQLATSQRRMRELDVLTDRDRIARDLHDHVIQ RLFAIGLALQGAVPHERNPEVQQRLSDVVDDLQDVIQEIRTTIYDLHGAS QGITRLRQRIDAAVAQFADSGLRTSVQFVGPLSVVDSALADQAEAVVREA VSNAVRHAKASTLTVRVKVDDDLCIEVTDNGRGLPDEFTGSGLTNLRQRA EQAGGEFTLASVPGASGTVLRWSAPLSQ |
| Rv3134c | 42 | MSDPRPARAVVVGIDGSRAATHAALWAVDEAVNRDIPLRLVYVIDPSQLS AAGEGGGQSAARAALHDASRKVEATGQPVKIETEVLCGRPLTKLMQESRS AAMLCVGSVGLDHVRGRRGSVAATLAGSALCPVAVIHPSPAEPATTSQVS AVVAEVDNGVVLRHAFEEEARLRGVPLRAVAVHAAETPDDVEQGSRLAHVH LSRRLAHWTRLYPEVRVDRAIAGGSACRHLAANAKPGQLFVADSHSAHEL CGAYQPGCAVLTVRSANL |
| Rv3841 | 43 | MTEYEGPKTKFHALMQEQIHNEFTAAQQYVAIAVYFDSEDLPQLAKHFYS QAVEERNHAMMLVQHLLDRDLRVEIPGVDTVRNQFDRPREALALALDQER |

TABLE 1-continued

Amino acid sequences of selected low oxygen induced antigens

| Rv no. | SEQ ID NO: | Sequence |
|---|---|---|
| | | TVTDQVGRLTAVARDEGDFLGEQFMQWFLQEQIEEVALMATLVRVADRAG
ANLFELENFVAREVDVAPAASGAPHAAGGRL |
| Rv3842c | 44 | MTWADEVLAGHPFVVAHRGASAARPEHTLAAYDLALKEGADGVECDVRLT
RDGHLVCVHDRRLDRTSTGAGLVSTMTLAQLRELEYGAWHDSWRPDGSHG
DTSLLTLDALVSLVLDWHRPVKIFVETKHPVRYGSLVENKLLALLHRFGI
AAPASADRSRAVVMSFSAAAVWRIRRAAPLLPTVLLGKTPRYLTSSAATA
VGATAVGPSLPALKEYPQLVDRSAAQGRAVYCWNVDEYEDIDFCREVGVA
WIGTHHPGRTKAWLEDGRANGTTR |
| Rv3908 | 45 | VSDGEQAKSRRRRGRRRGRRAAATAENHMDAQPAGDATPTPATAKRSRSR
SPRRGSTRMRTVHETSAGGLVIDGIDGPRDAQVAALIGRVDRRGRLLWSL
PKGHIELGETAEQTAIREVAEETGIRGSVLAALGRIDYWFVTDGRRVHKT
VHHYLMRFLGGELSDEDLEVAEVAWVPIRELPSRLAYADERRLAEVADEL
IDKLQSDGPAALPPLPPSSPRRRPQTHSRARHADDSAPGQHNGPGPGP |

TABLE 2

DNA sequences of selected low oxygen induced antigens

| Rv no. | SEQ ID NO: | Sequence |
|---|---|---|
| Rv0079 | 46 | gtggaaccgaaacgcagtcgcctcgtcgtatgtgcacccgagccatcgca
cgcgcgggaattcccggatgtcgccgtattctccggcggccgggctaacg
catcccaggccgaacggttggctcgtgccgtgggtcgcgtgttggccgat
cggggcgtcaccggggggtgctcggggtgcggctgaccatggcgaactgcgc
cgatgggccgacgctggtgcagataaacctgcaggtaggtgacaccccat
taagggcgcaggccgccaccgcgggcatcgatgatctgcgacccgcactg
atcagactggatcgacagatcgtgcgggcgtcggcacagtggtgcccccg
gccttggccggatcggccccgccggcgattgaccacgccggccgaggcgc
tagtcacccgccgcaaaccggtcgtgctaaggcgcgcaacccgttgcag
gcgattgccgctatggacgccatggactacgacgtgcatttgttcaccga
cgccgagacggggggaggacgctgtggtctatcgggctggaccgtcggggc
tgccggctggcccgccagcaccacgtatttcccccaggatggtcacgttgt
cgcgccccagccgggccgccggtgccgctgattgtgaattcgcgtccgac
accggttctcacggaggccgccgcggtggaccgggcgcgcgaacatggac
tgccattcctgttttttcaccgaccaggccaccggccgcggccagctgctc
tactcccgctacgacggcaacctcgggttgatcaccccgaccggtgacgg
cgttgccgacggtctggca |
| Rv0080 | 47 | atgagcccgggctcgcggcgcgccagcccgcaaagcgcccgggaggtggt
cgagctcgaccgtgacgaggcgatgcggttgctggccagcgttgaccatg
ggcgtgtggtgttcacccgcgcggcgctgccggcgatccgtccagtcaat
cacctcgtggtcgacggtcgggtgatcgggcgcacccgcctgacggccaa
ggtgtccgttgcggtgcgatcgagcgccgatgccggtgtcgtggtcgcct
acgaagccgacgaccttgatccgcggcgtcggacggggtggagtgtggtg
gtgacgggactggcgaccgaggtcagcgatcccgagcaggttgcccgcta
ccagcggctgctacacccgtgggtgaacatggcgatggacaccgtggtcg
cgatcgaacccgagatcgtcaccggcatccgcatcgttgctgactcgcgt
acgccg |
| Rv0081 | 48 | gtggagtccgaaccgctgtacaagctcaaggcggagttcttcaaaaccct
tgcgcatccggcgcggatcaggattttggagctgctggtcgagcgggacc
gttcggtcggtgagttgctgtcctcggacgtcggcctggagtcgtcgaac
ctgtcccagcagctgggtgtgctacgccgggcgggtgttgtcgcggcacg
tcgtgacggcaacgcgatgatctattcgattgccgcaccgatatcgccg
agctgctggcggtggcacgcaaggtgctggccagggtgctcagcgaccgg
gtggcggtgctagaggacctccgcgccggcggctcggccacg |
| Rv0363c | 49 | atgcctatcgcaacgcccgaggtctacgcggagatgctcggtcaggccaa
acaaaactcgtacgctttcccggctatcaactgcacctcctcggaaaccg
tcaacgccgcgatcaaaggtttcgccgacgccggcagtgacggaatcatc
cagttctcgaccggtggcgcagaattcggctccggcctcggggtcaaaga
catggtgaccggtgcggtcgccttggcggagttcacccacgttatcgcgg
ccaagtaccccggtcaacgtggcgctgcacaccgaccactgccccaaggac
aagttggacagccatgtccggcccttgctggcgatctcggcgcaacgcgt
gagcaaaggtggcaatccttttgttccagtcgcacatgtggacggctcgg
cagtgccaatcgatgagaacctggccatcgcccaggagctgctcaaggcg
gcggcggccgccaagatcattctggagatcgatcggcgtcgtcggcgg
cgaagaggacggcgtggcgaacgagatcaacgagaagctgtacaccagcc
cggaggacttcgagaaaaccatcgaggcgctgggcgccggtgagcacggc |

TABLE 2-continued

DNA sequences of selected low oxygen induced antigens

| Rv no. | SEQ ID NO: | Sequence |
|---|---|---|
|  |  | aaatacctgctggccgcgacgttcggcaacgtgcatggcgtctacaagcc<br>cggcaacgtcaagcttcgccccgacatccttgcgcaagggcaacaggtgg<br>cggcggccaagctcggactgccggccgacgccaagccgttcgacttcgtg<br>ttccacggcggctcgggttcgcttaagtcggagatcgaggaggcgctgcg<br>ctacggcgtggtgaagatgaacgtcgacaccgacacccagtacgcgttca<br>cccgcccgatcgccggtcacatgttcaccaactacgacggagtgctcaag<br>gtcgatggcgaggtgggtgtcaagaaggtctacgacccgcgcagctacct<br>caagaaggccgaagcttcgatgagccagcgggtcgttcaggcgtgcaatg<br>acctgcactgcgccggaaagtccctaacccac |
| Rv0572c | 50 | atgggtgagcacgccatcaagcggcacatgcggcaacggaagcctacgaa<br>gcatcccctagcccagaaacggggcgcgcggattctggtcttcaccgacg<br>atccccgcaggagcgtcctcatagtgcccggttgccacctggattccatg<br>cgccgagaaaagaacgcgtactacttccaggacggcaatgcgttggttgg<br>gatggttgtctcgggcggcacggttgagtacgacgccgacgaccgcacat<br>atgtcgtgcagctcaccgacggaaggcacaccactgagtcatctttcgaa<br>cactcatcgccgagtcgatcacctcaatccgatgaccta |
| Rv0574c | 51 | gtggctggcaatcctgatgtggtgacggtgctgctgggcggtgacgtcat<br>gctcggccgtggcgtcgatcagatcctgcctcatcccggcaaaccgcaat<br>tgcgcgaacggtatatgcgggatgcgaccggctatgttcgcctggccgag<br>cgggtgaacgggcgcattccgctccccgtggattggcgctggccctgggg<br>cgaggcgttggcggtccttgagaacaccgcgaccgacgtctgtttgatca<br>atctggagacgacgatcaccgccgacggtgaattcgccgaccgcaaaccg<br>gtctgctaccggatgcacccggataacaacgtgccggcgctgacggcattgcg<br>gccgcacgtgtgcgcgctggccaacaaccacattctcgatttcggctacc<br>aggggctgaccgatacggtcgcggctctcgccggtgcggggatccagagt<br>gtcggggcgggagccgatttgctcgccgctcgccgctcggcgctagtcac<br>ggttggccatgaacgccgggtgatcgtcggctcggtagcggcggaatcca<br>gcggcgtccccgaatcctgggccgcccgccgcgaccggcccggagtgtgg<br>ttgatccgggatccggcgcaacgcgacgtcgccgacgatgtggcggcaca<br>ggtgctggcggacaaacgccccggcgatatcgccatagtctcgatgcatt<br>ggggatccaattggggctatgcgaccgcaccccggcgacgtcgcgttcgcg<br>caccgactgatcgacgccggcatcgacatggtccacggacattcctcgca<br>ccatccgcggccaatcgagatatatcgcggtaaaccgatcctgtacggat<br>gcggtgacgtcgttgacgactacgaaggcatcggcgggcacgagtcgttc<br>cgcagtgaactgcgactgctgtatctgaccgtcaccgatcccgccagcgg<br>gaacctgatctcgctgcagatgcttccactgcgagtgtcgcggatgcgcc<br>tacagcgtgcctcccagaccgacaccgaatggctccgcaacaccaccgag<br>cgcatcagccgccggttcgggattcgagtcgtgactcgacccgacaacct<br>gctggaggtcgttcccgctgccaacctaacgagcaaggag |
| Rv1264 | 52 | gtgacagaccacgtgcgcgaggcggacgacgcgaacatcgacgatctgtt<br>gggcgacctgggcggtaccgcgcgcgccgagcgtgcgaagcttgtcgagt<br>ggttgctcgagcagggcatcacccccgacgagattcgggcgaccaaccg<br>ccgttgctgctggccaccgccacctcgtcggcgacgacggcacctacgt<br>atccgcaagggagattagcgagaactatggcgttgacctcgagctgctgc<br>agcgggtgcagcgcgctgtcggtctggccagagtggatgatcctgacgcg<br>gtggtgcacatgcgtgccgacggtgaggcggccgcacgcacagcggtt<br>cgttgagctggggctgaatcccgaccaagtcgtgctggtcgtgcgtgtgc<br>tcgccgagggcttgtcacacgccgccgaggccatgcgctacaccgcgctg<br>gaggccattatgcgccggggggctaccgagttggacatcgcgaaggggtc<br>gcaggcgctggtgagccagatcgtgccgctgctggggccgatgatccagg<br>acatgctgttcatgcagctgcggcacatgatggagacggaggccgtcaac<br>gccgagagcgtgcggccggcaagccgctaccgggagcgcgacaggtcac<br>cgttgccttcgccgacctggtcggtttcacccagctaggcgaagtggtgt<br>cggccgaagagctagggcacctcgccgggcggctggccggcctcgcgcgt<br>gacctgaccgctccgccggtgtggttcattaagacgatcggcgacgcggt<br>catgttggtctgtcctgatccggcgccattgctggacaccgtgctgaagc<br>tggtcgaggtcgtcgacaccgacaacaactttccccggctgcgagccggc<br>gtcgcctccgggatggcggttagccgggccggcgactggttcggcagccc<br>ggtcaacgtggcaagccgggtgaccggggtggcgcgcccgggtgccgtgc<br>tggtcgcggattcggtgcgggaggcccttggtgatgcccccgaagccgac<br>ggatttcagttggtccttcgccggccccgtcgcctcaggggaatccgggg<br>tgacgtcaggcttttttcgagtccggcgaggggccactcgcaccggctccg<br>gcggcgcggcccaagacgacgatttggccggctcgtcaccg |
| Rv1592c | 53 | atggtagagcccggcaatttggcaggcgcgaccggcgccgaatggatcgg<br>ccggccaccgcacgaggaattgcagcgcaaagtgcgcccgctgctgccat<br>ccgacgatccgttctacttcccaccctgccggctaccagcatgccggccc<br>ggaacggtgttgcgctcgcgcgatgtcgaactggcgtttatgggcttgat<br>tccgcagcccgtcaccgctaccagctgctgtaccggaccacgaacatgt<br>acggcaaccccgaggcgacggtgaccacggtgatcgtcccagcggagctt<br>gccccgggtcagacctgcccccttgctgtcgtaccagtgtgcgatcgatgc<br>catgtcgtcgcgctgttttccgtcatatgcccctgcgacgacgggccaagg |

TABLE 2-continued

DNA sequences of selected low oxygen induced antigens

| Rv no. | SEQ ID NO: | Sequence |
|---|---|---|
| | | ccctggggtcactgacccaaatggagctgttgatgatcagcgccgcactt<br>gccgaaggatgggcggtatcagtacccgaccatgaagggccgaaagggct<br>gtgggggtcgccgtatgaacccggttaccgagtcctcgacggaatccggg<br>ctgccttgaattccgagcgtgtcggttgtccccggcaacgccgatcggg<br>ctgtggggctactccggcggcgggctggccagcgcgtgggccgccgaagc<br>atgcggcgagtacgcaccggacctagacatcgtcggcgccgtgctgggat<br>cacccgtcggtgaccttggtcacacgttccgccggctcaatggcactctt<br>cttgccggtctgcccgcgttggtggtggccgcgctgcaacacagctaccc<br>cggcctggcccgggtgatcaaggagcacgccaacgacgaaggacgtcagc<br>tgctggagcaactgacggagatgacaacggtagacgcagtgatccggatg<br>gccggcagggacatgggtgacttcctcgacgaaccccttgaggacattct<br>gtcgacgccggaaatttcccatgtcttcggcgacaccaagctgggtagcg<br>cggtgcccacccccgccggtattgatcgtgcaggccgtgcatgactacctc<br>atcgacgtctctgacatcgacgcgctcgctgacagctatacagccggcgg<br>cgccaacgtcacctaccaccgcgacctgttcagcgaacatgtgtccctgc<br>acccgctgtcggccccaatgacgcttcgctggctcaccgaccggttcgcc<br>ggcaagccactgaccgaccaccgcgtccggaccacgtggccgaccatctt<br>caacccgatgacctacgccggcatggcgagactggccgtgatcgcggcca<br>aggtgatcaccggcaggaagttgagccgccgtccgctc |
| Rv1733c | 54 | atgatcgccacaacccgcgatcgtgaaggagccaccatgatcacgtttag<br>gctgcgcttgccgtgccggacgatactgcgggtgttcagccgcaatccgc<br>tggtgcgtgggacggatcgactcgaggcggtcgtcatgctgctggccgtc<br>acggtctcgctgctgactatcccgttcgccgccgcgggccggcaccgcagt<br>ccaggattcccgcagccacgtctatgccaccaggcccagaccgccatc<br>ccgcaaccgcgaccgtgatcgatcacgagggggtgatcgacagcaacacg<br>accgccacgtcagcgccgccgcgcacgaagatcaccgtgcctgcccgatg<br>ggtcgtgaacggaatagaacgcagcggtgaggtcaacgcgaagccgggaa<br>ccaaatccggtgaccgcgtcggcatttgggtcgacagtgccggtcagctg<br>gtcgatgaaccagctccgccgcccgtgccattgcggatgcggccctggc<br>cgccttgggactctggttgagcgtcgccgcggttgcgggcgccctgctgg<br>cgctcactcgggcgattctgatccgcgttcgcaacgccagttggcaacac<br>gacatcgacagcctgttctgcacgcagcgg |
| Rv1734c | 55 | atgaccaacgtcggtgaccaggggggttgacgcggtcttcggggtgatcta<br>cccacctcaggtcgcgctggtcagtttcggcaagccggcacaacgagttt<br>gcgccgtcgacggcgcgatccacgtcatgacgaccgtgctggctacgctg<br>cccgctgaccacggctgcagcgatgaccatcgcggcgcgctgttcttcct<br>gtcgatcaacgagctgacgcggtgcgccgcagtaacagga |
| Rv1736c | 56 | gtgacggtgacaccacggaccggcagccgcatcgaggagctgcttgcacg<br>cagcggccggttcttcatcccgggtgagatctcggcggatctgcgtaccg<br>tgacccgccgcggcggccgcgacggcgacgtgttctatcgagaccggtgg<br>agccacgacaaggtggtccgctccacacacgggtgaattgcaccgggtc<br>gtgttcttggaagatctacgtcaaagacgacatcatcacctgggagacgc<br>aggagaccgactatccgtcggtggggcccggaccggcccgagtatgagccc<br>cgcggctgcccgcgcggcgcggcgttttcctggtacacgtattcgccgac<br>gcgggtgcgccatccgtacgcccgcggcgtgcttgtcgagacgtatcggg<br>aggcgaaggcacgtttgggtgatccggtggcggcctgggccgacatccag<br>gccgaccgcggcggccgcgctaccagcgcgcccgcggcaagggcgg<br>gctggtccgggtcagctgggccgaggccaccgagatgatcgccgccgccc<br>acgtgcacaccatctccacatacggcccgaccgggttgccggcttctcc<br>cccatcccggcgatgtccatggtgagccacgccgcggggtcgcggttcgt<br>ggagctaatcggcggggtgatgacgtcgttctacgactggtacgccgacc<br>tgccggtggcctccccgcaggtgttcggcgaccagaccgacgtgccggag<br>tccggagattggtgggacgtggtgtggcaatgcgcctcggtgctgctgac<br>ctacccgaactcacggcaactcggcaccgcagaggaattgctggcccaca<br>tcgacggtccggccgcggatctgttggggcgcacggtctctgagctgcgc<br>cgtgccgatccgctgaccgcggcgacccgctacgtcgacaccttcgacct<br>gcgaggccgcgcaccctgtacctgacctactggaccgccggcgacaccc<br>gcaaccgcggccgggagatgctggccttcgcccagacctaccgcagcacc<br>gacgtcgcaccaccgcgcggcgagaccccggacttcctgccggtggtgct<br>cgaattcgccgcgaccgtcgaccccgaggcggggcgacggttgctgagcg<br>ggtaccgggtgcccatcgccgcgctgtgcaatgccctgaccgaggccgca<br>ttgccatacgcacacacggtggccgcggtatgccggacgggtgacatgat<br>gggcgaactcttctggaccgtcgtgccgtatgtgacgatgacgatcgtcg<br>cggtcggctcctggtggcgctaccgctatgacaaattcggctggaccacc<br>cgctcgtcccagctgtacgagtcgcggctgctgcggatcgccagcccgat<br>gtttcatttcggcatcctggtggtcatcgtcggccacggtatcgggctcg<br>tgatcccgcagtcgtggactcaggccgccggtttgagcgagggcgcatat<br>cacgtgcaggccgtcgtgctggggtcgatgccggcatcaccaccttggc<br>cggcgttacccctgctgatctaccggcggcgcaccccgcgggccggtgttca<br>tggctaccaccgtcaacgacaaggtgatgtacctcgtgctggtggcggcg<br>atcgtcgcgggactgggtgcgacggcgtttgggctccggcgttgtcggcga<br>ggcgtacaactaccgcgagacggtgtcggtgtggttccgctcggtgtggg |

TABLE 2-continued

DNA sequences of selected low oxygen induced antigens

| Rv no. | SEQ ID NO: | Sequence |
|---|---|---|
| | | tactgcaaccgcgcggggacctgatggccgaggctccgctgtattaccag<br>atccatgtgctgatcgggttggcgttgttcgcgttgtggccgttcacccg<br>gctggtacacgcgttcagcgccccgatcggctatctgttccgcccgtaca<br>tcatctaccgcagccgcgaggagctggtgctaacgcggccgcggcggcgc<br>gggtgg |
| Rv1737c | 57 | atgagagggcaagcggccaatctcgtgctggccacctggatctcggtggt<br>caacttctgggcgtggaacctgatcggcccgctgtcgaccagctacgcgc<br>gtgacatgtcactgtccagcgccgaggcgtcgctgctcgtcgccaccccg<br>atcctggtgggtgcccttggccgcatcgtcaccgggccgctcaccgaccg<br>cttcggcgggcgcgccatgctcatcgcggtgacgctggcgtcgatcctcc<br>cggcgctcgcggtcgggtcgcggcaaccatgggctcctacgcgttgctg<br>gtgttttttcgggctcttcctgggcgttgccggcacgatcttcgcgtcgg<br>catcccgttcgccaacaactggtaccagccggcgcggcgcggtttctcca<br>ccgcgtgttcggtatgggcatggtcggcaccgcgctctcggcgttcttc<br>accccgcggtttgtacggtggttcggcctgttcaccacccacgccatcgt<br>cgcggccgcgctcgcgtcgaccgccgtggtggccatggtcgtgcttcgtg<br>atgcaccctactttcggcccaacgccgaccggtgctgcccaggctcaag<br>gccgcggcacggttgccggtgacctgggagatgtcgtttctgtacgcgat<br>cgtgttcggcgggttcgtggcgttcagcaactacctgcccacctacatca<br>ccacgatctacgggttctccacgctcgacgcgggcgctcgcaccgccggg<br>ttcgccctggcggcggtgctggcccggccggtgggcgggtggctctccga<br>ccggatcgcaccgaggcacgtggtgctggcctcgctcgccgggaccgcgc<br>tgctggcgttcgccgcggcgttgcagccgccgccggaggtgtggtcggcg<br>gccaccttcatcaccctggcggtctgcctcggcgtgggcaccggcggcgt<br>gttcgcgtgggtggcccgccgcgcccggccgcatcggtcggctcggtca<br>ccggaatcgtcgccgcggcaggcggattgggcggttacttccgccgctg<br>gtgatgggcgcgacctacgacccggtcgacaacgactacacggtcgggtt<br>gctgctgctggtggcgaccgcgctggtcgcgtgtacctacaccgcgctgc<br>acgcgcgggagccggtgagtgaggaggcgtccagg |
| Rv1738 | 58 | atgtgcggcgaccagtcggatcacgtgctgcagcactggaccgtcgacat<br>atcgatcgacgaacacgaaggattgactcgggcgaaggcacggctgcgtt<br>ggcgggaaaaggaattggtgggtgttggcctggcaaggctcaatccggcc<br>gaccgcaacgtccccgagatcggcgatgaactctcggtcgcccgagcctt<br>gtccgacttggggaagcgaatgttgaaggtgtcgacccacgacatcgaag<br>ctgttacccatcagccggcgcgattgttgtat |
| Rv1739c | 59 | atgattcccacgatgacatcggccggctgggcaccagggggtggtgcagtt<br>ccgcgaataccaacggcgttggctgcgcggcgatgtcctcgccggcctga<br>ccgtggccgcctatctgatcccgcaagcgatggcgtatgcgaccgtggcg<br>ggcctaccgccggcagccgggctgtgggcgtcgatcgcgccgcttgccat<br>ttacgcactgctcggatcgtcccggcagctttcaatcggcccggaatccg<br>ccaccgccttgatgacggcggccgtgctcgctccgatggccgccggggat<br>cttcgacgctatgccgttctggcggcaaccctcggattgctagtcggcct<br>tatctgcctactcgctggcacggcgcgactaggtttcctcgccagcctgc<br>gatcgcggccggtgctcgtcggatacatggccggcatcgcgcttgtcatg<br>atctccagccaactcggcactatcaccggcacctcggtcgaaggcaacga<br>attcttcagcgaagtacactcttcgcgactagcgtcacgcgagttcact<br>ggccgacttttgtgttagccatgtctgtcctagcgctgctaactatgctc<br>acgcggtgggcgccgcgcgccccggaccgatcatcgcggttcttgcggc<br>cacgatgctagtggccgttatgtccttggatgccaaaggtattgcgattg<br>tgggtcggataccttccggtctgccgacgccgggtgtgccgcccgtttcg<br>gtggaagacttgcgggcactgatcattccggctgccgggatcgcgattgt<br>taccttcaccgacggtgtgttgaccgcacgcgccttcgccgctcgtcgag<br>gtcaggaagtcaatgccaacgccgagctgcgcgcggtcggggcctgcaac<br>atcgccgccgggctgacacacggttttccggtgagttccagcagcagccg<br>taccgccctcgccgacgtcgtcggtggccgcaccagctgtactcgctga<br>tcgcgttggggcctgttgtcatcgtgatggttttcgcgagtgggctgctg<br>gccatgtttccgatcgccgctctgggcgctttggtggtatatgccgcgct<br>acgcttgatcgacttgtcagaattccggcgactggcgcggtttcggcgca<br>gcgaactcatgctggcactagccaccacagcagccgtgttaggcctagga<br>gtgttctatggagtcctcgccgcggttgccctgtccatcctcgaactgct<br>tcgtcggtcgcacatccgcatgacagcgttctcgggttcgtgccgggca<br>ttgccggcatgcacgacatcgatgactatccgcaggccaagcgcgtgccc<br>gggctggtggtgtatcgctatgacgcgccgtttgtgcttcgccaatgccga<br>agacttccgcaggcgagcactgaccgtggtcgatcaggatccggggcaag<br>tcgagtggttccgtactcaacgccgaatccaatgtggaggtcgacctgact<br>gcgctggatgcgctcgaccaactccgcaccgagctgctgcgtcggggaat<br>agtgttcgccatggcccgggtcaaacaagacttgcgtgaatcactcaggg<br>ccgcagtcttctcgataagattggcgaagaccatatctttatgacattg<br>cctaccgcagtgcaggcgttccgtcggcgc |
| Rv1813c | 60 | atgatcacaaacctccgacgccgaaccgcgatggcagccgccggcctagg<br>ggctgctctcggggctgggcatcctgctggttccgacggtggacgcccatc |

TABLE 2-continued

DNA sequences of selected low oxygen induced antigens

| Rv no. | SEQ ID NO: | Sequence |
|---|---|---|
| | | tcgccaacggttcgatgtcggaagtcatgatgtcggaaattgccgggttg<br>cctatccctccgattatccattacggggcgattgcctatgccccagcgg<br>cgcgtcgggcaaagcgtggcaccagcgcacaccggcgcgagcagagcaag<br>tcgcactagaaaagtgcggtgacaagacttgcaaagtggttagtcgcttc<br>accaggtgcggcgcggtcgcctacaacggctcgaaataccaaggcggaac<br>cggactcacgcgccgcgcggcagaagacgacgccgtgaaccgactcgaag<br>gcgggcggatcgtcaactgggcgtgcaac |
| Rv1997 | 61 | ttgtcggcgtcagtgtctgccacgacggctcatcatggcttgccagcaca<br>tgaagtggtgctgctgctggagagcgatccatatcacgggctgtccgacg<br>gcgaggccgcccaacgactagaacgcttcgggcccaacaccttggcggtg<br>gtaacgcgcgctagcttgctggcccgcatcctgcggcagtttcatcaccc<br>gctgatctacgttctgctcgttgccgggacgatcaccgccggtcttaagg<br>aattcgttgacgccgcagtgatcttcggtgtggtggtgatcaatgcgatc<br>gtgggtttcattcaagaatccaaggcagaggccgcactgcagggcctgcg<br>ctccatggtgcacacccacgccaaggtggtgcgcgagggtcacgagcaca<br>caatgccatccgaagagctggttcccggtgaccttgtgctgttagcggcc<br>ggtgacaaggttcccgccgatttgcggctggtgcgacagaccggattgag<br>cgtgaacgagtcagcacttaccggcgagtcgacgccggttcacaaggacg<br>aggtggcgttgccggagggcacaccggtcgctgatcgtcgcaatatcgcg<br>tattccggcacattggtaaccgcggggccatggcgccgggatcgtcgtcgc<br>gaccggcgccgaaaccgaactcggtgagattcatcggctcgttggggccg<br>ccgaggttgtcgccacaccgctgaccgcgaagctggcgtggttcagcaag<br>tttctgaccatcgccatcctgggtctggcagcgctcacgttcggcgtggg<br>tttgctgcgccggcaagatgccgtcgaaacgttcaccgctgcgatcgcgc<br>tggcggtcggggcaattcccgaaggtctgcccaccgccgtgaccatcacc<br>ttggccatcggcatggcccggatggccaagcgccgcgcggtcattcgacg<br>tctacccgcggtggaaacgctgggcagcaccacggtcatctgcgccgaca<br>agaccggaacgctgaccgagaatcagatgacggtccagtcgatctggaca<br>ccccacggtgagatccgggcgaccggaacgggctatgcacccgacgtcct<br>cctgtgcgacaccgacgacgcgccggttccggtgaatgccaatgcggccc<br>ttcgctggtcgctgctggccggtgcctgcagcaacgacgccgcactggtt<br>cgcgacggcacacgctggcagatcgtcggcgatcccaccgagggcgcgat<br>gctcgtcgtggccgccaaggccggcttcaacccggagcggctggcgacaa<br>ctctgccgcaagtggcagccataccgttcagttccgagcggcaatacatg<br>gccaccctgcatcgcgacgggacggatcatgtggtgctggccaagggtgc<br>tgtggagcgcatgctcgacctgtgcggcaccgagatgggcgccgacggcg<br>cattgcggccgctggaccgcgccaccgtgttgcgtgccaccgaaatgttg<br>actcccgggggttgcgggtgctggcaaccgggatgggtgccggcgccgg<br>cactcccgacgacttcgacgaaaacgtgataccaggttcgctggcgctga<br>ccggcctgcaagcgatgagcgatccaccacgagcggccgcggcatcgcgg<br>gtggcggcctgccacagtgccggcattgcggtaaaaatgattaccggtga<br>ccacgcgggcaccgccacggcgatcgcaaccgaggtgggggttgctcgaca<br>acactgaaccggcggcaggctcggtcctgacgggtgccgagctggccgcg<br>ctgagcgcagaccagtacccggaggccgtggatacagccagcgtgtttgc<br>cagggtctctcccgagcagaagctgcggttggtgcaagcattgcaggcca<br>ggggcacgtcgtcgcgatgaccggcgacggcgtcaacgacgccccggcc<br>ttgcgtcaggccaacattggcgtcgcgatgggccgcggtggcaccgaggt<br>cgccaaggatgccgccgacatggtgttgaccgacgacgacttcgccacca<br>tcgaagccgcggtcgaggaaggccgcgcggcgtattcgacaatctgaccaag<br>ttcatcacctggacgctgcccaccaacctcggtgagggcctagtgatctt<br>ggccgccatcgctgttggcgtcgccttgccgattctgcccacccaaattc<br>tgtggatcaacatgaccacagcgatcgcgctcggactcatgctcgcgttc<br>gagcccaaggaggccggaatcatgacccggccaccgcgcgaccccgacca<br>accgctgctgaccggctggcttgtcaggcggactcttctggtttccacct<br>tgctcgtcgccagcgcgtggtggctgtttgcatgggagctcgacaatggc<br>gcgggcctgcatgaggcgcgcacgcggcgctgaacctgttcgtcgtcgt<br>cgaggcgttctatctgttcagctgccggtcgctgacccgatcggcctggc<br>ggctcggcatgttcgccaaccgctggatcatcctcggcgtcagtgcgcag<br>gccatcgcgcaattcgcgatcacatatctacccgcgatgaatatggtgtt<br>cgacaccgcgccaatcgatatcggggtgtgggtgcgcatattcgctgtcg<br>cgaccgcaatcacgattgtggtggccaccgacacgctgctgccgagaata<br>cgggcgcaaccgcca |
| Rv1998c | 62 | atgagtttccacgatcttcatcaccaaggtgttccgttcgtgttgcccaa<br>cgcctggatgtgccgtcggccctggcctacctcgcggagggcttcacgg<br>ctatcggcacaaccagtttcggggtctcgtccagcggcgggcacccggac<br>gggcaccgcgccactcgcggcgccaacatcgcactggcgccgccctggc<br>accgctgcaatgctacgtcagcgtcgacatcgaggacggatacagcgacg<br>aacccgacgccattgctgagtacgtcgcacaactgtcgacacccggaatc<br>aatatcgaggacagtagcgccgaaaagctcatcgaccccgcctggcagc<br>cgctaaaatcgttgcgatcaaacaacgtaaccccgaggtgttcgtcaacg<br>cccgcgtcgacacctattggttgcgccagcacgccgataccaccagcacg<br>atccagcgcgcacttcgctacgtcgatgccggcgccgacggcgtcttgt<br>cccactggccaacgatcccgacgaacttgctgagctcactcgcaacattc |

TABLE 2-continued

DNA sequences of selected low oxygen induced antigens

| Rv no. | SEQ ID NO: | Sequence |
|---|---|---|
| | | cgtgcccggttaacacgttgcccgtgcccggcttgacgatcgccgaccttggtgagctcggggtggcccgggtgtcaaccggttcagtgccctacagcgcggggttgtatgcagcggccacgcggctcgggccgtgagcgacggagagcagctgccacggtccgtaccgtacgccgaactgcaggcacgcttggttgactacgagaaccgcacgagtacaacg |
| Rv2003c | 63 | gtggtcaagcgctctcgggcaacccgactttcgccgagcatctggtccggatgggaatcacctcagtgtcggtccattcgggcgcgattgctgctaccccggggtcggtcgcggccgccgaacgccgattgttgctggaatcagctcgcggtgacgcctgacaccggatgccggcatcgtcggccgccgggcgcgacgcggcggcctacgacgcctggtatgactcacccaccgggcggccgatcctggcgaccgaggtcgccgcgttgcggccgctcatcgaggtctttgcccagccacgcttggaaatcggtgtcggtacaggacgtttcgccgacctgctcggcgtgcggttcggactcgatccatcccgtgatgcgctgatgttcgcacgccggcgcggcgtcctggtcgccaatgccgtcggcgaggcggtcccttttcgtcagccggcacttcggggcggtcctcatggcattcacgctctgtttcgtcaccgacccggccgccatattccgggaaacgcggcgtctgctcgccgacggcggcgccttgttatcgggttcttgcctcgcgggacaccgtgggccgacctgtacgctctgcgcgcggcccgcggacagccaggctaccgcgacgcccgcttctacaccgcggccgaactcgaacaactgctcgcagactcgggattccgggtcatcgcccgccgctgcacgctgcaccaaccgccgggactcgcccggtacgacatcgaagccgcccatgacggtatccaagccggcgccggcttcgttgctatctcggcggtcgaccaagcgcacgagcctaaggatgatcacccactcgagtcggaa |
| Rv2005c | 64 | atgtctaaaccccgcaagcagcacggagttgtcgtcggggtagatggttcgctcgaatcggatgccgccgcctgttggggtgccaccgatgcggcgatgaggaacattccgctgaccgtggtccacgtggtaacgccgatgtagcgacgtggccgccgatgccgtatccggagacctgggggtttggcaggaggacgagggtcgccagatcgtcgccaacgccgtcaagctcgccaaagaggcggttggagcggatcgaaagctcagcgtaaagagcgagctcgtattttccacgccggtacctaccatggttgaaatctccaacgaggcagagatggtggtgttgggcagctcgggccggggagcgctggcccgaggcttgctcggttcggtcagctcgagcctggtgcgacgcgccgggtgcccggtcgcggtcatccacagcgatgatgcggtgatccctgatccgcagcacgctcccgtgctggtgggaatcgacggttcgccggtttcggagcttgcgacggcggtggcatttgacgaggcgtcgcgccgcggcgtcgaactgatcgccgtgcacgcgtggagtgacgtcgaagtggtggaacttccgggtttggacttctcggctgtacagcaggaagcggagcttagtctcgccgaacgcttggcaggttggcaagaacgctatcccgatgtgccggtgagccggttgtcgtttgcgatcgcccggcgcggaagctggtgcaaaagtcggcgtccgcccagcttgtcgtcgttggcagtcatggccgaggtggcttgaccggcatgcttctggggtcggtcagtaacgcggtcttacacgccgcgcgggtgccagtgatcgtggcacggcagtcg |
| Rv2007c | 65 | gtgacctatgtgatcggtagtgagtgcgtggatgtgatggacaagtcctgtgtgcaggagtgtccggtcgactgtatctatgagggcgcccgaatgctctacatcaaccccgacgagtgcgtggattgtggtgcgtgcaaaccggcctgccgcgtcgaggcgatctactgggaaggcgatctacccgacgatcaacaccagcatctgggggacaacgccgcctttttccaccaagtcctgccgggccgagtggctccgctgggttcgccgggtggtgccgcagcggcgggcccgatcggagtcgacacgcctctggtcgcggctatcccggtggagtgccct |
| Rv2028c | 66 | atgaaccaatcacacaaaccccatcgatcgtcgtcggtattgatggctcgaagccggccgtgcaagccgcactgtgggcggtcgacgaggcagccagcgtgacatcccgctgcgtctgctgtacgcgatcgaacccgacgatcccgggtacgccgcacacggcgcggcggctcgcaaactcgccgccgccgagaacgcggtgcgctacgcgttcacagcggtcgaggcggcgaccggccggtcaaggtcgaggtggagatcaccccaggagcggccggtcacctcgttgatccgcgctcggcggctgctgcccggtgtgcgttggcgctatcggcgtgcaccacttccgaccggagcgggtgggatctaccgcagcggccctggcgttatcggcgcagtgcccagtggcgatcgtgcgacccaccgggtccccatcggacgcgaccgccgcatggatcgtcgtcgaggcggacgggtcgtccgatatcggtgttttgctggggcggtgatgccgaagcacggctgcgcgactcgccggttcgggtggtcacctgccggcaatccggagtgggcgataccggggacgacgtccgtgccagcctggaccgctggcttgcccgttggcaaccacggtatcccgatgtgcgggtgcaatcggcggcagtgcacgcgagctgctggattatctggctgggctgggtcgatcggtacacatggtggtgctcagcgcgagcgaccaggagcatgtgggagcaacttgtgggagcgccgggcaacgccgtgttgcaggaggccggctgcaccctgctggtcgtcggtcagcagtatctg |
| Rv2029c | 67 | atgacggagccagcggcgtgggacgaaggcaagccgcgaatcatcactttgaccatgaaccccgccttggacatcacgacgagcgtcgacgtggtgcgcccgaccgagaaaatgcgttgtggcgcacctcgctacgatcccggcggcggcggtatcaatgtcgcccgcattgtgcatgtcctcggcggttgctcgacagcactgttcccggccggcgggtcgaccgggagcctgctgatggcgctgctcg |

TABLE 2-continued

DNA sequences of selected low oxygen induced antigens

| Rv no. | SEQ ID NO: | Sequence |
|---|---|---|
| | | gtgatgcgggagtgccatttcgcgtcattccgatcgcggcctcgacgcgg |
| | | gagagcttcacggtcaacgagtccaggaccgccaagcagtatcgtttcgt |
| | | gcttccggggccgtcgctgaccgtcgcggagcaggagcaatgcctcgacg |
| | | aactgcgcggtgcggcggcttcggccgccttttgtggtggccagtggcagc |
| | | ctgccgccaggtgtggctgccgactactatcagcgggttgccgacatctg |
| | | ccgccgatcgagcactccgctgatcctggatacatctggtggcgggttgc |
| | | agcacatttcgtccggggtgtttcttctcaaggcgagcgtgcgggaactg |
| | | cgcgagtgcgtcggatccgaactgctgaccgagcccgaacaactggccgc |
| | | cgcacacgaactcattgaccgtgggcgcgccgaggtcgtggtggtctcgc |
| | | ttggatctcagggcgcgctattggccacacgacatgcgagccatcgattt |
| | | cgtcgattccgatgaccgcggttagcggtgtcggcgccggcgacgcgat |
| | | ggtggccgcgattaccgtgggcctcagccgtggctggtcgtcatcaagt |
| | | ccgttcgcttgggaaacgcggcaggtgcagccatgctgctgacgccaggc |
| | | accgcggcctgcaatcgcgacgatgtggagaggttcttcgagctggcggc |
| | | cgaacccaccgaagtcgggcaggatcaatacgtttggcacccgatcgtta |
| | | acccggaagcctcgcca |
| Rv2030c | 68 | gtgctgatgaccgcagcggctgatgtcacccggcgctcgccgcggcgcgt |
| | | gttccgtgaccgccgcgaggccggccgggtgctggcggaattactcgccg |
| | | cctatcgggaccagccggacgtgattgtgctcggcttggcccggggtggc |
| | | ctccccggtcgcatgggaggttgccgcggcactgcatgccccgctagacg |
| | | cttcgtcgtgcgcaaacttggtgccccggggcatgacgagttcgccgttg |
| | | gtgcactggccagcggcggccgcgtcgtggtcaatgacgacgtcgtgcgg |
| | | ggcctgcggatcacaccgcagcaactgcgcgacatcgccgaacgtgaggg |
| | | tcgggaactgcttcggcgcgagtccgcctaccgcggcgagcgcccgcca |
| | | ccgatatcaccggcaagacggtcattgtcgtcgatgacggtttggccacc |
| | | ggcgcaagcatgttcgcggcggtacaggcattgcgcgatgcgcaaccagc |
| | | gcagatcgtgattgccgtgccggcggcgcggagtccacgtgccgggagt |
| | | tcgccggcctcgtcgacgacgttgtgtgcgcgaccatgccgacccccgttc |
| | | ctggccgtcggtgagtcgtttttggacttccggcaggtcaccgacgagga |
| | | ggtccgccggctcctggccaccccgaccgctgggccgtcgctgcgccggc |
| | | ccgcggccgtcaacggcggccgatgttctgcgcagagtcgcgatcgacgcc |
| | | cccggggggtgttccgacgcacgaggtgttggcggagctggtcggcgatgc |
| | | acgaatcgtgttgatcggcgaaagctcgcacggcacacacgagttctacc |
| | | aggcccgggccgccatgacacagtggctgatcgaggagaagggctttggt |
| | | gcggtagccgccgaggcggactggcccgacgcctaccgggtcaatcggta |
| | | cgttcgcggcctcggcgaggacaccaacgctgacgaggcgcttagcggat |
| | | tcgagcggtttcccgcctggatgtggcgcaacaccgtggtccgagatttt |
| | | gtggaatggctgcgcacacgcaaccagcgctacgagtcgggcgcgctgcg |
| | | gcaagccggcttctacggtctggatctttacagcctgcatcggtcgatcc |
| | | aagaggtgatcagctatctcgacaaggtcgacccgcgtgcggcggcacgg |
| | | gcgcgggccggtatgcgcgcttcgaccatgcctgcgccgatgacggtca |
| | | ggcgtacggattcgcggccgcattcggcgccggtccgtcgtgcgaacgtg |
| | | aagccgtcgagcaactggtcgacgttcagcgcaatgccctggcgtatgcg |
| | | cgccaagacgggctgcttgccgaggacgaactgttctacgcccagcaaaa |
| | | cgcgcagacggtgcgcgacgcagaggtgtattaccgggccatgttcagtg |
| | | gacgcgttacctcgtggaacctgcgcgaccagcacatggcgcagaccctt |
| | | ggcagtttgctgacgcatttggaccgacacctcgatgcgccgccggcgcg |
| | | aatagtggtgtgggctcataactcccacgtgggtgacgcacgcgctaccg |
| | | aggtgtgggccgacgggcagctcaccctcggccagatagtccgtgagcga |
| | | tacggtgacgagtcgcgcagcatcggattcagcacgtacacgggcaccgt |
| | | caccgcggccagcgaatgggtggtatcgcccaacgcaaagcggttcggc |
| | | cggcactgcacggcagtgtcgaggagctcttccaccagactgcagacagt |
| | | ttcctggtgtcagcgcggctaagccgacgccgaagccccgctggacgt |
| | | tgtccggttgggacgtgccatcggcgtcgtttatctaccggcaacggaac |
| | | ggcaaagtcactacttgacgtgcggcccgccgaccagttcgacgccatg |
| | | atccacatcgatcagacccgtgccctggaacctctcgaggtgacgagccg |
| | | gtggatcgccggcgagaacccggaaacctacccgaccggtctg |
| Rv2031c | 69 | Atggccaccaccctttcccgttcagcgccaccgcggtccctcttccccga |
| | | gttttctgagctgttcgcggccttcccgtcattcgccggactccggccca |
| | | ccttcgacaccggttgatgcggctggaagacgagatgaaagaggggcgc |
| | | tacgaggtacgcgcggagcttcccggggtcgaccccgacaaggacgtcga |
| | | cattatggtccgcgatggtcagctgaccatcaaggccgagcgcaccgagc |
| | | agaaggacttcgacggtcgctcggaattcgcgtacggttccttcgttcgc |
| | | acggtgtcgctgccggtaggtgctgacgaggacgacattaaggccaccta |
| | | cgacaaggcatccttactgtgtcggtggcggtttcggaagggaagccaa |
| | | ccgaaaagcacattcagatccggtccaccaac |
| Rv2032 | 70 | atgccggacaccatggtgaccaccgatgtcatcaagagcgcggtgcagtt |
| | | ggcctgccgcgcaccgtcgctccacaacagccagccctggcgctggatag |
| | | ccgaggaccacacggttgcgctgttcctcgacaaggatcgggtgctttac |
| | | gcgaccgaccactccgccgggaagcgctgctggggtgcggcgccgtact |
| | | cgaccactttcgggtggcgatggcggccgcgggtaccaccgccaatgtgg |
| | | aacggtttcccaaccccaacgatcctttgcatctggcgtcaattgacttc |

TABLE 2-continued

DNA sequences of selected low oxygen induced antigens

| Rv no. | SEQ ID NO: | Sequence |
|---|---|---|
| | | agcccggccgatttcgtcaccgagggccaccgtctaagggcggatgcgat<br>cctactgcgccgtaccgaccggctgcctttcgccgagccgccggattggg<br>acttggtggagtcgcagttgcgcacgaccgtcaccgccgacacggtgcgc<br>atcgacgtcatcgccgacgatatgcgtcccgaactggcggcggcgtccaa<br>actcaccgaatcgctgcggctctacgattcgtcgtatcatgccgaactct<br>tttggtggacaggggcttttgagacttctgagggcataccgcacagttca<br>ttggtatcggcggccgaaagtgaccgggtcaccttcggacgcgacttccc<br>ggtcgtcgccaacaccgataggcgcccggagtttggcacgaccgctcta<br>aggtcctggtgctctccacctacgacaacgaacgcgccagcctactgcgc<br>tgcggcgagatgctttccgccgtattgcttgacgccaccatggctgggct<br>tgccacctgcacgctgacccacatcaccgaactgcacgccagccgagacc<br>tggtcgcagcgctgattgggcagcccgcaactccgcaagccttggttcgc<br>gtcggtctggccccggagatgaagagccgccaccggcaacgcctcggcg<br>accaatcgatgaagtgtttcacgttcgggctaaggatcaccgg |
| Rv2428 | 71 | atgccactgctaaccattggcgatcaattccccgcctaccagctcaccgc<br>tctcatcggcggtgacctgtccaaggtcgacgccaagcagcccggcgact<br>acttcaccactatcaccagtgacgaacacccaggcaagtggcgggtggtg<br>ttcttttggccgaaagacttcacgttcgtgtgccctaccgagatcgcggc<br>gttcagcaagctcaatgacgagttcgaggaccgcgacgcccagatcctgg<br>gggtttcgattgacagcgaattcgcgcatttccagtggcgtgcacagcac<br>aacgacctcaaaacgttacccttcccgatgctctccgacatcaagcgcga<br>actcagccaagccgcaggtgtcctcaacgccgacggtgtggccgaccgcg<br>tgacctttatcgtcgaccccaacaacgagatccagttcgtctcggccacc<br>gccggttcggtgggacgcaacgtcgatgaggtactgcgagtgctcgacgc<br>cctccagtccgacgagctgtgcgcatgcaactggcgcaagggcgacccga<br>cgctagacgctggcgaactcctcaaggcttcggcc |
| Rv2624c | 72 | atgtctgggagaggagagccgacgatgaaaacaatcattgttggtatcga<br>tggttcgcacgcggcgattacggccgcattgtgggggttgacgaggcca<br>tcagccgagcggtgccgctgcgactggtctcagtgatcaagccgacacat<br>ccgtccccggacgactacgaccgcgaccttgcgcatgctgaaagatcgct<br>tcgggaagcgcagtccgctgttgaggccgcgggcaagctcgtcaagatcg<br>aaaccgacatccccgcgggccagccggcccggtgcttgtggaggcatcg<br>cgcgacgccgagatgatctgcgtcggctccgtgggaatcgggcgctacgc<br>cagctcgatcttgggttcgacggcaaccgagctggccgaaaaggcgcatt<br>gcccggtcgccgtcatgcgctcaaaagtggaccagccagcgtctgacatc<br>aactggatcgtggtgcgcatgaccgacgcaccggataacgaggccgtgct<br>ggaatacgctgcccgggaagcgaagttgcggcaagcgcccatactggcac<br>tcggcggcgaccgaggagctccgggagattccggacggcgaattcgaa<br>cgtcgcgtgcaggattggcaccaccgtcatcccgatgtgcgcgtctaccc<br>gatcaccactcacacgggtattgcccggttcctggccgaccacgacgagc<br>gcgtacagctggcagtgatcggcggtggtgaggccggtcagctagcgcgg<br>ctggtcgggccatccggacatccggtgttccgtcacgccgagtgttcggt<br>gcttgtcgttcgccgc |
| Rv2625c | 73 | atgcgtgatgcgatcccgcttggcggatcgccgggtttgtggtgaacgt<br>ccactggagcgtgttggtgatcctgtggttgttcacctggagtctggcga<br>ccatgttgccgggtaccgtcggaggctacccggccgtggtctattggctt<br>ctcggcgcaggtggcgcggtcatgttgctggcgtcgctgttggctcatga<br>gctcgcgcacgccgtcgtcgctcgtcgcgccggggtatccgttgagagcg<br>tgacgttgtggctgttcggcggggtgaccgcgcttggcggcgaggcaaag<br>acgcccaaagccgctttccggatcgcgttcgcgggtccggctaccagcct<br>ggcgctgtcggcgacattcggtgcgttggccatcacgctcgccggcgtgc<br>ggaccccggccatcgtgatcagcgttgcttggtggttggctactgtcaac<br>ctgctgctggggctgttcaatctgctgcctggcgcgccgttggacggtgg<br>gcggttggtccgggcctatctgtggcgccgccacggcgatagtgtgcgcg<br>ccgggatcggtgcggcgggccggacgggtggttgcgctggtcttgatc<br>gcgttgggattggccgagtttgtggctggtggcctcgtcggtggggtctg<br>gttagccttcattggctggtttatcttcgctgccgctcgcgaggaggaga<br>cccggatttcgacccagcagctgtttgccggggtgcgtgtggccgatgcg<br>atgaccgcccaaccgcatacggctcccggatggataatgtcgaggattt<br>catccagcgttacgtgcttggtgaacggcactcggcatatccggttgccg<br>atcgggacggatcgatcacgggcctggtggcattgcggcagctgcgcgat<br>gttgcgcctagccggcgcagcactaccagcgtaggtgacattgcgctgcc<br>gctgcacagccgtgccgaccgcccgaccacaagagccgctgaccgcgctcc<br>tagagcggatggcaccgctcggcccgcgcagccgtgcgctggtcaccgaa<br>gggagcgcggtggtcggcaccgtcactcccagcgatgtcgcgcggctgac<br>tgacgtctaccggttggcccagccggaaccgaccttaccacgagtcccc<br>aagatgcggacaggttttccgatgcgggg |
| Rv2627c | 74 | atggcaagttctgcgagcgacggcaccccacgaacgctcggcttttcgcct<br>gagtccaccggtcttgagcggcgccatgggaccgttcatgcacaccggtc<br>tgtacgtcgctcaatcgtggcgcgactatctgggtcaacagcccgataaa<br>ctgccgatcgcacggcccactattgccttagcggcgcaagcctttcgaga |

TABLE 2-continued

DNA sequences of selected low oxygen induced antigens

| Rv no. | SEQ ID NO: | Sequence |
|---|---|---|
| | | cgaaatcgtcctgctgggcctcaaggcacgacgtccggtcagcaatcatc<br>gagtgttcgagcgcatcagccaagaagtggccgctggactggagttctat<br>gggaatcgcagatggctggagaagcctagcggattttttgcccagccccc<br>accgctcaccgaggtcgcggtccgaaaggtcaaggaccgcagacgctcct<br>tttatcgcatcttcttcgacagtgggtttacgccgcatccggtgaaccg<br>ggcagccaacggtggctctcatacactgcgaacaatcgcgagtacgccct<br>gttactgcggcacccagagccgcgtccctggctggtttgtgtacacggca<br>ccgagatgggcagggccccgttggatctcgcggtgttccgcgcctggaag<br>ctgcatgacgaactcggcctgaacattgtcatgccggttcttccgatgca<br>tggtccccgcgggcaaggtctgccgaagggcgccgttttccccggagaag<br>atgttctcgacgatgtgcatgggacggctcaagcggtgtgggatatccgg<br>cggctgttgtcctggatacgatcgcaggaggaggagtcgctgatcgggtt<br>gaacggtctctcgctgggcggctacatcgcgtcattggtcgccagcctcg<br>aagaaggtctcgcctgcgcgattctcggtgtcccagtggctgatctgatc<br>gagttgttgggccgccactgcggtcttcggcacaaagaccccgccgcca<br>caccgtcaagatggccgaaccgatcggccgaatgatctcgccgctctcac<br>ttacgccactggtgcccatgccgggccgctttatctacgcgggcattgcc<br>gaccgactcgtgcatccacgcgaacaggtgactcgcctctgggagcactg<br>gggcaaacccgaaatcgtgtggtatccaggcggtcacactggcttcttcc<br>agtcgcggccggtacgacggtttgtccaggctgcgctggagcagtcgggc<br>ctgttggacgcgccacggacacagcgcgaccgttccgcc |
| Rv2628 | 75 | Atgtccacgcaacgaccgaggcactccggtattcgggctgttggcccta<br>cgcatgggccggccgatgtggtcggataggcaggtgggggtgcaccagg<br>aggcgatgatgaatctagcgatatggcacccgcgcaaggtgcaatccgcc<br>accatctatcaggtgaccgatcgctcgcacgacgggcgcacagcacgggt<br>gcctggtgacgagatcactagcaccgtgtccggttggttgtcggagttgg<br>gcacccaaagcccgttggccgatgagcttgcgcgtgcggtgcggatcggc<br>gactggcccgctgcgtacgcaatcggtgagcacctgtccgttgagattgc<br>cgttgcggtc |
| Rv2629 | 76 | atgcgatcagaacgtctccggtggctggtagccgcagaaggtccgttcgc<br>ctcggtgtatttcgacgactcgcacgacactcttgatgcgtcggagcgcc<br>gggaagcgacgtggcgcgatgtccggaagcatctcgaaagccgcgacgcg<br>aagcaggagctcatcgacagcctcgaagaggcggtgcgggattctcgacc<br>ggccgtcggccagcgtggccgcgcgctgatcgcgaccggcgagcaagtac<br>tggtcaacgagcatctgatcggcccaccaccggctgcgctacggtgattcggctg<br>tcggattatccgtacgtcgtgccattgatagaccttgagatgcggcgacc<br>gacgtatgtatttgccgcggttgatcacaccggcgccgacgtcaagctgt<br>atcaggggccaccatcagttccacgaaaatcgatggggtcggctacccg<br>gtgcacaagccggtcaccgccggctggaacggctacggcgacttccagca<br>caccaccgaagaagccatccgaatgaactgccgcgcggtcgccgaccatc<br>tcacccgactggtagacgctgccgaccccgaggtggtgttcgtgtccggc<br>gaggtgcggtcacgcacagacctgctttccacattgccgcagcgggtggc<br>ggtccgggtgtcgcagctgcatgccggaccgcgcaaaagcgccttagacg<br>aggaagagatctgggacctgacatccgcggagttcacccggcggcggtac<br>gccgaaatcaccaatgtcgcacaacaatttgaggcggagatcggacgcgg<br>atcggggctggcggcccaagggttggcggaggtgtgtgcggctctgcgtg<br>acggcgacgtcgacacgctgatcgtcggagagctaggcgaggccaccgtg<br>gtcaccggtaaagcgctactacggtcgcgcgggatgccgacatgttgtc<br>cgaactcggcgaaccggtagatcgcgtggcaagggccgatgaggcgttgc<br>cattcgccgcgatcgcggtaggtgccgcattggtccgtgacgacaaccgg<br>atcgcgccactagatggggtgggcgcattgctgcgttatgccgccaccaa<br>ccgactcggcagccatagatcc |
| RV2630 | 77 | Atgctgcaccgcgacgatcacatcaatccgccgcggccccgcgggttgga<br>tgttccttgcgcccgcctacgagcgacaaatcccctgcgcgccttggcgc<br>gttgcgctcaggcgggcaagccgggcaccagttcagggcatcggtccgtg<br>ccgcatacggcggacttgcgaatcgaagcctgggcaccgaccgtgacgg<br>ctgtatccggcaggcggtgctgggtaccgtcgagagcttcctcgacctgg<br>aatccgcgcacgcggtccataccgggctgcgccggctgaccgcggatcgc<br>gacgacgatctactggtcgcggtgctcgaggaggtcatttatttgctgga<br>caccgtcggtgaaacgcctgtcgatctcaggctgcgcgacgttgacgggg<br>gtgtcgacgtcacattcgcaacgaccgatgcgagtacgctagttcaggtg<br>ggtgccgtgccgaaggcggtgtcactcaacgaacttcggttctcgcaggg<br>tcgccacggctggcgatgtgcggtaacgctcgatgtg |
| Rv2659c | 78 | Gtgacgcaaaccggcaagcgtcagagacgcaaattcggtcgcatccgaca<br>gttcaactccggccgctggcaagccagctacaccggccccgacggccgcg<br>tgtacatcgcccccaaaaaccttcaacgccaagatcgacgccgaagcatgg<br>ctcaccgaccgccgccgcgaaatcgaccgacaactatggtccccggcatc<br>gggtcaggaagaccgccccggagcccattcggtgagtacgccgaaggat<br>ggctgaagcagcgtggaatcaaggaccgcacccgcgcccactatcgcaaa<br>ctgctggacaaccacatcctggccaccttcgctgacaccgacctacgcga<br>catcaccccggccgccgtgcgccgctggtacgccaccaccgccgtgggca |

TABLE 2-continued

DNA sequences of selected low oxygen induced antigens

| Rv no. | SEQ ID NO: | Sequence |
|---|---|---|
| | | caccgaccatgcgggcacactcctacagcttgctgcgcgcaatcatgcag<br>accgccttggccgacgacctgatcgactccaaccctgccgcatctcagg<br>cgcgtccaccgcccgccgcgtccacaagatcaggcccgccaccctcgacg<br>agctggaaaccatcaccaaagccatgcccgaccctaccaggcgttcgtg<br>ctgatgcggcatggctggccatgcgctacggcgagctgaccgaattacg<br>ccgcaaagacatcgacctgcacggcgaggttgcgcgggtgcggcgggctg<br>tcgttcgggtgggcgaaggcttcaaggtgacgacaccgaaaagcgatgcg<br>ggagtcgcgacataagtatcccgccacatctgatacccgccatcgaaga<br>ccaccttcacaaacacgtcaacccccggccgggagtccctgctgttcccat<br>cggtcaacgaccccaaccgtcacctagcaccctcggcgctgtaccgtatg<br>ttctacaaggcccgaaaagccgccggccgaccagacttacggtgcacga<br>ccttcgacactccggcgccgtgttggctgcatccaccggcgccacactgg<br>ccgaactgatgcagcggctaggacacagcacagccggcgccgcactccgc<br>taccagcacgccgccaagggccgggaccgcgaaatcgccgcactgttaag<br>caaactggccgagaaccaggagatg |
| Rv2780 | 79 | Atgcgcgtcggtattccgaccgagaccaaaaacaacgaattccgggtggc<br>catcaccccggccggcgtcgcggaactaacccgtcgtggccatgaggtgc<br>tcatccaggcaggtgccggagagggctcggctatcaccgacgcggatttc<br>aaggcggcaggcgcgcaactggtcggcaccgccgaccaggcgtgggccga<br>cgctgatttattgctcaaggtcaaagaaccgatagcggcggaatacggcc<br>gcctgcgacacgggcagatcttgttcacgttcttgcatttggccgcgtca<br>cgtgcttgcaccgatgcgttgttggattccggcaccacgtcaattgccta<br>cgagaccgtccagaccgccgacggcgcactaccctgcttgccccgatga<br>gcgaagtcgccggtcgactcgccgcccaggttggcgcttaccacctgatg<br>cgaacccaaggggccgcggtgtgctgatgggcggggtgcccggcgtcga<br>accggccgacgtcgtggtgatcggcgccggcaccgccggctacaacgcag<br>cccgcatcgccaacggcatgggcgcgaccgttacggttctagacatcaac<br>atcgacaaacttcggcaactcgacgccgagttctgcggccggatccacac<br>tcgctactcatcggcctacgagctcgaggtgccgtcaaacgtgccgacc<br>tggtgattgggccgtcctggtgccaggcgccaaggcacccaaattagtc<br>tcgaattcacttgtcgcgcatatgaaaccaggtgcggtactggtggatat<br>agccatcgaccaggcggctgtttcgaaggctcacgaccgaccacctacg<br>accacccgacgttcgccgtgcacgacacgctgttttactgcgtggcgaac<br>atgcccgcctcggtgccgaagacgtcgacctacgcgctgaccaacgcgac<br>gatgccgtatgtgctcgagcttgccgaccatggctggcgggcggcgtgcc<br>ggtcgaatccggcactagccaaaggtctttcgacgcacgaaggggcgtta<br>ctgtccgaacgggtggccaccgacctgggggtgccgttcaccgagcccgc<br>cagcgtgctggcc |
| Rv3126c | 80 | Atggtcatccggtttgatcaaataggtcattggtcctctcaatgaaatc<br>ccttgcgccactgtcgtttcagcggtgtctgcgcgagaattctagcttgg<br>tcgcggcgctggaccggctcgatgctgcggtcgatgagctgagcgctttg<br>tcgtttgatgcgttgaccactccggagcgggatcgcgcccgtcgcgaccg<br>ggaccatcatccttggtcccgctcccgctcgcagttgtcgccacgaatgg<br>cgcacggtgcagtgcaccaatgccagtggccgaaggcggtttgggctgtc<br>attgacaatcca |
| Rv3127 | 81 | Gtgctcaagaacgcagtcttgctggcatgccgggcgccgtcggtgcacaa<br>cagccagccctggcgttgggtggccgaaagcggctccgagcacactactg<br>tgcacctgttcgtcaaccgccaccgaacggtgccggccaccgaccattcc<br>ggccggcaagcgatcatcagttgcggtgccgtactcgatcaccttcgcat<br>cgccatgacggccgcgcactggcaggcgaatatcactcgctttccccagc<br>cgaaccaacctgaccagttggccaccgtcgaattcagtcccatcgatcac<br>gtcacgcgggacagcgaaaccgcgcccaggcgattctgcagcgccgaac<br>cgatcggcttccgtttgacagcccgatgtactggcacctgtttgagcccg<br>cgctgcgcgacgccgtcgacaaagacgttgcgatgcttgatgtggtatcc<br>gacgaccagcgaacacgactggtggtagcgtcacaactcagcgaagtcct<br>gcggcgggacgatccgtactatcacgccgaactcgaatggtggacttcac<br>cgttcgtgctggcccatggtgtgccgccggatacgctggcatcggacgcc<br>gaacgcttgcgggttgacctgggccgtgacttcccggtccggagctacca<br>gaatcgccgtgccgagctagctgatgaccgatcgaaagtccttgtgccgt<br>cgaccccctagcgacacgcgagccgacgcactgaggtgtggcgaagtgctg<br>tcgaccatcctactcgagtgcaccacggccggcatggctacctgcacgtt<br>gacccatccgatcgaatccagtgacagtcgtgacatcgtgcggggcctga<br>cgaggcagcgaggcgagccgcaagcctttgatccgggtagggatagcccg<br>ccgttggcagcagttcccgcccccacaccacggcggccgctggacagcgt<br>cttgcagattcgccagacgcccgagaaagggcgtaatgcctcagatagaa<br>atgcccgtgaaacgggttggttcagcccgcct |
| Rv3128c | 82 | gtgtggtccgcctcgggtgggcagtgcgggaagtatcttgccgcctcgat<br>ggtgctgcagcttgatgggttggaacgtcacggtgtgttggagtttgggc<br>gtgaccgctatggccccgaggtgcgtgaggagctgttggcgatgagtgcg<br>gccagcatcgatcgttatctgaagaccgcgaaggccaaagaccagatatc<br>gggtgtgtcgacgacgaaaccctcaccactgctgcgtaattcgatcaagg |

TABLE 2-continued

DNA sequences of selected low oxygen induced antigens

| Rv no. | SEQ ID NO: | Sequence |
|---|---|---|
| | | ttcgcagggccggcgatgaggtcgaggcggagccggggttcttcgagggc<br>gacaccgtcgcccattgcggtccgacgctcaaaggcgagttcgcccacac<br>cctgaacttgaccgacgtgcacatcggatgggtgttcacccgcaccgtcc<br>gcaacaacgcccgtacccacatcctcgccgggctcaaagcttctgtcacc<br>gagatcccgcatgggataacgggtttagatttcgacaacggcaccgtgtt<br>tctcaacaagccggtcatcagctgggccggcgacaacggtatctacttca<br>cccgctttcgcccgtacaagaaaaaccactaggccaccatcgagtccaag<br>aacaaccacctggtccgcaagtacgcgttctactaccgctatgacaccgc<br>cgaggaacgcgccgtgctcaaccggatgtggaagctggtcaacgaccgcc<br>tcaactacctcaccccgaccatcaaaccgatcgggtatgccagcagcgcc<br>gacggccgccgcgacgcctctacgatgccccacagacgccgctggaccg<br>gccactggccgcaagggtgctctccgcgggcccagcaggccgacctgatca<br>cctaccgagacagcctcaaccccgcccagatcggccgcaaaatcgccgac<br>ctgcagaaccgactcctcatcttggccaaggagaaaaccgagcagctcta<br>cctcgctaacatccccaccgccctacccgacatccacaaaggcatcctga<br>tcaaggcgggc |
| RV3129 | 83 | Gtggtgcaaggccgcaccgtgctgtttcgtaccgcggagggcgccaaatt<br>attttcagccgtcgcgaagtgcgcggtggcttcgaggcggacgaccaca<br>acgttgccgagggctggagcgtgatcgtcaaggttcgcgcccaggtgctg<br>acgaccgacgcgggggtccgcgaagccgaacgcgcccagttactaccgtg<br>gaccgcgacgctgaaacgtcactgtgtgcgggtgatcccgtgggagatca<br>ccggccgccacttcaggttcggtccggaaccggaccgcagccagaccctt<br>gcctgcgaggcctcgtcacacaaccagcga |
| Rv3130c | 84 | atgaatcacctaacgacacttgacgccgggtttctcaaggcagaagacgt<br>ggatcggcacgtgagtctggcaatcggcgctctggcggtcatcgagggc<br>cggctcccgatcaggaagccttcttatcgtcgctcgctcaacgcctacgt<br>ccctgtaccgggttcgggcagcggtcacgcctgcgcccgttcgacctcgg<br>tgcacccaaatgggtggacgatcccgacttcgatcttggccgtcatgtgt<br>ggcgcatcgccttgccgcggcctggcaacgaagaccagttattcgagctg<br>atcgccgatctgacggcgcgtcgtttggaccggggtcgaccgctgtggga<br>ggtctgggtcatcgaaggcctggcggacagcaagtgggcgatcctgacca<br>aactgcaccactgcatggccgacggaatcgcggcgactcacctgctagct<br>gggctctccgatgaaagtatgagcgacagcttcgcgagcaacatccacac<br>gaccatgcagtcgcaatccgcatctgtgcggcggggtggattccgtgtca<br>atccaagcgaggcgttgaccgcgtcgaccgccgtgatggcaggcatcgtt<br>cgcgcggccaagggtgccagtgagatcgcggccggcgtgctaagtcccgc<br>cgcgtcgtcgttgaacgggccgatcagtgatttgcgtcgctacagcgcag<br>caaaggtccctctcgccgacgtcgaacaggtgtgccggaaattcgacgtc<br>accatcaatgatgttgcgcttgccgcgattacggaaagctaccgcaacgt<br>cctcatccagcggggtgagcggcctaggttttgattcgctgcgtacgctag<br>tgccggtctcgacgcgttccaacagcgctttgagcaagaccgataaccgt<br>gtttcgttaatgctgcccaacctgccggtggatcaagagaacccgctgca<br>gcggctgcggatcgtgcactcgcggctgactcgggccaaggcgggggac<br>agagacaattcggaaatactttgatggcgattgccaaccgccttccgttc<br>cccatgaccgcatggggcggtcgggctgttgatgcggctgccgcagcgtgg<br>tgttgtcaccgtggcgacaaatgtgccgggtccacgacggccgctgcaga<br>ttatgggcagacgggtgcttgacctataccggtttcgccgatcgcgatg<br>caactgcgcaccagtgtcgcgatgctcagctacgccgacgacctgtactt<br>cgggatcctggccgactacgacgtggtagcagatgccggccagctggcgc<br>gaggaattgaagacgccgtcgcacggctggtggcgatcagtaagcggcgc<br>aaggtgactcgcaggcgcggagcgctatcgctggttgtg |
| Rv3131 | 85 | atgaacacccatttcccggacgccgaaaccgtgcgaacggttctcaccct<br>ggccgtccgggccccctccatccacaacacgcagccgtggcggtggcggg<br>tatgcccgacgagtctggagctgttctctagacccgatatgcagctgcgt<br>agcaccgatccggacgggcgtgagttgatcctcagctgtggtgtggcatt<br>gcaccactgcgtcgtcgctttggcgtcgctgggctggcaggccaaggtaa<br>accgtttccccgatcccaaggaccgctgccatctggccaccatcggggta<br>caaccgcttgttcccgatcaggccgatgtcgccttggcggcggccatacc<br>gcggcgacgcaccgatcggcgcgcccacagttgctggccggtgccaggag<br>gtgacatcgcgttgatggccgcaagagcagcccgtggcggggtcatgctg<br>cggcaggtcagtgccctagaccgaatgaaagccattgtggcgcaggctgt<br>cttggaccacgtgaccgacgaggaatatctgcgcgagctcaccatttgga<br>gtgggcgctacggttcagtggccggggttcccgcccgcaacgagccgcca<br>tcagaccccagtgccccgatccccggtcgcctgttcgccgggccggtct<br>gtctcagccgtccgacgtcttaccgctgacgacggcgccgcgatcctgg<br>cactaggcaccgagacagacgaccggttggcccggctgcgcgccggcgag<br>gccgccagcatcgtcttgttgaccgcgacggcaatggggctggcgtgctg<br>cccgatcaccgaaccgctggagatcgccaagacccgcgacgcggtccgtg<br>ccgaggtgttcggcgccggcggctaccccagatgctgctgcgagtgggt<br>tgggcaccgatcaatgccgaccgttgccaccgacgccacggcgcgaact<br>gtcccaggtcgttgagtggccggaagagctactgcgacaacggtgc |

TABLE 2-continued

DNA sequences of selected low oxygen induced antigens

| Rv no. | SEQ ID NO: | Sequence |
|---|---|---|
| Rv3132c | 86 | atgacaacaggggggcctcgtcgacgaaaacgacggcgccgcaatgcgtcc<br>actgcgtcacacgctctcccaactacgcctgcacgagctgctggtcgagg<br>tgcaggaccgggtcgagcagatcgtcgagggccgggaccgcctcgatggt<br>ctggtggaggccatgctcgtggtcacagcgggcctggacctggaggcaac<br>cctacgcgctatcgtgcattcagcgaccagccttgtcgatgcgcgctatg<br>gcgctatggaggtgcacgaccggcagcatcgggtattgcactttgtctat<br>gaaggcatcgacgaggagaccgttcggcggatcggccacctaccgaaagg<br>cctaggcgtcatcgggctgctcatcgaagatcccaaaccgttacggctgg<br>acgatgtttctgcgcacccggcctcgattggttttccgccgtatcatccg<br>ccgacgcgtaccttccccggggtaccggttcgggtgcgcgatgaatcgtt<br>cggcactctgtacctgactgacaagaccaacgggcaaccgttcagcgacg<br>acgacgaggttctggtccaggcgctggcggccgccgcgggtatcgcagtc<br>gcgaatgcccggctctaccagcaggctaaggcgcgtcagtcgtggatcga<br>ggccaccgtgacatcgccaccgagttgttgcccggcaccgaacccgcga<br>cggtgttccggcttgtcgccgcggaggcgctcaagctgacggcggctgac<br>gctgccctggtagccgttccccgtcgacgaggacatgcctgccgctgacgt<br>gggggagctgctggtgattgaaacagtcggcagcgctgtggcttccattg<br>ttgggcgaacgattccggtggcgggcgcggtgctgcgggaggtcttcgtc<br>aacggcattccgcgacgggtcgaccgggtcgatttggaaggcctggacga<br>actggccgacgcaggtccggcgctgctgttgccgctgcgggccagaggta<br>ccgtagcgggtgtcgttgttgtgctgagtcaaggcggtccaggggctttc<br>accgacgaacaactcgagatgatggccgcgttcgccgaccaggccgcgct<br>ggcttggcaattggccacttcgcaacgtcggatgcgcgaactcgacgtac<br>tgaccgaccgggatcgtatcgcccgtgacctccatgaccatgtcatccag<br>cggctcttcgcgattggcctggcttttgcagggtgctgtcccgcacgaacg<br>taatcctgaagtgcagcaacgactctcggacgtggtagacgatctgcaag<br>acgttatacaggaaatccggaccaccatttatgacctgcacggagcatcg<br>cagggtatcactcggctccggcagcgaatcgatgcggccgtagcccaatt<br>tgccgactcggggttgcgcaccagcgttcaattcgtgggtccattgtcgg<br>tggtcgacagcgcgctcgccgatcaggccgaggcggtggttcgggaagcg<br>gtcagcaacgcggttcgccatgcgaaggccagcacgttgaccgtccgggt<br>caaagtcgacgacgacttgtgcatcgaggtgaccgacaacggccgcgggc<br>tgcccgacgagttcaccggaagcggcttaacgaacctgcggcagcgggca<br>gagcaggccggcggcgaattcaccctcgcgagcgtaccgggcgcgagcgg<br>aacagtgctgcgatggtcagcaccgttgtcgcag |
| Rv3134c | 87 | atgagcgatcctcggccagctcgggcagtggtcgttggtatcgacgggtc<br>aagggcggcaacgcatgcggcgttgtgggcggtcgatgaggcggtgaacc<br>gagacattccgctgcgactggtgtacgtcatcgatccgtcccaactgtcc<br>gccgccggcgagggcggtgggcaatcagcggcccgagcggcgctgcacga<br>cgcctctcggaaggtcgaggccaccgggcaaccggtcaagatcgaaacgg<br>aggttctgtgcggcaggccgctcaccaagctgatgcaggagtccaggtcc<br>gcggcgatgctgtgcgtcggttcggtggggcttgatcatgtccgcggtcg<br>ccgggggttcggtcgcggagaccctggctgggtcggccttatgccccgtgg<br>cggtgattcacccgtcgccggccgagccagcgacaacctcccaggtcagc<br>gcggttgtcgcggaggtggacaatggtgtggtgctgcggcacgcattcga<br>ggaggccaggctgcgcggagttccgctgcgggccgtggctgtccacgctg<br>ctgaaacacccgatgacgtcgaacagggcagccggctggcgcatgtacac<br>ctgagccgtcggctcgcccactggacccggctctaccccgagtgcgggt<br>ggatcgggccatcgccggcgggcagtgcgtgccgtcatctggccgccaacg<br>caaagcgggtcagctgttcgtcgcggactcacactccgcgcacgaattg<br>tgcggtgcataccagcccggatgcgccgtacttacggtacgcagtgccaa<br>cttg |
| RV3841 | 88 | atgacagaatacgaagggcctaagacaaaattccacgcgttaatgcagga<br>acagattcataacgaattcacagcggcacaacaatatgtcgcgatcgcgg<br>tttatttcgacagcgaagacctgccgcagttggcgaagcattttttacagc<br>caagcggtcgaggaacgaaaaccatgcaatgatgctcgtgcaacacctgct<br>cgaccgcgaccttcgtgtcgaaattcccggcgtagacacggtgcgaaacc<br>agttcgacagaccccgcgaggcactggcgctggcgctcgatcaggaacgc<br>acagtcaccgaccaggtcggtcggctgacagcggtggcccgcgacgaggg<br>cgatttcctcggcgagcagttcatgcagtggttcttgcaggaacagatca<br>aagaggtggccttgatggcaaccctggtgcgggttgccgatcggccgggg<br>gccaacctgttcgagctagagaacttcgtcgcacgtgaagtggatgtggc<br>gccggccgcatcaggcgccccgcacgctgccgggggccgcctc |
| Rv3842c | 89 | atgacatggggccgacgaggtgctcgccggacatcccttttgtggttgctca<br>ccgtggtgcgtcggcggctcggccggagcataccttgccgcctacgacc<br>tggcgctcaaagagggcgccgacggcgtggaatgtgatgtgcggttgacc<br>cgggacgggcatctggtctgtgtgcatgaccgccgcctggaccgaaccctc<br>gacgggagccggcgcttggtcagcacgatgacgctggcccagctacgcgagc<br>tggagtacggcgcgtggcacgacagctggcgccccgacggttcgcacggc<br>gacaccagtctgctgacccctggacgcgcttgtttcgctggttttggactg<br>gcaccggccggtgaagatcttcgtcgagaccaagcatcccgtccgatacg<br>gctcgctggtggaaaacaagctgctggcgctgctacaccggttcggtatt |

TABLE 2-continued

DNA sequences of selected low oxygen induced antigens

| Rv no. | SEQ ID NO: | Sequence |
|---|---|---|
| | | gccgcaccgcctccgcagatcgatcccgtgcggtggtgatgtcgttttc |
| | | ggccgccgcggtctggcggatccggcgggctgcaccgctgctgccgacgg |
| | | tgttgctcggcaagaccccccgatacctgaccagcagtgcggccacggcg |
| | | gtcggggcaaccgccgtgggaccctcactgcctgcgttaaaggaatatcc |
| | | gcaactcgttgaccgctcggcagctcagggccgggcggtgtactgctgga |
| | | acgtcgatgagtacgaggacatcgacttttgccgggaggtcggggtggcc |
| | | tggattggtactcaccaccccggccgcaccaaggcctggctggaagacgg |
| | | gcgggcgaacgggaccactcgc |
| Rv3908 | 90 | gtgtccgacggcgaacaagccaaatcacgtcgacgccggggcggcgccg |
| | | cgggcggcgcgctgcggctacagccgagaatcacatggacgcccaaccgg |
| | | ccggcgacgccaccccgaccccggcaacggcgaagcggtcccggtcccgc |
| | | tcacctcgtcgcgggtcgactcggatgcgcaccgtgcacgaaacatcggc |
| | | tggagggttggtcattgacggtatcgacggtccacgagacgcgcaggtcg |
| | | cggctctgatcggccgcgtcgaccggcgcggccggctgctgtggtcgcta |
| | | cccaaggggcacatcgagttgggcgagaccgccgagcagaccgccatccg |
| | | cgaggtcgccgaggagaccggcatccgcggcagtgtgctcgccgcgctgg |
| | | ggcgcatcgactactggttcgtcaccgacggccggcgggtgcacaagacc |
| | | gtccaccattatttgatgcggttttaggcggagagctgtccgacgaaga |
| | | cctcgaggtagccgaggtagcctgggtgccgatccgggaactgccgtctc |
| | | gactggcctacgccgacgaacgtcgactagccgaggtggccgacgaactg |
| | | atcgacaagctgcagagcgacggcccccgccgcgcttccgccgctaccacc |
| | | cagctcgcctcgtcgacggccgcaaacgcattcacgcgctcgtcatgccg |
| | | atgactcagcaccgggtcagcacaacggtcccgggccggggccg |

Preferably the immunogenic portions are selected from the group consisting of the sequences presented in Table 1 and the nucleic acid sequences are selected from the sequences presented in Table 2.

In another embodiment, the vaccine is a multiphase vaccine, where the polypeptides or fragments hereof are fused to other antigens with efficacy as prophylactic vaccines, where the fusion partner is selected from e.g. the group consisting of ESAT-6, TB10.4, CFP10, RD1-ORF5, RD1-ORF2, Rv1036, MPB64, MPT64, Ag85A, Ag85B (MPT59), MPB59, Ag85C, 19 kDa lipoprotein, MPT32.

The invention further discloses a therapeutic vaccine against *tuberculosis* comprising one or more polypeptides or fragments hereof, which polypeptides are expressed during the latent stage of the mycobacteria infection, which stage is characterized by low-oxygen tension in the microenvironment of the mycobacteria, or nucleic acids encoding these polypeptides.

Preferably, the therapeutic and multiphase vaccine comprises an additional delivery system selected from among, live recombinant vaccines, that is gene-modified organisms such as bacteria or viruses expressing mycobacteria genes, or immunogenic delivery systems such as, DNA vaccines, that is plasmids expressing genes or gene fragments for the proteins described above, or protein vaccines, that is the proteins themselves or synthetic peptides derived from the proteins themselves delivered in a delivery system such as an adjuvant.

The invention further discloses a therapeutic vaccine in which the amino acid sequence is lipidated so as to allow a self-adjuvanting effect of the polypeptide.

The invention also discloses a method for treating an animal, including a human being, with *tuberculosis* caused by virulent mycobacteria, e.g., by *Mycobacterium tuberculosis, Mycobacterium africanum* or *Mycobacterium bovis*, comprising administering to the animal the above-mentioned vaccine.

The invention also discloses a method for immunizing an animal, including a human being, against *tuberculosis* caused by virulent mycobacteria, e.g., by *Mycobacterium tuberculosis, Mycobacterium africanum* or *Mycobacterium bovis*, comprising administering to the animal the above mentioned vaccine.

In a still further embodiment, the invention discloses an immunogenic composition comprising a polypeptide as defined above, preferably in the form of a vaccine or in the form of a diagnostic reagent. The diagnostic reagent can be in the form of a skin test reagent (administered by the transcutaneous, subcutaneous or intradermal routes), a serological reagent or a reagent for stimulating a cell-mediated reaction.

In another embodiment, the invention discloses a nucleic acid fragment in isolated form which
(a) comprises a nucleic acid sequence which encodes a polypeptide as defined above, or comprises a nucleic acid sequence complementary thereto; or
(b) has a length of at least 10 nucleotides and hybridizes readily under stringent hybridization conditions with a nucleotide sequence selected from the nucleotide sequences presented in Table 2 or a sequence complementary thereto, or with a nucleotide sequence selected from a sequence in (a)

The nucleic acid fragment is preferably a DNA fragment. The fragment can be used as a pharmaceutical.

In another embodiment, the invention discloses a vaccine comprising a nucleic acid fragment according to the invention, optionally inserted in a vector, the vaccine effecting in vivo expression of antigen by a human being or other mammal or animal, to whom the vaccine has been administered, the amount of expressed antigen being effective to confer substantially increased resistance to *tuberculosis* caused by virulent mycobacteria, e.g. by *Mycobacterium tuberculosis, Mycobacterium africanum* or *Mycobacterium bovis*, in an animal, including a human being.

In a further embodiment, the invention discloses the use of a nucleic acid fragment according to the invention for the preparation of a composition for the diagnosis of *tuberculosis* caused by virulent mycobacteria, e.g., by *Mycobacterium tuberculosis, Mycobacterium africanum* or *Mycobacterium bovis*, and the use of a nucleic acid fragment according to the invention for the preparation of a pharmaceutical composition for the vaccination against *tuberculosis* caused by virulent mycobacteria, e.g., by *Mycobacterium tuberculosis, Mycobacterium africanum* or *Mycobacterium bovis*.

In a still further embodiment, the invention discloses a vaccine for immunizing an human being or other mammal or animal, against *tuberculosis* caused by virulent mycobacteria, e.g. by *Mycobacterium tuberculosis, Mycobacterium africanum* or *Mycobacterium bovis*, comprising as the effective component a non-pathogenic microorganism, wherein at least one copy of a DNA fragment comprising a DNA sequence encoding a polypeptide as defined above has been incorporated into the microorganism (e.g., placed on a plasmid or in the genome) in a manner allowing the microorganism to express and optionally secrete the polypeptide.

In another embodiment, the invention discloses a replicable expression vector, which comprises a nucleic acid fragment according to the invention, and a transformed cell harboring at least one such vector.

In another embodiment, the invention discloses a method for producing a polypeptide as defined above, comprising (a) inserting a nucleic acid fragment according to the invention into a vector that is able to replicate in a host cell, introducing the resulting recombinant vector into the host cell, culturing the host cell in a culture medium under conditions sufficient to effect expression of the polypeptide, and recovering the polypeptide from the host cell or culture medium;

(b) isolating the polypeptide from a whole *mycobacterium*, e.g. *Mycobacterium tuberculosis, Mycobacterium africanum* or *Mycobacterium bovis*, from culture filtrate or from lysates or fractions thereof; or (c) synthesizing the polypeptide e.g. by solid or liquid phase peptide synthesis.

The invention also discloses a method of diagnosing *tuberculosis* caused by virulent mycobacteria, e.g. by *Mycobacterium tuberculosis, Mycobacterium africanum* or *Mycobacterium bovis*, in an animal, including a human being, comprising intradermally injecting, in the animal, a polypeptide as defined above or an immunogenic composition as defined above, a positive skin response at the location of injection being indicative of the animal having *tuberculosis*, and a negative skin response at the location of injection being indicative of the animal not having *tuberculosis*.

In another embodiment, the invention discloses a method for immunizing an animal, including a human being, against *tuberculosis* caused by virulent mycobacteria, e.g. by *Mycobacterium tuberculosis, Mycobacterium africanum* or *Mycobacterium bovis*, comprising administering to the animal the polypeptide as defined above, the immunogenic composition according to the invention, or the vaccine according to the invention.

Another embodiment of the invention discloses a monoclonal or polyclonal antibody, which is specifically reacting with a polypeptide as defined above in an immuno assay, or a specific binding fragment of said antibody. Preferably, said antibody is for use as a diagnostic reagent, e.g. for detection of mycobacteria antigens in sputum, urine or other body fluids of an infected animal, including a human being.

In a further embodiment the invention discloses a pharmaceutical composition that comprises an immunologically responsive amount of at least one member selected from the group consisting of:

(a) a polypeptide selected from the sequences presented in Table 1, or an immunogenic portion thereof;

(b) an amino acid sequence which has a sequence identity of at least 70% to any one of said polypeptides in (a) and is immunogenic;

(c) a fusion polypeptide comprising at least one polypeptide or amino acid sequence according to (a) or (b) and at least one fusion partner;

(d) a nucleic acid sequence which encodes a polypeptide or amino acid sequence according to (a), (b) or (c);

(e) a nucleic acid sequence which is complementary to a sequence according to (d);

(f) a nucleic acid sequence which has a length of at least 10 nucleotides and which hybridizes under stringent conditions with a nucleic acid sequence according to (d) or (e); and (g) a non-pathogenic micro-organism which has incorporated (e.g. placed on a plasmid or in the genome) therein a nucleic acid sequence according to (d), (e) or (f) in a manner to permit expression of a polypeptide encoded thereby.

In a still further embodiment the invention discloses a method for stimulating an immunogenic response in an animal which comprises administering to said animal an immunologically stimulating amount of at least one member selected from the group consisting of:

(a) a polypeptide selected from the sequences presented in Table 1, or an immunogenic portion thereof;

(b) an amino acid sequence which has a sequence identity of at least 70% to any one of said polypeptides in (a) and is immunogenic;

(c) a fusion polypeptide comprising at least one polypeptide or amino acid sequence according to (a) or (b) and at least one fusion partner;

(d) a nucleic acid sequence which encodes a polypeptide or amino acid sequence according to (a), (b) or (c);

(e) a nucleic acid sequence that is complementary to a sequence according to (d);

(f) a nucleic acid sequence which has a length of at least 10 nucleotides and which hybridizes under stringent conditions with a nucleic acid sequence according to (d) or (e); and (g) a non-pathogenic micro-organism which has incorporated therein (e.g. placed on a plasmid or in the genome) a nucleic acid sequence according to (d), (e) or (f) in a manner to permit expression of a polypeptide encoded thereby.

The vaccine, immunogenic composition and pharmaceutical composition according to the invention can be used therapeutically in a subject infected with a virulent *mycobacterium* combined with a prophylactic composition in a subject to prevent further infection with a virulent *mycobacterium*.

The invention also discloses a method for diagnosing previous or ongoing infection with a virulent *mycobacterium*, said method comprising (a) contacting a sample, e.g. a blood sample, with a composition comprising an antibody according to the invention, a nucleic acid fragment according to the invention and/or a polypeptide as defined above, or (b) contacting a sample, e.g. a blood sample comprising mononuclear cells (e.g. T-lymphocytes), with a composition comprising one or more polypeptides as defined above in order to detect a positive reaction, e.g. proliferation of the cells or release of cytokines such as IFN-γ.

Finally, the invention, discloses a method of diagnosing *Mycobacterium tuberculosis* infection in a subject comprising:

(a) contacting a polypeptide as defined above with a bodily fluid of the subject;

(b) detecting binding of a antibody to said polypeptide, said binding being an indication that said subject is infected by *Mycobacterium tuberculosis* or is susceptible to *Mycobacterium tuberculosis* infection.

DEFINITIONS

Polypeptides

The word "polypeptide" in the present invention should have its usual meaning. That is an amino acid chain of any length, including a full-length protein, oligopeptides, short peptides and fragments thereof, wherein the amino acid residues are linked by covalent peptide bonds.

The polypeptide may be chemically modified by being glycosylated, by being lipidated (e.g. by chemical lipidation with palmitoyloxy succinimide as described by Mowat et al. 1991 or with dodecanoyl chloride as described by Lustig et al. 1976), by comprising prosthetic groups, or by containing additional amino acids such as e.g. a his-tag or a signal peptide.

Each polypeptide may thus be characterized by specific amino acids and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". These are defined according to the following table. Amino acids in the same block in the second column and preferably in the same line in the third column may be substituted for each other. The amino acids in the third column are indicated in one-letter code.

| | | |
|---|---|---|
| ALIPHATIC | Non-polar | GAP |
| | | ILV |
| | Polar-uncharged | CSTM |
| | | NQ |
| | Polar-charged | DE |
| | | KR |
| AROMATIC | | HFWY |

A preferred polypeptide within the present invention is an immunogenic antigen from *M. tuberculosis* produced when the organism is subjected to the stresses associated with latent infection. Such antigen can for example also be derived from the *M. tuberculosis* cell and/or *M. tuberculosis* culture filtrate. Thus, a polypeptide comprising an immunogenic portion of one of the above antigens may consist entirely of the immunogenic portion, or may contain additional sequences. The additional sequences may be derived from the native *M. tuberculosis* antigen or be heterologous and such sequences may, but need not, be immunogenic.

Each polypeptide is encoded by a specific nucleic acid sequence. It will be understood that such sequences include analogues and variants hereof wherein such nucleic acid sequences have been modified by substitution, insertion, addition or deletion of one or more nucleic acids. Substitutions are preferably silent substitutions in the codon usage that will not lead to any change in the amino acid sequence, but may be introduced to enhance the expression of the protein.

In the present context the term "substantially pure polypeptide fragment" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is in "essentially pure form", i.e. that the polypeptide fragment is essentially free of any other antigen with which it is natively associated, i.e. free of any other antigen from bacteria belonging to the tuberculosis complex or a virulent *mycobacterium*. This can be accomplished by preparing the polypeptide fragment by means of recombinant methods in a non-mycobacterial host cell as will be described in detail below, or by synthesizing the polypeptide fragment by the well-known methods of solid or liquid phase peptide synthesis, e.g. by the method described by Merrifield, 1963, or variations thereof.

By the term "virulent *mycobacterium*" is understood a bacterium capable of causing the *tuberculosis* disease in an animal or in a human being. Examples of virulent mycobacteria include but are not limited to *M. tuberculosis, M. africanum,* and *M. bovis*. Examples of relevant animals are cattle, possums, badgers and kangaroos.

By "a TB patient" is understood an individual with culture or microscopically proven infection with virulent mycobacteria, and/or an individual clinically diagnosed with TB and who is responsive to anti-TB chemotherapy. Culture, microscopy and clinical diagnosis of TB are well known by any person skilled in the art.

By the term "PPD-positive individual" is understood an individual with a positive Mantoux test or an individual where PPD induces a positive in vitro recall response determined by release of IFN-γ.

By "a latently infected individual" is understood an individual, who has been infected by a virulent *mycobacterium*, e.g. *M. tuberculosis*, but shows no sign of active *tuberculosis*. It is likely that individuals who have been vaccinated, e.g. by BCG, or treated for TB may still retain the mycobacteria within their bodies, although this is currently impossible to prove since such individuals would be expected to be positive if tested for PPD reactivity. Nonetheless, in its most accurate sense, "latently-infected" may be used to describe any individual who has *M. tuberculosis* residing in their tissues but who is not clinically ill.

By the term "delayed type hypersensitivity reaction" (DTH) is understood a T-cell mediated inflammatory response elicited after the injection of a polypeptide into, or application to, the skin, said inflammatory response appearing 72-96 hours after the polypeptide injection or application.

By the term "IFN-γ" is understood interferon-gamma. The measurement of IFN-γ is used as an indication of an immunological response.

By the terms "nucleic acid fragment" and "nucleic acid sequence" are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length e.g. from 10 to 10000 nucleotides, depending on the use. When the nucleic acid molecule is for use as a pharmaceutical, e.g. in DNA therapy, or for use in a method for producing a polypeptide according to the invention, a molecule encoding at least one epitope is preferably used, having a length from about 18 to about 1000 nucleotides, the molecule being optionally inserted into a vector. When the nucleic acid molecule is used as a probe, as a primer or in antisense therapy, a molecule having a length of 10-100 is preferably used. According to the invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, 30 or 20 nucleotides (or nucleotide derivatives).

The term "stringent" when used in conjunction with hybridization conditions is as defined in the art, i.e. the hybridization is performed at a temperature not more than 15-20° C. under the melting point $T_m$, cf. Sambrook et al, 1989, pages 11.45-11.49. Preferably, the conditions are "highly stringent", i.e. 5-10° C. under the melting point $T_m$.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

Sequence Identity

The term "sequence identity" indicates a quantitative measure of the degree of homology between two amino acid sequences of equal length or between two nucleotide sequences of equal length. The two sequences to be compared must be aligned to best possible fit allowing the insertion of gaps or alternatively, truncation at the ends of the protein sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC [SEQ ID NO: 184] will have a sequence identity of 75% with the sequence AATCAATC, SEQ ID NO: 185 ($N_{dif}$=2 and $N_{ref}$=8). A gap is counted as non-identity of the specific residue(s), i.e. the DNA sequence AGTGTC [SEQ ID NO: 186] will have a sequence identity of 75% with the DNA sequence AGTCAGTC, SEQ ID NO: 187, ($N_{dif}$=2 and $N_{ref}$=8). Sequence identity can alternatively be calculated by the BLAST program e.g. the BLASTP program (Pearson, 1988, or online through the NIH website). In one aspect of the invention, alignment is performed with the sequence alignment method ClustalW with default parameters as described by Thompson J., et al. 1994 and as available through online sources.

A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%.

Immunogenic Portion

In a preferred embodiment of the invention, the polypeptide comprises an immunogenic portion of the polypeptide, such as an epitope for a B-cell or T-cell.

The immunogenic portion of a polypeptide is a part of the polypeptide, which elicits an immune response in an animal or a human being, and/or in a biological sample determined by any of the biological assays described herein. The immunogenic portion of a polypeptide may be a T-cell epitope or a B-cell epitope. Immunogenic portions can be related to one or a few relatively small parts of the polypeptide, they can be scattered throughout the polypeptide sequence or be situated in specific parts of the polypeptide. For a few polypeptides, epitopes have even been demonstrated to be scattered throughout the polypeptide covering the full sequence (Ravn et al 1999). In order to identify relevant T-cell epitopes which are recognized during an immune response, it is possible to use overlapping oligopeptides for the detection of MHC class II epitopes, preferably synthetic, having a length of e.g. 20 amino acid residues derived from the polypeptide. These peptides can be tested in biological assays (e.g. the IFN-γ assay as described herein) and some of these will give a positive response (and thereby be immunogenic) as evidence for the presence of a T cell epitope in the peptide. For the detection of MHC class I epitopes it is possible to predict peptides that will bind (Stryhn et al. 1996) and hereafter produce these peptides synthetic and test them in relevant biological assays, e.g. the IFN-γ assay as described herein. The peptides preferably having a length of, e.g., 8 to 11 amino acid residues derived from the polypeptide. B-cell epitopes can be determined by analyzing the B cell recognition to overlapping peptides covering the polypeptide of interest as, e.g., described in Harboe et al 1998.

Although the minimum length of a T-cell epitope has been shown to be at least 6 amino acids; it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, and at least 30 amino acid residues. Hence, in important embodiments of the inventive method, it is preferred that the polypeptide fragment has a length of at most 50 amino acid residues, such as at most 40, 35, 30, 25, and 20 amino acid residues. It is expected that the peptides having a length of from 10 to 20 amino acid residues will prove to be most efficient as MHC class II epitopes and therefore especially preferred lengths of the polypeptide fragment used in the inventive method are 18, such as 15, 14, 13, 12 and even 11 amino acid residues. It is expected that the peptides having a length of from 7 to 12 amino acid residues will prove to be most efficient as MHC class I epitopes and therefore especially preferred lengths of the polypeptide fragment used in the inventive method are 11, such as 10, 9, 8 and even 7 amino acid residues.

Immunogenic portions of polypeptides may be recognized by a broad part (high frequency) or by a minor part (low frequency) of the genetically heterogeneous human population. In addition some immunogenic portions induce high immunological responses (dominant), whereas others induce lower, but still significant, responses (subdominant). High frequency or low frequency can be related to the immunogenic portion binding to widely distributed MHC molecules (HLA type) or even by multiple MHC molecules (Sinigaglia, 1988, Kilgus, 1991).

In the context of providing candidate molecules for a new vaccine against *tuberculosis*, the subdominant epitopes are however as relevant as are the dominant epitopes since it has been shown (Olsen, 2000) that such epitopes can induce protection regardless of the fact that they are not as strongly or broadly recognized.

Variants

A common feature of the polypeptides of the invention is their capability to induce an immunological response as illustrated in the examples. It is understood that a variant of a polypeptide of the invention produced by substitution, insertion, addition or deletion may also be immunogenic as determined by any of the assays described herein.

Immune Individual

An immune individual is defined as a person or an animal, which has cleared or controlled an infection with virulent mycobacteria or has received a vaccination with *M. bovis* BCG.

Immune Response

The immune response may be monitored by one of the following methods:

An in vitro cellular response is determined by induction of the release of a relevant cytokine such as IFN-γ from, or the induction of proliferation in lymphocytes withdrawn from an animal or human being currently or previously infected with virulent mycobacteria or immunized with the relevant polypeptide. The induction being performed by the addition of the polypeptide or the immunogenic portion of the polypeptide to a suspension comprising from $2\times10^5$ cells to $4\times10^5$ cells per well. The cells being isolated from either the blood, the spleen, the liver or the lung and the addition of the polypeptide or the immunogenic portion resulting in a concentration of not more than 20 μg per ml suspension and the stimulation being performed from two to five days. For monitoring cell proliferation the cells are pulsed with radioactive labeled Thymidine and after 16-22 hours of incubation detecting the proliferation by liquid scintillation counting. A positive response is defined as being a response more than background plus two standard deviations. The release of IFN-γ can be determined by the ELISA method, which is well known to a person skilled in the art. A positive response being a response more than background plus two standard deviations. Other cytokines than IFN-γ could be relevant when monitoring the immunological response to the polypeptide, such as IL-12, TNF-α, IL-4, IL-5, IL-10, IL-6, TGF-β. Another and more sensitive method for detecting the immune response is the ELISpot method, in which the frequency of IFN-γ producing cells is determined. In an ELIspot plate (MAHA, Millipore) precoated with anti-murine IFN-γ antibodies (PharMingen) graded numbers of cells isolated from either blood, spleen, or lung (typically between 1 to $4\times10^5$ cells/well) are incubated for 24-32 hrs in the presence of the polypeptide or the immunogenic portion resulting in a concentration of not more than 20 μg per ml. The plates are subsequently incubated with biotinylated anti-IFN-γ antibodies followed by a streptavidin-alkaline phosphatase incubation. The IFN-γ producing cells are identified by adding BCIP/NBT (Sigma), the relevant substrate giving rise to spots. These spots can be enumerated using a dissection microscope. It is also a possibility to determine the presence of mRNA coding for the relevant cytokine by the use of the PCR technique. Usually one or more cytokines will be measured utilizing for example PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or an *M. tuberculosis*-infected person where the T cell lines have been driven with either live mycobacteria, extracts from the bacterial cell or culture filtrate for 10 to 20 days with the addition of IL-2. The induction being performed by addition of not more than 20 μg polypeptide per ml suspension to the T cell lines containing from $1\times10^5$ cells to $3\times10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both assays a positive response being a response more than background plus two standard deviations.

An in vivo cellular response may be determined as a positive DTH response after intradermal injection or local application patch of at most 100 μg of the polypeptide or the immunogenic portion to an individual who is clinically or subclinically infected with a virulent *mycobacterium*, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the OD e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of a virulent *Mycobacterium*. Readout for induced protection could be decrease of the bacterial load in target organs compared to non-vaccinated animals, prolonged survival times compared to non-vaccinated animals and diminished weight loss compared to non-vaccinated animals.

Preparation Methods

In general, *M. tuberculosis* antigens, and DNA sequences encoding such antigens, may be prepared using any one of a variety of procedures.

They may be purified as native proteins from the *M. tuberculosis* cell or culture filtrate by procedures such as those described above. Immunogenic antigens may also be produced recombinantly using a DNA sequence encoding the antigen, which has been inserted into an expression vector and expressed in an appropriate host. Examples of host cells are *E. coli*. The polypeptides or immunogenic portion hereof can also be produced synthetically having fewer than about 100 amino acids, and generally fewer than 50 amino acids and may be generated using techniques well known to those ordinarily skilled in the art, such as commercially available solid-phase techniques where amino acids are sequentially added to a growing amino acid chain.

In the construction and preparation of plasmid DNA encoding the polypeptide as defined for DNA vaccination a host strain such as *E. coli* can be used. Plasmid DNA can then be prepared from cultures of the host strain carrying the plasmid of interest, and purified using e.g. the Qiagen Giga-Plasmid column kit (Qiagen, Santa Clarita, Calif., USA) including an endotoxin removal step. It is preferred that plasmid DNA used for DNA vaccination is endotoxin free.

Fusion Proteins

The immunogenic polypeptides may also be produced as fusion proteins, by which methods superior characteristics of the polypeptide of the invention can be achieved. For instance, fusion partners that facilitate export of the polypeptide when produced recombinantly, fusion partners that facilitate purification of the polypeptide, and fusion partners which enhance the immunogenicity of the polypeptide fragment of the invention are all interesting possibilities. Therefore, the invention also pertains to a fusion polypeptide comprising at least one polypeptide or immunogenic portion defined above and at least one fusion partner. The fusion partner can, in order to enhance immunogenicity, be another polypeptide derived from *M. tuberculosis*, such as of a polypeptide fragment derived from a bacterium belonging to the *tuberculosis* complex, such as ESAT-6, TB10.4, CFP10, RD1-ORF5, RD1-ORF2, Rv1036, MPB64, MPT64, Ag85A, Ag85B (MPT59), MPB59, Ag85C, 19 kDa lipoprotein, MPT32 and alpha-crystalline, or at least one T-cell epitope of any of the above mentioned antigens (Skjøt et al 2000; Danish Patent application PA 2000 00666; Danish Patent application PA 1999 01020; U.S. patent application Ser. No. 09/505,739; Rosenkrands et al 1998; Nagai et al 1991). The invention also pertains to a fusion polypeptide comprising mutual fusions of two or more of the polypeptides (or immunogenic portions thereof) of the invention.

Other fusion partners, which could enhance the immunogenicity of the product, are lymphokines such as IFN-γ, IL-2 and IL-12. In order to facilitate expression and/or purification, the fusion partner can e.g. be a bacterial fimbrial protein, e.g. the pilus components pilin and papA; protein A; the ZZ-peptide (ZZ-fusions are marketed by Pharmacia in Sweden); the maltose binding protein; glutathione S-transferase; β-galactosidase; or poly-histidine. Fusion proteins can be produced recombinantly in a host cell, which could be *E. coli*, and it is a possibility to induce a linker region between the different fusion partners.

Other interesting fusion partners are polypeptides, which are lipidated so that the immunogenic polypeptide is presented in a suitable manner to the immune system. This effect is e.g. known from vaccines based on the *Borrelia burgdorferi* OspA polypeptide as described in e.g. WO 96/40718 A or vaccines based on the *Pseudomonas aeruginosa* OprI lipoprotein (Cote-Sierra J 1998). Another possibility is N-terminal fusion of a known signal sequence and an N-terminal cystein to the immunogenic polypeptide. Such a fusion results in lipidation of the immunogenic polypeptide at the N-terminal cystein, when produced in a suitable production host.

Uses

Protein Vaccine

Another part of the invention pertains to a vaccine composition comprising a polypeptide (or at least one immunogenic portion thereof) or fusion polypeptide according to the invention. In order to ensure optimum performance of such a vaccine composition it is preferred that it comprises an immunologically and pharmaceutically acceptable carrier, vehicle or adjuvant.

An effective vaccine, wherein a polypeptide of the invention is recognized by the animal, will in an animal model be able to decrease bacterial load in target organs, prolong survival times and/or diminish weight loss after challenge with a virulent *Mycobacterium*, compared to non-vaccinated animals Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyldioctadecylammonium bromide (DDA), Quil A, poly I:C, aluminum hydroxide, Freund's incomplete adjuvant, IFN-γ, IL-2, IL-12, monophosphoryl lipid A (MPL), Trehalose Dimycolate (TDM), Trehalose Dibehenate and muramyl dipeptide (MDP).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-γ inducers such as poly I:C in combination with the above-mentioned adjuvants.

Another interesting possibility for achieving adjuvant effect is to employ the technique described in Gosselin et al., 1992 (which is hereby incorporated by reference herein). In brief, a relevant antigen such as an, antigen of the present invention can be conjugated to an antibody (or antigen binding antibody fragment) against the Fcγ receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

In many instances, it will be necessary to have multiple administrations of the vaccine. Especially, vaccines can be administered to prevent an infection with virulent mycobacteria, a prophylactic vaccine, and/or to treat established mycobacterial infection, a therapeutic vaccine. When administered to prevent an infection, the vaccine is given prophylactically, before definitive clinical signs, diagnosis or identification of an infection TB are present. Since the current vaccine BCG appears to induce an effective, but short-lived immune response, prophylactic vaccines may also be designed to be used as booster vaccines. Such booster vaccines are given to individuals who have previously received a vaccination, with the intention of prolonging the period of protection. In instances where the individual has already become infected or is suspected to have become infected, the previous vaccination may have provided sufficient immunity to prevent primary disease, but as discussed previously, boosting this immune response will not help against the latent infection. In such a situation, the vaccine will necessarily have to be a therapeutic vaccine designed for efficacy against the latent stage of infection. A combination of a prophylactic vaccine and a therapeutic vaccine, which is active against both primary and latent infection, constitutes a multiphase vaccine.

Due to genetic variation, different individuals may react with immune responses of varying strength to the same polypeptide. Therefore, the vaccine according to the invention may comprise several different polypeptides in order to increase the immune response. The vaccine may comprise two or more polypeptides or immunogenic portions, where all of the polypeptides are as defined above, or some but not all of the peptides may be derived from virulent mycobacteria. In the latter example, the polypeptides not necessarily fulfilling the criteria set forth above for polypeptides may either act due to their own immunogenicity or merely act as adjuvants.

The vaccine may comprise 1-20, such as 2-20 or even 3-20 different polypeptides or fusion polypeptides, such as 3-10 different polypeptides or fusion polypeptides.

The invention also pertains to a method for immunizing an animal, including a human being, against TB caused by virulent mycobacteria, comprising administering to the animal the polypeptide of the invention, or a vaccine composition of the invention as described above, or a living vaccine described above.

The invention also pertains to a method for producing an immunologic composition according to the invention, the method comprising preparing, synthesizing or isolating a polypeptide according to the invention, and solubilizing or dispersing the polypeptide in a medium for a vaccine, and optionally adding other *M. tuberculosis* antigens and/or a carrier, vehicle and/or adjuvant substance.

DNA Vaccine.

The nucleic acid fragments of the invention may be used for effecting in vivo expression of antigens, i.e. the nucleic acid fragments may be used in so-called DNA vaccines as reviewed in Ulmer et al 1993, which is included by reference.

Hence, the invention also relates to a vaccine comprising a nucleic acid fragment according to the invention, the vaccine effecting in vivo expression of antigen by an animal, including a human being, to whom the vaccine has been administered, the amount of expressed antigen being effective to confer substantially increased resistance to infections caused by virulent mycobacteria in an animal, including a human being.

The above mentioned definitions and distinctions of prophylactic-, booster-, therapeutic- and multiphase vaccines also applies for DNA vaccines The efficacy of such a DNA vaccine can possibly be enhanced by administering the gene encoding the expression product together with a DNA fragment encoding a polypeptide that has the capability of modulating an immune response.

Live Recombinant Vaccines

One possibility for effectively activating a cellular immune response for a vaccine can be achieved by expressing the relevant antigen in a vaccine in a non-pathogenic microorganism or virus. Well-known examples of such microorganisms are *Mycobacterium bovis* BCG, *Salmonella* and *Pseudomona* and examples of viruses are Vaccinia Virus and Adenovirus.

Therefore, another important aspect of the present invention is an improvement of the living BCG vaccine presently available, wherein one or more copies of a DNA sequence encoding one or more polypeptide as defined above has been incorporated into the genome of the micro-organism in a manner allowing the micro-organism to express and secrete the polypeptide. The incorporation of more than one copy of a nucleotide sequence of the invention is contemplated to enhance the immune response.

Another possibility is to integrate the DNA encoding the polypeptide according to the invention in an attenuated virus such as the vaccinia virus or Adenovirus (Rolph et al 1997). The recombinant vaccinia virus is able to replicate within the cytoplasma of the infected host cell and the polypeptide of interest can therefore induce an immune response, which is envisioned to induce protection against TB.

Therapeutic Vaccine.

The invention also relates to the use of a polypeptide or nucleic acid of the invention for use as therapeutic vaccines as have been described by D. Lowrie (Lowrie, 1999) using DNA vaccine encoding HSP65 from *M. leprae*. Antigens with therapeutic properties may be identified based on their ability to diminish the severity of *M. tuberculosis* infection in experimental animals or prevent reactivation of previous infection, when administered as a vaccine. The composition used for therapeutic vaccines can be prepared as described above for vaccines.

Diagnostic Protein

The invention also relates to a method of diagnosing latent TB caused by a virulent *mycobacterium* in an animal, including a human being, comprising intradermally injecting, in the animal, a polypeptide according to the invention, a positive skin response at the location of injection being indicative of the animal having TB, and a negative skin response at the location of injection being indicative of the animal not having TB.

When diagnosis of latent infection with virulent mycobacteria is the aim, a blood sample comprising mononuclear cells (i.e. T-lymphocytes) from a patient is contacted with a sample of one or more polypeptides of the invention. This contacting can be performed in vitro and a positive reaction could e.g. be proliferation of the T-cells or release of cytokines such as IFN-γ into the extracellular phase. It is also conceivable to contact a serum sample from a subject with a polypeptide of the invention, the demonstration of a binding between antibodies in the serum sample and the polypeptide being indicative of previous or ongoing infection.

The invention therefore also relates to an in vitro method for diagnosing latent infection in an animal or a human being with a virulent *mycobacterium*, the method comprising providing a blood sample from the animal or human being, and contacting the sample from the animal with the polypeptide of the invention, a significant release into the extracellular phase of at least one cytokine by mononuclear cells in the blood sample being indicative of the animal being sensitized. A positive response being a response more than release from a blood sample derived from a patient without the TB diagnosis plus two standard deviations. The invention also relates to the in vitro method for diagnosing ongoing or previous sensitization in an animal or a human being with a virulent *mycobacterium*, the method comprising providing a blood sample from the animal or human being, and by contacting the sample from the animal with the polypeptide of the invention demonstrating the presence of antibodies recognizing the polypeptide of the invention in the serum sample.

The immunogenic composition used for diagnosing may comprise 1-20, such as 2-20 or even 3-20 different polypeptides or fusion polypeptides, such as 3-10 different polypeptides or fusion polypeptides.

Diagnostic DNA

The nucleic acid probes encoding the polypeptide of the invention can be used in a variety of diagnostic assays for detecting the presence of pathogenic organisms in a given sample.

A method of determining the presence of mycobacterial nucleic acids in an animal, including a human being, or in a sample, comprising administering a nucleic acid fragment of the invention to the animal or incubating the sample with the nucleic acid fragment of the invention or a nucleic acid fragment complementary thereto, and detecting the presence of hybridized nucleic acids resulting from the incubation (by using the hybridization assays which are well-known in the art), is also included in the invention. Such a method of diagnosing TB might involve the use of a composition comprising at least a part of a nucleotide sequence as defined above and detecting the presence of nucleotide sequences in a sample from the animal or human being to be tested which hybridize with the nucleic acid fragment (or a complementary fragment) by the use of PCR technique.

Antibodies

A monoclonal or polyclonal antibody, which is specifically reacting with a polypeptide of the invention in an immunoassay, or a specific binding fragment of said antibody, is also a part of the invention. The antibodies can be produced by methods known to a person skilled in the art. Polyclonal antibodies can be raised in a mammal, for example, by one or more injections of a polypeptide according to the present invention and, if desired, an adjuvant. The monoclonal antibodies according to the present invention may, for example, be produced by the hybridoma method first described by Kohler and Milstein (Kohler and Milstein, 1975), or may be produced by recombinant DNA methods such as described in U.S. Pat. No. 4,816,567. The monoclonal antibodies may also be isolated from phage libraries generated using the techniques described by McCafferty et al (McCafferty, 1990), for example. Methods for producing antibodies are described in the literature, e.g. in U.S. Pat. No. 6,136,958.

A sample of a potentially infected organ or body fluid from an infected individual may be contacted with such an antibody recognizing a polypeptide of the invention. The demonstration of the reaction by means of methods well known in the art between the sample and the antibody will be indicative of an ongoing infection. It is of course also a possibility to demonstrate the presence of anti-mycobacterial antibodies in serum or other body fluids by contacting a serum sample from a subject with at least one of the polypeptide fragments of the invention and using well-known methods for visualizing the reaction between the antibody and antigen.

In diagnostics, an antibody, a nucleic acid fragment and/or a polypeptide of the invention can be used either alone, or as a constituent in a composition. Such compositions are known in the art, and comprise compositions in which the antibody, the nucleic acid fragment or the polypeptide of the invention is coupled, preferably covalently, to at least one other molecule, e.g. a label (e.g. radioactive or fluorescent) or a carrier molecule.

It will be understood that the following examples are illustrative of the present invention and are not a limitation thereof. A number of variations on the techniques, reagents, and conditions described in the following examples will be readily apparent to one of skill in the art.

EXAMPLE 1

Cloning and Expression of Low Oxygen Induced *M. tuberculosis* Antigens in *E. coli*

A number of *M. tuberculosis* genes are induced under low oxygen conditions. The up-regulation of the genes listed in table 2 has been determined at either the mRNA (Sherman, 2001) or protein (Boon, 2001, Rosenkrands, 2002) level. The coding region of these selected antigens is amplified by PCR using the primer sets listed in Table 3.

TABLE 3

Primer sequences for PCR amplification of selected low oxygen induced antigens

| Rv no. | | SEQ ID NO: | Primer sequence |
|---|---|---|---|
| Rv0079 | Fwd | 92 | CACCGTGGAACCGAAACGCAGTCG |
|  | Rvs | 93 | TTATGCCAGACCGTCGGCA |
| Rv0080 | Fwd | 94 | CACCATGAGCCCGGGCTCG |
|  | Rvs | 95 | TTACGGCGTACGCGAGTCAG |
| Rv0081 | Fwd | 96 | CACCGTGGAGTCCGAACCGCTGTA |
|  | Rvs | 97 | TTACGTGGCCGAGCCGC |
| Rv0363c (fba) | Fwd | 98 | CACCATGCCTATCGCAACGCCC |
|  | Rvs | 99 | TTAGTGGGTTAGGGACTTTCCGG |

TABLE 3-continued

Primer sequences for PCR amplification of selected low oxygen induced antigens

| Rv no. | | SEQ ID NO: | Primer sequence |
|---|---|---|---|
| Rv0569 | Fwd | 100 | GGGGACAAGTTTGTACAAAAAAGCAGGCTTAAAGGCAAAGGTCGGGGAC |
| | Rvs | 101 | GGGGACCACTTTGTACAAGAAAGCTGGGTCCTACGTTCCCCTGGCATGGA |
| Rv0572c | Fwd | 102 | CACCATGGGTGAGCACGCCATC |
| | Rvs | 103 | TTATAGGTCATCGGATTGAGGTGATC |
| Rv0574c | Fwd | 104 | CACCGTGGCTGGCAATCCTGATGT |
| | Rvs | 105 | TTACTCCTTGCTCGTTAGGTTGGC |
| Rv1264 | Fwd | 106 | CACCGTGACAGACCACGTGCGC |
| | Rvs | 107 | TTACGGTGACGAGCCGGC |
| Rv1592c | Fwd | 108 | CACCATGGTAGAGCCCGGCAATTTG |
| | Rvs | 109 | TTAGAGCGGACGGCGGCT |
| Rv1733c | Fwd | 110 | CACCATGATCGCCACAACCCGC |
| | Rvs | 111 | TTACCGCTGCGTGCAGAACA |
| Rv1734c | Fwd | 112 | CACCATGACCAACGTCGGTGACCA |
| | Rvs | 113 | TTATCCTGTTACTGCGGCGCA |
| Rv1736c (narX) | Fwd | 114 | CACCGTGACGGTGACACCACGGAC |
| | Rvs | 115 | TTACCACCCGCGCCGC |
| Rv1737c (narK2) | Fwd | 116 | CACCATGAGAGGGCAAGCGGC |
| | Rvs | 117 | TTACCTGGACGCCTCCTCACTC |
| Rv1738 | Fwd | 118 | CACCATGTGCGGCGACCAGTC |
| | Rvs | 119 | TTAATACAACAATCGCGCCGG |
| Rv1739c | Fwd | 120 | CACCATGATTCCCACGATGACATCG |
| | Rvs | 121 | TTAGCGCCGACGGAACG |
| Rv1813c | Fwd | 122 | GGGGACAAGTTTGTACAAAAAAGCAGGCTTAATCACAAACCTCCGACGC |
| | Rvs | 123 | GGGGACCACTTTGTACAAGAAAGCTGGGTCCTAGTTGCACGCCCAGTTGAC |
| Rv1997 (ctpF) | Fwd | 124 | CACCTTGTCGGCGTCAGTGTCTGC |
| | Rvs | 125 | TTATGGCGGTTGCGCCC |
| Rv1998c | Fwd | 126 | CACCATGAGTTTCCACGATCTTCATCACC |
| | Rvs | 127 | TTACGTTGTACTCGTGCGGTTCTC |
| Rv2003c | Fwd | 128 | CACCGTGGTCAAGCGCTCTCGG |
| | Rvs | 129 | TTATTCCGACTCGAGTGGGTGA |
| Rv2005c | Fwd | 130 | CACCATGTCTAAACCCCGCAAGCA |
| | Rvs | 131 | TTACGACTGCCGTGCCACG |
| Rv2007c (fdxA) | Fwd | 132 | CACCGTGACCTATGTGATCGGTAGTGAGTG |
| | Rvs | 133 | TTAAGGGCACTCCACCGGGA |
| Rv2028c | Fwd | 134 | CACCATGAACCAATCACACAAACCCC |
| | Rvs | 135 | TTACAGATACTGCTGACCGACGACC |
| Rv2029c (pfkB) | Fwd | 136 | CACCATGACGGAGCCAGCGG |
| | Rvs | 137 | TTATGGCGAGGCTTCCGG |
| Rv2030c | Fwd | 138 | GGGGACAAGTTTGTACAAAAAAGCAGGCTTACTGATGACCGCAGCGGCT |
| | Rvs | 139 | GGGGACCACTTTGTACAAGAAAGCTGGGTCCTACAGACCGGTCGGGTAGGTTT |
| Rv2031c (hspX) | Fwd | 140 | GGGGACAAGTTTGTACAAAAAAGCAGGCTTAGCCACCACCCTTCCCGT |
| | Rvs | 141 | GGGGACCACTTTGTACAAGAAAGCTGGGTCCTAGTTGGTGGACCGGATCTGAAT |
| Rv2032 | Fwd | 142 | CACCATGCCGGACACCATGGTG |
| | Rvs | 143 | TTAGTGATCCTTAGCCCGAACGTG |

TABLE 3-continued

Primer sequences for PCR amplification of selected low oxygen induced antigens

| Rv no. | | SEQ ID NO: | Primer sequence |
|---|---|---|---|
| Rv2428 (ahpC) | Fwd | 144 | GGGGACAAGTTTGTACAAAAAAGCAGGCTTAATGCCACTGCTAACCATTGGC |
| | Rvs | 145 | GGGGACCACTTTGTACAAGAAAGCTGGGTCCTAGGCCGAAGCCTTGAGGAGT |
| Rv2624c | Fwd | 146 | CACCATGTCTGGGAGAGGAGAGCCG |
| | Rvs | 147 | TTAGCGAACGACAAGCACCGA |
| Rv2625c | Fwd | 148 | GGGGACAAGTTTGTACAAAAAAGCAGGCTTACGTGATGCGATCCCGCT |
| | Rvs | 149 | GGGGACCACTTTGTACAAGAAAGCTGGGTCCTACCCCGCATCGGAAACC |
| Rv2627c | Fwd | 150 | GGGGACAAGTTTGTACAAAAAAGCAGGCTTAATGGCAAGTTCTGCGAGCGA |
| | Rvs | 151 | GGGGACCACTTTGTACAAGAAAGCTGGGTCCTAGGAACGGTCGCGCTGTGT |
| Rv2628 | Fwd | 152 | CACCATGTCCACGCAACGACCG |
| | Rvs | 153 | TTAACCGCAACGGCAATCTCA |
| Rv2629 | Fwd | 154 | CACCATGCGATCAGAACGTCTCCG |
| | Rvs | 155 | TTAGGATCTATGGCTGCCGAGTC |
| Rv2630 | Fwd | 156 | CACCATGCTGCACCGCGACGA |
| | Rvs | 157 | TTACACATCGAGCGTTACCGCAC |
| Rv2659c | Fwd | 158 | GGGGACAAGTTTGTACAAAAAAGCAGGCTTAGTGACGCAAACCGGCAA |
| | Rvs | 159 | GGGGACCACTTTGTACAAGAAAGCTGGGTCCTACATCTCCTGGTTCTCGGCC |
| Rv2780 | Fwd | 160 | GGGGACAAGTTTGTACAAAAAAGCAGGCTTACGCGTCGGTATTCCGACC |
| | Rvs | 161 | GGGGACCACTTTGTACAAGAAAGCTGGGTCCTACACGCTGGCGGGCTC |
| Rv3126c | Fwd | 162 | CACCATGGTCATCCGGTTTGATCAAATA |
| | Rvs | 163 | TTATGGATTGTCAATGACAGCCCA |
| Rv3127 | Fwd | 164 | CACCGTGCTCAAGAACGCAGTCTTGC |
| | Rvs | 165 | TTAAGGCGGGCTGAACCAACC |
| Rv3128c | Fwd | 166 | CACCGTGTGGTCCGCCTCGG |
| | Rvs | 167 | TTAGCCCGCCTTGATCAGGA |
| Rv3129 | Fwd | 168 | CACCGTGGTGCAAGGCCGCA |
| | Rvs | 169 | TTATCGCTGGTTGTGTGACGAG |
| Rv3130c | Fwd | 170 | CACCATGAATCACCTAACGACACTTGACG |
| | Rvs | 171 | TTACACAACCAGCGATAGCGCTC |
| Rv3131 | Fwd | 172 | CACCATGAACACCCATTTCCCGG |
| | Rvs | 173 | TTAGCACCGTTGTCGCAGTAGCT |
| Rv3132c | Fwd | 174 | CACCATGACAACAGGGGGCCTCG |
| | Rvs | 175 | TTACTGCGACAACGGTGCTGAC |
| Rv3134c | Fwd | 176 | CACCATGAGCGATCCTCGGCCA |
| | Rvs | 177 | TTACAAGTTGGCACTGCGTACCG |
| Rv3841 (bfrB) | Fwd | 178 | CCGGCTGAGATCTATGACAGAATACGAAGGGC |
| | Rvs | 179 | CCCCGCCAGGGAACTAGAGGCGGC |
| Rv3842c (glpQ1) | Fwd | 180 | CACCATGACATGGGCCGACGAG |
| | Rvs | 181 | TTAGCGAGTGGTCCCGTTCG |
| Rv3908 | Fwd | 182 | CACCGTGTCCGACGGCGAACAA |
| | Rvs | 183 | TTACGGCCCCGGCCC |

PCR reactions were carried out using Platinum Taq DNA Polymerase (GIBCO BRL) in a 50 µl reaction volume containing 60 mM Tris-SO$_4$(pH 8.9), 18 mM Ammonium Sulfate, 0.2 mM of each of the four nucleotides, 0.2 µM of each primer and 10 ng of *M. tuberculosis* H37Rv chromosomal DNA. The reaction mixtures were initially heated to 95° C. for 5 min., followed by 35 cycles of: 95° C. for 45 sec, 60° C. for 45 sec and 72° C. for 2 min. The amplification products were precipitated by PEG/MgCl$_2$, and dissolved in 50 µL TE buffer.

DNA fragments were cloned and expressed in Gateway Cloning system (Life Technology). First, to create Entry Clones, 5 µL of DNA fragment was mixed with 1 µL of pDONR201, 2 µL of BP CLONASE enzyme mix and 2 µL of BP reaction buffer. The recombination reactions were carried out at 25° C. for 60 min. After Proteinase K treatment at 37° C. for 10 min., 5 µL of each sample was used to transform *E. coli* DH5α competent cells. Transformants were selected on LB plates containing 50 µg/mL kanamycin. One bacterial clone from each transformation was grown in 3 mL LB medium containing 50 µg/mL kanamycin and plasmid DNA was isolated (Qiagen).

Second, to create expression clones, 2 µL of each entry clone DNA was mixed with 1 µL of His-tagged expression vector (pDest17), 2 µL LR reaction buffer, 2 µL LR CLO-NASE enzyme mix and 3 µL TE. After recombination at 25° C. for 60 min, and Proteinase K treatment at 37° C. for 10 min., 54 µL of each sample was used to transform *E. coli* BL21-SI competent cells. Transformants were selected on LBON (LB without NaCl) plates containing 100 µg/mL ampicillin. The resulting *E. coli* clones express recombinant proteins carrying a 6-histine tag at the N-terminal. All clones were confirmed by DNA sequencing.

Recombinant proteins were purified from transformed *E. coli* BL21-SI cells cultured in 900 mL LBON medium containing 100 µg/mL at 30° C. until OD$_{600}$=0.4-0.6. At this point 100 mL 3 M NaCl was added and 3 hours later bacteria were harvested by centrifugation. Bacteria pellets were resuspended in 20 mL bacterial protein extraction reagent (Pierce) incubated for 10 min. at room temperature and pelleted by centrifugation. Bacteria were lysed and their DNA digested by treating with lysozyme (0.1 mg/mL) and DNase I (2.5 µg/mL) at room temperature for 30 minutes, with gentle agitation. The recombinant protein forms inclusion bodies and can be pelleted by centrifugation at 27.000×g for 15 min. Protein pellets were solubilized by adding 20 ml of sonication buffer (8 M urea, 50 mM Na$_2$HPO$_4$, 100 mM Tris-HCl, pH 8.0) and sonicating 5×30 sec pulses interrupted by a 30 sec pause. After another centrifugation at 27.000×g for 15 min., supernatants were applied to 10 mL TALON columns (Clontech). The columns were washed with 50 mL sonication buffer. Bound proteins were eluted by lowering pH (8 M urea, 50 mM Na$_2$HPO$_4$, 100 mM Tris-HCl, pH 4.5). 5 mL fractions were collected and analyzed by SDS-PAGE. Fractions containing recombinant protein were pooled. Further purification was achieved by anion- or cation-exchange chromatography on Hitrap columns (Pharmacia). Bound protein was eluted using a NaCl gradient from 0-500 mM in 3 M urea, 10 mM Tris-HCl, pH 8.0. All fractions were collected and analyzed on SDS-PAGE using Coomassie staining. Fractions containing recombinant protein were pooled. Final protein concentrations were determined by micro BCA (Pierce).

EXAMPLE 2

Prophylactic Versus Therapeutic Vaccine

Murine Vaccination Models.

A prophylactic vaccine given prior to infection should induce an immune response sufficiently strong to prevent or dampen the initial proliferation of the bacteria in the acute phase and thereby reduce the ensuing disease. In the murine prophylactic vaccine model outlined in FIG. 1A, naïve mice are immunized 3 times, 2 weeks apart with recombinant antigens. Six weeks after the last immunization, the mice are given an aerosol infection with approximately 250 *M. tuberculosis* bacilli. The protective capacity of the vaccine is evaluated by enumeration of the bacteria in spleen and lung 6 weeks post-infection.

To define the optimal components for a therapeutic vaccine, a murine reactivation model of latent TB has been established (van Pinxteren, 2000) (FIG. 1B). An aerosol infection with approximately 250 *M. tuberculosis* bacilli is given and at the peak of infection 6 weeks later, the mice receive an 8-week course of anti-mycobacterial drug treatment of isoniazid and rifabutin given in the drinking water. This reduces the bacterial load in spleen and lung to a low level (about 500 bacteria per organ). This latent phase of low chronic infection is stable for 9-10 weeks after which a slow spontaneous reactivation occurs. The therapeutic vaccine is given as 3 subcutaneous (s.c.) immunizations about 5 weeks after cessation of drug treatment. The effect of the therapeutic vaccine is evaluated as protection against reactivation determined by enumeration of bacteria in spleen and lung 7 weeks after the last immunization.

The effect of the antigens in a prophylactic or a therapeutic vaccine.

BCG, ESAT6, and Rv2031c, one of the most prominent proteins induced under low oxygen conditions (Rosenkrands, 2002), were analyzed for their prophylactic and therapeutic vaccine potential. Naïve or latently infected C57Bl mice were immunized with one s.c. injection of 2.5×10$^5$ BCG, or 3 s.c. immunizations of 10 µg of either recombinant ESAT6 or recombinant Rv2031c in a DDA/MPL adjuvant. The vaccinations were done in groups of 5 mice and protective capacity of the vaccines was evaluated as described above. FIG. 2 shows the bacterial load in the lung in the acute phase (A) and in the reactivation phase (B), after prophylactic and therapeutic vaccination respectively. ESAT6 (as previously described by Brandt, 2000) offers protection against acute phase infection at the level of BCG (FIG. 2A). However, neither of the two shows any protective effect against reactivation of the infection when given during latent infection (FIG. 2B). In contrast, Rv2031c, the low oxygen induced antigen, offers no protection against the acute phase of the infection when given as a prophylactic vaccine, but gives some protection against reactivation when given as a therapeutic vaccine. That is, some antigens, here exemplified by ESAT6, though potent as prophylactic vaccines have no effect as therapeutic vaccines. In contrast, other antigens, here exemplified by Rv2031c, can be efficient therapeutic vaccines although they have no effect or only negligible effect as prophylactic vaccines.

EXAMPLE 3

Low Oxygen Induced Antigens, Rv2031c, as Therapeutic Vaccines

Figure 3:
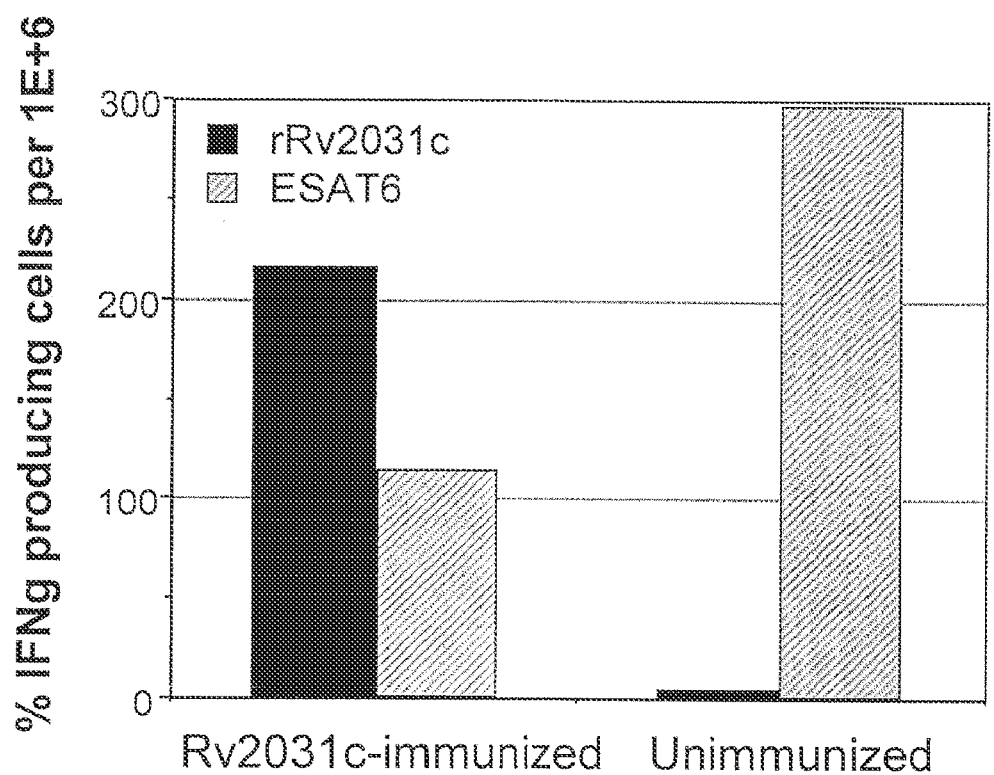
FIG. 3 illustrates Rv2031c specific IFN-γ responses. Latent infected C57Bl/6j mice were either not immunized or immunized with 3 μg recombinant Rv2031 3 times with a two-week interval. One and two weeks post immunization mice were bleed and PBMCs isolated. The frequency of IFN-γ producing cells specific for either ESAT6 or Rv2031c was determined for both the rRv2031c immunized and the unimmunized group. In an ELIspot plate precoated with anti-IFN-γ antibodies graded numbers of PBMCs were incubated with either 2 μg/ml rRv2031c or 2 μg/ml rESAT6. After 32 h the plate was washed and incubated with biotinylated anti-INF-γ antibodies followed by a streptavidin-alkalinephosphatase incubation. The INFγ spots, representing individual IFN-γ producing cells were visualized using BCIP/NBT substrate. The results are shown as number Rv2031c specific IFN-γ producing cell (black bars) and number of ESAT6 specific IFN-γ producing cell (hatch bars) per $10^6$ PBMCs.

There is a high variability in bacterial load intrinsic to the reactivation model in the latent and reactivation phase. The analysis of Rv2031c as a therapeutic vaccine was therefore repeated in groups of eight mice. As in the previous experiments the mice were given 3 s.c. immunizations of 10 μg rRv2031c in DDA/MPL. The induced immune responses were analyzed one week post immunization. The mice were partially bled and the PBMC from the blood purified and analyzed for Rv2031c- and ESAT6 specific recall responses. Using ELIspot technique, the frequency of Rv2031c-specific and ESAT6-specific IFN-γ-producing cells were determined in both the rRv2031c immunized and the unimmunized group (FIG. 3). The rRv2031c immunization has increased the frequency of Rv2031c-specific IFN-γ producing cells by a factor of 43 as compared to the unimmunized group. In contrast, the frequency of ESAT6-specific IFN-γ producing cells is significantly higher in the unimmunized group. ESAT6 is an antigen produced in high amounts by the actively-growing *M. tuberculosis* bacteria. The level of the ESAT6 specific immune response in infected mice could therefore be indicative the degree of actively-growing infection in the animals. Recent reports have in fact demonstrated such a correlation between the level of ESAT6 response and degree of disease in both *M. tuberculosis*-infected humans and *M. bovis*-infected cattle (Doherty, 2002, Vordermeier, 2002). Therefore, the higher ESAT6 response in the unimmunized group of latently-infected mice could be indicative of a transition into the reactivation phase, where the bacteria are again beginning to multiply.

Figure 4A:
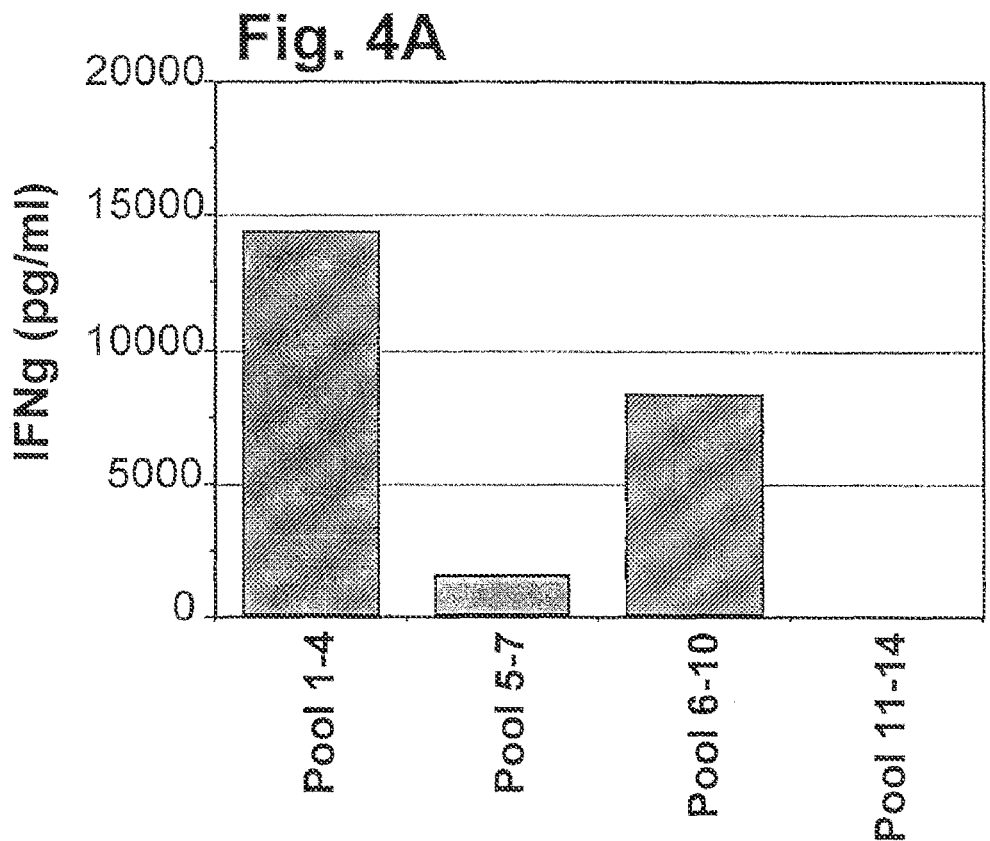
FIGS. 4A and 4B illustrate the results of epitope screening of Rv2031c. PBMCs from rRv2031c immunized latently infected C57Bl/6j mice were analyzed for recognition of 20' mer overlapping peptides scanning through Rv2031c.
Figure 4B:
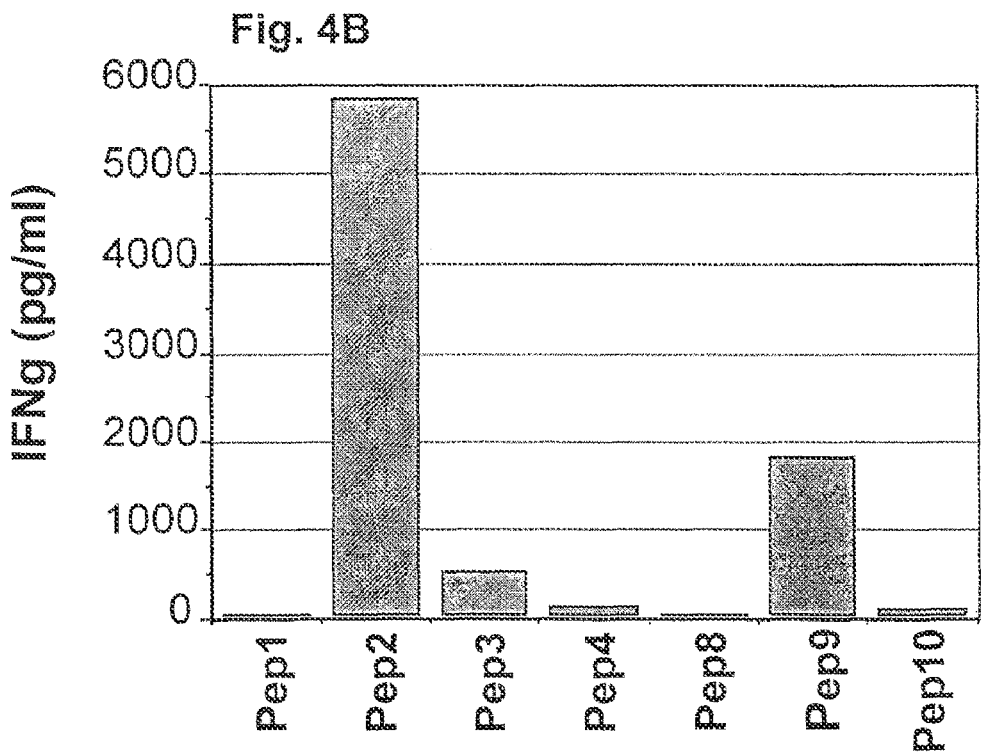

To analyze the epitope recognition pattern of Rv2031c, fourteen overlapping peptides (each 20 amino acids long) covering the whole Rv2031c protein were synthesized. Initially the peptides were analyzed in 4 pools of 3-4 peptides. PBMCs from rRv2031c immunized latently-infected mice were incubated with the peptide pools (5 μg/ml per peptide) for 72 h. The specific peptide-induced IFN-γ production was quantitated in the supernatant in a standard sandwich ELISA using paired anti-murine IFN-γ antibodies (PharMingen) and recombinant IFN-γ (PharMingen) as standard. Both peptide pool 1-4 and 8-10 stimulated a significant IFN-γ response (FIG. 4A). The individual peptides of these two pools were re-analyzed (FIG. 4B). This clearly shows that the response to Rv2031c contains a dominant epitope, peptide 2 (PRSLF-PEFSELFAAFPSFAG, aa 11-30 of SEQ ID NO:24), and a subdominant epitope, peptide 9 (RTEQKDFDGRSEFAYGS-FVR, aa 81-100 of SEQ ID NO:24).

The therapeutic effect of the rRv2031c immunizations was analyzed 7 weeks after the last immunization. FIG. 5 shows the bacterial load in the lung (A) and the spleen (B) of both rRv2031c-immunized and unimmunized mice. There is a clear reduction in the level of bacteria in both organs in the rRv2031c-immunized group. That is, the induction of Rv2031c T cell responses can participate in keeping the latent infection in check.

EXAMPLE 4

Low Oxygen Induced Antigens, Rv0569, as Therapeutic Vaccines

Rv0569 is also a low oxygen induced antigen described in WO0179274 and illustrates very well the potential as a therapeutic vaccine.

We have established a murine reactivation model of latent TB [van Pinxteren et al, 2000, 30:3689-98], which is a variant of the so-called Cornell model. An aerosol infection is allowed to be established and at the peak of infection 6 weeks after, the mice receive an 8-week course of anti-mycobacterial drug treatment of isoniazid and rifabutin given in the drinking water. This reduces the bacterial load in spleen and lung to a low level. This latent phase of low chronic infection is stable for 9-10 weeks after which a slow spontaneous reactivation can be detected. This model is used to analyze the protective effect of a post exposure vaccine on reactivation.

Rv0569, which is highly up regulated under low oxygen growth conditions [Rosenkrands et al, 2002, 184(13): 3485-91], was analyzed for its ability to protect against reactivation given as a therapeutic vaccine in the latent phase of TB infection. Latent infected C57B1 mice were vaccinated with 3 s.c. injections of 3 μg recombinant Rv0569 and for comparison with 3 s.c. injections of 3 μg recombinant ESAT6 or one s.c. injection of BCG. The effect of the vaccine is evaluated 7 weeks after the last immunization. The induced immune responses were analyzed for Rv0569 or ESAT6 specific responses in an in vitro recall assay. Isolated splenocytes were incubated with 1 μg/ml of Rv0569 or 1 μg/ml of ESAT6 for 72 h. The produced IFNγ in the culture supernatant was quantitated in a standard sandwich ELISA. FIG. 6 shows a nice Rv0569 specific IFNγ response induced in the Rv0569 vaccinated group with practically no response in the un-vaccinated group. The ESAT6 vaccination enhanced the ESAT6 specific response though a significant ESAT6 response persisted in the un-vaccinated latent infected group.

The Rv0569 induced protection against reactivation was determined by enumeration of bacteria in spleen and lung 7 weeks after the last immunization. FIG. 7 shows the bacterial load in the lung and the spleen of both Rv0569-vaccinated, ESAT6-vaccinated, BCG vaccinated and un-vaccinated latently infected mice. There is a clear reduction in the level of viable bacteria in both spleen and lungs of the Rv0569 vaccinated mice, whereas neither ESAT6 nor BCG are able to inhibit the growth of the *M. tuberculosis* bacteria when given as a vaccine during latent infection. That is, the induction of Rv0569 T cell responses can participate in keeping the latent infection in check.

REFERENCES

Anon. 2001. Global *Tuberculosis* Control. WHO Report.
Boon, C., et al. 2001. J. Bacteriol, 183, 2677-2676.
Brandt, L., et al. 2000 Infect. Immun. 68:2; 791-795.
Cote-Sierra J, et al 1998, Gene Oct. 9; 221(1):25-34
Doherty T M et al., 2002, J Clin Microbiol. February; 40(2): 704-6.
Florczyk, M. A., et al. 2001. Infect Immun, 69, 5777-5785.
Gosselin et al., 1992. J. Immunol. 149: 3477-3481
Harboe, M., et al 1998 Infect. Immun. 66:2; 717-723
Honer zu Bentrup, K. et al., 2001. Trens Immunol. 9 597-605
Kilgus J et al, J Immunol. 1991 Jan. 1; 146(1):307-15
Kohler and Milstein, Nature, 256:495 (1975)
Lowrie, D. B. et al 1999, Nature 400: 269-71
Lustig et al 1976, Cell Immunol 24(1):164-7
Manganelli, et al. 2001. Mol Microbiol, 41, 423-437.
McCafferty, et al. 1990. Nature, 348, 552-554.
Merrifield, R. B. Fed. Proc. Am. Soc. Ex. Biol. 21: 412, 1962 and J. Am. Chem. Soc. 85: 2149, 1963
Monahan, I. M. et al. 2001. Microbiology, 147, 459-471.
Mowat et al 1991, Immunology 72(3):317-22
Nagai et al 1991, Infect. Immun 59:1; 372-382
Olsen A. W et al, Eur J Immunol. 2000 June; 30(6):1724-32
Danish Patent application PA 2000 00666 "Nucleic acid fragments and polypeptide fragments derived from *M. tuberculosis*"
Danish Patent application PA 1999 01020 (WO 01/23388) "*Tuberculosis* vaccine and diagnostic based on the *Mycobacterium tuberculosis* esat-6 gene family".

U.S. patent application Ser. No. 09/0505,739 "Nucleic acid fragments and polypeptide fragments derived from *M. tuberculosis*"
Pearson, W. R. et al. 1988. Proc Natl Acad Sci USA, 85, 2444-2448.
Ravn, P. et al 1999. J. Infect. Dis. 179:637-645
Rolph, M. S, and I. A. Ramshaw. 1997. Curr. Opin. Immunol. 9:517-24
Rosenkrands, I., et al 1998, Infect. Immun 66:6; 2728-2735
Rosenkrands, I., et al. 2002. Journal of Bacteriology, 184: 3485-3491.
Sambrook et al Molecular Cloning; A laboratory manual, Cold Spring Harbor Laboratories, N.Y., 1989
Sherman, D. R., et al. 2001. PNAS, 98, 7534-7539.
Sinigaglia F et al. Nature 1988 Dec. 22-29; 336(6201):778-80
Skjøt, R. L. V., et al 2000, Infect. Immun 68:1; 214-220
Stryhn, A., et al 1996 Eur. J. Immunol. 26:1911-1918
Thompson J., et al Nucleic Acids Res 1994 22: 4673-4680
Ulmer J. B et al 1993, Curr. Opin. Invest. Drugs 2(9): 983-989
van Pinxteren L. et al. *Eur J Immunol* 2000, 30: 3689-3698.
Vordermeier, H. M. et al. 2002. Infect. Immun., 70, 3026-3032.

All documents listed above, and the sequence listing, are incorporated by reference herein. A variety of modifications and variations on the processes, conditions, reagents and compositions described herein will be readily apparent to one of skill in the art given the teachings of the present invention. Such modifications and variations are within the scope of the invention as set forth in the following claims.

The invention claimed is:

1. A therapeutic vaccine against tuberculosis comprising a mycobacteria polypeptide having amino acid sequence SEQ ID NO: 33 and a pharmaceutically acceptable polymeric carrier bound to the polypeptide or a pharmaceutically acceptable adjuvant.

2. The therapeutic vaccine according to claim 1, wherein said polypeptide is fused to at least one fusion partner which is an antigen expressed by bacteria within the mycobacteria family, wherein said at least one fusion partner is heterologous to said polypeptide.

3. The therapeutic vaccine according to claim 1, wherein said polypeptide is lipidated thereby providing a self-adjuvanting effect of the polypeptide.

4. The therapeutic vaccine according to claim 1, which comprises a polymeric carrier bound by covalent or non-covalent interactions to said polypeptide.

5. The therapeutic vaccine according to claim 4, wherein the polymeric carrier is a polystyrene.

6. The therapeutic vaccine according to claim 2, wherein the fusion partner is selected from the polypeptides of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, and 45.

7. The therapeutic vaccine according to claim 6, wherein the polypeptides are recombinant or synthetic and are delivered in a delivery system comprising an adjuvant.

8. The therapeutic vaccine according to claim 2, wherein said at least one fusion partner is an antigen expressed by bacteria within the mycobacteria family other than a polypeptide selected from SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, and 45.

9. The therapeutic vaccine according to claim 8, wherein said at least one fusion partner is selected from the group consisting of ESAT-6, ESAT-6-Ag85B, TB10.4, CFP10, RD1-ORF5, RD1-ORF2, Rv1036, MPB64, MPT64, Ag85A, Ag85B (MPT59), MPB59, Ag85C, 19 kDa lipoprotein, and MPT32.

10. The therapeutic vaccine according to claim 8, wherein the polypeptides are recombinant or synthetic and are delivered in a delivery system comprising an adjuvant.

11. A therapeutic vaccine against tuberculosis comprising one or more mycobacteria polypeptides which are upregulated or expressed during the latent stage of the mycobacteria infection which is characterized by low-oxygen tension in the microenvironment of the mycobacteria and (i) a pharmaceutically acceptable polymeric carrier bound to the one or more polypeptides or (ii) a pharmaceutically acceptable adjuvant, wherein said one or more polypeptides has the amino acid sequence of SEQ ID NO: 33, wherein said one or more polypeptides is fused to at least one mycobacteria fusion partner.

12. The therapeutic vaccine according to claim 11, where the polypeptides are recombinant or synthetic and are delivered in a delivery system comprising an adjuvant.

13. The therapeutic vaccine according to claim 11, wherein the fusion partner is selected from SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, and 45.

14. The therapeutic vaccine according to claim 13, wherein the fusion partner is an antigen expressed by bacteria within the mycobacteria family other than a polypeptide selected from SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, and 45.

15. The therapeutic vaccine according to claim 14, wherein the fusion partner is selected from the group consisting of ESAT-6, ESAT-6-Ag85B, TB10.4, CFP10, RD1-ORF5, RD1-ORF2, Rv1036, MPB64, MPT64, Ag85A, Ag85B (MPT59), MPB59, Ag85C, 19 kDa lipoprotein, and MPT32.

* * * * *

SEQUENCE LISTING

```
<160> NUMBER OF SEQ ID NOS: 187

<210> SEQ ID NO 1
<211> LENGTH: 273
<212> TYPE: PRT
<213> ORGANISM: Mycobacterium tuberculosis

<400> SEQUENCE: 1

Val Glu Pro Lys Arg Ser Arg Leu Val Val Cys Ala Pro Glu Pro Ser
1               5                   10                  15

His Ala Arg Glu Phe Pro Asp Val Ala Val Phe Ser Gly Gly Arg Ala
            20                  25                  30

Asn Ala Ser Gln Ala Glu Arg Leu Ala Arg Ala Val Gly Arg Val Leu
        35                  40                  45

Ala Asp Arg Gly Val Thr Gly Gly Ala Arg Val Arg Leu Thr Met Ala
    50                  55                  60

Asn Cys Ala Asp Gly Pro Thr Leu Val Gln Ile Asn Leu Gln Val Gly
65                  70                  75                  80

Asp Thr Pro Leu Arg Ala Gln Ala Ala Thr Ala Gly Ile Asp Asp Leu
                85                  90                  95

Arg Pro Ala Leu Ile Arg Leu Asp Arg Gln Ile Val Arg Ala Ser Ala
            100                 105                 110

Gln Trp Cys Pro Arg Pro Trp Pro Asp Arg Pro Arg Arg Arg Leu Thr
        115                 120                 125

Thr Pro Ala Glu Ala Leu Val Thr Arg Arg Lys Pro Val Val Leu Arg
    130                 135                 140

Arg Ala Thr Pro Leu Gln Ala Ile Ala Ala Met Asp Ala Met Asp Tyr
145                 150                 155                 160

Asp Val His Leu Phe Thr Asp Ala Glu Thr Gly Glu Asp Ala Val Val
                165                 170                 175

Tyr Arg Ala Gly Pro Ser Gly Leu Arg Leu Ala Arg Gln His His Val
            180                 185                 190

Phe Pro Pro Gly Trp Ser Arg Cys Arg Ala Pro Ala Gly Pro Pro Val
        195                 200                 205

Pro Leu Ile Val Asn Ser Arg Pro Thr Pro Val Leu Thr Glu Ala Ala
    210                 215                 220

Ala Val Asp Arg Ala Arg Glu His Gly Leu Pro Phe Leu Phe Phe Thr
225                 230                 235                 240

Asp Gln Ala Thr Gly Arg Gly Gln Leu Leu Tyr Ser Arg Tyr Asp Gly
                245                 250                 255

Asn Leu Gly Leu Ile Thr Pro Thr Gly Asp Gly Val Ala Asp Gly Leu
```

```
                    260                 265                 270

Ala

<210> SEQ ID NO 2
<211> LENGTH: 152
<212> TYPE: PRT
<213> ORGANISM: Mycobacterium tuberculosis

<400> SEQUENCE: 2

Met Ser Pro Gly Ser Arg Arg Ala Ser Pro Gln Ser Ala Arg Glu Val
1               5                   10                  15

Val Glu Leu Asp Arg Asp Glu Ala Met Arg Leu Leu Ala Ser Val Asp
            20                  25                  30

His Gly Arg Val Val Phe Thr Arg Ala Ala Leu Pro Ala Ile Arg Pro
        35                  40                  45

Val Asn His Leu Val Val Asp Gly Arg Val Ile Gly Arg Thr Arg Leu
    50                  55                  60

Thr Ala Lys Val Ser Val Ala Val Arg Ser Ser Ala Asp Ala Gly Val
65                  70                  75                  80

Val Val Ala Tyr Glu Ala Asp Asp Leu Asp Pro Arg Arg Arg Thr Gly
                85                  90                  95

Trp Ser Val Val Thr Gly Leu Ala Thr Glu Val Ser Asp Pro Glu
            100                 105                 110

Gln Val Ala Arg Tyr Gln Arg Leu Leu His Pro Trp Val Asn Met Ala
        115                 120                 125

Met Asp Thr Val Val Ala Ile Glu Pro Glu Ile Val Thr Gly Ile Arg
    130                 135                 140

Ile Val Ala Asp Ser Arg Thr Pro
145                 150

<210> SEQ ID NO 3
<211> LENGTH: 114
<212> TYPE: PRT
<213> ORGANISM: Mycobacterium tuberculosis

<400> SEQUENCE: 3

Val Glu Ser Glu Pro Leu Tyr Lys Leu Lys Ala Glu Phe Phe Lys Thr
1               5                   10                  15

Leu Ala His Pro Ala Arg Ile Arg Ile Leu Glu Leu Leu Val Glu Arg
            20                  25                  30

Asp Arg Ser Val Gly Glu Leu Leu Ser Ser Val Gly Leu Glu Ser
        35                  40                  45

Ser Asn Leu Ser Gln Gln Leu Gly Val Leu Arg Arg Ala Gly Val Val
    50                  55                  60

Ala Ala Arg Arg Asp Gly Asn Ala Met Ile Tyr Ser Ile Ala Ala Pro
65                  70                  75                  80

Asp Ile Ala Glu Leu Leu Ala Val Ala Arg Lys Val Leu Ala Arg Val
                85                  90                  95

Leu Ser Asp Arg Val Ala Val Leu Glu Asp Leu Arg Ala Gly Gly Ser
            100                 105                 110

Ala Thr

<210> SEQ ID NO 4
<211> LENGTH: 344
<212> TYPE: PRT
<213> ORGANISM: Mycobacterium tuberculosis

<400> SEQUENCE: 4
```

```
Met Pro Ile Ala Thr Pro Glu Val Tyr Ala Glu Met Leu Gly Gln Ala
1               5                   10                  15

Lys Gln Asn Ser Tyr Ala Phe Pro Ala Ile Asn Cys Thr Ser Ser Glu
            20                  25                  30

Thr Val Asn Ala Ala Ile Lys Gly Phe Ala Asp Ala Gly Ser Asp Gly
        35                  40                  45

Ile Ile Gln Phe Ser Thr Gly Gly Ala Glu Phe Gly Ser Gly Leu Gly
50                  55                  60

Val Lys Asp Met Val Thr Gly Ala Val Ala Leu Ala Glu Phe Thr His
65                  70                  75                  80

Val Ile Ala Ala Lys Tyr Pro Val Asn Val Ala Leu His Thr Asp His
                85                  90                  95

Cys Pro Lys Asp Lys Leu Asp Ser Tyr Val Arg Pro Leu Leu Ala Ile
            100                 105                 110

Ser Ala Gln Arg Val Ser Lys Gly Gly Asn Pro Leu Phe Gln Ser His
        115                 120                 125

Met Trp Asp Gly Ser Ala Val Pro Ile Asp Glu Asn Leu Ala Ile Ala
130                 135                 140

Gln Glu Leu Leu Lys Ala Ala Ala Ala Lys Ile Ile Leu Glu Ile
145                 150                 155                 160

Glu Ile Gly Val Val Gly Gly Glu Glu Asp Gly Val Ala Asn Glu Ile
                165                 170                 175

Asn Glu Lys Leu Tyr Thr Ser Pro Glu Asp Phe Glu Lys Thr Ile Glu
            180                 185                 190

Ala Leu Gly Ala Gly Glu His Gly Lys Tyr Leu Leu Ala Ala Thr Phe
        195                 200                 205

Gly Asn Val His Gly Val Tyr Lys Pro Gly Asn Val Lys Leu Arg Pro
210                 215                 220

Asp Ile Leu Ala Gln Gly Gln Val Ala Ala Lys Leu Gly Leu
225                 230                 235                 240

Pro Ala Asp Ala Lys Pro Phe Asp Phe Val Phe His Gly Gly Ser Gly
                245                 250                 255

Ser Leu Lys Ser Glu Ile Glu Glu Ala Leu Arg Tyr Gly Val Val Lys
            260                 265                 270

Met Asn Val Asp Thr Asp Thr Gln Tyr Ala Phe Thr Arg Pro Ile Ala
        275                 280                 285

Gly His Met Phe Thr Asn Tyr Asp Gly Val Leu Lys Val Asp Gly Glu
290                 295                 300

Val Gly Val Lys Lys Val Tyr Asp Pro Arg Ser Tyr Leu Lys Lys Ala
305                 310                 315                 320

Glu Ala Ser Met Ser Gln Arg Val Val Gln Ala Cys Asn Asp Leu His
                325                 330                 335

Cys Ala Gly Lys Ser Leu Thr His
            340

<210> SEQ ID NO 5
<211> LENGTH: 113
<212> TYPE: PRT
<213> ORGANISM: Mycobacterium tuberculosis

<400> SEQUENCE: 5

Met Gly Glu His Ala Ile Lys Arg His Met Arg Gln Arg Lys Pro Thr
1               5                   10                  15

Lys His Pro Leu Ala Gln Lys Arg Gly Ala Arg Ile Leu Val Phe Thr
            20                  25                  30
```

```
Asp Asp Pro Arg Arg Ser Val Leu Ile Val Pro Gly Cys His Leu Asp
            35                  40                  45

Ser Met Arg Arg Glu Lys Asn Ala Tyr Tyr Phe Gln Asp Gly Asn Ala
 50                  55                  60

Leu Val Gly Met Val Val Ser Gly Gly Thr Val Glu Tyr Asp Ala Asp
 65                  70                  75                  80

Asp Arg Thr Tyr Val Val Gln Leu Thr Asp Gly Arg His Thr Thr Glu
                 85                  90                  95

Ser Ser Phe Glu His Ser Ser Pro Ser Arg Ser Pro Gln Ser Asp Asp
                100                 105                 110

Leu

<210> SEQ ID NO 6
<211> LENGTH: 380
<212> TYPE: PRT
<213> ORGANISM: Mycobacterium tuberculosis

<400> SEQUENCE: 6

Val Ala Gly Asn Pro Asp Val Val Thr Val Leu Leu Gly Gly Asp Val
 1               5                  10                  15

Met Leu Gly Arg Gly Val Asp Gln Ile Leu Pro His Pro Gly Lys Pro
                20                  25                  30

Gln Leu Arg Glu Arg Tyr Met Arg Asp Ala Thr Gly Tyr Val Arg Leu
            35                  40                  45

Ala Glu Arg Val Asn Gly Arg Ile Pro Leu Pro Val Asp Trp Arg Trp
 50                  55                  60

Pro Trp Gly Glu Ala Leu Ala Val Leu Glu Asn Thr Ala Thr Asp Val
 65                  70                  75                  80

Cys Leu Ile Asn Leu Glu Thr Thr Ile Thr Ala Asp Gly Glu Phe Ala
                 85                  90                  95

Asp Arg Lys Pro Val Cys Tyr Arg Met His Pro Asp Asn Val Pro Ala
                100                 105                 110

Leu Thr Ala Leu Arg Pro His Val Cys Ala Leu Ala Asn Asn His Ile
            115                 120                 125

Leu Asp Phe Gly Tyr Gln Gly Leu Thr Asp Thr Val Ala Ala Leu Ala
130                 135                 140

Gly Ala Gly Ile Gln Ser Val Gly Ala Gly Ala Asp Leu Leu Ala Ala
145                 150                 155                 160

Arg Arg Ser Ala Leu Val Thr Val Gly His Glu Arg Arg Val Ile Val
                165                 170                 175

Gly Ser Val Ala Ala Glu Ser Ser Gly Val Pro Glu Ser Trp Ala Ala
                180                 185                 190

Arg Arg Asp Arg Pro Gly Val Trp Leu Ile Arg Asp Pro Ala Gln Arg
            195                 200                 205

Asp Val Ala Asp Val Ala Ala Gln Val Leu Ala Asp Lys Arg Pro
 210                 215                 220

Gly Asp Ile Ala Ile Val Ser Met His Trp Gly Ser Asn Trp Gly Tyr
225                 230                 235                 240

Ala Thr Ala Pro Gly Asp Val Ala Phe Ala His Arg Leu Ile Asp Ala
                245                 250                 255

Gly Ile Asp Met Val His Gly His Ser Ser His Pro Arg Pro Ile
                260                 265                 270

Glu Ile Tyr Arg Gly Lys Pro Ile Leu Tyr Gly Cys Gly Asp Val Val
            275                 280                 285
```

Asp Asp Tyr Glu Gly Ile Gly Gly His Glu Ser Phe Arg Ser Glu Leu
            290                 295                 300

Arg Leu Leu Tyr Leu Thr Val Thr Asp Pro Ala Ser Gly Asn Leu Ile
305                 310                 315                 320

Ser Leu Gln Met Leu Pro Leu Arg Val Ser Arg Met Arg Leu Gln Arg
                325                 330                 335

Ala Ser Gln Thr Asp Thr Glu Trp Leu Arg Asn Thr Ile Glu Arg Ile
                340                 345                 350

Ser Arg Arg Phe Gly Ile Arg Val Thr Arg Pro Asp Asn Leu Leu
                355                 360                 365

Glu Val Val Pro Ala Ala Asn Leu Thr Ser Lys Glu
            370                 375                 380

<210> SEQ ID NO 7
<211> LENGTH: 397
<212> TYPE: PRT
<213> ORGANISM: Mycobacterium tuberculosis

<400> SEQUENCE: 7

Val Thr Asp His Val Arg Glu Ala Asp Ala Asn Ile Asp Asp Leu
1               5                   10                  15

Leu Gly Asp Leu Gly Gly Thr Ala Arg Ala Glu Arg Ala Lys Leu Val
                20                  25                  30

Glu Trp Leu Leu Glu Gln Gly Ile Thr Pro Asp Glu Ile Arg Ala Thr
            35                  40                  45

Asn Pro Pro Leu Leu Leu Ala Thr Arg His Leu Val Gly Asp Asp Gly
        50                  55                  60

Thr Tyr Val Ser Ala Arg Glu Ile Ser Glu Asn Tyr Gly Val Asp Leu
65                  70                  75                  80

Glu Leu Leu Gln Arg Val Arg Gln Ala Val Gly Leu Ala Arg Val Asp
                85                  90                  95

Asp Pro Asp Ala Val Val His Met Arg Ala Asp Gly Glu Ala Ala Ala
            100                 105                 110

Arg Ala Gln Arg Phe Val Glu Leu Gly Leu Asn Pro Asp Gln Val Val
        115                 120                 125

Leu Val Val Arg Val Leu Ala Glu Gly Leu Ser His Ala Ala Glu Ala
    130                 135                 140

Met Arg Tyr Thr Ala Leu Glu Ala Ile Met Arg Pro Gly Ala Thr Glu
145                 150                 155                 160

Leu Asp Ile Ala Lys Gly Ser Gln Ala Leu Val Ser Gln Ile Val Pro
                165                 170                 175

Leu Leu Gly Pro Met Ile Gln Asp Met Leu Phe Met Gln Leu Arg His
            180                 185                 190

Met Met Glu Thr Glu Ala Val Asn Ala Gly Glu Arg Ala Ala Gly Lys
        195                 200                 205

Pro Leu Pro Gly Ala Arg Gln Val Thr Val Ala Phe Ala Asp Leu Val
    210                 215                 220

Gly Phe Thr Gln Leu Gly Glu Val Val Ser Ala Glu Glu Leu Gly His
225                 230                 235                 240

Leu Ala Gly Arg Leu Ala Gly Leu Ala Arg Asp Leu Thr Ala Pro Pro
                245                 250                 255

Val Trp Phe Ile Lys Thr Ile Gly Asp Ala Val Met Leu Val Cys Pro
            260                 265                 270

Asp Pro Ala Pro Leu Leu Asp Thr Val Leu Lys Leu Val Glu Val Val
        275                 280                 285

-continued

Asp Thr Asp Asn Asn Phe Pro Arg Leu Arg Ala Gly Val Ala Ser Gly
            290                 295                 300

Met Ala Val Ser Arg Ala Gly Asp Trp Phe Gly Ser Pro Val Asn Val
305                 310                 315                 320

Ala Ser Arg Val Thr Gly Val Ala Arg Pro Gly Ala Val Leu Val Ala
                325                 330                 335

Asp Ser Val Arg Glu Ala Leu Gly Asp Ala Pro Glu Ala Asp Gly Phe
                340                 345                 350

Gln Trp Ser Phe Ala Gly Pro Arg Arg Leu Arg Gly Ile Arg Gly Asp
            355                 360                 365

Val Arg Leu Phe Arg Val Arg Arg Gly Ala Thr Arg Thr Gly Ser Gly
            370                 375                 380

Gly Ala Ala Gln Asp Asp Asp Leu Ala Gly Ser Ser Pro
385                 390                 395

<210> SEQ ID NO 8
<211> LENGTH: 446
<212> TYPE: PRT
<213> ORGANISM: Mycobacterium tuberculosis

<400> SEQUENCE: 8

Met Val Glu Pro Gly Asn Leu Ala Gly Ala Thr Gly Ala Glu Trp Ile
1               5                   10                  15

Gly Arg Pro Pro His Glu Glu Leu Gln Arg Lys Val Arg Pro Leu Leu
                20                  25                  30

Pro Ser Asp Asp Pro Phe Tyr Phe Pro Pro Ala Gly Tyr Gln His Ala
            35                  40                  45

Val Pro Gly Thr Val Leu Arg Ser Arg Asp Val Glu Leu Ala Phe Met
    50                  55                  60

Gly Leu Ile Pro Gln Pro Val Thr Ala Thr Gln Leu Leu Tyr Arg Thr
65                  70                  75                  80

Thr Asn Met Tyr Gly Asn Pro Glu Ala Thr Val Thr Thr Val Ile Val
                85                  90                  95

Pro Ala Glu Leu Ala Pro Gly Gln Thr Cys Pro Leu Leu Ser Tyr Gln
            100                 105                 110

Cys Ala Ile Asp Ala Met Ser Ser Arg Cys Phe Pro Ser Tyr Ala Leu
        115                 120                 125

Arg Arg Arg Ala Lys Ala Leu Gly Ser Leu Thr Gln Met Glu Leu Leu
130                 135                 140

Met Ile Ser Ala Ala Leu Ala Glu Gly Trp Ala Val Ser Val Pro Asp
145                 150                 155                 160

His Glu Gly Pro Lys Gly Leu Trp Gly Ser Pro Tyr Glu Pro Gly Tyr
                165                 170                 175

Arg Val Leu Asp Gly Ile Arg Ala Ala Leu Asn Ser Glu Arg Val Gly
            180                 185                 190

Leu Ser Pro Ala Thr Pro Ile Gly Leu Trp Gly Tyr Ser Gly Gly Gly
        195                 200                 205

Leu Ala Ser Ala Trp Ala Ala Glu Ala Cys Gly Glu Tyr Ala Pro Asp
210                 215                 220

Leu Asp Ile Val Gly Ala Val Leu Gly Ser Pro Val Gly Asp Leu Gly
225                 230                 235                 240

His Thr Phe Arg Arg Leu Asn Gly Thr Leu Leu Ala Gly Leu Pro Ala
                245                 250                 255

Leu Val Val Ala Ala Leu Gln His Ser Tyr Pro Gly Leu Ala Arg Val
            260                 265                 270

```
Ile Lys Glu His Ala Asn Asp Glu Gly Arg Gln Leu Leu Glu Gln Leu
        275                 280                 285

Thr Glu Met Thr Thr Val Asp Ala Val Ile Arg Met Ala Gly Arg Asp
        290                 295                 300

Met Gly Asp Phe Leu Asp Glu Pro Leu Glu Asp Ile Leu Ser Thr Pro
305                 310                 315                 320

Glu Ile Ser His Val Phe Gly Asp Thr Lys Leu Gly Ser Ala Val Pro
                325                 330                 335

Thr Pro Pro Val Leu Ile Val Gln Ala Val His Asp Tyr Leu Ile Asp
            340                 345                 350

Val Ser Asp Ile Asp Ala Leu Ala Asp Ser Tyr Thr Ala Gly Gly Ala
        355                 360                 365

Asn Val Thr Tyr His Arg Asp Leu Phe Ser Glu His Val Ser Leu His
    370                 375                 380

Pro Leu Ser Ala Pro Met Thr Leu Arg Trp Leu Thr Asp Arg Phe Ala
385                 390                 395                 400

Gly Lys Pro Leu Thr Asp His Arg Val Arg Thr Thr Trp Pro Thr Ile
                405                 410                 415

Phe Asn Pro Met Thr Tyr Ala Gly Met Ala Arg Leu Ala Val Ile Ala
                420                 425                 430

Ala Lys Val Ile Thr Gly Arg Lys Leu Ser Arg Pro Leu
        435                 440                 445

<210> SEQ ID NO 9
<211> LENGTH: 210
<212> TYPE: PRT
<213> ORGANISM: Mycobacterium tuberculosis

<400> SEQUENCE: 9

Met Ile Ala Thr Thr Arg Asp Arg Glu Gly Ala Thr Met Ile Thr Phe
1               5                   10                  15

Arg Leu Arg Leu Pro Cys Arg Thr Ile Leu Arg Val Phe Ser Arg Asn
            20                  25                  30

Pro Leu Val Arg Gly Thr Asp Arg Leu Glu Ala Val Val Met Leu Leu
        35                  40                  45

Ala Val Thr Val Ser Leu Leu Thr Ile Pro Phe Ala Ala Ala Ala Gly
    50                  55                  60

Thr Ala Val Gln Asp Ser Arg Ser His Val Tyr Ala His Gln Ala Gln
65                  70                  75                  80

Thr Arg His Pro Ala Thr Ala Thr Val Ile Asp His Glu Gly Val Ile
                85                  90                  95

Asp Ser Asn Thr Thr Ala Thr Ser Ala Pro Pro Arg Thr Lys Ile Thr
            100                 105                 110

Val Pro Ala Arg Trp Val Val Asn Gly Ile Glu Arg Ser Gly Glu Val
        115                 120                 125

Asn Ala Lys Pro Gly Thr Lys Ser Gly Asp Arg Val Gly Ile Trp Val
    130                 135                 140

Asp Ser Ala Gly Gln Leu Val Asp Glu Pro Ala Pro Ala Arg Ala
145                 150                 155                 160

Ile Ala Asp Ala Ala Leu Ala Ala Leu Gly Leu Trp Leu Ser Val Ala
                165                 170                 175

Ala Val Ala Gly Ala Leu Leu Ala Leu Thr Arg Ala Ile Leu Ile Arg
            180                 185                 190

Val Arg Asn Ala Ser Trp Gln His Asp Ile Asp Ser Leu Phe Cys Thr
        195                 200                 205
```

Gln Arg
    210

<210> SEQ ID NO 10
<211> LENGTH: 80
<212> TYPE: PRT
<213> ORGANISM: Mycobacterium tuberculosis

<400> SEQUENCE: 10

Met Thr Asn Val Gly Asp Gln Gly Val Asp Ala Val Phe Gly Val Ile
1               5                   10                  15

Tyr Pro Pro Gln Val Ala Leu Val Ser Phe Gly Lys Pro Ala Gln Arg
            20                  25                  30

Val Cys Ala Val Asp Gly Ala Ile His Val Met Thr Thr Val Leu Ala
        35                  40                  45

Thr Leu Pro Ala Asp His Gly Cys Ser Asp Asp His Arg Gly Ala Leu
    50                  55                  60

Phe Phe Leu Ser Ile Asn Glu Leu Thr Arg Cys Ala Ala Val Thr Gly
65                  70                  75                  80

<210> SEQ ID NO 11
<211> LENGTH: 652
<212> TYPE: PRT
<213> ORGANISM: Mycobacterium tuberculosis

<400> SEQUENCE: 11

Val Thr Val Thr Pro Arg Thr Gly Ser Arg Ile Glu Glu Leu Leu Ala
1               5                   10                  15

Arg Ser Gly Arg Phe Phe Ile Pro Gly Glu Ile Ser Ala Asp Leu Arg
            20                  25                  30

Thr Val Thr Arg Arg Gly Gly Arg Asp Gly Asp Val Phe Tyr Arg Asp
        35                  40                  45

Arg Trp Ser His Asp Lys Val Val Arg Ser Thr His Gly Val Asn Cys
    50                  55                  60

Thr Gly Ser Cys Ser Trp Lys Ile Tyr Val Lys Asp Asp Ile Ile Thr
65                  70                  75                  80

Trp Glu Thr Gln Glu Thr Asp Tyr Pro Ser Val Gly Pro Asp Arg Pro
                85                  90                  95

Glu Tyr Glu Pro Arg Gly Cys Pro Arg Gly Ala Ala Phe Ser Trp Tyr
            100                 105                 110

Thr Tyr Ser Pro Thr Arg Val Arg His Pro Tyr Ala Arg Gly Val Leu
        115                 120                 125

Val Glu Met Tyr Arg Glu Ala Lys Ala Arg Leu Gly Asp Pro Val Ala
    130                 135                 140

Ala Trp Ala Asp Ile Gln Ala Asp Pro Arg Arg Arg Arg Arg Tyr Gln
145                 150                 155                 160

Arg Ala Arg Gly Lys Gly Gly Leu Val Arg Val Ser Trp Ala Glu Ala
            165                 170                 175

Thr Glu Met Ile Ala Ala Ala His Val His Thr Ile Ser Thr Tyr Gly
        180                 185                 190

Pro Asp Arg Val Ala Gly Phe Ser Pro Ile Pro Ala Met Ser Met Val
    195                 200                 205

Ser His Ala Ala Gly Ser Arg Phe Val Glu Leu Ile Gly Gly Val Met
    210                 215                 220

Thr Ser Phe Tyr Asp Trp Tyr Ala Asp Leu Pro Val Ala Ser Pro Gln
225                 230                 235                 240

Val Phe Gly Asp Gln Thr Asp Val Pro Glu Ser Gly Asp Trp Trp Asp

```
                245                 250                 255
Val Val Trp Gln Cys Ala Ser Val Leu Leu Thr Tyr Pro Asn Ser Arg
            260                 265                 270
Gln Leu Gly Thr Ala Glu Glu Leu Leu Ala His Ile Asp Gly Pro Ala
            275                 280                 285
Ala Asp Leu Leu Gly Arg Thr Val Ser Glu Leu Arg Arg Ala Asp Pro
            290                 295                 300
Leu Thr Ala Ala Thr Arg Tyr Val Asp Thr Phe Asp Leu Arg Gly Arg
305                 310                 315                 320
Ala Thr Leu Tyr Leu Thr Tyr Trp Thr Ala Gly Asp Thr Arg Asn Arg
                325                 330                 335
Gly Arg Glu Met Leu Ala Phe Ala Gln Thr Tyr Arg Ser Thr Asp Val
            340                 345                 350
Ala Pro Pro Arg Gly Glu Thr Pro Asp Phe Leu Pro Val Val Leu Glu
            355                 360                 365
Phe Ala Ala Thr Val Asp Pro Glu Ala Gly Arg Arg Leu Leu Ser Gly
            370                 375                 380
Tyr Arg Val Pro Ile Ala Ala Leu Cys Asn Ala Leu Thr Glu Ala Ala
385                 390                 395                 400
Leu Pro Tyr Ala His Thr Val Ala Ala Val Cys Arg Thr Gly Asp Met
                405                 410                 415
Met Gly Glu Leu Phe Trp Thr Val Pro Tyr Val Thr Met Thr Ile
            420                 425                 430
Val Ala Val Gly Ser Trp Trp Arg Tyr Arg Tyr Asp Lys Phe Gly Trp
            435                 440                 445
Thr Thr Arg Ser Ser Gln Leu Tyr Glu Ser Arg Leu Leu Arg Ile Ala
            450                 455                 460
Ser Pro Met Phe His Phe Gly Ile Leu Val Val Ile Val Gly His Gly
465                 470                 475                 480
Ile Gly Leu Val Ile Pro Gln Ser Trp Thr Gln Ala Ala Gly Leu Ser
                485                 490                 495
Glu Gly Ala Tyr His Val Gln Ala Val Val Leu Gly Ser Ile Ala Gly
            500                 505                 510
Ile Thr Thr Leu Ala Gly Val Thr Leu Leu Ile Tyr Arg Arg Arg Thr
            515                 520                 525
Arg Gly Pro Val Phe Met Ala Thr Thr Val Asn Asp Lys Val Met Tyr
            530                 535                 540
Leu Val Leu Val Ala Ala Ile Val Ala Gly Leu Gly Ala Thr Ala Leu
545                 550                 555                 560
Gly Ser Gly Val Val Gly Glu Ala Tyr Asn Tyr Arg Glu Thr Val Ser
                565                 570                 575
Val Trp Phe Arg Ser Val Trp Val Leu Gln Pro Arg Gly Asp Leu Met
            580                 585                 590
Ala Glu Ala Pro Leu Tyr Tyr Gln Ile His Val Leu Ile Gly Leu Ala
            595                 600                 605
Leu Phe Ala Leu Trp Pro Phe Thr Arg Leu Val His Ala Phe Ser Ala
            610                 615                 620
Pro Ile Gly Tyr Leu Phe Arg Pro Tyr Ile Ile Tyr Arg Ser Arg Glu
625                 630                 635                 640
Glu Leu Val Leu Thr Arg Pro Arg Arg Gly Trp
                645                 650

<210> SEQ ID NO 12
<211> LENGTH: 395
```

```
<212> TYPE: PRT
<213> ORGANISM: Mycobacterium tuberculosis

<400> SEQUENCE: 12

Met Arg Gly Gln Ala Ala Asn Leu Val Leu Ala Thr Trp Ile Ser Val
1               5                   10                  15

Val Asn Phe Trp Ala Trp Asn Leu Ile Gly Pro Leu Ser Thr Ser Tyr
            20                  25                  30

Ala Arg Asp Met Ser Leu Ser Ser Ala Glu Ala Ser Leu Leu Val Ala
        35                  40                  45

Thr Pro Ile Leu Val Gly Ala Leu Gly Arg Ile Val Thr Gly Pro Leu
    50                  55                  60

Thr Asp Arg Phe Gly Gly Arg Ala Met Leu Ile Ala Val Thr Leu Ala
65                  70                  75                  80

Ser Ile Leu Pro Val Leu Ala Val Gly Val Ala Ala Thr Met Gly Ser
                85                  90                  95

Tyr Ala Leu Leu Val Phe Phe Gly Leu Phe Leu Gly Val Ala Gly Thr
            100                 105                 110

Ile Phe Ala Val Gly Ile Pro Phe Ala Asn Asn Trp Tyr Gln Pro Ala
        115                 120                 125

Arg Arg Gly Phe Ser Thr Gly Val Phe Gly Met Gly Met Val Gly Thr
    130                 135                 140

Ala Leu Ser Ala Phe Phe Thr Pro Arg Phe Val Arg Trp Phe Gly Leu
145                 150                 155                 160

Phe Thr Thr His Ala Ile Val Ala Ala Leu Ala Ser Thr Ala Val
                165                 170                 175

Val Ala Met Val Val Leu Arg Asp Ala Pro Tyr Phe Arg Pro Asn Ala
            180                 185                 190

Asp Pro Val Leu Pro Arg Leu Lys Ala Ala Arg Leu Pro Val Thr
        195                 200                 205

Trp Glu Met Ser Phe Leu Tyr Ala Ile Val Phe Gly Gly Phe Val Ala
    210                 215                 220

Phe Ser Asn Tyr Leu Pro Thr Tyr Ile Thr Thr Ile Tyr Gly Phe Ser
225                 230                 235                 240

Thr Val Asp Ala Gly Ala Arg Thr Ala Gly Phe Ala Leu Ala Ala Val
                245                 250                 255

Leu Ala Arg Pro Val Gly Gly Trp Leu Ser Asp Arg Ile Ala Pro Arg
            260                 265                 270

His Val Val Leu Ala Ser Leu Ala Gly Thr Ala Leu Leu Ala Phe Ala
        275                 280                 285

Ala Ala Leu Gln Pro Pro Glu Val Trp Ser Ala Ala Thr Phe Ile
    290                 295                 300

Thr Leu Ala Val Cys Leu Gly Val Gly Thr Gly Gly Val Phe Ala Trp
305                 310                 315                 320

Val Ala Arg Arg Ala Pro Ala Ala Ser Val Gly Ser Val Thr Gly Ile
                325                 330                 335

Val Ala Ala Ala Gly Gly Leu Gly Gly Tyr Phe Pro Pro Leu Val Met
            340                 345                 350

Gly Ala Thr Tyr Asp Pro Val Asp Asn Asp Tyr Thr Val Gly Leu Leu
        355                 360                 365

Leu Leu Val Ala Thr Ala Leu Val Ala Cys Thr Tyr Thr Ala Leu His
    370                 375                 380

Ala Arg Glu Pro Val Ser Glu Glu Ala Ser Arg
385                 390                 395
```

<210> SEQ ID NO 13
<211> LENGTH: 94
<212> TYPE: PRT
<213> ORGANISM: Mycobacterium tuberculosis

<400> SEQUENCE: 13

Met Cys Gly Asp Gln Ser Asp His Val Leu Gln His Trp Thr Val Asp
1               5                   10                  15

Ile Ser Ile Asp Glu His Glu Gly Leu Thr Arg Ala Lys Ala Arg Leu
            20                  25                  30

Arg Trp Arg Glu Lys Glu Leu Val Gly Val Gly Leu Ala Arg Leu Asn
        35                  40                  45

Pro Ala Asp Arg Asn Val Pro Glu Ile Gly Asp Glu Leu Ser Val Ala
    50                  55                  60

Arg Ala Leu Ser Asp Leu Gly Lys Arg Met Leu Lys Val Ser Thr His
65                  70                  75                  80

Asp Ile Glu Ala Val Thr His Gln Pro Ala Arg Leu Leu Tyr
                85                  90

<210> SEQ ID NO 14
<211> LENGTH: 560
<212> TYPE: PRT
<213> ORGANISM: Mycobacterium tuberculosis

<400> SEQUENCE: 14

Met Ile Pro Thr Met Thr Ser Ala Gly Trp Ala Pro Gly Val Val Gln
1               5                   10                  15

Phe Arg Glu Tyr Gln Arg Arg Trp Leu Arg Gly Asp Val Leu Ala Gly
            20                  25                  30

Leu Thr Val Ala Ala Tyr Leu Ile Pro Gln Ala Met Ala Tyr Ala Thr
        35                  40                  45

Val Ala Gly Leu Pro Pro Ala Ala Gly Leu Trp Ala Ser Ile Ala Pro
    50                  55                  60

Leu Ala Ile Tyr Ala Leu Leu Gly Ser Ser Arg Gln Leu Ser Ile Gly
65                  70                  75                  80

Pro Glu Ser Ala Thr Ala Leu Met Thr Ala Ala Val Leu Ala Pro Met
                85                  90                  95

Ala Ala Gly Asp Leu Arg Arg Tyr Ala Val Leu Ala Thr Leu Gly
            100                 105                 110

Leu Leu Val Gly Leu Ile Cys Leu Leu Ala Gly Thr Ala Arg Leu Gly
        115                 120                 125

Phe Leu Ala Ser Leu Arg Ser Arg Pro Val Leu Val Gly Tyr Met Ala
    130                 135                 140

Gly Ile Ala Leu Val Met Ile Ser Ser Gln Leu Gly Thr Ile Thr Gly
145                 150                 155                 160

Thr Ser Val Glu Gly Asn Glu Phe Phe Ser Glu Val His Ser Phe Ala
                165                 170                 175

Thr Ser Val Thr Arg Val His Trp Pro Thr Phe Val Leu Ala Met Ser
            180                 185                 190

Val Leu Ala Leu Leu Thr Met Leu Thr Arg Trp Ala Pro Arg Ala Pro
        195                 200                 205

Gly Pro Ile Ile Ala Val Leu Ala Ala Thr Met Leu Val Ala Val Met
    210                 215                 220

Ser Leu Asp Ala Lys Gly Ile Ala Ile Val Gly Arg Ile Pro Ser Gly
225                 230                 235                 240

Leu Pro Thr Pro Gly Val Pro Pro Val Ser Val Glu Asp Leu Arg Ala

```
                        245                 250                 255
Leu Ile Ile Pro Ala Ala Gly Ile Ala Ile Val Thr Phe Thr Asp Gly
                260                 265                 270

Val Leu Thr Ala Arg Ala Phe Ala Ala Arg Arg Gly Gln Glu Val Asn
            275                 280                 285

Ala Asn Ala Glu Leu Arg Ala Val Gly Ala Cys Asn Ile Ala Ala Gly
        290                 295                 300

Leu Thr His Gly Phe Pro Val Ser Ser Ser Ser Arg Thr Ala Leu
305                 310                 315                 320

Ala Asp Val Val Gly Gly Arg Thr Gln Leu Tyr Ser Leu Ile Ala Leu
                325                 330                 335

Gly Leu Val Val Ile Val Met Val Phe Ala Ser Gly Leu Leu Ala Met
                340                 345                 350

Phe Pro Ile Ala Ala Leu Gly Ala Leu Val Val Tyr Ala Ala Leu Arg
            355                 360                 365

Leu Ile Asp Leu Ser Glu Phe Arg Arg Leu Ala Arg Phe Arg Arg Ser
        370                 375                 380

Glu Leu Met Leu Ala Leu Ala Thr Thr Ala Ala Val Leu Gly Leu Gly
385                 390                 395                 400

Val Phe Tyr Gly Val Leu Ala Ala Val Ala Leu Ser Ile Leu Glu Leu
                405                 410                 415

Leu Arg Arg Val Ala His Pro His Asp Ser Val Leu Gly Phe Val Pro
                420                 425                 430

Gly Ile Ala Gly Met His Asp Ile Asp Asp Tyr Pro Gln Ala Lys Arg
            435                 440                 445

Val Pro Gly Leu Val Val Tyr Arg Tyr Asp Ala Pro Leu Cys Phe Ala
        450                 455                 460

Asn Ala Glu Asp Phe Arg Arg Ala Leu Thr Val Asp Gln Asp
465                 470                 475                 480

Pro Gly Gln Val Glu Trp Phe Val Leu Asn Ala Glu Ser Asn Val Glu
                485                 490                 495

Val Asp Leu Thr Ala Leu Asp Ala Leu Asp Gln Leu Arg Thr Glu Leu
                500                 505                 510

Leu Arg Arg Gly Ile Val Phe Ala Met Ala Arg Val Lys Gln Asp Leu
            515                 520                 525

Arg Glu Ser Leu Arg Ala Ala Ser Leu Leu Asp Lys Ile Gly Glu Asp
        530                 535                 540

His Ile Phe Met Thr Leu Pro Thr Ala Val Gln Ala Phe Arg Arg Arg
545                 550                 555                 560

<210> SEQ ID NO 15
<211> LENGTH: 143
<212> TYPE: PRT
<213> ORGANISM: Mycobacterium tuberculosis

<400> SEQUENCE: 15

Met Ile Thr Asn Leu Arg Arg Arg Thr Ala Met Ala Ala Ala Gly Leu
1               5                   10                  15

Gly Ala Ala Leu Gly Leu Gly Ile Leu Leu Val Pro Thr Val Asp Ala
                20                  25                  30

His Leu Ala Asn Gly Ser Met Ser Glu Val Met Met Ser Glu Ile Ala
            35                  40                  45

Gly Leu Pro Ile Pro Pro Ile Ile His Tyr Gly Ala Ile Ala Tyr Ala
        50                  55                  60

Pro Ser Gly Ala Ser Gly Lys Ala Trp His Gln Arg Thr Pro Ala Arg
```

```
                65                  70                  75                  80
Ala Glu Gln Val Ala Leu Glu Lys Cys Gly Asp Lys Thr Cys Lys Val
                    85                  90                  95

Val Ser Arg Phe Thr Arg Cys Gly Ala Val Ala Tyr Asn Gly Ser Lys
                100                 105                 110

Tyr Gln Gly Gly Thr Gly Leu Thr Arg Arg Ala Ala Glu Asp Asp Ala
                115                 120                 125

Val Asn Arg Leu Glu Gly Gly Arg Ile Val Asn Trp Ala Cys Asn
                130                 135                 140

<210> SEQ ID NO 16
<211> LENGTH: 905
<212> TYPE: PRT
<213> ORGANISM: Mycobacterium tuberculosis

<400> SEQUENCE: 16

Leu Ser Ala Ser Val Ser Ala Thr Thr Ala His His Gly Leu Pro Ala
1               5                   10                  15

His Glu Val Val Leu Leu Leu Glu Ser Asp Pro Tyr His Gly Leu Ser
                20                  25                  30

Asp Gly Glu Ala Ala Gln Arg Leu Glu Arg Phe Gly Pro Asn Thr Leu
            35                  40                  45

Ala Val Val Thr Arg Ala Ser Leu Leu Ala Arg Ile Leu Arg Gln Phe
        50                  55                  60

His His Pro Leu Ile Tyr Val Leu Leu Val Ala Gly Thr Ile Thr Ala
65                  70                  75                  80

Gly Leu Lys Glu Phe Val Asp Ala Ala Val Ile Phe Gly Val Val Val
                85                  90                  95

Ile Asn Ala Ile Val Gly Phe Ile Gln Glu Ser Lys Ala Glu Ala Ala
                100                 105                 110

Leu Gln Gly Leu Arg Ser Met Val His Thr His Ala Lys Val Val Arg
            115                 120                 125

Glu Gly His Glu His Thr Met Pro Ser Glu Glu Leu Val Pro Gly Asp
        130                 135                 140

Leu Val Leu Leu Ala Ala Gly Asp Lys Val Pro Ala Asp Leu Arg Leu
145                 150                 155                 160

Val Arg Gln Thr Gly Leu Ser Val Asn Glu Ser Ala Leu Thr Gly Glu
                165                 170                 175

Ser Thr Pro Val His Lys Asp Glu Val Ala Leu Pro Glu Gly Thr Pro
                180                 185                 190

Val Ala Asp Arg Arg Asn Ile Ala Tyr Ser Gly Thr Leu Val Thr Ala
            195                 200                 205

Gly His Gly Ala Gly Ile Val Val Ala Thr Gly Ala Glu Thr Glu Leu
        210                 215                 220

Gly Glu Ile His Arg Leu Val Gly Ala Ala Glu Val Val Ala Thr Pro
225                 230                 235                 240

Leu Thr Ala Lys Leu Ala Trp Phe Ser Lys Phe Leu Thr Ile Ala Ile
                245                 250                 255

Leu Gly Leu Ala Ala Leu Thr Phe Gly Val Gly Leu Leu Arg Arg Gln
                260                 265                 270

Asp Ala Val Glu Thr Phe Thr Ala Ala Ile Ala Leu Ala Val Gly Ala
            275                 280                 285

Ile Pro Glu Gly Leu Pro Thr Ala Val Thr Ile Thr Leu Ala Ile Gly
        290                 295                 300

Met Ala Arg Met Ala Lys Arg Arg Ala Val Ile Arg Arg Leu Pro Ala
```

-continued

```
                305                 310                 315                 320
Val Glu Thr Leu Gly Ser Thr Thr Val Ile Cys Ala Asp Lys Thr Gly
                    325                 330                 335

Thr Leu Thr Glu Asn Gln Met Thr Val Gln Ser Ile Trp Thr Pro His
                    340                 345                 350

Gly Glu Ile Arg Ala Thr Gly Thr Gly Tyr Ala Pro Asp Val Leu Leu
                    355                 360                 365

Cys Asp Thr Asp Ala Pro Val Pro Val Asn Ala Asn Ala Ala Leu
                    370                 375                 380

Arg Trp Ser Leu Leu Ala Gly Ala Cys Ser Asn Asp Ala Ala Leu Val
385                 390                 395                 400

Arg Asp Gly Thr Arg Trp Gln Ile Val Gly Asp Pro Thr Glu Gly Ala
                    405                 410                 415

Met Leu Val Val Ala Ala Lys Ala Gly Phe Asn Pro Glu Arg Leu Ala
                    420                 425                 430

Thr Thr Leu Pro Gln Val Ala Ala Ile Pro Phe Ser Ser Glu Arg Gln
                    435                 440                 445

Tyr Met Ala Thr Leu His Arg Asp Gly Thr Asp His Val Val Leu Ala
                    450                 455                 460

Lys Gly Ala Val Glu Arg Met Leu Asp Leu Cys Gly Thr Glu Met Gly
465                 470                 475                 480

Ala Asp Gly Ala Leu Arg Pro Leu Asp Arg Ala Thr Val Leu Arg Ala
                    485                 490                 495

Thr Glu Met Leu Thr Ser Arg Gly Leu Arg Val Leu Ala Thr Gly Met
                    500                 505                 510

Gly Ala Gly Ala Gly Thr Pro Asp Asp Phe Asp Glu Asn Val Ile Pro
                    515                 520                 525

Gly Ser Leu Ala Leu Thr Gly Leu Gln Ala Met Ser Asp Pro Pro Arg
                    530                 535                 540

Ala Ala Ala Ala Ser Ala Val Ala Ala Cys His Ser Ala Gly Ile Ala
545                 550                 555                 560

Val Lys Met Ile Thr Gly Asp His Ala Gly Thr Ala Thr Ala Ile Ala
                    565                 570                 575

Thr Glu Val Gly Leu Leu Asp Asn Thr Glu Pro Ala Ala Gly Ser Val
                    580                 585                 590

Leu Thr Gly Ala Glu Leu Ala Ala Leu Ser Ala Asp Gln Tyr Pro Glu
                    595                 600                 605

Ala Val Asp Thr Ala Ser Val Phe Ala Arg Val Ser Pro Glu Gln Lys
                    610                 615                 620

Leu Arg Leu Val Gln Ala Leu Gln Ala Arg Gly His Val Val Ala Met
625                 630                 635                 640

Thr Gly Asp Gly Val Asn Asp Ala Pro Ala Leu Arg Gln Ala Asn Ile
                    645                 650                 655

Gly Val Ala Met Gly Arg Gly Thr Glu Val Ala Lys Asp Ala Ala
                    660                 665                 670

Asp Met Val Leu Thr Asp Asp Phe Ala Thr Ile Glu Ala Ala Val
                    675                 680                 685

Glu Gly Gly Arg Gly Val Phe Asp Asn Leu Thr Lys Phe Ile Thr Trp
                    690                 695                 700

Thr Leu Pro Thr Asn Leu Gly Glu Gly Leu Val Ile Leu Ala Ala Ile
705                 710                 715                 720

Ala Val Gly Val Ala Leu Pro Ile Leu Pro Thr Gln Ile Leu Trp Ile
                    725                 730                 735
```

```
Asn Met Thr Thr Ala Ile Ala Leu Gly Leu Met Leu Ala Phe Glu Pro
            740                 745                 750

Lys Glu Ala Gly Ile Met Thr Arg Pro Pro Arg Asp Pro Asp Gln Pro
            755                 760                 765

Leu Leu Thr Gly Trp Leu Val Arg Arg Thr Leu Leu Val Ser Thr Leu
            770                 775                 780

Leu Val Ala Ser Ala Trp Trp Leu Phe Ala Trp Glu Leu Asp Asn Gly
785                 790                 795                 800

Ala Gly Leu His Glu Ala Arg Thr Ala Ala Leu Asn Leu Phe Val Val
                805                 810                 815

Val Glu Ala Phe Tyr Leu Phe Ser Cys Arg Ser Leu Thr Arg Ser Ala
            820                 825                 830

Trp Arg Leu Gly Met Phe Ala Asn Arg Trp Ile Ile Leu Gly Val Ser
            835                 840                 845

Ala Gln Ala Ile Ala Gln Phe Ala Ile Thr Tyr Leu Pro Ala Met Asn
            850                 855                 860

Met Val Phe Asp Thr Ala Pro Ile Asp Ile Gly Val Trp Val Arg Ile
865                 870                 875                 880

Phe Ala Val Ala Thr Ala Ile Thr Ile Val Val Ala Thr Asp Thr Leu
                885                 890                 895

Leu Pro Arg Ile Arg Ala Gln Pro Pro
            900                 905

<210> SEQ ID NO 17
<211> LENGTH: 258
<212> TYPE: PRT
<213> ORGANISM: Mycobacterium tuberculosis

<400> SEQUENCE: 17

Met Ser Phe His Asp Leu His His Gln Gly Val Pro Phe Val Leu Pro
1               5                   10                  15

Asn Ala Trp Asp Val Pro Ser Ala Leu Ala Tyr Leu Ala Glu Gly Phe
            20                  25                  30

Thr Ala Ile Gly Thr Thr Ser Phe Gly Val Ser Ser Ser Gly Gly His
            35                  40                  45

Pro Asp Gly His Arg Ala Thr Arg Gly Ala Asn Ile Ala Leu Ala Ala
50                  55                  60

Ala Leu Ala Pro Leu Gln Cys Tyr Val Ser Val Asp Ile Glu Asp Gly
65                  70                  75                  80

Tyr Ser Asp Glu Pro Asp Ala Ile Ala Asp Tyr Val Ala Gln Leu Ser
                85                  90                  95

Thr Ala Gly Ile Asn Ile Glu Asp Ser Ser Ala Glu Lys Leu Ile Asp
            100                 105                 110

Pro Ala Leu Ala Ala Ala Lys Ile Val Ala Ile Lys Gln Arg Asn Pro
            115                 120                 125

Glu Val Phe Val Asn Ala Arg Val Asp Thr Tyr Trp Leu Arg Gln His
            130                 135                 140

Ala Asp Thr Thr Ser Thr Ile Gln Arg Ala Leu Arg Tyr Val Asp Ala
145                 150                 155                 160

Gly Ala Asp Gly Val Phe Val Pro Leu Ala Asn Asp Pro Asp Glu Leu
                165                 170                 175

Ala Glu Leu Thr Arg Asn Ile Pro Cys Pro Val Asn Thr Leu Pro Val
            180                 185                 190

Pro Gly Leu Thr Ile Ala Asp Leu Gly Glu Leu Gly Val Ala Arg Val
            195                 200                 205
```

-continued

Ser Thr Gly Ser Val Pro Tyr Ser Ala Gly Leu Tyr Ala Ala His
        210                 215                 220

Ala Ala Arg Ala Val Ser Asp Gly Glu Gln Leu Pro Arg Ser Val Pro
225                 230                 235                 240

Tyr Ala Glu Leu Gln Ala Arg Leu Val Asp Tyr Glu Asn Arg Thr Ser
                245                 250                 255

Thr Thr

<210> SEQ ID NO 18
<211> LENGTH: 285
<212> TYPE: PRT
<213> ORGANISM: Mycobacterium tuberculosis

<400> SEQUENCE: 18

Val Val Lys Arg Ser Arg Ala Thr Arg Leu Ser Pro Ser Ile Trp Ser
1               5                   10                  15

Gly Trp Glu Ser Pro Gln Cys Arg Ser Ile Arg Ala Arg Leu Leu Leu
                20                  25                  30

Pro Arg Gly Arg Ser Arg Pro Pro Asn Ala Asp Cys Cys Trp Asn Gln
            35                  40                  45

Leu Ala Val Thr Pro Asp Thr Arg Met Pro Ala Ser Ser Ala Ala Gly
50                  55                  60

Arg Asp Ala Ala Ala Tyr Asp Ala Trp Tyr Asp Ser Pro Thr Gly Arg
65                  70                  75                  80

Pro Ile Leu Ala Thr Glu Val Ala Ala Leu Arg Pro Leu Ile Glu Val
                85                  90                  95

Phe Ala Gln Pro Arg Leu Glu Ile Gly Val Gly Thr Gly Arg Phe Ala
            100                 105                 110

Asp Leu Leu Gly Val Arg Phe Gly Leu Asp Pro Ser Arg Asp Ala Leu
        115                 120                 125

Met Phe Ala Arg Arg Arg Gly Val Leu Val Ala Asn Ala Val Gly Glu
130                 135                 140

Ala Val Pro Phe Val Ser Arg His Phe Gly Ala Val Leu Met Ala Phe
145                 150                 155                 160

Thr Leu Cys Phe Val Thr Asp Pro Ala Ala Ile Phe Arg Glu Thr Arg
                165                 170                 175

Arg Leu Leu Ala Asp Gly Gly Leu Val Ile Gly Phe Leu Pro Arg
            180                 185                 190

Gly Thr Pro Trp Ala Asp Leu Tyr Ala Leu Arg Ala Ala Arg Gly Gln
        195                 200                 205

Pro Gly Tyr Arg Asp Ala Arg Phe Tyr Thr Ala Ala Glu Leu Glu Gln
210                 215                 220

Leu Leu Ala Asp Ser Gly Phe Arg Val Ile Ala Arg Arg Cys Thr Leu
225                 230                 235                 240

His Gln Pro Pro Gly Leu Ala Arg Tyr Asp Ile Glu Ala Ala His Asp
                245                 250                 255

Gly Ile Gln Ala Gly Ala Gly Phe Val Ala Ile Ser Ala Val Asp Gln
            260                 265                 270

Ala His Glu Pro Lys Asp Asp His Pro Leu Glu Ser Glu
        275                 280                 285

<210> SEQ ID NO 19
<211> LENGTH: 285
<212> TYPE: PRT
<213> ORGANISM: Mycobacterium tuberculosis

<400> SEQUENCE: 19

```
Val Val Lys Arg Ser Arg Ala Thr Arg Leu Ser Pro Ser Ile Trp Ser
1               5                   10                  15

Gly Trp Glu Ser Pro Gln Cys Arg Ser Ile Arg Ala Arg Leu Leu Leu
            20                  25                  30

Pro Arg Gly Arg Ser Arg Pro Asn Ala Asp Cys Cys Trp Asn Gln
        35                  40                  45

Leu Ala Val Thr Pro Asp Thr Arg Met Pro Ala Ser Ser Ala Ala Gly
    50                  55                  60

Arg Asp Ala Ala Ala Tyr Asp Ala Trp Tyr Asp Ser Pro Thr Gly Arg
65                  70                  75                  80

Pro Ile Leu Ala Thr Glu Val Ala Ala Leu Arg Pro Leu Ile Glu Val
                85                  90                  95

Phe Ala Gln Pro Arg Leu Glu Ile Gly Val Gly Thr Gly Arg Phe Ala
                100                 105                 110

Asp Leu Leu Gly Val Arg Phe Gly Leu Asp Pro Ser Arg Asp Ala Leu
            115                 120                 125

Met Phe Ala Arg Arg Arg Gly Val Leu Val Ala Asn Ala Val Gly Glu
    130                 135                 140

Ala Val Pro Phe Val Ser Arg His Phe Gly Ala Val Leu Met Ala Phe
145                 150                 155                 160

Thr Leu Cys Phe Val Thr Asp Pro Ala Ala Ile Phe Arg Glu Thr Arg
                165                 170                 175

Arg Leu Leu Ala Asp Gly Gly Leu Val Ile Gly Phe Leu Pro Arg
            180                 185                 190

Gly Thr Pro Trp Ala Asp Leu Tyr Ala Leu Arg Ala Ala Arg Gly Gln
    195                 200                 205

Pro Gly Tyr Arg Asp Ala Arg Phe Tyr Thr Ala Ala Glu Leu Glu Gln
    210                 215                 220

Leu Leu Ala Asp Ser Gly Phe Arg Val Ile Ala Arg Arg Cys Thr Leu
225                 230                 235                 240

His Gln Pro Pro Gly Leu Ala Arg Tyr Asp Ile Glu Ala Ala His Asp
                245                 250                 255

Gly Ile Gln Ala Gly Ala Gly Phe Val Ala Ile Ser Ala Val Asp Gln
    260                 265                 270

Ala His Glu Pro Lys Asp Asp His Pro Leu Glu Ser Glu
    275                 280                 285

<210> SEQ ID NO 20
<211> LENGTH: 114
<212> TYPE: PRT
<213> ORGANISM: Mycobacterium tuberculosis

<400> SEQUENCE: 20

Val Thr Tyr Val Ile Gly Ser Glu Cys Val Asp Val Met Asp Lys Ser
1               5                   10                  15

Cys Val Gln Glu Cys Pro Val Asp Cys Ile Tyr Glu Gly Ala Arg Met
            20                  25                  30

Leu Tyr Ile Asn Pro Asp Glu Cys Val Asp Cys Gly Ala Cys Lys Pro
        35                  40                  45

Ala Cys Arg Val Glu Ala Ile Tyr Trp Glu Gly Asp Leu Pro Asp Asp
    50                  55                  60

Gln His Gln His Leu Gly Asp Asn Ala Ala Phe Phe His Gln Val Leu
65                  70                  75                  80

Pro Gly Arg Val Ala Pro Leu Gly Ser Pro Gly Gly Ala Ala Ala Val
                85                  90                  95
```

```
Gly Pro Ile Gly Val Asp Thr Pro Leu Val Ala Ala Ile Pro Val Glu
            100                 105                 110

Cys Pro

<210> SEQ ID NO 21
<211> LENGTH: 279
<212> TYPE: PRT
<213> ORGANISM: Mycobacterium tuberculosis

<400> SEQUENCE: 21

Met Asn Gln Ser His Lys Pro Pro Ser Ile Val Val Gly Ile Asp Gly
1               5                   10                  15

Ser Lys Pro Ala Val Gln Ala Ala Leu Trp Ala Val Asp Glu Ala Ala
            20                  25                  30

Ser Arg Asp Ile Pro Leu Arg Leu Leu Tyr Ala Ile Glu Pro Asp Asp
        35                  40                  45

Pro Gly Tyr Ala Ala His Gly Ala Ala Ala Arg Lys Leu Ala Ala Ala
    50                  55                  60

Glu Asn Ala Val Arg Tyr Ala Phe Thr Ala Val Glu Ala Ala Asp Arg
65                  70                  75                  80

Pro Val Lys Val Glu Val Glu Ile Thr Gln Glu Arg Pro Val Thr Ser
                85                  90                  95

Leu Ile Arg Ala Ser Ala Ala Ala Leu Val Cys Val Gly Ala Ile
            100                 105                 110

Gly Val His His Phe Arg Pro Glu Arg Val Gly Ser Thr Ala Ala Ala
        115                 120                 125

Leu Ala Leu Ser Ala Gln Cys Pro Val Ala Ile Val Arg Pro His Arg
    130                 135                 140

Val Pro Ile Gly Arg Asp Ala Ala Trp Ile Val Val Glu Ala Asp Gly
145                 150                 155                 160

Ser Ser Asp Ile Gly Val Leu Leu Gly Ala Val Met Ala Glu Ala Arg
                165                 170                 175

Leu Arg Asp Ser Pro Val Arg Val Val Thr Cys Arg Gln Ser Gly Val
            180                 185                 190

Gly Asp Thr Gly Asp Val Arg Ala Ser Leu Asp Arg Trp Leu Ala
        195                 200                 205

Arg Trp Gln Pro Arg Tyr Pro Asp Val Arg Val Gln Ser Ala Ala Val
    210                 215                 220

His Gly Glu Leu Leu Asp Tyr Leu Ala Gly Leu Gly Arg Ser Val His
225                 230                 235                 240

Met Val Val Leu Ser Ala Ser Asp Gln Glu His Val Glu Gln Leu Val
                245                 250                 255

Gly Ala Pro Gly Asn Ala Val Leu Gln Glu Ala Gly Cys Thr Leu Leu
            260                 265                 270

Val Val Gly Gln Gln Tyr Leu
        275

<210> SEQ ID NO 22
<211> LENGTH: 339
<212> TYPE: PRT
<213> ORGANISM: Mycobacterium tuberculosis

<400> SEQUENCE: 22

Met Thr Glu Pro Ala Ala Trp Asp Glu Gly Lys Pro Arg Ile Ile Thr
1               5                   10                  15

Leu Thr Met Asn Pro Ala Leu Asp Ile Thr Thr Ser Val Asp Val Val
```

```
            20                  25                  30
Arg Pro Thr Glu Lys Met Arg Cys Gly Ala Pro Arg Tyr Asp Pro Gly
         35                  40                  45

Gly Gly Gly Ile Asn Val Ala Arg Ile Val His Val Leu Gly Gly Cys
 50                  55                  60

Ser Thr Ala Leu Phe Pro Ala Gly Gly Ser Thr Gly Ser Leu Leu Met
65                  70                  75                  80

Ala Leu Leu Gly Asp Ala Gly Val Pro Phe Arg Val Ile Pro Ile Ala
                 85                  90                  95

Ala Ser Thr Arg Glu Ser Phe Thr Val Asn Glu Ser Arg Thr Ala Lys
            100                 105                 110

Gln Tyr Arg Phe Val Leu Pro Gly Pro Ser Leu Thr Val Ala Glu Gln
        115                 120                 125

Glu Gln Cys Leu Asp Glu Leu Arg Gly Ala Ala Ser Ala Ala Phe
    130                 135                 140

Val Val Ala Ser Gly Ser Leu Pro Pro Gly Val Ala Ala Asp Tyr Tyr
145                 150                 155                 160

Gln Arg Val Ala Asp Ile Cys Arg Arg Ser Ser Thr Pro Leu Ile Leu
                165                 170                 175

Asp Thr Ser Gly Gly Leu Gln His Ile Ser Ser Gly Val Phe Leu
            180                 185                 190

Leu Lys Ala Ser Val Arg Glu Leu Arg Glu Cys Val Gly Ser Glu Leu
        195                 200                 205

Leu Thr Glu Pro Glu Gln Leu Ala Ala Ala His Glu Leu Ile Asp Arg
    210                 215                 220

Gly Arg Ala Glu Val Val Val Ser Leu Gly Ser Gln Gly Ala Leu
225                 230                 235                 240

Leu Ala Thr Arg His Ala Ser His Arg Phe Ser Ser Ile Pro Met Thr
                245                 250                 255

Ala Val Ser Gly Val Gly Ala Gly Asp Ala Met Val Ala Ala Ile Thr
            260                 265                 270

Val Gly Leu Ser Arg Gly Trp Ser Leu Ile Lys Ser Val Arg Leu Gly
        275                 280                 285

Asn Ala Ala Gly Ala Ala Met Leu Leu Thr Pro Gly Thr Ala Ala Cys
    290                 295                 300

Asn Arg Asp Asp Val Glu Arg Phe Phe Glu Leu Ala Ala Glu Pro Thr
305                 310                 315                 320

Glu Val Gly Gln Asp Gln Tyr Val Trp His Pro Ile Val Asn Pro Glu
                325                 330                 335

Ala Ser Pro

<210> SEQ ID NO 23
<211> LENGTH: 681
<212> TYPE: PRT
<213> ORGANISM: Mycobacterium tuberculosis

<400> SEQUENCE: 23

Val Leu Met Thr Ala Ala Asp Val Thr Arg Ser Pro Arg Arg
1               5                   10                  15

Val Phe Arg Asp Arg Arg Glu Ala Gly Arg Val Leu Ala Glu Leu Leu
            20                  25                  30

Ala Ala Tyr Arg Asp Gln Pro Asp Val Ile Val Leu Gly Leu Ala Arg
        35                  40                  45

Gly Gly Leu Pro Val Ala Trp Glu Val Ala Ala Ala Leu His Ala Pro
    50                  55                  60
```

-continued

```
Leu Asp Ala Phe Val Val Arg Lys Leu Gly Ala Pro Gly His Asp Glu
 65                  70                  75                  80

Phe Ala Val Gly Ala Leu Ala Ser Gly Gly Arg Val Val Asn Asp
                 85                  90                  95

Asp Val Val Arg Gly Leu Arg Ile Thr Pro Gln Gln Leu Arg Asp Ile
                100                 105                 110

Ala Glu Arg Glu Gly Arg Glu Leu Leu Arg Arg Glu Ser Ala Tyr Arg
                115                 120                 125

Gly Glu Arg Pro Pro Thr Asp Ile Thr Gly Lys Thr Val Ile Val Val
130                 135                 140

Asp Asp Gly Leu Ala Thr Gly Ala Ser Met Phe Ala Ala Val Gln Ala
145                 150                 155                 160

Leu Arg Asp Ala Gln Pro Ala Gln Ile Val Ile Ala Val Pro Ala Ala
                165                 170                 175

Pro Glu Ser Thr Cys Arg Glu Phe Ala Gly Leu Val Asp Asp Val Val
                180                 185                 190

Cys Ala Thr Met Pro Thr Pro Phe Leu Ala Val Gly Glu Ser Phe Trp
                195                 200                 205

Asp Phe Arg Gln Val Thr Asp Glu Glu Val Arg Arg Leu Leu Ala Thr
                210                 215                 220

Pro Thr Ala Gly Pro Ser Leu Arg Arg Pro Ala Ala Ser Thr Ala Ala
225                 230                 235                 240

Asp Val Leu Arg Arg Val Ala Ile Asp Ala Pro Gly Gly Val Pro Thr
                245                 250                 255

His Glu Val Leu Ala Glu Leu Val Gly Asp Ala Arg Ile Val Leu Ile
                260                 265                 270

Gly Glu Ser Ser His Gly Thr His Glu Phe Tyr Gln Ala Arg Ala Ala
                275                 280                 285

Met Thr Gln Trp Leu Ile Glu Glu Lys Gly Phe Gly Ala Val Ala Ala
                290                 295                 300

Glu Ala Asp Trp Pro Asp Ala Tyr Arg Val Asn Arg Tyr Val Arg Gly
305                 310                 315                 320

Leu Gly Glu Asp Thr Asn Ala Asp Glu Ala Leu Ser Gly Phe Glu Arg
                325                 330                 335

Phe Pro Ala Trp Met Trp Arg Asn Thr Val Val Arg Asp Phe Val Glu
                340                 345                 350

Trp Leu Arg Thr Arg Asn Gln Arg Tyr Glu Ser Gly Ala Leu Arg Gln
                355                 360                 365

Ala Gly Phe Tyr Gly Leu Asp Leu Tyr Ser Leu His Arg Ser Ile Gln
                370                 375                 380

Glu Val Ile Ser Tyr Leu Asp Lys Val Asp Pro Arg Ala Ala Ala Arg
385                 390                 395                 400

Ala Arg Ala Arg Tyr Ala Cys Phe Asp His Ala Cys Ala Asp Asp Gly
                405                 410                 415

Gln Ala Tyr Gly Phe Ala Ala Ala Phe Gly Ala Gly Pro Ser Cys Glu
                420                 425                 430

Arg Glu Ala Val Glu Gln Leu Val Asp Val Gln Arg Asn Ala Leu Ala
                435                 440                 445

Tyr Ala Arg Gln Asp Gly Leu Leu Ala Glu Asp Glu Leu Phe Tyr Ala
                450                 455                 460

Gln Gln Asn Ala Gln Thr Val Arg Asp Ala Glu Val Tyr Tyr Arg Ala
465                 470                 475                 480

Met Phe Ser Gly Arg Val Thr Ser Trp Asn Leu Arg Asp Gln His Met
```

```
                                485                 490                 495
Ala Gln Thr Leu Gly Ser Leu Leu Thr His Leu Asp Arg His Leu Asp
                500                 505                 510

Ala Pro Pro Ala Arg Ile Val Val Trp Ala His Asn Ser His Val Gly
                515                 520                 525

Asp Ala Arg Ala Thr Glu Val Trp Ala Asp Gly Gln Leu Thr Leu Gly
                530                 535                 540

Gln Ile Val Arg Glu Arg Tyr Gly Asp Glu Ser Arg Ser Ile Gly Phe
545                 550                 555                 560

Ser Thr Tyr Thr Gly Thr Val Thr Ala Ala Ser Glu Trp Gly Gly Ile
                565                 570                 575

Ala Gln Arg Lys Ala Val Arg Pro Ala Leu His Gly Ser Val Glu Glu
                580                 585                 590

Leu Phe His Gln Thr Ala Asp Ser Phe Leu Val Ser Ala Arg Leu Ser
                595                 600                 605

Arg Asp Ala Glu Ala Pro Leu Asp Val Val Arg Leu Gly Arg Ala Ile
                610                 615                 620

Gly Val Val Tyr Leu Pro Ala Thr Glu Arg Gln Ser His Tyr Leu His
625                 630                 635                 640

Val Arg Pro Ala Asp Gln Phe Asp Ala Met Ile His Ile Asp Gln Thr
                645                 650                 655

Arg Ala Leu Glu Pro Leu Glu Val Thr Ser Arg Trp Ile Ala Gly Glu
                660                 665                 670

Asn Pro Glu Thr Tyr Pro Thr Gly Leu
                675                 680

<210> SEQ ID NO 24
<211> LENGTH: 144
<212> TYPE: PRT
<213> ORGANISM: Mycobacterium tuberculosis

<400> SEQUENCE: 24

Met Ala Thr Thr Leu Pro Val Gln Arg His Pro Arg Ser Leu Phe Pro
1               5                   10                  15

Glu Phe Ser Glu Leu Phe Ala Ala Phe Pro Ser Phe Ala Gly Leu Arg
                20                  25                  30

Pro Thr Phe Asp Thr Arg Leu Met Arg Leu Glu Asp Glu Met Lys Glu
                35                  40                  45

Gly Arg Tyr Glu Val Arg Ala Glu Leu Pro Gly Val Asp Pro Asp Lys
            50                  55                  60

Asp Val Asp Ile Met Val Arg Asp Gly Gln Leu Thr Ile Lys Ala Glu
65              70                  75                  80

Arg Thr Glu Gln Lys Asp Phe Asp Gly Arg Ser Glu Phe Ala Tyr Gly
                85                  90                  95

Ser Phe Val Arg Thr Val Ser Leu Pro Val Gly Ala Asp Glu Asp Asp
                100                 105                 110

Ile Lys Ala Thr Tyr Asp Lys Gly Ile Leu Thr Val Ser Val Ala Val
                115                 120                 125

Ser Glu Gly Lys Pro Thr Glu Lys His Ile Gln Ile Arg Ser Thr Asn
            130                 135                 140

<210> SEQ ID NO 25
<211> LENGTH: 331
<212> TYPE: PRT
<213> ORGANISM: Mycobacterium tuberculosis

<400> SEQUENCE: 25
```

```
Met Pro Asp Thr Met Val Thr Thr Asp Val Ile Lys Ser Ala Val Gln
1               5                   10                  15

Leu Ala Cys Arg Ala Pro Ser Leu His Asn Ser Gln Pro Trp Arg Trp
            20                  25                  30

Ile Ala Glu Asp His Thr Val Ala Leu Phe Leu Asp Lys Asp Arg Val
                35                  40                  45

Leu Tyr Ala Thr Asp His Ser Gly Arg Glu Ala Leu Leu Gly Cys Gly
    50                  55                  60

Ala Val Leu Asp His Phe Arg Val Ala Met Ala Ala Gly Thr Thr
65                  70                  75                  80

Ala Asn Val Glu Arg Phe Pro Asn Pro Asn Asp Pro Leu His Leu Ala
                85                  90                  95

Ser Ile Asp Phe Ser Pro Ala Asp Phe Val Thr Glu Gly His Arg Leu
                100                 105                 110

Arg Ala Asp Ala Ile Leu Leu Arg Arg Thr Asp Arg Leu Pro Phe Ala
            115                 120                 125

Glu Pro Pro Asp Trp Asp Leu Val Glu Ser Gln Leu Arg Thr Thr Val
            130                 135                 140

Thr Ala Asp Thr Val Arg Ile Asp Val Ile Ala Asp Asp Met Arg Pro
145                 150                 155                 160

Glu Leu Ala Ala Ala Ser Lys Leu Thr Glu Ser Leu Arg Leu Tyr Asp
                165                 170                 175

Ser Ser Tyr His Ala Glu Leu Phe Trp Trp Thr Gly Ala Phe Glu Thr
                180                 185                 190

Ser Glu Gly Ile Pro His Ser Ser Leu Val Ser Ala Ala Glu Ser Asp
            195                 200                 205

Arg Val Thr Phe Gly Arg Asp Phe Pro Val Val Ala Asn Thr Asp Arg
    210                 215                 220

Arg Pro Glu Phe Gly His Asp Arg Ser Lys Val Leu Val Leu Ser Thr
225                 230                 235                 240

Tyr Asp Asn Glu Arg Ala Ser Leu Leu Arg Cys Gly Glu Met Leu Ser
                245                 250                 255

Ala Val Leu Leu Asp Ala Thr Met Ala Gly Leu Ala Thr Cys Thr Leu
            260                 265                 270

Thr His Ile Thr Glu Leu His Ala Ser Arg Asp Leu Val Ala Ala Leu
            275                 280                 285

Ile Gly Gln Pro Ala Thr Pro Gln Ala Leu Val Arg Val Gly Leu Ala
        290                 295                 300

Pro Glu Met Glu Glu Pro Pro Ala Thr Pro Arg Arg Pro Ile Asp
305                 310                 315                 320

Glu Val Phe His Val Arg Ala Lys Asp His Arg
                325                 330
```

<210> SEQ ID NO 26
<211> LENGTH: 195
<212> TYPE: PRT
<213> ORGANISM: Mycobacterium tuberculosis

<400> SEQUENCE: 26

```
Met Pro Leu Leu Thr Ile Gly Asp Gln Phe Pro Ala Tyr Gln Leu Thr
1               5                   10                  15

Ala Leu Ile Gly Gly Asp Leu Ser Lys Val Asp Ala Lys Gln Pro Gly
            20                  25                  30

Asp Tyr Phe Thr Thr Ile Thr Ser Asp Glu His Pro Gly Lys Trp Arg
                35                  40                  45
```

Val Val Phe Phe Trp Pro Lys Asp Phe Thr Phe Val Cys Pro Thr Glu
            50                  55                  60

Ile Ala Ala Phe Ser Lys Leu Asn Asp Glu Phe Glu Asp Arg Asp Ala
 65                  70                  75                  80

Gln Ile Leu Gly Val Ser Ile Asp Ser Glu Phe Ala His Phe Gln Trp
                85                  90                  95

Arg Ala Gln His Asn Asp Leu Lys Thr Leu Pro Phe Pro Met Leu Ser
               100                 105                 110

Asp Ile Lys Arg Glu Leu Ser Gln Ala Ala Gly Val Leu Asn Ala Asp
               115                 120                 125

Gly Val Ala Asp Arg Val Thr Phe Ile Val Asp Pro Asn Asn Glu Ile
            130                 135                 140

Gln Phe Val Ser Ala Thr Ala Gly Ser Val Gly Arg Asn Val Asp Glu
145                 150                 155                 160

Val Leu Arg Val Leu Asp Ala Leu Gln Ser Asp Glu Leu Cys Ala Cys
                165                 170                 175

Asn Trp Arg Lys Gly Asp Pro Thr Leu Asp Ala Gly Glu Leu Leu Lys
                180                 185                 190

Ala Ser Ala
       195

<210> SEQ ID NO 27
<211> LENGTH: 272
<212> TYPE: PRT
<213> ORGANISM: Mycobacterium tuberculosis

<400> SEQUENCE: 27

Met Ser Gly Arg Gly Glu Pro Thr Met Lys Thr Ile Ile Val Gly Ile
 1               5                  10                  15

Asp Gly Ser His Ala Ala Ile Thr Ala Ala Leu Trp Gly Val Asp Glu
                20                  25                  30

Ala Ile Ser Arg Ala Val Pro Leu Arg Leu Val Ser Val Ile Lys Pro
                35                  40                  45

Thr His Pro Ser Pro Asp Asp Tyr Asp Arg Asp Leu Ala His Ala Glu
     50                  55                  60

Arg Ser Leu Arg Glu Ala Gln Ser Ala Val Glu Ala Ala Gly Lys Leu
 65                  70                  75                  80

Val Lys Ile Glu Thr Asp Ile Pro Arg Gly Pro Ala Gly Pro Val Leu
                85                  90                  95

Val Glu Ala Ser Arg Asp Ala Glu Met Ile Cys Val Gly Ser Val Gly
               100                 105                 110

Ile Gly Arg Tyr Ala Ser Ser Ile Leu Gly Ser Thr Ala Thr Glu Leu
               115                 120                 125

Ala Glu Lys Ala His Cys Pro Val Ala Val Met Arg Ser Lys Val Asp
           130                 135                 140

Gln Pro Ala Ser Asp Ile Asn Trp Ile Val Val Arg Met Thr Asp Ala
145                 150                 155                 160

Pro Asp Asn Glu Ala Val Leu Glu Tyr Ala Ala Arg Glu Ala Lys Leu
                165                 170                 175

Arg Gln Ala Pro Ile Leu Ala Leu Gly Gly Arg Pro Glu Glu Leu Arg
                180                 185                 190

Glu Ile Pro Asp Gly Glu Phe Glu Arg Arg Val Gln Asp Trp His His
            195                 200                 205

Arg His Pro Asp Val Arg Val Tyr Pro Ile Thr Thr His Thr Gly Ile
        210                 215                 220

```
Ala Arg Phe Leu Ala Asp His Asp Glu Arg Val Gln Leu Ala Val Ile
225                 230                 235                 240

Gly Gly Gly Glu Ala Gly Gln Leu Ala Arg Leu Val Gly Pro Ser Gly
            245                 250                 255

His Pro Val Phe Arg His Ala Glu Cys Ser Val Leu Val Arg Arg
        260                 265                 270

<210> SEQ ID NO 28
<211> LENGTH: 393
<212> TYPE: PRT
<213> ORGANISM: Mycobacterium tuberculosis

<400> SEQUENCE: 28

Met Arg Asp Ala Ile Pro Leu Gly Arg Ile Ala Gly Phe Val Val Asn
1               5                   10                  15

Val His Trp Ser Val Leu Val Ile Leu Trp Leu Phe Thr Trp Ser Leu
            20                  25                  30

Ala Thr Met Leu Pro Gly Thr Val Gly Gly Tyr Pro Ala Val Val Tyr
        35                  40                  45

Trp Leu Leu Gly Ala Gly Ala Val Met Leu Leu Ala Ser Leu Leu
    50                  55                  60

Ala His Glu Leu Ala His Ala Val Val Ala Arg Arg Ala Gly Val Ser
65                  70                  75                  80

Val Glu Ser Val Thr Leu Trp Leu Phe Gly Val Thr Ala Leu Gly
                85                  90                  95

Gly Glu Ala Lys Thr Pro Lys Ala Phe Arg Ile Ala Phe Ala Gly
            100                 105                 110

Pro Ala Thr Ser Leu Ala Leu Ser Ala Thr Phe Gly Ala Leu Ala Ile
        115                 120                 125

Thr Leu Ala Gly Val Arg Thr Pro Ala Ile Val Ile Ser Val Ala Trp
    130                 135                 140

Trp Leu Ala Thr Val Asn Leu Leu Leu Gly Leu Phe Asn Leu Leu Pro
145                 150                 155                 160

Gly Ala Pro Leu Asp Gly Gly Arg Leu Val Arg Ala Tyr Leu Trp Arg
                165                 170                 175

Arg His Gly Asp Ser Val Arg Ala Gly Ile Gly Ala Ala Arg Ala Gly
            180                 185                 190

Arg Val Val Ala Leu Val Leu Ile Ala Leu Gly Leu Ala Glu Phe Val
        195                 200                 205

Ala Gly Gly Leu Val Gly Gly Val Trp Leu Ala Phe Ile Gly Trp Phe
    210                 215                 220

Ile Phe Ala Ala Ala Arg Glu Glu Glu Thr Arg Ile Ser Thr Gln Gln
225                 230                 235                 240

Leu Phe Ala Gly Val Arg Val Ala Asp Ala Met Thr Ala Gln Pro His
                245                 250                 255

Thr Ala Pro Gly Trp Ile Asn Val Glu Asp Phe Ile Gln Arg Tyr Val
            260                 265                 270

Leu Gly Glu Arg His Ser Ala Tyr Pro Val Ala Asp Arg Asp Gly Ser
        275                 280                 285

Ile Thr Gly Leu Val Ala Leu Arg Gln Leu Arg Asp Val Ala Pro Ser
    290                 295                 300

Arg Arg Ser Thr Thr Ser Val Gly Asp Ile Ala Leu Pro Leu His Ser
305                 310                 315                 320

Val Pro Thr Ala Arg Pro Gln Glu Pro Leu Thr Ala Leu Leu Glu Arg
                325                 330                 335
```

```
Met Ala Pro Leu Gly Pro Arg Ser Arg Ala Leu Val Thr Glu Gly Ser
                340                 345                 350

Ala Val Gly Ile Val Thr Pro Ser Asp Val Ala Arg Leu Ile Asp
            355                 360                 365

Val Tyr Arg Leu Ala Gln Pro Glu Pro Thr Phe Thr Thr Ser Pro Gln
370                 375                 380

Asp Ala Asp Arg Phe Ser Asp Ala Gly
385                 390

<210> SEQ ID NO 29
<211> LENGTH: 413
<212> TYPE: PRT
<213> ORGANISM: Mycobacterium tuberculosis

<400> SEQUENCE: 29

Met Ala Ser Ser Ala Ser Asp Gly Thr His Glu Arg Ser Ala Phe Arg
1               5                   10                  15

Leu Ser Pro Pro Val Leu Ser Gly Ala Met Gly Pro Phe Met His Thr
                20                  25                  30

Gly Leu Tyr Val Ala Gln Ser Trp Arg Asp Tyr Leu Gly Gln Gln Pro
            35                  40                  45

Asp Lys Leu Pro Ile Ala Arg Pro Thr Ile Ala Leu Ala Ala Gln Ala
        50                  55                  60

Phe Arg Asp Glu Ile Val Leu Leu Gly Leu Lys Ala Arg Arg Pro Val
65                  70                  75                  80

Ser Asn His Arg Val Phe Glu Arg Ile Ser Gln Glu Val Ala Ala Gly
                85                  90                  95

Leu Glu Phe Tyr Gly Asn Arg Arg Trp Leu Glu Lys Pro Ser Gly Phe
            100                 105                 110

Phe Ala Gln Pro Pro Leu Thr Glu Val Ala Val Arg Lys Val Lys
        115                 120                 125

Asp Arg Arg Ser Phe Tyr Arg Ile Phe Phe Asp Ser Gly Phe Thr
130                 135                 140

Pro His Pro Gly Glu Pro Gly Ser Gln Arg Trp Leu Ser Tyr Thr Ala
145                 150                 155                 160

Asn Asn Arg Glu Tyr Ala Leu Leu Arg His Pro Glu Pro Arg Pro
                165                 170                 175

Trp Leu Val Cys Val His Gly Thr Glu Met Gly Arg Ala Pro Leu Asp
            180                 185                 190

Leu Ala Val Phe Arg Ala Trp Lys Leu His Asp Glu Leu Gly Leu Asn
        195                 200                 205

Ile Val Met Pro Val Leu Pro Met His Gly Pro Arg Gly Gln Gly Leu
210                 215                 220

Pro Lys Gly Ala Val Phe Pro Gly Glu Asp Val Leu Asp Val His
225                 230                 235                 240

Gly Thr Ala Gln Ala Val Trp Asp Ile Arg Arg Leu Leu Ser Trp Ile
                245                 250                 255

Arg Ser Gln Glu Glu Ser Leu Ile Gly Leu Asn Gly Leu Ser Leu
            260                 265                 270

Gly Gly Tyr Ile Ala Ser Leu Val Ala Ser Leu Glu Glu Gly Leu Ala
        275                 280                 285

Cys Ala Ile Leu Gly Val Pro Val Ala Asp Leu Ile Glu Leu Leu Gly
290                 295                 300

Arg His Cys Gly Leu Arg His Lys Asp Pro Arg Arg His Thr Val Lys
305                 310                 315                 320
```

```
Met Ala Glu Pro Ile Gly Arg Met Ile Ser Pro Leu Ser Leu Thr Pro
                325                 330                 335

Leu Val Pro Met Pro Gly Arg Phe Ile Tyr Ala Gly Ile Ala Asp Arg
            340                 345                 350

Leu Val His Pro Arg Glu Gln Val Thr Arg Leu Trp Glu His Trp Gly
        355                 360                 365

Lys Pro Glu Ile Val Trp Tyr Pro Gly Gly His Thr Gly Phe Phe Gln
    370                 375                 380

Ser Arg Pro Val Arg Arg Phe Val Gln Ala Ala Leu Glu Gln Ser Gly
385                 390                 395                 400

Leu Leu Asp Ala Pro Arg Thr Gln Arg Asp Arg Ser Ala
                405                 410

<210> SEQ ID NO 30
<211> LENGTH: 120
<212> TYPE: PRT
<213> ORGANISM: Mycobacterium tuberculosis

<400> SEQUENCE: 30

Met Ser Thr Gln Arg Pro Arg His Ser Gly Ile Arg Ala Val Gly Pro
1               5                   10                  15

Tyr Ala Trp Ala Gly Arg Cys Gly Arg Ile Gly Arg Trp Gly Val His
            20                  25                  30

Gln Glu Ala Met Met Asn Leu Ala Ile Trp His Pro Arg Lys Val Gln
        35                  40                  45

Ser Ala Thr Ile Tyr Gln Val Thr Asp Arg Ser His Asp Gly Arg Thr
    50                  55                  60

Ala Arg Val Pro Gly Asp Glu Ile Thr Ser Thr Val Ser Gly Trp Leu
65                  70                  75                  80

Ser Glu Leu Gly Thr Gln Ser Pro Leu Ala Asp Glu Leu Ala Arg Ala
                85                  90                  95

Val Arg Ile Gly Asp Trp Pro Ala Ala Tyr Ala Ile Gly Glu His Leu
            100                 105                 110

Ser Val Glu Ile Ala Val Ala Val
        115                 120

<210> SEQ ID NO 31
<211> LENGTH: 374
<212> TYPE: PRT
<213> ORGANISM: Mycobacterium tuberculosis

<400> SEQUENCE: 31

Met Arg Ser Glu Arg Leu Arg Trp Leu Val Ala Ala Glu Gly Pro Phe
1               5                   10                  15

Ala Ser Val Tyr Phe Asp Asp Ser His Asp Thr Leu Asp Ala Val Glu
            20                  25                  30

Arg Arg Glu Ala Thr Trp Arg Asp Val Arg Lys His Leu Glu Ser Arg
        35                  40                  45

Asp Ala Lys Gln Glu Leu Ile Asp Ser Leu Glu Glu Ala Val Arg Asp
    50                  55                  60

Ser Arg Pro Ala Val Gly Gln Arg Gly Arg Ala Leu Ile Ala Thr Gly
65                  70                  75                  80

Glu Gln Val Leu Val Asn Glu His Leu Ile Gly Pro Pro Pro Ala Thr
                85                  90                  95

Val Ile Arg Leu Ser Asp Tyr Pro Tyr Val Val Pro Leu Ile Asp Leu
            100                 105                 110
```

Glu Met Arg Arg Pro Thr Tyr Val Phe Ala Ala Val Asp His Thr Gly
    115                 120                 125

Ala Asp Val Lys Leu Tyr Gln Gly Ala Thr Ile Ser Ser Thr Lys Ile
130                 135                 140

Asp Gly Val Gly Tyr Pro Val His Lys Pro Val Thr Ala Gly Trp Asn
145                 150                 155                 160

Gly Tyr Gly Asp Phe Gln His Thr Thr Glu Glu Ala Ile Arg Met Asn
                165                 170                 175

Cys Arg Ala Val Ala Asp His Leu Thr Arg Leu Val Asp Ala Ala Asp
                180                 185                 190

Pro Glu Val Val Phe Val Ser Gly Glu Val Arg Ser Arg Thr Asp Leu
            195                 200                 205

Leu Ser Thr Leu Pro Gln Arg Val Ala Val Arg Val Ser Gln Leu His
    210                 215                 220

Ala Gly Pro Arg Lys Ser Ala Leu Asp Glu Glu Ile Trp Asp Leu
225                 230                 235                 240

Thr Ser Ala Glu Phe Thr Arg Arg Tyr Ala Glu Ile Thr Asn Val
                245                 250                 255

Ala Gln Gln Phe Glu Ala Glu Ile Gly Arg Gly Ser Gly Leu Ala Ala
            260                 265                 270

Gln Gly Leu Ala Glu Val Cys Ala Ala Leu Arg Asp Gly Asp Val Asp
    275                 280                 285

Thr Leu Ile Val Gly Glu Leu Gly Glu Ala Thr Val Val Thr Gly Lys
    290                 295                 300

Ala Arg Thr Thr Val Ala Arg Asp Ala Asp Met Leu Ser Glu Leu Gly
305                 310                 315                 320

Glu Pro Val Asp Arg Val Ala Arg Ala Asp Glu Ala Leu Pro Phe Ala
                325                 330                 335

Ala Ile Ala Val Gly Ala Ala Leu Val Arg Asp Asp Asn Arg Ile Ala
            340                 345                 350

Pro Leu Asp Gly Val Gly Ala Leu Leu Arg Tyr Ala Ala Thr Asn Arg
    355                 360                 365

Leu Gly Ser His Arg Ser
    370

<210> SEQ ID NO 32
<211> LENGTH: 179
<212> TYPE: PRT
<213> ORGANISM: Mycobacterium tuberculosis

<400> SEQUENCE: 32

Met Leu His Arg Asp Asp His Ile Asn Pro Pro Arg Pro Arg Gly Leu
1               5                   10                  15

Asp Val Pro Cys Ala Arg Leu Arg Ala Thr Asn Pro Leu Arg Ala Leu
                20                  25                  30

Ala Arg Cys Val Gln Ala Gly Lys Pro Gly Thr Ser Ser Gly His Arg
            35                  40                  45

Ser Val Pro His Thr Ala Asp Leu Arg Ile Glu Ala Trp Ala Pro Thr
    50                  55                  60

Arg Asp Gly Cys Ile Arg Gln Ala Val Leu Gly Thr Val Glu Ser Phe
65              70                  75                  80

Leu Asp Leu Glu Ser Ala His Ala Val His Thr Arg Leu Arg Arg Leu
                85                  90                  95

Thr Ala Asp Arg Asp Asp Asp Leu Leu Val Ala Val Leu Glu Glu Val
            100                 105                 110

```
Ile Tyr Leu Leu Asp Thr Val Gly Glu Thr Pro Val Asp Leu Arg Leu
        115                 120                 125

Arg Asp Val Asp Gly Val Asp Val Thr Phe Ala Thr Thr Asp Ala
130                 135                 140

Ser Thr Leu Val Gln Val Gly Ala Val Pro Lys Ala Val Ser Leu Asn
145                 150                 155                 160

Glu Leu Arg Phe Ser Gln Gly Arg His Gly Trp Arg Cys Ala Val Thr
                165                 170                 175

Leu Asp Val

<210> SEQ ID NO 33
<211> LENGTH: 375
<212> TYPE: PRT
<213> ORGANISM: Mycobacterium tuberculosis

<400> SEQUENCE: 33

Val Thr Gln Thr Gly Lys Arg Gln Arg Lys Phe Gly Arg Ile Arg
1               5                   10                  15

Gln Phe Asn Ser Gly Arg Trp Gln Ala Ser Tyr Thr Gly Pro Asp Gly
                20                  25                  30

Arg Val Tyr Ile Ala Pro Lys Thr Phe Asn Ala Lys Ile Asp Ala Glu
            35                  40                  45

Ala Trp Leu Thr Asp Arg Arg Glu Ile Asp Arg Gln Leu Trp Ser
    50                  55                  60

Pro Ala Ser Gly Gln Glu Asp Arg Pro Gly Ala Pro Phe Gly Glu Tyr
65                  70                  75                  80

Ala Glu Gly Trp Leu Lys Gln Arg Gly Ile Lys Asp Arg Thr Arg Ala
                85                  90                  95

His Tyr Arg Lys Leu Leu Asp Asn His Ile Leu Ala Thr Phe Ala Asp
            100                 105                 110

Thr Asp Leu Arg Asp Ile Thr Pro Ala Ala Val Arg Arg Trp Tyr Ala
        115                 120                 125

Thr Thr Ala Val Gly Thr Pro Thr Met Arg Ala His Ser Tyr Ser Leu
130                 135                 140

Leu Arg Ala Ile Met Gln Thr Ala Leu Ala Asp Asp Leu Ile Asp Ser
145                 150                 155                 160

Asn Pro Cys Arg Ile Ser Gly Ala Ser Thr Ala Arg Arg Val His Lys
                165                 170                 175

Ile Arg Pro Ala Thr Leu Asp Glu Leu Glu Thr Ile Thr Lys Ala Met
            180                 185                 190

Pro Asp Pro Tyr Gln Ala Phe Val Leu Met Ala Ala Trp Leu Ala Met
        195                 200                 205

Arg Tyr Gly Glu Leu Thr Glu Leu Arg Arg Lys Asp Ile Asp Leu His
210                 215                 220

Gly Glu Val Ala Arg Val Arg Arg Ala Val Val Arg Val Gly Glu Gly
225                 230                 235                 240

Phe Lys Val Thr Thr Pro Lys Ser Asp Ala Gly Val Arg Asp Ile Ser
                245                 250                 255

Ile Pro Pro His Leu Ile Pro Ala Ile Glu Asp His Leu His Lys His
            260                 265                 270

Val Asn Pro Gly Arg Glu Ser Leu Leu Phe Pro Ser Val Asn Asp Pro
        275                 280                 285

Asn Arg His Leu Ala Pro Ser Ala Leu Tyr Arg Met Phe Tyr Lys Ala
290                 295                 300

Arg Lys Ala Ala Gly Arg Pro Asp Leu Arg Val His Asp Leu Arg His
```

```
                305                 310                 315                 320
Ser Gly Ala Val Leu Ala Ala Ser Thr Gly Ala Thr Leu Ala Glu Leu
                    325                 330                 335

Met Gln Arg Leu Gly His Ser Thr Ala Gly Ala Ala Leu Arg Tyr Gln
                340                 345                 350

His Ala Ala Lys Gly Arg Asp Arg Glu Ile Ala Ala Leu Leu Ser Lys
            355                 360                 365

Leu Ala Glu Asn Gln Glu Met
        370                 375

<210> SEQ ID NO 34
<211> LENGTH: 371
<212> TYPE: PRT
<213> ORGANISM: Mycobacterium tuberculosis

<400> SEQUENCE: 34

Met Arg Val Gly Ile Pro Thr Glu Thr Lys Asn Asn Glu Phe Arg Val
1               5                   10                  15

Ala Ile Thr Pro Ala Gly Val Ala Glu Leu Thr Arg Arg Gly His Glu
                20                  25                  30

Val Leu Ile Gln Ala Gly Ala Gly Gly Ser Ala Ile Thr Asp Ala
            35                  40                  45

Asp Phe Lys Ala Ala Gly Ala Gln Leu Val Gly Thr Ala Asp Gln Val
    50                  55                  60

Trp Ala Asp Ala Asp Leu Leu Leu Lys Val Lys Glu Pro Ile Ala Ala
65                  70                  75                  80

Glu Tyr Gly Arg Leu Arg His Gly Gln Ile Leu Phe Thr Phe Leu His
                85                  90                  95

Leu Ala Ala Ser Arg Ala Cys Thr Asp Ala Leu Leu Asp Ser Gly Thr
            100                 105                 110

Thr Ser Ile Ala Tyr Glu Thr Val Gln Thr Ala Asp Gly Ala Leu Pro
        115                 120                 125

Leu Leu Ala Pro Met Ser Glu Val Ala Gly Arg Leu Ala Ala Gln Val
    130                 135                 140

Gly Ala Tyr His Leu Met Arg Thr Gln Gly Gly Arg Gly Val Leu Met
145                 150                 155                 160

Gly Gly Val Pro Gly Val Glu Pro Ala Asp Val Val Ile Gly Ala
                165                 170                 175

Gly Thr Ala Gly Tyr Asn Ala Ala Arg Ile Ala Asn Gly Met Gly Ala
            180                 185                 190

Thr Val Thr Val Leu Asp Ile Asn Ile Asp Lys Leu Arg Gln Leu Asp
        195                 200                 205

Ala Glu Phe Cys Gly Arg Ile His Thr Arg Tyr Ser Ser Ala Tyr Glu
    210                 215                 220

Leu Glu Gly Ala Val Lys Arg Ala Asp Leu Val Ile Gly Ala Val Leu
225                 230                 235                 240

Val Pro Gly Ala Lys Ala Pro Lys Leu Val Ser Asn Ser Leu Val Ala
                245                 250                 255

His Met Lys Pro Gly Ala Val Leu Val Asp Ile Ala Ile Asp Gln Gly
            260                 265                 270

Gly Cys Phe Glu Gly Ser Arg Pro Thr Thr Tyr Asp His Pro Thr Phe
        275                 280                 285

Ala Val His Asp Thr Leu Phe Tyr Cys Val Ala Asn Met Pro Ala Ser
    290                 295                 300

Val Pro Lys Thr Ser Thr Tyr Ala Leu Thr Asn Ala Thr Met Pro Tyr
```

```
                305                 310                 315                 320
Val Leu Glu Leu Ala Asp His Gly Trp Arg Ala Cys Arg Ser Asn
                    325                 330                 335

Pro Ala Leu Ala Lys Gly Leu Ser Thr His Glu Gly Ala Leu Leu Ser
                340                 345                 350

Glu Arg Val Ala Thr Asp Leu Gly Val Pro Phe Thr Glu Pro Ala Ser
                355                 360                 365

Val Leu Ala
        370

<210> SEQ ID NO 35
<211> LENGTH: 104
<212> TYPE: PRT
<213> ORGANISM: Mycobacterium tuberculosis

<400> SEQUENCE: 35

Met Val Ile Arg Phe Asp Gln Ile Gly Ser Leu Val Leu Ser Met Lys
1               5                   10                  15

Ser Leu Ala Ser Leu Ser Phe Gln Arg Cys Leu Arg Glu Asn Ser Ser
            20                  25                  30

Leu Val Ala Ala Leu Asp Arg Leu Asp Ala Ala Val Asp Glu Leu Ser
        35                  40                  45

Ala Leu Ser Phe Asp Ala Leu Thr Thr Pro Glu Arg Asp Arg Ala Arg
    50                  55                  60

Arg Asp Arg Asp His His Pro Trp Ser Arg Ser Arg Ser Gln Leu Ser
65                  70                  75                  80

Pro Arg Met Ala His Gly Ala Val His Gln Cys Gln Trp Pro Lys Ala
                85                  90                  95

Val Trp Ala Val Ile Asp Asn Pro
            100

<210> SEQ ID NO 36
<211> LENGTH: 344
<212> TYPE: PRT
<213> ORGANISM: Mycobacterium tuberculosis

<400> SEQUENCE: 36

Val Leu Lys Asn Ala Val Leu Ala Cys Arg Ala Pro Ser Val His
1               5                   10                  15

Asn Ser Gln Pro Trp Arg Trp Val Ala Glu Ser Gly Ser Glu His Thr
            20                  25                  30

Thr Val His Leu Phe Val Asn Arg His Arg Thr Val Pro Ala Thr Asp
        35                  40                  45

His Ser Gly Arg Gln Ala Ile Ile Ser Cys Gly Ala Val Leu Asp His
    50                  55                  60

Leu Arg Ile Ala Met Thr Ala Ala His Trp Gln Ala Asn Ile Thr Arg
65                  70                  75                  80

Phe Pro Gln Pro Asn Gln Pro Asp Gln Leu Ala Thr Val Glu Phe Ser
                85                  90                  95

Pro Ile Asp His Val Thr Ala Gly Gln Arg Asn Arg Ala Gln Ala Ile
            100                 105                 110

Leu Gln Arg Arg Thr Asp Arg Leu Pro Phe Asp Ser Pro Met Tyr Trp
        115                 120                 125

His Leu Phe Glu Pro Ala Leu Arg Asp Ala Val Asp Lys Asp Val Ala
    130                 135                 140

Met Leu Asp Val Val Ser Asp Asp Gln Arg Thr Arg Leu Val Val Ala
145                 150                 155                 160
```

```
Ser Gln Leu Ser Glu Val Leu Arg Arg Asp Pro Tyr Tyr His Ala
                165                 170                 175

Glu Leu Glu Trp Trp Thr Ser Pro Phe Val Leu Ala His Gly Val Pro
            180                 185                 190

Pro Asp Thr Leu Ala Ser Asp Ala Glu Arg Leu Arg Val Asp Leu Gly
            195                 200                 205

Arg Asp Phe Pro Val Arg Ser Tyr Gln Asn Arg Ala Glu Leu Ala
        210                 215                 220

Asp Asp Arg Ser Lys Val Leu Val Leu Ser Thr Pro Ser Asp Thr Arg
225                 230                 235                 240

Ala Asp Ala Leu Arg Cys Gly Glu Val Leu Ser Thr Ile Leu Leu Glu
            245                 250                 255

Cys Thr Met Ala Gly Met Ala Thr Cys Thr Leu Thr His Leu Ile Glu
            260                 265                 270

Ser Ser Asp Ser Arg Asp Ile Val Arg Gly Leu Thr Arg Gln Arg Gly
        275                 280                 285

Glu Pro Gln Ala Leu Ile Arg Val Gly Ile Ala Pro Pro Leu Ala Ala
        290                 295                 300

Val Pro Ala Pro Thr Pro Arg Arg Pro Leu Asp Ser Val Leu Gln Ile
305                 310                 315                 320

Arg Gln Thr Pro Glu Lys Gly Arg Asn Ala Ser Asp Arg Asn Ala Arg
                325                 330                 335

Glu Thr Gly Trp Phe Ser Pro Pro
            340

<210> SEQ ID NO 37
<211> LENGTH: 336
<212> TYPE: PRT
<213> ORGANISM: Mycobacterium tuberculosis

<400> SEQUENCE: 37

Val Trp Ser Ala Ser Gly Gly Gln Cys Gly Lys Tyr Leu Ala Ala Ser
1               5                   10                  15

Met Val Leu Gln Leu Asp Gly Leu Glu Arg His Gly Val Leu Glu Phe
            20                  25                  30

Gly Arg Asp Arg Tyr Gly Pro Glu Val Arg Glu Glu Leu Leu Ala Met
        35                  40                  45

Ser Ala Ala Ser Ile Asp Arg Tyr Leu Lys Thr Ala Lys Ala Lys Asp
    50                  55                  60

Gln Ile Ser Gly Val Ser Thr Thr Lys Pro Ser Pro Leu Leu Arg Asn
65                  70                  75                  80

Ser Ile Lys Val Arg Arg Ala Gly Asp Glu Val Glu Ala Glu Pro Gly
                85                  90                  95

Phe Phe Glu Gly Asp Thr Val Ala His Cys Gly Pro Thr Leu Lys Gly
            100                 105                 110

Glu Phe Ala His Thr Leu Asn Leu Thr Asp Val His Ile Gly Trp Val
        115                 120                 125

Phe Thr Arg Thr Val Arg Asn Asn Ala Arg Thr His Ile Leu Ala Gly
            130                 135                 140

Leu Lys Ala Ser Val Thr Glu Ile Pro His Gly Ile Thr Gly Leu Asp
145                 150                 155                 160

Phe Asp Asn Gly Thr Val Phe Leu Asn Lys Pro Val Ile Ser Trp Ala
                165                 170                 175

Gly Asp Asn Gly Ile Tyr Phe Thr Arg Phe Arg Pro Tyr Lys Lys Asn
            180                 185                 190
```

```
His Ala Thr Ile Glu Ser Lys Asn Asn His Leu Val Arg Lys Tyr Ala
        195                 200                 205

Phe Tyr Tyr Arg Tyr Asp Thr Ala Glu Glu Arg Ala Val Leu Asn Arg
    210                 215                 220

Met Trp Lys Leu Val Asn Asp Arg Leu Asn Tyr Leu Thr Pro Thr Ile
225                 230                 235                 240

Lys Pro Ile Gly Tyr Ala Ser Ser Ala Asp Gly Arg Arg Arg Arg Leu
                245                 250                 255

Tyr Asp Ala Pro Gln Thr Pro Leu Asp Arg Pro Leu Ala Ala Arg Val
            260                 265                 270

Leu Ser Ala Ala Gln Gln Ala Asp Leu Ile Thr Tyr Arg Asp Ser Leu
        275                 280                 285

Asn Pro Ala Gln Ile Gly Arg Lys Ile Ala Asp Leu Gln Asn Arg Leu
    290                 295                 300

Leu Ile Leu Ala Lys Glu Lys Thr Glu Gln Leu Tyr Leu Ala Asn Ile
305                 310                 315                 320

Pro Thr Ala Leu Pro Asp Ile His Lys Gly Ile Leu Ile Lys Ala Gly
                325                 330                 335

<210> SEQ ID NO 38
<211> LENGTH: 110
<212> TYPE: PRT
<213> ORGANISM: Mycobacterium tuberculosis
<400> SEQUENCE: 38

Val Val Gln Gly Arg Thr Val Leu Phe Arg Thr Ala Glu Gly Ala Lys
1               5                   10                  15

Leu Phe Ser Ala Val Ala Lys Cys Ala Val Ala Phe Glu Ala Asp Asp
            20                  25                  30

His Asn Val Ala Glu Gly Trp Ser Val Ile Val Lys Val Arg Ala Gln
        35                  40                  45

Val Leu Thr Thr Asp Ala Gly Val Arg Glu Ala Glu Arg Ala Gln Leu
    50                  55                  60

Leu Pro Trp Thr Ala Thr Leu Lys Arg His Cys Val Arg Val Ile Pro
65                  70                  75                  80

Trp Glu Ile Thr Gly Arg His Phe Arg Phe Gly Pro Glu Pro Asp Arg
                85                  90                  95

Ser Gln Thr Phe Ala Cys Glu Ala Ser Ser His Asn Gln Arg
            100                 105                 110

<210> SEQ ID NO 39
<211> LENGTH: 463
<212> TYPE: PRT
<213> ORGANISM: Mycobacterium tuberculosis
<400> SEQUENCE: 39

Met Asn His Leu Thr Thr Leu Asp Ala Gly Phe Leu Lys Ala Glu Asp
1               5                   10                  15

Val Asp Arg His Val Ser Leu Ala Ile Gly Ala Leu Ala Val Ile Glu
            20                  25                  30

Gly Pro Ala Pro Asp Gln Glu Ala Phe Leu Ser Ser Leu Ala Gln Arg
        35                  40                  45

Leu Arg Pro Cys Thr Arg Phe Gly Gln Arg Leu Arg Leu Arg Pro Phe
    50                  55                  60

Asp Leu Gly Ala Pro Lys Trp Val Asp Asp Pro Asp Phe Asp Leu Gly
65                  70                  75                  80
```

Arg His Val Trp Arg Ile Ala Leu Pro Arg Pro Gly Asn Glu Asp Gln
            85                  90                  95

Leu Phe Glu Leu Ile Ala Asp Leu Met Ala Arg Arg Leu Asp Arg Gly
            100                 105                 110

Arg Pro Leu Trp Glu Val Trp Val Ile Glu Gly Leu Ala Asp Ser Lys
            115                 120                 125

Trp Ala Ile Leu Thr Lys Leu His His Cys Met Ala Asp Gly Ile Ala
130                 135                 140

Ala Thr His Leu Leu Ala Gly Leu Ser Asp Glu Ser Met Ser Asp Ser
145                 150                 155                 160

Phe Ala Ser Asn Ile His Thr Thr Met Gln Ser Gln Ser Ala Ser Val
            165                 170                 175

Arg Arg Gly Gly Phe Arg Val Asn Pro Ser Glu Ala Leu Thr Ala Ser
            180                 185                 190

Thr Ala Val Met Ala Gly Ile Val Arg Ala Ala Lys Gly Ala Ser Glu
            195                 200                 205

Ile Ala Ala Gly Val Leu Ser Pro Ala Ala Ser Ser Leu Asn Gly Pro
210                 215                 220

Ile Ser Asp Leu Arg Arg Tyr Ser Ala Ala Lys Val Pro Leu Ala Asp
225                 230                 235                 240

Val Glu Gln Val Cys Arg Lys Phe Asp Val Thr Ile Asn Asp Val Ala
            245                 250                 255

Leu Ala Ala Ile Thr Glu Ser Tyr Arg Asn Val Leu Ile Gln Arg Gly
            260                 265                 270

Glu Arg Pro Arg Phe Asp Ser Leu Arg Thr Leu Val Pro Val Ser Thr
            275                 280                 285

Arg Ser Asn Ser Ala Leu Ser Lys Thr Asp Asn Arg Val Ser Leu Met
290                 295                 300

Leu Pro Asn Leu Pro Val Asp Gln Glu Asn Pro Leu Gln Arg Leu Arg
305                 310                 315                 320

Ile Val His Ser Arg Leu Thr Arg Ala Lys Ala Gly Gly Gln Arg Gln
            325                 330                 335

Phe Gly Asn Thr Leu Met Ala Ile Ala Asn Arg Leu Pro Phe Pro Met
            340                 345                 350

Thr Ala Trp Ala Val Gly Leu Leu Met Arg Leu Pro Gln Arg Gly Val
            355                 360                 365

Val Thr Val Ala Thr Asn Val Pro Gly Pro Arg Pro Leu Gln Ile
            370                 375                 380

Met Gly Arg Arg Val Leu Asp Leu Tyr Pro Val Ser Pro Ile Ala Met
385                 390                 395                 400

Gln Leu Arg Thr Ser Val Ala Met Leu Ser Tyr Ala Asp Asp Leu Tyr
            405                 410                 415

Phe Gly Ile Leu Ala Asp Tyr Asp Val Val Ala Asp Ala Gly Gln Leu
            420                 425                 430

Ala Arg Gly Ile Glu Asp Ala Val Ala Arg Leu Val Ala Ile Ser Lys
            435                 440                 445

Arg Arg Lys Val Thr Arg Arg Gly Ala Leu Ser Leu Val Val
450                 455                 460

<210> SEQ ID NO 40
<211> LENGTH: 332
<212> TYPE: PRT
<213> ORGANISM: Mycobacterium tuberculosis

<400> SEQUENCE: 40

Met Asn Thr His Phe Pro Asp Ala Glu Thr Val Arg Thr Val Leu Thr
1               5                   10                  15

Leu Ala Val Arg Ala Pro Ser Ile His Asn Thr Gln Pro Trp Arg Trp
            20                  25                  30

Arg Val Cys Pro Thr Ser Leu Glu Leu Phe Ser Arg Pro Asp Met Gln
        35                  40                  45

Leu Arg Ser Thr Asp Pro Asp Gly Arg Glu Leu Ile Leu Ser Cys Gly
50                  55                  60

Val Ala Leu His His Cys Val Val Ala Leu Ala Ser Leu Gly Trp Gln
65                  70                  75                  80

Ala Lys Val Asn Arg Phe Pro Asp Pro Lys Asp Arg Cys His Leu Ala
                85                  90                  95

Thr Ile Gly Val Gln Pro Leu Val Pro Asp Gln Ala Asp Val Ala Leu
            100                 105                 110

Ala Ala Ala Ile Pro Arg Arg Thr Asp Arg Arg Ala Tyr Ser Cys
        115                 120                 125

Trp Pro Val Pro Gly Gly Asp Ile Ala Leu Met Ala Ala Arg Ala Ala
    130                 135                 140

Arg Gly Gly Val Met Leu Arg Gln Val Ser Ala Leu Asp Arg Met Lys
145                 150                 155                 160

Ala Ile Val Ala Gln Ala Val Leu Asp His Val Thr Asp Glu Glu Tyr
                165                 170                 175

Leu Arg Glu Leu Thr Ile Trp Ser Arg Tyr Gly Ser Val Ala Gly
            180                 185                 190

Val Pro Ala Arg Asn Glu Pro Pro Ser Asp Pro Ser Ala Pro Ile Pro
            195                 200                 205

Gly Arg Leu Phe Ala Gly Pro Gly Leu Ser Gln Pro Ser Asp Val Leu
    210                 215                 220

Pro Ala Asp Asp Gly Ala Ala Ile Leu Ala Leu Gly Thr Glu Thr Asp
225                 230                 235                 240

Asp Arg Leu Ala Arg Leu Arg Ala Gly Glu Ala Ala Ser Ile Val Leu
                245                 250                 255

Leu Thr Ala Thr Ala Met Gly Leu Ala Cys Cys Pro Ile Thr Glu Pro
            260                 265                 270

Leu Glu Ile Ala Lys Thr Arg Asp Ala Val Arg Ala Glu Val Phe Gly
    275                 280                 285

Ala Gly Gly Tyr Pro Gln Met Leu Leu Arg Val Gly Trp Ala Pro Ile
    290                 295                 300

Asn Ala Asp Pro Leu Pro Pro Thr Pro Arg Arg Glu Leu Ser Gln Val
305                 310                 315                 320

Val Glu Trp Pro Glu Glu Leu Leu Arg Gln Arg Cys
            325                 330

<210> SEQ ID NO 41
<211> LENGTH: 578
<212> TYPE: PRT
<213> ORGANISM: Mycobacterium tuberculosis

<400> SEQUENCE: 41

Met Thr Thr Gly Gly Leu Val Asp Glu Asn Asp Gly Ala Ala Met Arg
1               5                   10                  15

Pro Leu Arg His Thr Leu Ser Gln Leu Arg Leu His Glu Leu Leu Val
            20                  25                  30

Glu Val Gln Asp Arg Val Glu Gln Ile Val Glu Gly Arg Asp Arg Leu
        35                  40                  45

-continued

```
Asp Gly Leu Val Glu Ala Met Leu Val Val Thr Ala Gly Leu Asp Leu
 50                  55                  60
Glu Ala Thr Leu Arg Ala Ile Val His Ser Ala Thr Ser Leu Val Asp
 65                  70                  75                  80
Ala Arg Tyr Gly Ala Met Glu Val His Asp Arg Gln His Arg Val Leu
                 85                  90                  95
His Phe Val Tyr Glu Gly Ile Asp Glu Glu Thr Val Arg Arg Ile Gly
                100                 105                 110
His Leu Pro Lys Gly Leu Gly Val Ile Gly Leu Leu Ile Glu Asp Pro
            115                 120                 125
Lys Pro Leu Arg Leu Asp Asp Val Ser Ala His Pro Ala Ser Ile Gly
130                 135                 140
Phe Pro Pro Tyr His Pro Pro Met Arg Thr Phe Leu Gly Val Pro Val
145                 150                 155                 160
Arg Val Arg Asp Glu Ser Phe Gly Thr Leu Tyr Leu Thr Asp Lys Thr
                165                 170                 175
Asn Gly Gln Pro Phe Ser Asp Asp Glu Val Leu Val Gln Ala Leu
                180                 185                 190
Ala Ala Ala Ala Gly Ile Ala Val Ala Asn Ala Arg Leu Tyr Gln Gln
            195                 200                 205
Ala Lys Ala Arg Gln Ser Trp Ile Glu Ala Thr Arg Asp Ile Ala Thr
210                 215                 220
Glu Leu Leu Ser Gly Thr Glu Pro Ala Thr Val Phe Arg Leu Val Ala
225                 230                 235                 240
Ala Glu Ala Leu Lys Leu Thr Ala Ala Asp Ala Ala Leu Val Ala Val
                245                 250                 255
Pro Val Asp Glu Asp Met Pro Ala Ala Asp Val Gly Glu Leu Leu Val
            260                 265                 270
Ile Glu Thr Val Gly Ser Ala Val Ala Ser Ile Val Gly Arg Thr Ile
            275                 280                 285
Pro Val Ala Gly Ala Val Leu Arg Glu Val Phe Val Asn Gly Ile Pro
290                 295                 300
Arg Arg Val Asp Arg Val Asp Leu Glu Gly Leu Asp Glu Leu Ala Asp
305                 310                 315                 320
Ala Gly Pro Ala Leu Leu Leu Pro Leu Arg Ala Arg Gly Thr Val Ala
                325                 330                 335
Gly Val Val Val Leu Ser Gln Gly Gly Pro Gly Ala Phe Thr Asp
            340                 345                 350
Glu Gln Leu Glu Met Met Ala Ala Phe Ala Asp Gln Ala Ala Leu Ala
            355                 360                 365
Trp Gln Leu Ala Thr Ser Gln Arg Arg Met Arg Glu Leu Asp Val Leu
370                 375                 380
Thr Asp Arg Asp Arg Ile Ala Arg Asp Leu His Asp His Val Ile Gln
385                 390                 395                 400
Arg Leu Phe Ala Ile Gly Leu Ala Leu Gln Gly Ala Val Pro His Glu
                405                 410                 415
Arg Asn Pro Glu Val Gln Gln Arg Leu Ser Asp Val Val Asp Asp Leu
            420                 425                 430
Gln Asp Val Ile Gln Glu Ile Arg Thr Thr Ile Tyr Asp Leu His Gly
            435                 440                 445
Ala Ser Gln Gly Ile Thr Arg Leu Arg Gln Ile Asp Ala Ala Val
            450                 455                 460
Ala Gln Phe Ala Asp Ser Gly Leu Arg Thr Ser Val Gln Phe Val Gly
465                 470                 475                 480
```

```
Pro Leu Ser Val Val Asp Ser Ala Leu Ala Asp Gln Ala Glu Ala Val
                485                 490                 495

Val Arg Glu Ala Val Ser Asn Ala Val Arg His Ala Lys Ala Ser Thr
            500                 505                 510

Leu Thr Val Arg Val Lys Val Asp Asp Leu Cys Ile Glu Val Thr
            515                 520                 525

Asp Asn Gly Arg Gly Leu Pro Asp Glu Phe Thr Gly Ser Gly Leu Thr
        530                 535                 540

Asn Leu Arg Gln Arg Ala Glu Gln Ala Gly Gly Glu Phe Thr Leu Ala
545                 550                 555                 560

Ser Val Pro Gly Ala Ser Gly Thr Val Leu Arg Trp Ser Ala Pro Leu
                565                 570                 575

Ser Gln

<210> SEQ ID NO 42
<211> LENGTH: 268
<212> TYPE: PRT
<213> ORGANISM: Mycobacterium tuberculosis

<400> SEQUENCE: 42

Met Ser Asp Pro Arg Pro Ala Arg Ala Val Val Gly Ile Asp Gly
1               5                   10                  15

Ser Arg Ala Ala Thr His Ala Ala Leu Trp Ala Val Asp Glu Ala Val
                20                  25                  30

Asn Arg Asp Ile Pro Leu Arg Leu Val Tyr Val Ile Asp Pro Ser Gln
            35                  40                  45

Leu Ser Ala Ala Gly Glu Gly Gly Gln Ser Ala Ala Arg Ala Ala
        50                  55                  60

Leu His Asp Ala Ser Arg Lys Val Glu Ala Thr Gly Gln Pro Val Lys
65                  70                  75                  80

Ile Glu Thr Glu Val Leu Cys Gly Arg Pro Leu Thr Lys Leu Met Gln
                85                  90                  95

Glu Ser Arg Ser Ala Ala Met Leu Cys Val Gly Ser Val Gly Leu Asp
            100                 105                 110

His Val Arg Gly Arg Arg Gly Ser Val Ala Ala Thr Leu Ala Gly Ser
        115                 120                 125

Ala Leu Cys Pro Val Ala Val Ile His Pro Ser Pro Ala Glu Pro Ala
130                 135                 140

Thr Thr Ser Gln Val Ser Ala Val Ala Glu Val Asp Asn Gly Val
145                 150                 155                 160

Val Leu Arg His Ala Phe Glu Glu Ala Arg Leu Arg Gly Val Pro Leu
                165                 170                 175

Arg Ala Val Ala Val His Ala Ala Glu Thr Pro Asp Asp Val Glu Gln
            180                 185                 190

Gly Ser Arg Leu Ala His Val His Leu Ser Arg Arg Leu Ala His Trp
        195                 200                 205

Thr Arg Leu Tyr Pro Glu Val Arg Val Asp Arg Ala Ile Ala Gly Gly
210                 215                 220

Ser Ala Cys Arg His Leu Ala Ala Asn Ala Lys Pro Gly Gln Leu Phe
225                 230                 235                 240

Val Ala Asp Ser His Ser Ala His Glu Leu Cys Gly Ala Tyr Gln Pro
                245                 250                 255

Gly Cys Ala Val Leu Thr Val Arg Ser Ala Asn Leu
            260                 265
```

<210> SEQ ID NO 43
<211> LENGTH: 181
<212> TYPE: PRT
<213> ORGANISM: Mycobacterium tuberculosis

<400> SEQUENCE: 43

Met Thr Glu Tyr Glu Gly Pro Lys Thr Lys Phe His Ala Leu Met Gln
1               5                   10                  15

Glu Gln Ile His Asn Glu Phe Thr Ala Ala Gln Gln Tyr Val Ala Ile
            20                  25                  30

Ala Val Tyr Phe Asp Ser Glu Asp Leu Pro Gln Leu Ala Lys His Phe
        35                  40                  45

Tyr Ser Gln Ala Val Glu Glu Arg Asn His Ala Met Met Leu Val Gln
    50                  55                  60

His Leu Leu Asp Arg Asp Leu Arg Val Glu Ile Pro Gly Val Asp Thr
65                  70                  75                  80

Val Arg Asn Gln Phe Asp Arg Pro Arg Glu Ala Leu Ala Leu Ala Leu
                85                  90                  95

Asp Gln Glu Arg Thr Val Thr Asp Gln Val Gly Arg Leu Thr Ala Val
            100                 105                 110

Ala Arg Asp Glu Gly Asp Phe Leu Gly Glu Gln Phe Met Gln Trp Phe
        115                 120                 125

Leu Gln Glu Gln Ile Glu Glu Val Ala Leu Met Ala Thr Leu Val Arg
    130                 135                 140

Val Ala Asp Arg Ala Gly Ala Asn Leu Phe Glu Leu Glu Asn Phe Val
145                 150                 155                 160

Ala Arg Glu Val Asp Val Ala Pro Ala Ala Ser Gly Ala Pro His Ala
                165                 170                 175

Ala Gly Gly Arg Leu
            180

<210> SEQ ID NO 44
<211> LENGTH: 274
<212> TYPE: PRT
<213> ORGANISM: Mycobacterium tuberculosis

<400> SEQUENCE: 44

Met Thr Trp Ala Asp Glu Val Leu Ala Gly His Pro Phe Val Val Ala
1               5                   10                  15

His Arg Gly Ala Ser Ala Ala Arg Pro Glu His Thr Leu Ala Ala Tyr
            20                  25                  30

Asp Leu Ala Leu Lys Glu Gly Ala Asp Gly Val Glu Cys Asp Val Arg
        35                  40                  45

Leu Thr Arg Asp Gly His Leu Val Cys Val His Asp Arg Arg Leu Asp
    50                  55                  60

Arg Thr Ser Thr Gly Ala Gly Leu Val Ser Thr Met Thr Leu Ala Gln
65                  70                  75                  80

Leu Arg Glu Leu Glu Tyr Gly Ala Trp His Asp Ser Trp Arg Pro Asp
                85                  90                  95

Gly Ser His Gly Asp Thr Ser Leu Leu Thr Leu Asp Ala Leu Val Ser
            100                 105                 110

Leu Val Leu Asp Trp His Arg Pro Val Lys Ile Phe Val Glu Thr Lys
        115                 120                 125

His Pro Val Arg Tyr Gly Ser Leu Val Glu Asn Lys Leu Leu Ala Leu
    130                 135                 140

Leu His Arg Phe Gly Ile Ala Ala Pro Ala Ser Ala Asp Arg Ser Arg

```
                145                 150                 155                 160
Ala Val Val Met Ser Phe Ser Ala Ala Val Trp Arg Ile Arg Arg
                    165                 170                 175

Ala Ala Pro Leu Leu Pro Thr Val Leu Leu Gly Lys Thr Pro Arg Tyr
                180                 185                 190

Leu Thr Ser Ser Ala Ala Thr Ala Val Gly Ala Thr Ala Val Gly Pro
            195                 200                 205

Ser Leu Pro Ala Leu Lys Glu Tyr Pro Gln Leu Val Asp Arg Ser Ala
        210                 215                 220

Ala Gln Gly Arg Ala Val Tyr Cys Trp Asn Val Asp Glu Tyr Glu Asp
225                 230                 235                 240

Ile Asp Phe Cys Arg Glu Val Gly Val Ala Trp Ile Gly Thr His His
                    245                 250                 255

Pro Gly Arg Thr Lys Ala Trp Leu Glu Asp Gly Arg Ala Asn Gly Thr
                260                 265                 270

Thr Arg

<210> SEQ ID NO 45
<211> LENGTH: 248
<212> TYPE: PRT
<213> ORGANISM: Mycobacterium tuberculosis

<400> SEQUENCE: 45

Val Ser Asp Gly Glu Gln Ala Lys Ser Arg Arg Arg Gly Arg Arg
1               5                   10                  15

Arg Gly Arg Arg Ala Ala Ala Thr Ala Glu Asn His Met Asp Ala Gln
                20                  25                  30

Pro Ala Gly Asp Ala Thr Pro Thr Pro Ala Thr Ala Lys Arg Ser Arg
            35                  40                  45

Ser Arg Ser Pro Arg Arg Gly Ser Thr Arg Met Arg Thr Val His Glu
        50                  55                  60

Thr Ser Ala Gly Gly Leu Val Ile Asp Gly Ile Asp Gly Pro Arg Asp
65                  70                  75                  80

Ala Gln Val Ala Ala Leu Ile Gly Arg Val Asp Arg Arg Gly Arg Leu
                85                  90                  95

Leu Trp Ser Leu Pro Lys Gly His Ile Glu Leu Gly Glu Thr Ala Glu
            100                 105                 110

Gln Thr Ala Ile Arg Glu Val Ala Glu Glu Thr Gly Ile Arg Gly Ser
        115                 120                 125

Val Leu Ala Ala Leu Gly Arg Ile Asp Tyr Trp Phe Val Thr Asp Gly
    130                 135                 140

Arg Arg Val His Lys Thr Val His His Tyr Leu Met Arg Phe Leu Gly
145                 150                 155                 160

Gly Glu Leu Ser Asp Glu Asp Leu Glu Val Ala Glu Val Ala Trp Val
                165                 170                 175

Pro Ile Arg Glu Leu Pro Ser Arg Leu Ala Tyr Ala Asp Glu Arg Arg
            180                 185                 190

Leu Ala Glu Val Ala Asp Glu Leu Ile Asp Lys Leu Gln Ser Asp Gly
        195                 200                 205

Pro Ala Ala Leu Pro Pro Leu Pro Ser Ser Pro Arg Arg Arg Pro
    210                 215                 220

Gln Thr His Ser Arg Ala Arg His Ala Asp Asp Ser Ala Pro Gly Gln
225                 230                 235                 240

His Asn Gly Pro Gly Pro Gly Pro
                245
```

<210> SEQ ID NO 46
<211> LENGTH: 819
<212> TYPE: DNA
<213> ORGANISM: Mycobacterium tuberculosis

<400> SEQUENCE: 46

| | | | | | |
|---|---|---|---|---|---|
| gtggaaccga | aacgcagtcg | cctcgtcgta | tgtgcacccg | agccatcgca | cgcgcgggaa | 60 |
| ttcccggatg | tcgccgtatt | ctccggcggc | cgggctaacg | catcccaggc | cgaacggttg | 120 |
| gctcgtgccg | tgggtcgcgt | gttggccgat | cggggcgtca | ccgggggtgc | tcgggtgcgg | 180 |
| ctgaccatgg | cgaactgcgc | cgatgggccg | acgctggtgc | agataaacct | gcaggtaggt | 240 |
| gacaccccat | taagggcgca | ggccgccacc | gcgggcatcg | atgatctgcg | acccgcactg | 300 |
| atcagactgg | atcgacagat | cgtgcgggcg | tcggcacagt | ggtgccccg | gccttggccg | 360 |
| gatcggcccc | gccggcgatt | gaccacgccg | gccgaggcgc | tagtcacccg | ccgcaaaccg | 420 |
| gtcgtgctaa | ggcgcgcaac | cccgttgcag | gcgattgccg | ctatggacgc | catggactac | 480 |
| gacgtgcatt | tgttcaccga | cgccgagacg | ggggaggacg | ctgtggtcta | tcgggctgga | 540 |
| ccgtcggggc | tgcggctggc | ccgccagcac | cacgtatttc | ccccaggatg | gtcacgttgt | 600 |
| cgcgccccag | ccgggccgcc | ggtgccgctg | attgtgaatt | cgcgtccgac | accggttctc | 660 |
| acggaggccg | ccgcggtgga | ccgggcgcgc | gaacatggac | tgccattcct | gtttttcacc | 720 |
| gaccaggcca | ccggccgcgg | ccagctgctc | tactcccgct | acgacggcaa | cctcgggttg | 780 |
| atcaccccga | ccggtgacgg | cgttgccgac | ggtctggca | | | 819 |

<210> SEQ ID NO 47
<211> LENGTH: 819
<212> TYPE: DNA
<213> ORGANISM: Mycobacterium tuberculosis

<400> SEQUENCE: 47

| | | | | | |
|---|---|---|---|---|---|
| gtggaaccga | aacgcagtcg | cctcgtcgta | tgtgcacccg | agccatcgca | cgcgcgggaa | 60 |
| ttcccggatg | tcgccgtatt | ctccggcggc | cgggctaacg | catcccaggc | cgaacggttg | 120 |
| gctcgtgccg | tgggtcgcgt | gttggccgat | cggggcgtca | ccgggggtgc | tcgggtgcgg | 180 |
| ctgaccatgg | cgaactgcgc | cgatgggccg | acgctggtgc | agataaacct | gcaggtaggt | 240 |
| gacaccccat | taagggcgca | ggccgccacc | gcgggcatcg | atgatctgcg | acccgcactg | 300 |
| atcagactgg | atcgacagat | cgtgcgggcg | tcggcacagt | ggtgccccg | gccttggccg | 360 |
| gatcggcccc | gccggcgatt | gaccacgccg | gccgaggcgc | tagtcacccg | ccgcaaaccg | 420 |
| gtcgtgctaa | ggcgcgcaac | cccgttgcag | gcgattgccg | ctatggacgc | catggactac | 480 |
| gacgtgcatt | tgttcaccga | cgccgagacg | ggggaggacg | ctgtggtcta | tcgggctgga | 540 |
| ccgtcggggc | tgcggctggc | ccgccagcac | cacgtatttc | ccccaggatg | gtcacgttgt | 600 |
| cgcgccccag | ccgggccgcc | ggtgccgctg | attgtgaatt | cgcgtccgac | accggttctc | 660 |
| acggaggccg | ccgcggtgga | ccgggcgcgc | gaacatggac | tgccattcct | gtttttcacc | 720 |
| gaccaggcca | ccggccgcgg | ccagctgctc | tactcccgct | acgacggcaa | cctcgggttg | 780 |
| atcaccccga | ccggtgacgg | cgttgccgac | ggtctggca | | | 819 |

<210> SEQ ID NO 48
<211> LENGTH: 342
<212> TYPE: DNA
<213> ORGANISM: Mycobacterium tuberculosis

<400> SEQUENCE: 48

```
gtggagtccg aaccgctgta caagctcaag gcggagttct tcaaaaccct tgcgcatccg      60
gcgcggatca ggattttgga gctgctggtc gagcgggacc gttcggtcgg tgagttgctg     120
tcctcggacg tcggcctgga gtcgtcgaac ctgtcccagc agctgggtgt gctacgccgg     180
gcgggtgttg tcgcggcacg tcgtgacggc aacgcgatga tctattcgat tgccgcaccc     240
gatatcgccg agctgctggc ggtggcacgc aaggtgctgg ccagggtgct cagcgaccgg     300
gtggcggtgc tagaggacct ccgcgccggc ggctcggcca cg                        342

<210> SEQ ID NO 49
<211> LENGTH: 1032
<212> TYPE: DNA
<213> ORGANISM: Mycobacterium tuberculosis

<400> SEQUENCE: 49
atgcctatcg caacgcccga ggtctacgcg gagatgctcg gtcaggccaa acaaaactcg      60
tacgctttcc cggctatcaa ctgcacctcc tcggaaaccg tcaacgccgc gatcaaaggt     120
ttcgccgacg ccggcagtga cggaatcatc cagttctcga ccggtggcgc agaattcggc     180
tccggcctcg gggtcaaaga catggtgacc ggtgcggtcg ccttggcgga gttcacccac     240
gttatcgcgg ccaagtaccc ggtcaacgtg gcgctgcaca ccgaccactg ccccaaggac     300
aagttggaca gctatgtccg gcccttgctg gcgatctcgg cgcaacgcgt gagcaaaggt     360
ggcaatcctt tgttccagtc gcacatgtgg gacggctcgg cagtgccaat cgatgagaac     420
ctggccatcg cccaggagct gctcaaggcg gcggcggccg ccaagatcat tctggagatc     480
gagatcggcg tcgtcggcgg cgaagaggac ggcgtggcga acgagatcaa cgagaagctg     540
tacaccagcc cggaggactt cgagaaaacc atcgaggcgc tgggcgccgg tgagcacggc     600
aaatacctgc tggccgcgac gttcggcaac gtgcatggcg tctacaagcc cggcaacgtc     660
aagcttcgcc ccgacatcct tgcgcaaggg caacaggtgg cggcggccaa gctcggactg     720
ccggccgacg ccaagccgtt cgacttcgtg ttccacggcg gctcgggttc gcttaagtcg     780
gagatcgagg aggcgctgcg ctacggcgtg gtgaagatga acgtcgacac cgacacccag     840
tacgcgttca cccgcccgat cgccggtcac atgttcacca actacgacgg agtgctcaag     900
gtcgatggcg aggtgggtgt caagaaggtc tacgacccgc gcagctacct caagaaggcc     960
gaagcttcga tgagccagcg ggtcgttcag gcgtgcaatg acctgcactg cgccggaaag    1020
tccctaaccc ac                                                        1032

<210> SEQ ID NO 50
<211> LENGTH: 339
<212> TYPE: DNA
<213> ORGANISM: Mycobacterium tuberculosis

<400> SEQUENCE: 50
atgggtgagc acgccatcaa gcggcacatg cggcaacgga agcctacgaa gcatccccta      60
gcccagaaac ggggcgcgcg gattctggtc ttcaccgacg atccccgcag gagcgtcctc     120
atagtgcccg gttgccacct ggattccatg cgccgagaaa agaacgcgta ctacttccag     180
gacggcaatg cgttggttgg gatggttgtc tcggcggca cggttgagta cgacgccgac      240
gaccgcacat atgtcgtgca gctcaccgac ggaaggcaca ccactgagtc atctttcgaa     300
cactcatcgc cgagtcgatc acctcaatcc gatgaccta                            339

<210> SEQ ID NO 51
<211> LENGTH: 1140
```

<212> TYPE: DNA
<213> ORGANISM: Mycobacterium tuberculosis

<400> SEQUENCE: 51

```
gtggctggca atcctgatgt ggtgacggtg ctgctgggcg gtgacgtcat gctcggccgt      60
ggcgtcgatc agatcctgcc tcatcccggc aaaccgcaat tgcgcgaacg gtatatgcgg     120
gatgcgaccg gctatgttcg cctggccgag cgggtgaacg ggcgcattcc gctccccgtg     180
gattggcgct ggccctgggg cgaggcgttg gcggtccttg agaacaccgc gaccgacgtc     240
tgtttgatca atctggagac gacgatcacc gccgacggtg aattcgccga ccgcaaaccg     300
gtctgctacc ggatgcaccc ggataacgtg ccggcgctga cggcattgcg gccgcacgtg     360
tgcgcgctgg ccaacaacca cattctcgat ttcggctacc aggggctgac cgatacggtc     420
gcggctctcg ccggtgcggg gatccagagt gtcggggcgg gagccgattt gctcgccgct     480
cgccgctcgg cgctagtcac ggttggccat gaacgccggg tgatcgtcgg ctcggtagcg     540
gcggaatcca gcgcgtccc cgaatcctgg ccgcccgcc gcgaccggcc cggagtgtgg     600
ttgatccggg atccggcgca acgcgacgtc gccgacgatg tggcggcaca ggtgctggcg     660
gacaaacgcc ccggcgatat cgccatagtc tcgatgcatt ggggatccaa ttggggctat     720
gcgaccgcac ccggcgacgt cgcgttcgcg caccgactga tcgacgccgg catcgacatg     780
gtccacggac attcctcgca ccatccgcgg ccaatcgaga tatatcgcgg taaaccgatc     840
ctgtacggat gcggtgacgt cgttgacgac tacgaaggca tcggcgggca cgagtcgttc     900
cgcagtgaac tgcgactgct gtatctgacc gtcaccgatc ccgccagcgg gaacctgatc     960
tcgctgcaga tgcttccact gcgagtgtcg cggatgcgcc tacagcgtgc ctcccagacc    1020
gacaccgaat ggctccgcaa caccattgag cgcatcagcc gccggttcgg gattcgagtc    1080
gtgactcgac ccgacaacct gctggaggtc gttcccgctg ccaacctaac gagcaaggag    1140
```

<210> SEQ ID NO 52
<211> LENGTH: 1191
<212> TYPE: DNA
<213> ORGANISM: Mycobacterium tuberculosis

<400> SEQUENCE: 52

```
gtgacagacc acgtgcgcga ggcggacgac gcgaacatcg acgatctgtt gggcgacctg      60
ggcggtaccg cgcgcgccga gcgtgcgaag cttgtcgagt ggttgctcga gcagggcatc     120
accccccgacg agattcgggc gaccaacccg ccgttgctgc tggccacccg ccacctcgtc     180
ggcgacgacg gcacctacgt atccgcaagg gagattagcg agaactatgg cgttgacctc     240
gagctgctgc agcgggtgca gcgcgctgtc ggtctggcca gagtggatga tcctgacgcg     300
gtggtgcaca tgcgtgccga cggtgaggcg gccgcacgcg cacagcggtt cgttgagctg     360
gggctgaatc ccgaccaagt cgtgctggtc gtgcgtgtgc tcgccgaggg cttgtcacac     420
gccgccgagg ccatgcgcta caccgcgctg gaggccatta tgcggccggg ggctaccgag     480
ttggacatcg cgaagggggtc gcaggcgctg gtgagccaga tcgtgccgct gctgggccg     540
atgatccagg acatgctgtt catgcagctg cggcacatga tggagacgga ggccgtcaac     600
gccggagagc gtgcggccgg caagccgcta ccgggagcgc gacaggtcac cgttgccttc     660
gccgacctgg tcggtttcac ccagctaggc gaagtggtgt cggccgaaga gctagggcac     720
ctcgccgggc ggctggccgg cctcgcgcgt gacctgaccg ctccgccggt gtggttcatt     780
aagacgatcg gcgacgcggt catgttggtc tgtcctgatc cggcgccatt gctggacacc     840
gtgctgaagc tggtcgaggt cgtcgacacc gacaacaact ttccccggct gcgagccggc     900
```

```
gtcgcctccg ggatggcggt tagccgggcc ggcgactggt tcggcagccc ggtcaacgtg      960
gcaagccggg tgaccggggt ggcgcgcccg ggtgccgtgc tggtcgcgga ttcggtgcgg     1020
gaggcccttg gtgatgcccc cgaagccgac ggatttcagt ggtccttcgc cggcccccgt     1080
cgcctcaggg gaatccgggg tgacgtcagg cttttttcgag tccggcgagg ggccactcgc    1140
accggctccg gcggcgcggc caagacgac gatttggccg gctcgtcacc g                1191

<210> SEQ ID NO 53
<211> LENGTH: 1338
<212> TYPE: DNA
<213> ORGANISM: Mycobacterium tuberculosis

<400> SEQUENCE: 53
atggtagagc ccggcaattt ggcaggcgcg accggcgccg aatggatcgg ccggccaccg      60
cacgaggaat tgcagcgcaa agtgcgcccg ctgctgccat ccgacgatcc gttctacttc     120
ccacctgccg gctaccagca tgccgtgccc ggaacggtgt tgcgctcgcg cgatgtcgaa     180
ctggcgttta tgggcttgat tccgcagccc gtcaccgcta cccagctgct gtaccggacc     240
acgaacatgt acggcaaccc cgaggcgacg gtgaccacgg tgatcgtccc agcggagctt     300
gccccgggtc agacctgccc cttgctgtcg taccagtgtg cgatcgatgc catgtcgtcg     360
cgctgttttc cgtcatatgc cctgcgacga cgggccaagg ccctggggtc actgacccaa     420
atggagctgt tgatgatcag cgccgcactt gccgaaggat gggcggtatc agtacccgac     480
catgaagggc cgaaagggct gtgggggtcg ccgtatgaac ccggttaccg agtcctcgac     540
ggaatccggg ctgccttgaa ttccgagcgt gtcgggttgt ccccggcaac gccgatcggg     600
ctgtggggct actccggcgg cgggctggcc agcgcgtggg ccgccgaagc atgcggcgag     660
tacgcaccgg acctagacat cgtcggcgcc gtgctgggat cacccgtcgg tgaccttggt     720
cacacgttcc gccggctcaa tggcactctt cttgccggtc tgcccgcgtt ggtggtggcc     780
gcgctgcaac acagctaccc cggcctggcc cgggtgatca aggagcacgc caacgacgaa     840
ggacgtcagc tgctggagca actgacggag atgacaacgg tagacgcagt gatccggatg     900
gccggcaggg acatgggtga cttcctcgac gaaccccttg aggacattct gtcgacgccg     960
gaaatttccc atgtcttcgg cgacaccaag ctgggtagcg cggtgcccac ccgccggta    1020 ttgatcgtgc aggccgtgca tgactacctc atcgacgtct ctgacatcga cgcgctcgct    1080
gacagctata cagccggcgg cgccaacgtc acctaccacc gcgacctgtt cagcgaacat    1140
gtgtccctgc acccgctgtc ggccccaatg acgcttcgct ggctcaccga ccggttcgcc    1200
ggcaagccac tgaccgacca ccgcgtccgg accacgtggc cgaccatctt caacccgatg    1260
acctacgccg gcatggcgag actggccgtg atcgcggcca aggtgatcac cggcaggaag    1320
ttgagccgcc gtccgctc                                                   1338

<210> SEQ ID NO 54
<211> LENGTH: 630
<212> TYPE: DNA
<213> ORGANISM: Mycobacterium tuberculosis

<400> SEQUENCE: 54
atgatcgcca caacccgcga tcgtgaagga gccaccatga tcacgtttag gctgcgcttg      60
ccgtgccgga cgatactgcg ggtgttcagc cgcaatccgc tggtgcgtgg gacggatcga     120 ctcgaggcg tcgtcatgct gctggccgtc acggtctcgc tgctgactat cccgttcgcc     180
gccgcggccg gcaccgcagt ccaggattcc cgcagccacg tctatgccca ccaggcccag     240
```

-continued

| | |
|---|---|
| acccgccatc ccgcaaccgc gaccgtgatc gatcacgagg gggtgatcga cagcaacacg | 300 |
| accgccacgt cagcgccgcc gcgcacgaag atcaccgtgc ctgcccgatg ggtcgtgaac | 360 |
| ggaatagaac gcagcggtga ggtcaacgcg aagcccgggaa ccaaatccgg tgaccgcgtc | 420 |
| ggcatttggg tcgacagtgc cggtcagctg gtcgatgaac cagctccgcc ggcccgtgcc | 480 |
| attgcggatg cggccctggc cgccttggga ctctggttga gcgtcgccgc ggttgcgggc | 540 |
| gccctgctgg cgctcactcg ggcgattctg atccgcgttc gcaacgccag ttggcaacac | 600 |
| gacatcgaca gcctgttctg cacgcagcgg | 630 |

<210> SEQ ID NO 55
<211> LENGTH: 240
<212> TYPE: DNA
<213> ORGANISM: Mycobacterium tuberculosis

<400> SEQUENCE: 55

| | |
|---|---|
| atgaccaacg tcggtgacca gggggttgac gcggtcttcg ggtgatcta cccacctcag | 60 |
| gtcgcgctgg tcagtttcgg caagccggca caacgagttt gcgccgtcga cggcgcgatc | 120 |
| cacgtcatga cgaccgtgct ggctacgctg cccgctgacc acggctgcag cgatgaccat | 180 |
| cgcggcgcgc tgttcttcct gtcgatcaac gagctgacgc ggtgcgccgc agtaacagga | 240 |

<210> SEQ ID NO 56
<211> LENGTH: 1956
<212> TYPE: DNA
<213> ORGANISM: Mycobacterium tuberculosis

<400> SEQUENCE: 56

| | |
|---|---|
| gtgacggtga caccacggac cggcagccgc atcgaggagc tgcttgcacg cagcggccgg | 60 |
| ttcttcatcc cgggtgagat ctcggcggat ctgcgtaccg tgacccgccg cggcggccgc | 120 |
| gacggcgacg tgttctatcg agaccggtgg agccacgaca aggtggtccg ctccacacac | 180 |
| ggggtgaatt gcaccgggtc gtgttcttgg aagatctacg tcaaagacga catcatcacc | 240 |
| tgggagacgc aggagaccga ctatccgtcg gtgggcccgg accggcccga gtatgagccc | 300 |
| cgcggctgcc cgcgcggcgc ggcgtttttcc tggtacacgt attcgccgac gcgggtgcgc | 360 |
| catccgtacg cccgcggcgt gcttgtcgag atgtatcggg aggcgaaggc acgtttgggt | 420 |
| gatccggtgg cggcctgggc cgacatccag gccgaccgc ggcggcgccg ccgctaccag | 480 |
| cgcgcccgcg gcaagggcgg gctggtccgg gtcagctggg ccgaggccac cgagatgatc | 540 |
| gccgccgccc acgtgcacac catctccaca tacggcccgg accgggttgc cggcttctcc | 600 |
| cccatcccgg cgatgtccat ggtgagccac gccgcgggt cgcggttcgt ggagctaatc | 660 |
| ggcggggtga tgacgtcgtt ctacgactgg tacgccgacc tgccggtggc ctccccgcag | 720 |
| gtgttcggcg accagaccga cgtgccgag tccggagatt ggtgggacgt ggtgtggcaa | 780 |
| tgcgcctcgg tgctgctgac ctacccgaac tcacggcaac tcggcaccgc agaggaattg | 840 |
| ctggcccaca tcgacggtcc ggccgcggat ctgttgggc gcacggtctc tgagctgcgc | 900 |
| cgtgccgatc cgctgaccgc ggcgaccgc tacgtcgaca ccttcgacct gcgaggccgc | 960 |
| gccaccctgt acctgaccta ctggaccgcc ggcgacaccc gcaaccgcgg ccgggagatg | 1020 |
| ctggccttcg cccagaccta ccgcagcacc gacgtcgcac caccgcgcgg cgagaccccg | 1080 |
| gacttcctgc cggtggtgct cgaattcgcc gcgaccgtcg accccgaggc ggggcgacgg | 1140 |
| ttgctgagcg ggtaccgggt gcccatcgcc gcgctgtgca atgccctgac cgaggccgca | 1200 |
| ttgccatacg cacacacggt ggccgcggta tgccggacgg gtgacatgat gggcgaactc | 1260 |

-continued

```
ttctggaccg tcgtgccgta tgtgacgatg acgatcgtcg cggtcggctc ctggtggcgc      1320
taccgctatg acaaattcgg ctggaccacc cgctcgtccc agctgtacga gtcgcggctg      1380
ctgcggatcg ccagcccgat gtttcatttc ggcatcctgg tggtcatcgt cggccacggt      1440
atcgggctcg tgatcccgca gtcgtggact caggccgccg gtttgagcga gggcgcatat      1500
cacgtgcagg ccgtcgtgct ggggtcgatc gccggcatca ccaccttggc cggcgttacc      1560
ctgctgatct accggcggcg cacccgcggg ccggtgttca tggctaccac cgtcaacgac      1620
aaggtgatgt acctcgtgct ggtggcggcg atcgtcgcgg gactgggtgc gacggcgttg      1680
ggctccggcg ttgtcggcga ggcgtacaac taccgcgaga cggtgtcggt gtggttccgc      1740
tcggtgtggg tactgcaacc gcgcggggac ctgatggccg aggctccgct gtattaccag      1800
atccatgtgc tgatcgggtt ggcgttgttc cgttgtggc cgttcacccg gctggtacac       1860
gcgttcagcg ccccgatcgg ctatctgttc cgcccgtaca tcatctaccg cagccgcgag      1920
gagctggtgc taacgcggcc gcggcggcgc gggtgg                                1956
```

\<210\> SEQ ID NO 57
\<211\> LENGTH: 1185
\<212\> TYPE: DNA
\<213\> ORGANISM: Mycobacterium tuberculosis

\<400\> SEQUENCE: 57

```
atgagagggc aagcggccaa tctcgtgctg gccacctgga tctcggtggt caacttctgg      60
gcgtggaacc tgatcggccc gctgtcgacc agctacgcgc gtgacatgtc actgtccagc      120
gccgaggcgt cgctgctcgt cgccaccccg atcctggtgg gtgcccttgg ccgcatcgtc      180
accgggccgc tcaccgaccg cttcggcggg cgcgccatgc tcatcgcggt gacgctggcg      240
tcgatcctcc cggtgctcgc ggtcggggtc gcggcaacca tgggctccta cgcgttgctg      300 gtgttttttcg ggctcttcct gggcgttgcc ggcacgatct tcgccgtcgg catcccgttc      360
gccaacaact ggtaccagcc ggcgcggcgc ggtttctcca ccggcgtgtt cggtatgggc      420
atggtcggca ccgcgctctc ggcgttcttc accccgcggt ttgtacggtg gttcggcctg      480
ttcaccaccc acgccatcgt cgcggccgcg ctcgcgtcga ccgccgtggt ggccatggtc      540
gtgcttcgtg atgcacccta ctttcggccc aacgccgacc cggtgctgcc caggctcaag      600
gccgcggcac ggttgccggt gacctgggag atgtcgtttc tgtacgcgat cgtgttcggc      660
gggttcgtgg cgttcagcaa ctacctgccc acctacatca ccacgatcta cgggttctcc      720
acggtcgacg cgggcgctcg caccgccggg ttcgccctgg cggcggtgct ggcccggccg      780
gtgggcgggt ggctctccga ccggatcgca ccgaggcacg tggtgctggc ctcgctcgcc      840
gggaccgcgc tgctggcgtt cgccgcgcg ttgcagccgc cgccggaggt gtggtcggcg       900
gccaccttca tcaccctggc ggtctgcctc ggcgtgggca ccggcggcgt gttcgcgtgg      960
gtggcccgcc gcgccccggc cgcatcgtc ggctcggtca ccggaatcgt cgccgcggca       1020
ggcggattgg gcggttactt cccgccgctg tgatgggcg cgacctacga cccggtcgac       1080
aacgactaca cggtcgggtt gctgctgctg gtggcgaccg cgctggtcgc gtgtacctac      1140
accgcgctgc acgcgcggga gccggtgagt gaggaggcgt ccagg                      1185
```

\<210\> SEQ ID NO 58
\<211\> LENGTH: 282
\<212\> TYPE: DNA
\<213\> ORGANISM: Mycobacterium tuberculosis

\<400\> SEQUENCE: 58

```
atgtgcggcg accagtcgga tcacgtgctg cagcactgga ccgtcgacat atcgatcgac    60
gaacacgaag gattgactcg ggcgaaggca cggctgcgtt ggcgggaaaa ggaattggtg   120
ggtgttggcc tggcaaggct caatccggcc gaccgcaacg tccccgagat cggcgatgaa   180
ctctcggtcg cccgagcctt gtccgacttg gggaagcgaa tgttgaaggt gtcgacccac   240
gacatcgaag ctgttaccca tcagccggcg cgattgttgt at                      282

<210> SEQ ID NO 59
<211> LENGTH: 1680
<212> TYPE: DNA
<213> ORGANISM: Mycobacterium tuberculosis

<400> SEQUENCE: 59
atgattccca cgatgacatc ggccggctgg gcaccagggg tggtgcagtt ccgcgaatac    60
caacggcgtt ggctgcgcgg cgatgtcctc gccggcctga ccgtggccgc ctatctgatc   120
ccgcaagcga tggcgtatgc gaccgtggcg ggcctaccgc cggcagccgg gctgtgggcg   180
tcgatcgcgc cgcttgccat ttacgcactg ctcggatcgt cccggcagct ttcaatcggc   240
ccggaatccg ccaccgcctt gatgacgcg gccgtgctcg ctccgatggc cgccggggat    300
cttcgacgct atgccgttct ggcggcaacc ctcggattgc tagtcggcct tatctgccta   360
ctcgctggca cggcgcgact aggtttcctc gccagcctgc gatcgcgcc ggtgctcgtc    420 ggatacatgg ccggcatcgc gcttgtcatg atctccagcc aactcggcac tatcaccggc   480
acctcggtcg aaggcaacga attcttcagc gaagtacact ctttcgcgac tagcgtcacg   540
cgagttcact ggccgacttt tgtgttagcc atgtctgtcc tagcgctgct aactatgctc   600
acgcggtggg cgccgcgcgc ccccggaccg atcatcgcgg ttcttgcggc cacgatgcta   660
gtggccgtta tgtccttgga tgccaaaggt attgcgattg tgggtcggat accttccggt   720
ctgccgacgc cggtgtgcc gcccgtttcg gtggaagact gcgggcact gatcattccg     780 gctgccggga tcgcgattgt taccttcacc gacggtgtgt tgaccgcacg cgccttcgcc   840
gctcgtcgag gtcaggaagt caatgccaac gccgagctgc gcgcggtcgg ggcctgcaac   900
atcgccgccg ggctgacaca cggttttccg gtgagttcca gcagcagccg taccgccctc   960
gccgacgtcg tcgtggccg cacccagctg tactcgctga tcgcgttggg gcttgttgtc  1020
atcgtgatgg ttttcgcgag tgggctgctg gccatgtttc cgatcgccgc tctgggcgct  1080
ttggtggtat atgccgcgct acgcttgatc gacttgtcag aattccggcg actggcgcgg  1140
tttcggcgca gcgaactcat gctggcacta gccaccacag cagccgtgtt aggcctagga  1200
gtgttctatg gagtcctcgc cgcggttgcc ctgtccatcc tcgaactgct tgtcgggtc   1260 gcacatccgc atgacagcgt tctcgggttc gtgccgggca ttgccggcat gcacgacatc  1320
gatgactatc gcgcaggcca agcgcgtgcc gggctggtgg tgtatcgcta tgacgcgccg  1380
ttgtgcttcg ccaatgccga agacttccgc aggcgagcac tgaccgtggt cgatcaggat  1440
ccggggcaag tcgagtggtt cgtactcaac gccgaatcca atgtggaggt cgacctgact  1500
gcgctggatg cgctcgacca actccgcacc gagctgctgc gtcggggaat agtgttcgcc  1560
atggcccggg tcaaacaaga cttgcgtgaa tcactcaggg ccgccagtct tctcgataag  1620
attggcgaag accatatctt tatgacattg cctaccgcag tgcaggcgtt ccgtcggcgc  1680

<210> SEQ ID NO 60
<211> LENGTH: 429
<212> TYPE: DNA
<213> ORGANISM: Mycobacterium tuberculosis
```

```
<400> SEQUENCE: 60
atgatcacaa acctccgacg ccgaaccgcg atggcagccg ccggcctagg ggctgctctc      60
gggctgggca tcctgctggt tccgacggtg gacgcccatc tcgccaacgg ttcgatgtcg     120
gaagtcatga tgtcggaaat tgccgggttg cctatccctc cgattatcca ttacggggcg     180
attgcctatg ccccagcgg cgcgtcgggc aaagcgtggc accagcgcac accggcgcga     240
gcagagcaag tcgcactaga aaagtgcggt gacaagactt gcaaagtggt tagtcgcttc     300
accaggtgcg gcgcggtcgc ctacaacggc tcgaaatacc aaggcggaac cggactcacg     360
cgccgcgcgg cagaagacga cgccgtgaac cgactcgaag gcgggcggat cgtcaactgg     420
gcgtgcaac                                                            429

<210> SEQ ID NO 61
<211> LENGTH: 2715
<212> TYPE: DNA
<213> ORGANISM: Mycobacterium tuberculosis

<400> SEQUENCE: 61
ttgtcggcgt cagtgtctgc cacgacggct catcatggct tgccagcaca tgaagtggtg      60
ctgctgctgg agagcgatcc atatcacggg ctgtccgacg gcgaggccgc ccaacgacta     120
gaacgcttcg ggcccaacac cttggcggtg gtaacgcgcg ctagcttgct ggcccgcatc     180
ctgcggcagt ttcatcaccc gctgatctac gttctgctcg ttgccgggac gatcaccgcc     240
ggtcttaagg aattcgttga cgccgcagtg atcttcggtg tggtggtgat caatgcgatc     300 gtgggttca ttcaagaatc caaggcagag gccgcactgc agggcctgcg ctccatggtg     360
cacacccacg ccaaggtggt gcgcgagggt cacgagcaca caatgccatc gaagagctg     420 gttcccggtg accttgtgct gttagcggcc ggtgacaagg ttcccgccga tttgcggctg     480
gtgcgacaga ccggattgag cgtgaacgag tcagcactta ccggcgagtc gacgccggtt     540
cacaaggacg aggtggcgtt gccggagggc acaccggtcg ctgatcgtcg caatatcgcg     600
tattccggca cattggtaac cgcgggccat ggcgccggga tcgtcgtcgc gaccggcgcc     660
gaaaccgaac tcggtgagat tcatcggctc gttggggccg ccgaggttgt cgccacaccg     720
ctgaccgcga agctggcgtg gttcagcaag tttctgacca tcgccatcct gggtctggca     780
gcgctcacgt tcggcgtggg tttgctgcgc cggcaagatg ccgtcgaaac gttcaccgct     840
gcgatcgcgc tggcggtcgg ggcaattccc gaaggtctgc ccaccgccgt gaccatcacc     900
ttggccatcg gcatggcccg gatggccaag cgccgcgcgg tcattcgacg tctacccgcg     960
gtggaaacgc tgggcagcac cacggtcatc tgcgccgaca agaccggaac gctgaccgag    1020
aatcagatga cggtccagtc gatctggaca ccccacggtg agatccgggc gaccggaacg    1080
ggctatgcac ccgacgtcct cctgtgcgac accgacgacg cgccggttcc ggtgaatgcc    1140
aatgcggccc ttcgctggtc gctgctgccc ggtgcctgca gcaacgacgc cgcactggtt    1200
cgcgacggca cacgctggca gatcgtcggc gatcccaccg agggcgcgat gctcgtcgtg    1260
gccgccaagg ccggcttcaa cccggagcgg ctggcgacaa ctctgccgca agtggcagcc    1320
ataccgttca gttccgagcg gcaatacatg gccaccctgc atcgcgacgg gacggatcat    1380
gtggtgctgc ccaagggtgc tgtggagcgc atgctcgacc tgtgcggcac cgagatgggc    1440
gccgacggcg cattgcggcc gctggccgcg ccaccgtgt tgcgtgccac cgaaatgttg    1500
acttcccggg ggttgcgggt gctggcaacc gggatgggtg ccggcgccgg cactcccgac    1560
gacttcgacg aaaacgtgat accaggttcg ctggcgctga ccggcctgca agcgatgagc    1620
```

```
gatccaccac gagcggccgc ggcatcggcg gtggcggcct gccacagtgc cggcattgcg      1680
gtaaaaatga ttaccggtga ccacgcgggc accgccacgg cgatcgcaac cgaggtgggg      1740
ttgctcgaca acactgaacc ggcggcaggc tcggtcctga cgggtgccga gctggccgcg      1800
ctgagcgcag accagtaccc ggaggccgtg gatacagcca gcgtgtttgc cagggtctct      1860
cccgagcaga agctgcggtt ggtgcaagca ttgcaggcca gggggcacgt cgtcgcgatg      1920
accggcgacg gcgtcaacga cgccccggcc ttgcgtcagg ccaacattgg cgtcgcgatg      1980
ggccgcggtg gcaccgaggt cgccaaggat gccgccgaca tggtgttgac cgacgacgac      2040
ttcgccacca tcgaagccgc ggtcgaggaa ggccgcggcg tattcgacaa tctgaccaag      2100
ttcatcacct ggacgctgcc caccaacctc ggtgagggcc tagtgatctt ggccgccatc      2160
gctgttggcg tcgccttgcc gattctgccc acccaaattc tgtggatcaa catgaccaca      2220
gcgatcgcgc tcggactcat gctcgcgttc gagcccaagg aggccggaat catgacccgg      2280
ccaccgcgcg accccgacca accgctgctg accggctggc ttgtcaggcg gactcttctg      2340
gtttccacct tgctcgtcgc cagcgcgtgg tggctgtttg catgggagct cgacaatggc      2400
gcgggcctgc atgaggcgcg cacggcggcg ctgaacctgt tcgtcgtcgt cgaggcgttc      2460
tatctgttca gctgccggtc gctgacccga tcggcctggc ggctcggcat gttcgccaac      2520
cgctggatca tcctcggcgt cagtgcgcag gccatcgcgc aattcgcgat acatatctca      2580
cccgcgatga atatggtgtt cgacaccgcg ccaatcgata tcgggggtgtg ggtgcgcata      2640 ttcgctgtcg cgaccgcaat cacgattgtg gtggccaccg acacgctgct gccgagaata      2700
cgggcgcaac cgcca                                                      2715

<210> SEQ ID NO 62
<211> LENGTH: 774
<212> TYPE: DNA
<213> ORGANISM: Mycobacterium tuberculosis

<400> SEQUENCE: 62
atgagtttcc acgatcttca tcaccaaggt gttccgttcg tgttgcccaa cgcctgggat        60
gtgccgtcgg ccctggccta cctcgcggag ggcttcacgg ctatcggcac aaccagtttc       120
ggggtctcgt ccagcggcgg gcaccccgac gggcaccgcg ccactcgcgg cgccaacatc       180
gcactggcgg ccgcccctggc accgctgcaa tgctacgtca gcgtcgacat cgaggacgga       240
tacagcgacg aacccgacgc cattgctgac tacgtcgcac aactgtcgac agccggaatc       300
aatatcgagg acagtagcgc cgaaaagctc atcgaccccg ccctggcagc cgctaaaatc       360
gttgcgatca acaacgtaa ccccgaggtg ttcgtcaacg cccgcgtcga cacctattgg       420
ttgcgccagc acgccgatac caccagcacg atccagcgcg cacttcgcta cgtcgatgcc       480
ggcgccgacg gcgtctttgt cccactggcc aacgatcccg acgaacttgc tgagctcact       540
cgcaacattc cgtgcccggt taacacgttg cccgtgcccg gcttgacgat cgccgacctt       600
ggtgagctcg gggtggcccg ggtgtcaacc ggttcagtgc cctacagcgc ggggttgtat       660
gcagcggccc acgcggctcg ggccgtgagc gacggagagc agctgccacg gtccgtaccg       720
tacgccgaac tgcaggcacg cttggttgac tacgagaacc gcacgagtac aacg            774

<210> SEQ ID NO 63
<211> LENGTH: 855
<212> TYPE: DNA
<213> ORGANISM: Mycobacterium tuberculosis

<400> SEQUENCE: 63
```

```
gtggtcaagc gctctcgggc aacccgactt tcgccgagca tctggtccgg atgggaatca 60
cctcagtgtc ggtccattcg ggcgcgattg ctgctacccc ggggtcggtc gcggccgccg 120
aacgccgatt gttgctggaa tcagctcgcg gtgacgcctg acacccggat gccggcatcg 180
tcggccgccg ggcgcgacgc ggcggcctac gacgcctggt atgactcacc caccgggcgg 240
ccgatcctgg cgaccgaggt cgccgcgttg cggccgctca tcgaggtctt tgcccagcca 300
cgcttggaaa tcggtgtcgg tacaggacgt ttcgccgacc tgctcggcgt gcggttcgga 360
ctcgatccat cccgtgatgc gctgatgttc gcacgccggc gcggcgtcct ggtcgccaat 420
gccgtcggcg aggcggtccc tttcgtcagc cggcacttcg gggcggtcct catggcattc 480
acgctctgtt tcgtcaccga cccggccgcc atattccggg aaacgcggcg tctgctcgcc 540
gacggcggcg gccttgttat cgggttcttg cctcgcggga caccgtgggc cgacctgtac 600
gctctgcgcg cggcccgcgg acagccaggc taccgcgacg cccgcttcta caccgcggcc 660
gaactcgaac aactgctcgc agactcggga ttccgggtca tcgcccgccg ctgcacgctg 720
caccaaccgc cgggactcgc ccggtacgac atcgaagccg cccatgacgg tatccaagcc 780
ggcgccggct tcgttgctat ctcggcggtc gaccaagcgc acgagcctaa ggatgatcac 840
ccactcgagt cggaa 855

<210> SEQ ID NO 64
<211> LENGTH: 885
<212> TYPE: DNA
<213> ORGANISM: Mycobacterium tuberculosis
<400> SEQUENCE: 64
atgtctaaac cccgcaagca gcacggagtt gtcgtcgggg tagatggttc gctcgaatcg 60
gatgccgccg cctgttgggg tgccaccgat gcggcgatga ggaacattcc gctgaccgtg 120
gtccacgtgg tgaacgccga tgtagcgacg tggccgccga tgccgtatcc ggagacctgg 180
ggggtttggc aggaggacga gggtcgccag atcgtcgcca acgccgtcaa gctcgccaaa 240
gaggcggttg gagcggatcg aaagctcagc gtaaagagcg agctcgtatt ttccacgccg 300
gtacctacca tggttgaaat ctccaacgag gcagagatgg tggtgttggg cagctcgggc 360
cggggagcgc tggcccgagg cttgctcggt tcggtcagct cgagcctggt gcgacgcgcc 420
gggtgcccgg tcgcggtcat ccacagcgat gatgcggtga tccctgatcc gcagcacgct 480
cccgtgctgg tgggaatcga cggttcgccg gtttcggagc ttgcgacggc ggtggcattt 540
gacgaggcgt cgcgccgcgg cgtcgaactg atcgccgtgc acgcgtggag tgacgtcgaa 600
gtggtggaac ttccgggttt ggacttctcg gctgtacagc aggaagcgga gcttagtctc 660
gccgaacgct tggcaggttg gcaagaacgc tatcccgatg tgccggtgag ccgggttgtc 720
gtttgcgatc gcccggcgcg gaagctggtg caaaagtcgg cgtccgccca gcttgtcgtc 780
gttggcagtc atggccgagg tggcttgacc ggcatgcttc tggggtcggt cagtaacgcg 840
gtcttacacg ccgcgcgggt gccagtgatc gtggcacggc agtcg 885

<210> SEQ ID NO 65
<211> LENGTH: 342
<212> TYPE: DNA
<213> ORGANISM: Mycobacterium tuberculosis
<400> SEQUENCE: 65
gtgacctatg tgatcggtag tgagtgcgtg gatgtgatgg acaagtcctg tgtgcaggag 60
tgtccggtcg actgtatcta tgagggcgcc cgaatgctct acatcaaccc cgacgagtgc 120
```

| | |
|---|---|
| gtggattgtg gtgcgtgcaa accggcctgc cgcgtcgagg cgatctactg ggaaggcgat | 180 |
| ctacccgacg atcaacacca gcatctgggg gacaacgccg cctttttcca ccaagtcctg | 240 |
| ccgggccgag tggctccgct gggttcgccg ggtggtgccg cagcggtggg cccgatcgga | 300 |
| gtcgacacgc ctctggtcgc ggctatcccg gtggagtgcc ct | 342 |

<210> SEQ ID NO 66
<211> LENGTH: 837
<212> TYPE: DNA
<213> ORGANISM: Mycobacterium tuberculosis

<400> SEQUENCE: 66

| | |
|---|---|
| atgaaccaat cacacaaacc cccatcgatc gtcgtcggta ttgatggctc gaagccggcc | 60 |
| gtgcaagccg cactgtgggc ggtcgacgag gcagccagcc gtgacatccc gctgcgtctg | 120 |
| ctgtacgcga tcgaacccga cgatcccggg tacgccgcac acggcgcggc ggctcgcaaa | 180 |
| ctcgccgccg ccgagaacgc ggtgcgctac gcgttcacag cggtcgaggc ggcggaccgg | 240 |
| ccggtcaagg tcgaggtgga gatcacccag gagcggccgg tcacctcgtt gatccgcgct | 300 |
| tcggcggctg ctgccctggt gtgcgttggc gctatcggcg tgcaccactt ccgaccggag | 360 |
| cgggtgggat ctaccgcagc ggccctggcg ttatcggcgc agtgcccagt ggcgatcgtg | 420 |
| cgaccccacc gggtccccat cggacgcgac gccgcatgga tcgtcgtcga ggcggacggg | 480 |
| tcgtccgata tcggtgtttt gctggggggcg gtgatggccg aagcacggct gcgcgactcg | 540 |
| ccggttcggg tggtcacctg ccggcaatcc ggagtgggcg ataccgggga cgacgtccgt | 600 |
| gccagcctgg accgctggct tgcccgttgg caaccacggt atcccgatgt gcgggtgcaa | 660 |
| tcggcggcag tgcacggcga gctgctggat tatctggctg ggctgggtcg atcggtacac | 720 |
| atggtggtgc tcagcgcgag cgaccaggag catgtggagc aacttgtggg agcgccgggc | 780 |
| aacgccgtgt tgcaggaggc cggctgcacc ctgctggtcg tcggtcagca gtatctg | 837 |

<210> SEQ ID NO 67
<211> LENGTH: 1017
<212> TYPE: DNA
<213> ORGANISM: Mycobacterium tuberculosis

<400> SEQUENCE: 67

| | |
|---|---|
| atgacggagc cagcggcgtg ggacgaaggc aagccgcgaa tcatcacttt gaccatgaac | 60 |
| cccgccttgg acatcacgac gagcgtcgac gtggtgcgcc cgaccgagaa aatgcgttgt | 120 |
| ggcgcacctc gctacgatcc cggcggcggc ggtatcaatg tcgcccgcat tgtgcatgtc | 180 |
| ctcggcggtt gctcgacagc actgttcccg gccggcgggt cgaccgggag cctgctgatg | 240 |
| gcgctgctcg gtgatgcggg agtgccattt cgcgtcattc cgatcgcggc ctcgacgcgg | 300 |
| gagagcttca cggtcaacga gtccaggacc gccaagcagt atcgtttcgt gcttccgggg | 360 |
| ccgtcgctga ccgtcgcgga gcaggagcaa tgcctcgacg aactgcgcgg tcggcggct | 420 |
| tcggccgcct ttgtggtggc cagtggcagc ctgccgccag gtgtggctgc cgactactat | 480 |
| cagcgggttg ccgacatctg ccgccgatcg agcactccgc tgatcctgga tacatctggt | 540 |
| ggcgggttgc agcacatttc gtccggggtg tttcttctca aggcgagcgt gcgggaactg | 600 |
| cgcgagtgcg tcggatccga actgctgacc gagcccgaac aactgccgcc cgcacacgaa | 660 |
| ctcattgacc gtgggcgcgc cgaggtcgtg gtggtctcgc ttggatctca gggcgcgcta | 720 |
| ttggccacac gacatgcgag ccatcgattt tcgtcgattc cgatgaccgc ggttagcggt | 780 |
| gtcggcgccg gcgacgcgat ggtggccgcg attaccgtgg gcctcagccg tggctggtcg | 840 |

```
ctcatcaagt ccgttcgctt gggaaacgcg gcaggtgcag ccatgctgct gacgccaggc     900
accgcggcct gcaatcgcga cgatgtggag aggttcttcg agctggcggc cgaacccacc     960
gaagtcgggc aggatcaata cgtttggcac ccgatcgtta acccggaagc ctcgcca       1017
```

<210> SEQ ID NO 68
<211> LENGTH: 2043
<212> TYPE: DNA
<213> ORGANISM: Mycobacterium tuberculosis

<400> SEQUENCE: 68

```
gtgctgatga ccgcagcggc tgatgtcacc cggcgctcgc cgcggcgcgt gttccgtgac      60
cgccgcgagg ccggccgggt gctggcggaa ttactcgccg cctatcggga ccagccggac     120
gtgattgtgc tcggcttggc ccggggtggc ctcccggtcg catgggaggt tgccgcggca     180
ctgcatgccc cgctagacgc cttcgtcgtg cgcaaacttg gtgccccggg gcatgacgag     240
ttcgccgttg gtgcactggc cagcggcggc cgcgtcgtgg tcaatgacga cgtcgtgcgg     300
ggcctgcgga tcacaccgca gcaactgcgc gacatcgccg aacgtgaggg tcgggaactg     360
cttcggcgcg agtccgccta ccgcggcgag cgcccgccca ccgatatcac cggcaagacg     420
gtcattgtcg tcgatgacgg tttggccacc ggcgcaagca tgttcgcggc ggtacaggca     480
ttgcgcgatg cgcaaccagc gcagatcgtg attgccgtgc cggcggcgcc ggagtccacg     540
tgccgggagt tcgccggcct cgtcgacgac gttgtgtgcg cgaccatgcc gaccccgttc     600
ctggccgtcg gtgagtcgtt ttgggacttc cggcaggtca ccgacgagga ggtccgccgg     660
ctcctggcca ccccgaccgc tggccgtcg ctgcgccggc ccgcggcgtc aacggcggcc      720
gatgttctgc gcagagtcgc gatcgacgcc cccgggggtg ttccgacgca cgaggtgttg     780
gcggagctgg tcggcgatgc acgaatcgtg ttgatcggcg aaagctcgca cggcacacac     840
gagttctacc aggcccgggc cgccatgaca cagtggctga tcgaggagaa gggctttggt     900
gcggtagccg ccgaggcgga ctggcccgac gcctaccggg tcaatcggta cgttcgcggc     960
ctcggcgagg acaccaacgc tgacgaggcg cttagcggat tcgagcggtt tcccgcctgg    1020
atgtggcgca acaccgtggt ccgagatttt gtggaatggc tgcgcacacg caaccagcgc    1080
tacgagtcgg gcgcgctgcg gcaagccggc ttctacggtc tggatcttta cagcctgcat    1140
cggtcgatcc aagaggtgat cagctatctc gacaaggtcg acccgcgtgc ggcggcacgg    1200
gcgcgggccc ggtatgcgtg cttcgaccat gcctgcgccg atgacggtca ggcgtacgga    1260
ttcgcggccg cattcggcgc cggtccgtcg tgcgaacgtg aagccgtcga gcaactggtc    1320
gacgttcagc gcaatgccct ggcgtatgcg cgccaagacg ggctgcttgc cgaggacgaa    1380
ctgttctacg cccagcaaaa cgcgcagacg gtgcgcgacg cagaggtgta ttaccgggcc    1440
atgttcagtg gacgcgttac ctcgtggaac ctgcgcgacc agcacatggc gcagaccctt    1500
ggcagtttgc tgacgcattt ggaccgacac ctcgatgcgc cgccggcgcg aatagtggtg    1560
tgggctcata actcccacgt gggtgacgca cgcgctaccg aggtgtgggc cgacgggcag    1620
ctcaccctcg gccagatagt ccgtgagcga tacggtgacg agtcgcgcag catcggattc    1680
agcacgtaca cgggcaccgt caccgcggcc agcgaatggg gtggtatcgc ccaacgcaaa    1740
gcggttcggc cggcactgca cggcagtgtc gaggagctct tccaccagac tgcagacagt    1800
ttcctggtgt cagcgcggct aagccgcgac gccgaagccc cgctggacgt tgtccggttg    1860
ggacgtgcca tcggcgtcgt ttatctaccg gcaacggaac ggcaaagtca ctacttgcac    1920
gtgcggcccg ccgaccagtt cgacgccatg atccacatcg atcagacccg tgccctggaa    1980
```

```
cctctcgagg tgacgagccg gtggatcgcc ggcgagaacc cggaaaccta cccgaccggt   2040
ctg                                                                 2043

<210> SEQ ID NO 69
<211> LENGTH: 432
<212> TYPE: DNA
<213> ORGANISM: Mycobacterium tuberculosis

<400> SEQUENCE: 69
atggccacca cccttcccgt tcagcgccac ccgcggtccc tcttcccga gttttctgag     60 ctgttcgcgg ccttcccgtc attcgccgga ctccggccca ccttcgacac ccggttgatg   120
cggctggaag acgagatgaa agaggggcgc tacgaggtac gcgcggagct tccccggggtc  180 gacccccgaca aggacgtcga cattatggtc cgcgatggtc agctgaccat caaggccgag   240
cgcaccgagc agaaggactt cgacggtcgc tcggaattcg cgtacggttc cttcgttcgc   300
acggtgtcgc tgccggtagg tgctgacgag gacgacatta aggccaccta cgacaagggc   360
attcttactg tgtcggtggc ggtttcggaa gggaagccaa ccgaaaagca cattcagatc   420
cggtccacca ac                                                       432

<210> SEQ ID NO 70
<211> LENGTH: 993
<212> TYPE: DNA
<213> ORGANISM: Mycobacterium tuberculosis

<400> SEQUENCE: 70
atgccggaca ccatggtgac caccgatgtc atcaagagcg cggtgcagtt ggcctgccgc     60
gcaccgtcgc tccacaacag ccagccctgg cgctggatag ccgaggacca cacggttgcg   120
ctgttcctcg acaaggatcg ggtgctttac gcgaccgacc actccggccg ggaagcgctg   180
ctggggtgcg cgccgtact cgaccacttt cgggtggcga tggcggccgc gggtaccacc   240
gccaatgtgg aacggtttcc caaccccaac gatcctttgc atctggcgtc aattgacttc   300
agcccggccg atttcgtcac cgagggccac cgtctaaggg cggatgcgat cctactgcgc   360
cgtaccgacc ggctgccttt cgccgagccg ccggattggg acttggtgga gtcgcagttg   420
cgcacgaccg tcaccgccga cacggtgcgc atcgacgtca tcgccgacga tatgcgtccc   480
gaactggcgg cggcgtccaa actcaccgaa tcgctgcggc tctacgattc gtcgtatcat   540
gccgaactct tttggtggac aggggctttt gagacttctg agggcatacc gcacagttca   600
ttggtatcgg cggccgaaag tgaccgggtc accttcggac gcgacttccc ggtcgtcgcc   660
aacaccgata ggcgcccgga gtttggccac gaccgctcta aggtcctggt gctctccacc   720
tacgacaacg aacgcgccag cctactgcgc tgcggcgaga tgctttccgc cgtattgctt   780
gacgccacca tggctgggct tgccacctgc acgctgaccc acatcaccga actgcacgcc   840
agccgagacc tggtcgcagc gctgattggg cagcccgcaa ctccgcaagc cttggttcgc   900
gtcggtctgg ccccggagat ggaagagccg ccaccggcaa cgcctcggcg accaatcgat   960
gaagtgtttc acgttcgggc taaggatcac cgg                                993

<210> SEQ ID NO 71
<211> LENGTH: 585
<212> TYPE: DNA
<213> ORGANISM: Mycobacterium tuberculosis

<400> SEQUENCE: 71
atgccactgc taaccattgg cgatcaattc cccgcctacc agctcaccgc tctcatcggc     60
```

```
ggtgacctgt ccaaggtcga cgccaagcag cccggcgact acttcaccac tatcaccagt    120
gacgaacacc caggcaagtg gcgggtggtg ttcttttggc cgaaagactt cacgttcgtg    180
tgccctaccg agatcgcggc gttcagcaag ctcaatgacg agttcgagga ccgcgacgcc    240
cagatcctgg gggtttcgat tgacagcgaa ttcgcgcatt ccagtggcg tgcacagcac     300 aacgacctca aaacgttacc cttcccgatg ctctccgaca tcaagcgcga actcagccaa    360
gccgcaggtg tcctcaacgc cgacggtgtg gccgaccgcg tgacctttat cgtcgacccc    420
aacaacgaga tccagttcgt ctcggccacc gccggttcgg tgggacgcaa cgtcgatgag    480
gtactgcgag tgctcgacgc cctccagtcc gacgagctgt gcgcatgcaa ctggcgcaag    540
ggcgacccga cgctagacgc tggcgaactc ctcaaggctt cggcc                    585

<210> SEQ ID NO 72
<211> LENGTH: 816
<212> TYPE: DNA
<213> ORGANISM: Mycobacterium tuberculosis

<400> SEQUENCE: 72
atgtctggga gaggagagcc gacgatgaaa acaatcattg ttggtatcga tggttcgcac     60
gcggcgatta cggccgcatt gtgggggtt gacgaggcca tcagccgagc ggtgccgctg     120
cgactggtct cagtgatcaa gccgacacat ccgtccccgg acgactacga ccgcgacctt    180
gcgcatgctg aaagatcgct tcgggaagcg cagtccgctg ttgaggccgc gggcaagctc    240
gtcaagatcg aaaccgacat cccccgcggg ccagccggcc cggtgcttgt ggaggcatcg    300
cgcgacgccg agatgatctg cgtcggctcc gtgggaatcg ggcgctacgc cagctcgatc    360
ttgggttcga cggcaaccga gctggccgaa aaggcgcatt gcccggtcgc cgtcatgcgc    420
tcaaaagtgg accagccagc gtctgacatc aactggatcg tggtgcgcat gaccgacgca    480
ccggataacg aggccgtgct ggaatacgct gcccgggaag cgaagttgcg gcaagcgccc    540
atactggcac tcggcgggcg accggaggag ctccgggaga ttccggacgg cgaattcgaa    600
cgtcgcgtgc aggattggca ccaccgtcat cccgatgtgc gcgtctaccc gatcaccact    660
cacacgggta ttgcccggtt cctggccgac cacgacgagc gcgtacagct ggcagtgatc    720
ggcggtggtg aggccggtca gctagcgcgg ctggtcgggc catccggaca tccggtgttc    780
cgtcacgccg agtgttcggt gcttgtcgtt cgccgc                              816

<210> SEQ ID NO 73
<211> LENGTH: 1179
<212> TYPE: DNA
<213> ORGANISM: Mycobacterium tuberculosis

<400> SEQUENCE: 73
atgcgtgatg cgatcccgct tgggcggatc gccgggtttg tggtgaacgt ccactggagc     60
gtgttggtga tcctgtggtt gttcacctgg agtctggcga ccatgttgcc gggtaccgtc    120
ggaggctacc cggccgtggt ctattggctt ctcggcgcag gtggcgcggt catgttgctg    180
gcgtcgctgt tggctcatga gctcgcgcac gccgtcgtcg ctcgtcgcgc cggggtatcc    240
gttgagagcg tgacgttgtg gctgttcggc ggggtgaccg cgcttggcgg cgaggcaaag    300
acgcccaaag ccgctttccg gatcgcgttc gcgggtccgg ctaccagcct ggcgctgtcg    360
gcgacattcg gtgcgttggc catcacgctc gccggcgtgc ggaccccggc catcgtgatc    420
agcgttgctt ggtggttggc tactgtcaac ctgctgctgg ggctgttcaa tctgctgcct    480
ggcgcgccgt tggacggtgg gcggttggtc cgggcctatc tgtggcgccg ccacggcgat    540
```

```
agtgtgcgcg ccgggatcgg tgcggcgcgg gccggacggg tggttgcgct ggtcttgatc      600
gcgttgggat tggccgagtt tgtggctggt ggcctcgtcg gtggggtctg gttagccttc      660
attggctggt ttatcttcgc tgccgctcgc gaggaggaga cccggatttc gacccagcag      720
ctgtttgccg gggtgcgtgt ggccgatgcg atgaccgccc aaccgcatac ggctcccgga      780
tggatcaatg tcgaggattt catccagcgt tacgtgcttg gtgaacggca ctcggcatat      840
ccggttgccg atcgggacgg atcgatcacg ggcctggtgg cattgcggca gctgcgcgat      900
gttgcgccta ccggcgcag  cactaccagc gtaggtgaca ttgcgctgcc gctgcacagc      960
gtgccgaccg cccgaccaca agagccgctg accgcgctcc tagagcggat ggcaccgctc     1020
ggcccgcgca gccgtgcgct ggtcaccgaa gggagcgcgg tggtcggcat cgtcactccc     1080
agcgatgtcg cgcggctgat tgacgtctac cggttggccc agccggaacc gacctttacc     1140
acgagtcccc aagatgcgga caggttttcc gatgcgggg                            1179

<210> SEQ ID NO 74
<211> LENGTH: 1239
<212> TYPE: DNA
<213> ORGANISM: Mycobacterium tuberculosis

<400> SEQUENCE: 74
atggcaagtt ctgcgagcga cggcacccac gaacgctcgg cttttcgcct gagtccaccg       60
gtcttgagcg gcgccatggg accgttcatg cacaccggtc tgtacgtcgc tcaatcgtgg      120
cgcgactatc tgggtcaaca gcccgataaa ctgccgatcg cacggcccac tattgcctta      180
gcggcgcaag cctttcgaga cgaaatcgtc ctgctgggcc tcaaggcacg acgtccggtc      240
agcaatcatc gagtgttcga gcgcatcagc caagaagtgg ccgctggact ggagttctat      300
gggaatcgca gatggctgga gaagcctagc ggattttttg cccagccccc accgctcacc      360
gaggtcgcgg tccgaaaggt caaggaccgc agacgctcct tttatcgcat cttcttcgac      420
agtgggttta cgccgcatcc gggtgaaccg ggcagccaac ggtggctctc atacactgcg      480
aacaatcgcg agtacgccct gttactgcgg cacccagagc cgcgtccctg gctggtttgt      540
gtacacggca ccgagatggg cagggccccg ttggatctcg cggtgttccg cgcctggaag      600
ctgcatgacg aactcggcct gaacattgtc atgccggttc ttccgatgca tggtccccgc      660
gggcaaggtc tgccgaaggg cgccgttttt cccggagaag atgttctcga cgatgtgcat      720
gggacggctc aagcggtgtg ggatatccgg cggctgttgt cctggatacg atcgcaggag      780
gaggagtcgc tgatcgggtt gaacggtctc tcgctgggcg gctacatcgc gtcattggtc      840
gccagcctcg aagaaggtct cgcctgcgcg attctcggtg tcccagtggc tgatctgatc      900
gagttgttgg gccgccactg cggtcttcgg cacaaagacc cccgccgcca caccgtcaag      960
atggccgaac cgatcggccg aatgatctcg ccgctctcac ttacgccact ggtgcccatg     1020
ccgggccgct ttatctacgc gggcattgcc gaccgactcg tgcatccacg cgaacaggtg     1080
actcgcctct gggagcactg gggcaaaccc gaaatcgtgt ggtatccagg cggtcacact     1140
ggcttcttcc agtcgcggcc ggtacgacgg tttgtccagg ctgcgctgga gcagtcgggc     1200
ctgttggacg cgccacggac acagcgcgac cgttccgcc                           1239

<210> SEQ ID NO 75
<211> LENGTH: 360
<212> TYPE: DNA
<213> ORGANISM: Mycobacterium tuberculosis

<400> SEQUENCE: 75
```

```
atgtccacgc aacgaccgag gcactccggt attcgggctg ttggcccta cgcatgggcc      60 ggccgatgtg gtcggatagg caggtggggg gtgcaccagg aggcgatgat gaatctagcg     120
atatggcacc cgcgcaaggt gcaatccgcc accatctatc aggtgaccga tcgctcgcac     180
gacgggcgca cagcacgggt gcctggtgac gagatcacta gcaccgtgtc cggttggttg     240
tcggagttgg gcacccaaag cccgttggcc gatgagcttg cgcgtgcggt gcggatcggc     300
gactggcccg ctgcgtacgc aatcggtgag cacctgtccg ttgagattgc cgttgcggtc     360
```

<210> SEQ ID NO 76
<211> LENGTH: 1122
<212> TYPE: DNA
<213> ORGANISM: Mycobacterium tuberculosis

<400> SEQUENCE: 76

```
atgcgatcag aacgtctccg gtggctggta gccgcagaag gtccgttcgc ctcggtgtat      60
ttcgacgact cgcacgacac tcttgatgcc gtcgagcgcc gggaagcgac gtggcgcgat     120
gtccggaagc atctcgaaag ccgcgacgcg aagcaggagc tcatcgacag cctcgaagag     180
gcggtgcggg attctcgacc ggccgtcggc cagcgtggcc gcgcgctgat cgcgaccggc     240
gagcaagtac tggtcaacga gcatctgatc ggcccaccac cggctacggt gattcggctg     300
tcggattatc cgtacgtcgt gccattgata gaccttgaga tgcggcgacc gacgtatgta     360
tttgccgcgg ttgatcacac cggcgccgac gtcaagctgt atcaggggc caccatcagt     420 tccacgaaaa tcgatggggt cggctacccg gtgcacaagc cggtcaccgc cggctggaac     480
ggctacggcg acttccagca caccaccgaa gaagccatcc gaatgaactg ccgcgcggtc     540
gccgaccatc tcacccgact ggtagacgct gccgaccccg aggtggtgtt cgtgtccggc     600
gaggtgcggt cacgcacaga cctgctttcc acattgccgc agcgggtggc ggtccgggtg     660
tcgcagctgc atgccggacc gcgcaaaagc gccttagacg aggaagagat ctgggacctg     720
acatccgcgg agttcacccg gcggcggtac gccgaaatca ccaatgtcgc acaacaattt     780
gaggcggaga tcgacgcgg atcggggctg gcggcccaag ggttggcgga ggtgtgtgcg     840
gctctgcgtg acggcgacgt cgacacgctg atcgtcggag agctaggcga ggccaccgtg     900
gtcaccggta aagcgcgtac tacggtcgcg cgggatgccg acatgttgtc cgaactcggc     960
gaaccggtag atcgcgtggc aagggccgat gaggcgttgc cattcgccgc gatcgcggta    1020
ggtgccgcat tggtccgtga cgacaaccgg atcgcgccac tagatggggt gggcgcattg    1080
ctgcgttatg ccgccaccaa ccgactcggc agccatagat cc                       1122
```

<210> SEQ ID NO 77
<211> LENGTH: 537
<212> TYPE: DNA
<213> ORGANISM: Mycobacterium tuberculosis

<400> SEQUENCE: 77

```
atgctgcacc gcgacgatca catcaatccg ccgcggcccc gcgggttgga tgttccttgc      60
gcccgcctac gagcgacaaa tcccctgcgc gccttggcgc gttgcgttca ggcgggcaag     120
ccgggcacca gttcagggca tcggtccgtg ccgcatacgg cggacttgcg aatcgaagcc     180
tgggcaccga cccgtgacgg ctgtatccgg caggcggtgc tgggtaccgt cgagagcttc     240
ctcgacctgg aatccgcgca cgcggtccat accggctgc gccggctgac cgcggatcgc     300
gacgacgatc tactggtcgc ggtgctcgag gaggtcattt atttgctgga caccgtcggt     360
gaaacgcctg tcgatctcag gctgcgcgac gttgacgggg gtgtcgacgt cacattcgca     420
```

| | |
|---|---:|
| acgaccgatg cgagtacgct agttcaggtg ggtgccgtgc cgaaggcggt gtcactcaac | 480 |
| gaacttcggt tctcgcaggg tcgccacggc tggcgatgtg cggtaacgct cgatgtg | 537 |

<210> SEQ ID NO 78
<211> LENGTH: 1125
<212> TYPE: DNA
<213> ORGANISM: Mycobacterium tuberculosis

<400> SEQUENCE: 78

| | |
|---|---:|
| gtgacgcaaa ccggcaagcg tcagagacgc aaattcggtc gcatccgaca gttcaactcc | 60 |
| ggccgctggc aagccagcta caccggcccc gacggccgcg tgtacatcgc ccccaaaacc | 120 |
| ttcaacgcca agatcgacgc cgaagcatgg ctcaccgacc gccgccgcga aatcgaccga | 180 |
| caactatggt ccccggcatc gggtcaggaa gaccgccccg gagccccatt cggtgagtac | 240 |
| gccgaaggat ggctgaagca gcgtggaatc aaggaccgca cccgcgccca ctatcgcaaa | 300 |
| ctgctggaca ccacatcct ggccaccttc gctgacaccg acctacgcga catcaccccg | 360 |
| gccgccgtgc gccgctggta cgccaccacc gccgtgggca caccgaccat gcgggcacac | 420 |
| tcctacagct tgctgcgcgc aatcatgcag accgccttgg ccgacgacct gatcgactcc | 480 |
| aaccctgcc gcatctcagg cgcgtccacc gcccgccgcg tccacaagat caggcccgcc | 540 |
| accctcgacg agctggaaac catcaccaaa gccatgcccg acccctacca ggcgttcgtg | 600 |
| ctgatggcgg catggctggc catgcgctac ggcgagctga ccgaattacg ccgcaaagac | 660 |
| atcgacctgc acggcgaggt tgcgcgggtg cggcgggctg tcgttcgggt gggcgaaggc | 720 |
| ttcaaggtga cgacaccgaa aagcgatgcg ggagtgcgcg acataagtat cccgccacat | 780 |
| ctgatacccg ccatcgaaga ccaccttcac aaacacgtca accccggccg ggagtccctg | 840 |
| ctgttcccat cggtcaacga ccccaaccgt cacctagcac cctcggcgct gtaccgcatg | 900 |
| ttctacaagg cccgaaaagc cgccggccga ccagacttac gggtgcacga ccttcgacac | 960 |
| tccggcgccg tgttggctgc atccaccggc gccacactgg ccgaactgat gcagcggcta | 1020 |
| ggacacagca cagccggcgc cgcactccgc taccagcacg ccgccaaggg ccgggaccgc | 1080 |
| gaaatcgccg cactgttaag caaactggcc gagaaccagg agatg | 1125 |

<210> SEQ ID NO 79
<211> LENGTH: 1113
<212> TYPE: DNA
<213> ORGANISM: Mycobacterium tuberculosis

<400> SEQUENCE: 79

| | |
|---|---:|
| atgcgcgtcg gtattccgac cgagaccaaa acaacgaat tccgggtggc catcaccccg | 60 |
| gccgcgtcg cggaactaac ccgtcgtggc catgaggtgc tcatccaggc aggtgccgga | 120 |
| gagggctcgg ctataccga cgcggatttc aaggcggcag gcgcgcaact ggtcggcacc | 180 |
| gccgaccagg tgtgggccga cgctgattta ttgctcaagg tcaaagaacc gatagcggcg | 240 |
| gaatacggcc gcctgcgaca cgggcagatc ttgttcacgt tcttgcattt ggccgcgtca | 300 |
| cgtgcttgca ccgatgcgtt gttggattcc ggcaccacgt caattgccta cgagaccgtc | 360 |
| cagaccgccg acggcgcact accctgctt gccccgatga gcgaagtcgc cggtcgactc | 420 |
| gccgcccagg ttggcgctta ccacctgatg cgaacccaag ggggccgcgg tgtgctgatg | 480 |
| ggcggggtgc ccggcgtcga accgccgac gtcgtggtga tcggcgccgg caccgccggc | 540 |
| tacaacgcag cccgcatcgc caacggcatg gcgcgaccg ttacggttct agacatcaac | 600 |
| atcgacaaac ttcggcaact cgacgccgag ttctgcggcc ggatccacac tcgctactca | 660 |

```
tcggcctacg agctcgaggg tgccgtcaaa cgtgccgacc tggtgattgg ggccgtcctg      720
gtgccaggcg ccaaggcacc caaattagtc tcgaattcac ttgtcgcgca tatgaaacca      780
ggtgcggtac tggtggatat agccatcgac cagggcggct gtttcgaagg ctcacgaccg      840
accacctacg accacccgac gttcgccgtg cacgacacgc tgttttactg cgtggcgaac      900
atgcccgcct cggtgccgaa gacgtcgacc tacgcgctga ccaacgcgac gatgccgtat      960
gtgctcgagc ttgccgacca tggctggcgg gcggcgtgcc ggtcgaatcc ggcactagcc     1020
aaaggtcttt cgacgcacga aggggcgtta ctgtccgaac gggtggccac cgacctgggg     1080
gtgccgttca ccgagcccgc cagcgtgctg gcc                                  1113

<210> SEQ ID NO 80
<211> LENGTH: 312
<212> TYPE: DNA
<213> ORGANISM: Mycobacterium tuberculosis

<400> SEQUENCE: 80
atggtcatcc ggtttgatca aatagggtca ttggtcctct caatgaaatc ccttgcgtca       60
ctgtcgtttc agcggtgtct gcgcgagaat tctagtttgg tcgcggcgct ggaccggctc      120
gatgctgcgg tcgatgagct gagcgctttg tcgtttgatg cgttgaccac tccggagcgg      180
gatcgcgccc gtcgcgaccg ggaccatcat ccttggtccc gctcccgctc gcagttgtcg      240
ccacgaatgg cgcacggtgc agtgcaccaa tgccagtggc cgaaggcggt ttgggctgtc      300
attgacaatc ca                                                          312

<210> SEQ ID NO 81
<211> LENGTH: 1032
<212> TYPE: DNA
<213> ORGANISM: Mycobacterium tuberculosis

<400> SEQUENCE: 81
gtgctcaaga acgcagtctt gctggcatgc cgggcgccgt cggtgcacaa cagccagccc       60
tggcgttggg tggccgaaag cggctccgag cacactactg tgcacctgtt cgtcaaccgc      120
caccgaacgg tgccggccac cgaccattcc ggccggcaag cgatcatcag ttgcggtgcc      180
gtactcgatc accttcgcat cgccatgacg gccgcgcact ggcaggcgaa tatcactcgc      240
tttccccagc cgaaccaacc tgaccagttg gccaccgtcg aattcagtcc catcgatcac      300
gtcacggcgg gacagcgaaa ccgcgcccag gcgattctgc agcgccgaac cgatcggctt      360
ccgtttgaca gcccgatgta ctggcacctg tttgagcccg cgctgcgcga cgccgtcgac      420
aaagacgttg cgatgcttga tgtggtatcc gacgaccagc gaaacgcgact ggtggtagcg      480 tcacaactca gcgaagtcct gcggcgggac gatccgtact atcacgccga actcgaatgg      540
tggacttcac cgttcgtgct ggcccatggt gtgccgccgg atacgctggc atcagacgcc      600
gaacgcttgc gggttgacct gggccgtgac ttcccggtcc ggagctacca gaatcgccgt      660
gccgagctag ctgatgaccg atcgaaagtc cttgtgctgt cgaccccctag cgacacgcga      720 gccgacgcac tgaggtgtgg cgaagtgctg tcgaccatcc tactcgagtg caccatggcc      780
ggcatggcta cctgcacgtt gacccatctg atcgaatcca gtgacagtcg tgacatcgtg      840
cggggcctga cgaggcagcg aggcgagccg caagccttga tccgggtagg atagccccg      900 ccgttggcag cagttcccgc ccccacacca cggcggccgc tggacagcgt cttgcagatt      960
cgccagacgc ccgagaaagg gcgtaatgcc tcagatagaa atgcccgtga acgggttgg     1020 ttcagcccgc ct                                                         1032
```

<210> SEQ ID NO 82
<211> LENGTH: 1011
<212> TYPE: DNA
<213> ORGANISM: Mycobacterium tuberculosis

<400> SEQUENCE: 82

| | | | | | | |
|---|---|---|---|---|---|---|
| gtgtggtccg | cctcgggtgg | gcagtgcggg | aagtatcttg | ccgcctcgat | ggtgctgcag | 60 |
| cttgatgggt | tggaacgtca | cggtgtgttg | gagtttgggc | gtgaccgcta | tggccccgag | 120 |
| gtgcgtgagg | agctgttggc | gatgagtgcg | gccagcatcg | atcgttatct | gaagaccgcg | 180 |
| aaggccaaag | accagatatc | gggtgtgtcg | acgacgaaac | cctcaccact | gctgcgtaat | 240 |
| tcgatcaagg | ttcgcagggc | cggcgatgag | gtcgaggcgg | agccggggtt | cttcgagggc | 300 |
| gacaccgtcg | cccattgcgg | tccgacgctc | aaaggcgagt | tcgcccacac | cctgaacttg | 360 |
| accgacgtgc | acatcggatg | gtgttcacc | cgcaccgtcc | gcaacaacgc | ccgtacccac | 420 |
| atcctcgccg | ggctcaaagc | ttctgtcacc | gagatcccgc | atgggataac | gggtttagat | 480 |
| ttcgacaacg | gcaccgtgtt | tctcaacaag | ccggtcatca | gctgggccgg | cgacaacggt | 540 |
| atctacttca | cccgctttcg | cccgtacaag | aaaaaccact | aggccaccat | cgagtccaag | 600 |
| aacaaccacc | tggtccgcaa | gtacgcgttc | tactaccgct | atgacaccgc | cgaggaacgc | 660 |
| gccgtgctca | accggatgtg | gaagctggtc | aacgaccgcc | tcaactacct | cacccccgacc | 720 |
| atcaaaccga | tcgggtatgc | cagcagcgcc | gacggccgcc | gccgacgcct | ctacgatgcc | 780 |
| ccacagacgc | cgctggaccg | gccactggcc | gcaaggtgc | tctccgcggc | ccagcaggcc | 840 |
| gacctgatca | cctaccgaga | cagcctcaac | cccgcccaga | tcggccgcaa | aatcgccgac | 900 |
| ctgcagaacc | gactcctcat | cttggccaag | gagaaaaccg | agcagctcta | cctcgctaac | 960 |
| atccccaccg | ccctacccga | catccacaaa | ggcatcctga | tcaaggcggg | c | 1011 |

<210> SEQ ID NO 83
<211> LENGTH: 330
<212> TYPE: DNA
<213> ORGANISM: Mycobacterium tuberculosis

<400> SEQUENCE: 83

| | | | | | | |
|---|---|---|---|---|---|---|
| gtggtgcaag | gccgcaccgt | gctgtttcgt | accgcggagg | gcgccaaatt | attttcagcc | 60 |
| gtcgcgaagt | gcgcggtggc | tttcgaggcg | gacgaccaca | acgttgccga | gggctggagc | 120 |
| gtgatcgtca | aggttcgcgc | ccaggtgctg | acgaccgacg | cggggggtccg | cgaagccgaa | 180 |
| cgcgcccagt | tactaccgtg | gaccgcgacg | ctgaaacgtc | actgtgtgcg | ggtgatcccg | 240 |
| tgggagatca | ccggccgcca | cttcaggttc | ggtccggaac | cggaccgcag | ccagaccttt | 300 |
| gcctgcgagg | cctcgtcaca | caaccagcga | | | | 330 |

<210> SEQ ID NO 84
<211> LENGTH: 1389
<212> TYPE: DNA
<213> ORGANISM: Mycobacterium tuberculosis

<400> SEQUENCE: 84

| | | | | | | |
|---|---|---|---|---|---|---|
| atgaatcacc | taacgacact | tgacgccggg | tttctcaagg | cagaagacgt | ggatcggcac | 60 |
| gtgagtctgg | caatcggcgc | tctggcggtc | atcgagggggc | cggctcccga | tcaggaagcc | 120 |
| ttcttatcgt | cgctcgctca | acgcctacgt | ccctgtaccc | ggttcgggca | gcggttacgc | 180 |
| ctgcgcccgt | tcgacctcgg | tgcacccaaa | tgggtgacg | atcccgactt | cgatcttggc | 240 |
| cgtcatgtgt | ggcgcatcgc | cttgccgcgg | cctggcaacg | aagaccagtt | attcgagctg | 300 |

```
atcgccgatc tgatggcgcg tcgtttggac cggggtcgac cgctgtggga ggtctgggtc    360
atcgaaggcc tggcggacag caagtgggcg atcctgacca aactgcacca ctgcatggcc    420
gacggaatcg cggcgactca cctgctagct gggctctccg atgaaagtat gagcgacagc    480
ttcgcgagca acatccacac gaccatgcag tcgcaatccg catctgtgcg gcggggtgga    540
ttccgtgtca atccaagcga ggcgttgacc gcgtcgaccg ccgtgatggc aggcatcgtt    600
cgcgcggcca agggtgccag tgagatcgcg gccggcgtgc taagtcccgc cgcgtcgtcg    660
ttgaacgggc cgatcagtga tttgcgtcgc tacagcgcag caaaggtccc tctcgccgac    720
gtcgaacagg tgtgccggaa attcgacgtc accatcaatg atgttgcgct tgccgcgatt    780
acggaaagct accgcaacgt cctcatccag cggggtgagc ggcctaggtt tgattcgctg    840
cgtacgctag tgccggtctc gacgcgttcc aacagcgctt tgagcaagac cgataaccgt    900
gtttcgttaa tgctgcccaa cctgccggtg gatcaagaga cccgctgca gcggctgcgg    960 atcgtgcact cgcggctgac tcgggccaag gcggggggac agagacaatt cggaaatact   1020
ttgatggcga ttgccaaccg ccttccgttc cccatgaccg catgggcggt cgggctgttg   1080
atgcggctgc cgcagcgtgg tgttgtcacc gtggcgacaa atgtgccggg tccacgacgg   1140
ccgctgcaga ttatgggcag acgggtgctt gacctatacc cggtttcgcc gatcgcgatg   1200
caactgcgca ccagtgtcgc gatgctcagc tacgccgacg acctgtactt cgggatcctg   1260
gccgactacg acgtggtagc agatgccggc cagctggcgc gaggaattga agacgccgtc   1320
gcacggctgg tggcgatcag taagcggcgc aaggtgactc gcaggcgcgg agcgctatcg   1380
ctggttgtg                                                             1389

<210> SEQ ID NO 85
<211> LENGTH: 996
<212> TYPE: DNA
<213> ORGANISM: Mycobacterium tuberculosis

<400> SEQUENCE: 85
atgaacaccc atttcccgga cgccgaaacc gtgcgaacgg ttctcaccct ggccgtccgg     60 gcccccctcca tccacaacac gcagccgtgg cggtggcggg tatgcccgac gagtctggag    120
ctgttctcta gacccgatat gcagctgcgt agcaccgatc cggacgggcg tgagttgatc    180
ctcagctgtg gtgtggcatt gcaccactgc gtcgtcgctt tggcgtcgct gggctggcag    240
gccaaggtaa ccgttttccc cgatcccaag gaccgctgcc atctggccac catcggggta    300
caaccgcttg ttcccgatca ggccgatgtc gccttggcgg cggccatacc gcggcgacgc    360
accgatcggc gcgcctacag ttgctggccg gtgccaggag gtgacatcgc gttgatggcc    420
gcaagagcag cccgtggcgg ggtcatgctg cggcaggtca gtgccctaga ccgaatgaaa    480
gccattgtgg cgcaggctgt cttggaccac gtgaccgacg aggaatatct gcgcgagctc    540
accatttgga gtgggcgcta cggttcagtg gccggggttc ccgcccgcaa cgagccgcca    600
tcagacccca gtgccccgat ccccggtcgc ctgttcgccg ggcccggtct gtctcagccg    660
tccgacgtct tacccgctga cgacggcgcc gcgatcctgg cactaggcac cgagacagac    720
gaccggttgg cccggctgcg cgccggcgag gccgccagca tcgtcttgtt gaccgcgacg    780
gcaatggggc tggcgtgctg cccgatcacc gaaccgctgg agatcgccaa gacccgcgac    840
gcggtccgtg ccgaggtgtt cggccgcggc ggctaccccc agatgctgct gcgagtgggt    900
tgggcaccga tcaatgccga cccgttgcca ccgacgccac ggcgcgaact gtcccaggtc    960
gttgagtggc cggaagagct actgcgacaa cggtgc                               996
```

<210> SEQ ID NO 86
<211> LENGTH: 1734
<212> TYPE: DNA
<213> ORGANISM: Mycobacterium tuberculosis

<400> SEQUENCE: 86
atgacaacag gggcctcgt cgacgaaaac gacggcgccg caatgcgtcc actgcgtcac 60
acgctctccc aactacgcct gcacgagctg ctggtcgagg tgcaggaccg ggtcgagcag 120
atcgtcgagg gccgggaccg cctcgatggt ctggtggagg ccatgctcgt ggtcacagcg 180
ggcctggacc tggaggcaac cctacgcgct atcgtgcatt cagcgaccag ccttgtcgat 240
gcgcgctatg gcgctatgga ggtgcacgac cggcagcatc gggtattgca ctttgtctat 300
gaaggcatcg acgaggagac cgttcggcgg atcggccacc taccgaaagg cctaggcgtc 360
atcgggctgc tcatcgaaga tcccaaaccg ttacggctgg acgatgtttc tgcgcacccg 420
gcctcgattg gttttccgcc gtatcatccg ccgatgcgta ccttcctcgg ggtaccggtt 480
cgggtgcgcg atgaatcgtt cggcactctg tacctgactg acaagaccaa cgggcaaccg 540
ttcagcgacg acgacgaggt tctggtccag gcgctggcgg ccgccgcggg tatcgcagtc 600
gcgaatgccc ggctctacca gcaggctaag gcgcgtcagt cgtggatcga ggccacccgt 660
gacatcgcca ccgagttgtt gtccggcacc gaacccgcga cggtgttccg gcttgtcgcc 720
gcggaggcgc tcaagctgac ggcggctgac gctgccctgg tagccgttcc cgtcgacgag 780
gacatgcctg ccgctgacgt gggggagctg ctggtgattg aaacagtcgg cagcgctgtg 840
gcttccattg ttgggcgaac gattccggtg gcgggcgcgg tgctgcggga ggtcttcgtc 900
aacggcattc cgcgacgggt cgaccgggtc gatttggaag gcctggacga actggccgac 960
gcaggtccgg cgctgctgtt gccgctgcgg gccagaggta ccgtagcggg tgtcgttgtt 1020
gtgctgagtc aaggcggtcc aggggctttc accgacgaac aactcgagat gatggccgcg 1080
ttcgccgacc aggccgcgct ggcttggcaa ttggccactt cgcaacgtcg gatgcgcgaa 1140
ctcgacgtac tgaccgaccg ggatcgtatc gcccgtgacc tccatgacca tgtcatccag 1200
cggctcttcg cgattggcct ggctttgcag ggtgctgtcc cgcacgaacg taatcctgaa 1260
gtgcagcaac gactctcgga cgtggtagac gatctgcaag acgttataca ggaaatccgg 1320
accaccattt atgacctgca cggagcatcg cagggtatca ctcggctccg gcagcgaatc 1380
gatgcggccg tagcccaatt tgccgactcg ggttgcgca ccagcgttca attcgtgggt 1440
ccattgtcgg tggtcgacag cgcgctcgcc gatcaggccg aggcggtggt tcgggaagcg 1500
gtcagcaacg cggttcgcca tgcgaaggcc agcacgttga ccgtccgggt caaagtcgac 1560
gacgacttgt gcatcgaggt gaccgacaac ggccgcgggc tgcccgacga gttcaccgga 1620
agcggcttaa cgaacctgcg gcagcgggca gagcaggccg gcggcgaatt caccctcgcg 1680
agcgtaccgg gcgcgagcgg aacagtgctg cgatggtcag caccgttgtc gcag 1734

<210> SEQ ID NO 87
<211> LENGTH: 804
<212> TYPE: DNA
<213> ORGANISM: Mycobacterium tuberculosis

<400> SEQUENCE: 87
atgagcgatc ctcggccagc tcgggcagtg gtcgttggta tcgacgggtc aagggcggca 60
acgcatgcgg cgttgtgggc ggtcgatgag gcggtgaacc gagacattcc gctgcgactg 120
gtgtacgtca tcgatccgtc ccaactgtcc gccgccggcg agggcggtgg gcaatcagcg 180

```
gcccgagcgg cgctgcacga cgcctctcgg aaggtcgagg ccaccgggca accggtcaag      240
atcgaaacgg aggttctgtg cggcaggccg ctcaccaagc tgatgcagga gtccaggtcc      300
gcggcgatgc tgtgcgtcgg ttcgtggggg cttgatcatg tccgcggtcg ccggggttcg      360
gtcgcggcga ccctggctgg gtcggcctta tgccccgtgg cggtgattca cccgtcgccg      420
gccgagccag cgacaacctc ccaggtcagc gcggttgtcg cggaggtgga caatggtgtg      480
gtgctgcggc acgcattcga ggaggccagg ctgcgcggag ttccgctgcg ggccgtggct      540
gtccacgctg ctgaaacacc cgatgacgtc gaacagggca gccggttggc gcatgtacac      600
ctgagccgtc ggctcgccca ctggacccgg ctctaccccg aggtgcgggt ggatcgggcc      660
atcgccggcg gcagtgcgtg ccgtcatctg gccgccaacg caaagccggg tcagctgttc      720
gtcgcggact cacactccgc gcacgaattg tgcggtgcat accagcccgg atgcgccgta      780
cttacggtac gcagtgccaa cttg                                             804
```

<210> SEQ ID NO 88
<211> LENGTH: 543
<212> TYPE: DNA
<213> ORGANISM: Mycobacterium tuberculosis

<400> SEQUENCE: 88

```
atgacagaat acgaagggcc taagacaaaa ttccacgcgt taatgcagga acagattcat       60
aacgaattca cagcggcaca acaatatgtc gcgatcgcgg tttatttcga cagcgaagac      120
ctgccgcagt tggcgaagca ttttttacagc caagcggtcg aggaacgaaa ccatgcaatg      180
atgctcgtgc aacacctgct cgaccgcgac cttcgtgtcg aaattcccgg cgtagacacg      240
gtgcgaaacc agttcgacag accccgcgag gcactggcgc tggcgctcga tcaggaacgc      300
acagtcaccg accaggtcgg tcggctgaca gcggtggccc gcgacgaggg cgatttcctc      360
ggcgagcagt tcatgcagtg gttcttgcag gaacagatcg aagaggtggc cttgatggca      420
accctggtgc gggttgccga tcgggccggg gccaacctgt tcgagctaga gaacttcgtc      480
gcacgtgaag tggatgtggc gccggccgca tcaggcgccc cgcacgctgc cggggccgc       540 ctc                                                                    543
```

<210> SEQ ID NO 89
<211> LENGTH: 822
<212> TYPE: DNA
<213> ORGANISM: Mycobacterium tuberculosis

<400> SEQUENCE: 89

```
atgacatggg ccgacgaggt gctcgccgga catcccttig tggttgctca ccgtggtgcg       60
tcggcggctc ggccggagca taccctigcc gcctacgacc tggcgctcaa agagggcgcc      120
gacggcgtgg aatgtgatgt gcggttgacc cgggacgggc atctggtctg tgtgcatgac      180
cgccgcctgg accgaacctc gacgggagcc ggcttggtca gcacgatgac gctggcccag      240
ctacgcgagc tggagtacgg cgcgtggcac gacagctggc gccccgacgg ttcgcacggc      300
gacaccagtc tgctgaccct ggacgcgctt gtttcgctgg ttttggactg gcaccggccg      360
gtgaagatct tcgtcgagac caagcatccc gtccgatacg gctcgctggt ggaaaacaag      420
ctgctggcgc tgctacaccg gttcggtatt gccgcacccg cctccgcaga tcgatcccgt      480
gcggtggtga tgtcgttttc ggccgccgcg gtctggcgga tccggcgggc tgcaccgctg      540
ctgccgacgg tgttgctcgg caagaccccc cgatacctga ccagcagtgc ggccacggcg      600
gtcggggcaa ccgccgtggg accctcactg cctgcgttaa aggaatatcc gcaactcgtt      660
```

```
gaccgctcgg cagctcaggg ccgggcggtg tactgctgga acgtcgatga gtacgaggac    720
atcgactttt gccgggaggt cggggtggcc tggattggta ctcaccaccc cggccgcacc    780
aaggcctggc tggaagacgg gcgggcgaac gggaccactc gc                        822

<210> SEQ ID NO 90
<211> LENGTH: 744
<212> TYPE: DNA
<213> ORGANISM: Mycobacterium tuberculosis

<400> SEQUENCE: 90
gtgtccgacg gcgaacaagc caaatcacgt cgacgccggg ggcggcgccg cgggcggcgc     60
gctgcggcta cagccgagaa tcacatggac gcccaaccgg ccggcgacgc cacccccgacc   120 ccggcaacgg cgaagcggtc ccggtcccgc tcacctcgtc gcgggtcgac tcggatgcgc    180
accgtgcacg aaacatcggc tggagggttg gtcattgacg gtatcgacgg tccacgagac    240
gcgcaggtcg cggctctgat cggccgcgtc gaccggcgcg gccggctgct gtggtcgcta    300
cccaaggggc acatcgagtt gggcgagacc gccgagcaga ccgccatccg cgaggtcgcc    360
gaggagaccg gcatccgcgg cagtgtgctc gccgcgctgg ggcgcatcga ctactggttc    420
gtcaccgacg gccggcgggt gcacaagacc gtccaccatt atttgatgcg gttttttaggc   480 ggagagctgt ccgacgaaga cctcgaggta gccgaggtag cctgggtgcc gatccgggaa    540
ctgccgtctc gactggccta cgccgacgaa cgtcgactag ccgaggtggc cgacgaactg    600
atcgacaagc tgcagagcga cggccccgcc gcgcttccgc cgctaccacc cagctcgcct    660
cgtcgacggc cgcaaacgca ttcacgcgct cgtcatgccg atgactcagc accgggtcag    720
cacaacggtc ccgggccggg gccg                                           744

<210> SEQ ID NO 91
<211> LENGTH: 88
<212> TYPE: PRT
<213> ORGANISM: Mycobacterium tuberculosis

<400> SEQUENCE: 91

Met Lys Ala Lys Val Gly Asp Trp Leu Val Ile Lys Gly Ala Thr Ile
1               5                   10                  15

Asp Gln Pro Asp His Arg Gly Leu Ile Ile Glu Val Arg Ser Ser Asp
            20                  25                  30

Gly Ser Pro Pro Tyr Val Val Arg Trp Leu Glu Thr Asp His Val Ala
        35                  40                  45

Thr Val Ile Pro Gly Pro Asp Ala Val Val Val Thr Ala Glu Glu Gln
    50                  55                  60

Asn Ala Ala Asp Glu Arg Ala Gln His Arg Phe Gly Ala Val Gln Ser
65                  70                  75                  80

Ala Ile Leu His Ala Arg Gly Thr
                85

<210> SEQ ID NO 92
<211> LENGTH: 24
<212> TYPE: DNA
<213> ORGANISM: Artificial
<220> FEATURE:
<223> OTHER INFORMATION: primer sequence

<400> SEQUENCE: 92
caccgtggaa ccgaaacgca gtcg                                            24
```

```
<210> SEQ ID NO 93
<211> LENGTH: 19
<212> TYPE: DNA
<213> ORGANISM: Artificial
<220> FEATURE:
<223> OTHER INFORMATION: primer sequence

<400> SEQUENCE: 93
ttatgccaga ccgtcggca                                            19

<210> SEQ ID NO 94
<211> LENGTH: 19
<212> TYPE: DNA
<213> ORGANISM: Artificial
<220> FEATURE:
<223> OTHER INFORMATION: primer sequence

<400> SEQUENCE: 94
caccatgagc ccgggctcg                                            19

<210> SEQ ID NO 95
<211> LENGTH: 20
<212> TYPE: DNA
<213> ORGANISM: Artificial
<220> FEATURE:
<223> OTHER INFORMATION: primer sequence

<400> SEQUENCE: 95
ttacggcgta cgcgagtcag                                           20

<210> SEQ ID NO 96
<211> LENGTH: 24
<212> TYPE: DNA
<213> ORGANISM: Artificial
<220> FEATURE:
<223> OTHER INFORMATION: primer sequence

<400> SEQUENCE: 96
caccgtggag tccgaaccgc tgta                                      24

<210> SEQ ID NO 97
<211> LENGTH: 17
<212> TYPE: DNA
<213> ORGANISM: Artificial
<220> FEATURE:
<223> OTHER INFORMATION: primer sequence

<400> SEQUENCE: 97
ttacgtggcc gagccgc                                              17

<210> SEQ ID NO 98
<211> LENGTH: 22
<212> TYPE: DNA
<213> ORGANISM: Artificial
<220> FEATURE:
<223> OTHER INFORMATION: primer sequence

<400> SEQUENCE: 98
caccatgcct atcgcaacgc cc                                        22

<210> SEQ ID NO 99
<211> LENGTH: 23
<212> TYPE: DNA
<213> ORGANISM: Artificial
<220> FEATURE:
<223> OTHER INFORMATION: primer sequence

<400> SEQUENCE: 99
```
ttagtgggtt agggactttc cgg                    23

<210> SEQ ID NO 100
<211> LENGTH: 49
<212> TYPE: DNA
<213> ORGANISM: Artificial
<220> FEATURE:
<223> OTHER INFORMATION: primer sequence

<400> SEQUENCE: 100
ggggacaagt ttgtacaaaa aagcaggctt aaaggcaaag gtcggggac      49

<210> SEQ ID NO 101
<211> LENGTH: 50
<212> TYPE: DNA
<213> ORGANISM: Artificial
<220> FEATURE:
<223> OTHER INFORMATION: primer sequence

<400> SEQUENCE: 101
ggggaccact ttgtacaaga aagctgggtc ctacgttccc ctggcatgga     50

<210> SEQ ID NO 102
<211> LENGTH: 22
<212> TYPE: DNA
<213> ORGANISM: Artificial
<220> FEATURE:
<223> OTHER INFORMATION: primer sequence

<400> SEQUENCE: 102
caccatgggt gagcacgcca tc                     22

<210> SEQ ID NO 103
<211> LENGTH: 26
<212> TYPE: DNA
<213> ORGANISM: Artificial
<220> FEATURE:
<223> OTHER INFORMATION: primer sequence

<400> SEQUENCE: 103
ttataggtca tcggattgag gtgatc                 26

<210> SEQ ID NO 104
<211> LENGTH: 24
<212> TYPE: DNA
<213> ORGANISM: Artificial
<220> FEATURE:
<223> OTHER INFORMATION: primer sequence

<400> SEQUENCE: 104
caccgtggct ggcaatcctg atgt                   24

<210> SEQ ID NO 105
<211> LENGTH: 24
<212> TYPE: DNA
<213> ORGANISM: Artificial
<220> FEATURE:
<223> OTHER INFORMATION: primer sequence

<400> SEQUENCE: 105
ttactccttg ctcgttaggt tggc                   24

<210> SEQ ID NO 106
<211> LENGTH: 22
<212> TYPE: DNA
<213> ORGANISM: Artificial

```
<220> FEATURE:
<223> OTHER INFORMATION: primer sequence

<400> SEQUENCE: 106
caccgtgaca gaccacgtgc gc                                          22

<210> SEQ ID NO 107
<211> LENGTH: 18
<212> TYPE: DNA
<213> ORGANISM: Artificial
<220> FEATURE:
<223> OTHER INFORMATION: primer sequence

<400> SEQUENCE: 107
ttacggtgac gagccggc                                               18

<210> SEQ ID NO 108
<211> LENGTH: 25
<212> TYPE: DNA
<213> ORGANISM: Artificial
<220> FEATURE:
<223> OTHER INFORMATION: primer sequence

<400> SEQUENCE: 108
caccatggta gagcccggca atttg                                       25

<210> SEQ ID NO 109
<211> LENGTH: 18
<212> TYPE: DNA
<213> ORGANISM: Artificial
<220> FEATURE:
<223> OTHER INFORMATION: primer sequence

<400> SEQUENCE: 109
ttagagcgga cggcggct                                               18

<210> SEQ ID NO 110
<211> LENGTH: 22
<212> TYPE: DNA
<213> ORGANISM: Artificial
<220> FEATURE:
<223> OTHER INFORMATION: primer sequence

<400> SEQUENCE: 110
caccatgatc gccacaaccc gc                                          22

<210> SEQ ID NO 111
<211> LENGTH: 20
<212> TYPE: DNA
<213> ORGANISM: Artificial
<220> FEATURE:
<223> OTHER INFORMATION: primer sequence

<400> SEQUENCE: 111
ttaccgctgc gtgcagaaca                                             20

<210> SEQ ID NO 112
<211> LENGTH: 24
<212> TYPE: DNA
<213> ORGANISM: Artificial
<220> FEATURE:
<223> OTHER INFORMATION: primer sequence

<400> SEQUENCE: 112
caccatgacc aacgtcggtg acca                                        24
```

```
<210> SEQ ID NO 113
<211> LENGTH: 21
<212> TYPE: DNA
<213> ORGANISM: Artificial
<220> FEATURE:
<223> OTHER INFORMATION: primer sequence

<400> SEQUENCE: 113
ttatcctgtt actgcggcgc a                                              21

<210> SEQ ID NO 114
<211> LENGTH: 24
<212> TYPE: DNA
<213> ORGANISM: Artificial
<220> FEATURE:
<223> OTHER INFORMATION: primer sequence

<400> SEQUENCE: 114
caccgtgacg gtgacaccac ggac                                           24

<210> SEQ ID NO 115
<211> LENGTH: 16
<212> TYPE: DNA
<213> ORGANISM: Artificial
<220> FEATURE:
<223> OTHER INFORMATION: primer sequence

<400> SEQUENCE: 115
ttaccacccg cgccgc                                                    16

<210> SEQ ID NO 116
<211> LENGTH: 21
<212> TYPE: DNA
<213> ORGANISM: Artificial
<220> FEATURE:
<223> OTHER INFORMATION: primer sequence

<400> SEQUENCE: 116
caccatgaga gggcaagcgg c                                              21

<210> SEQ ID NO 117
<211> LENGTH: 22
<212> TYPE: DNA
<213> ORGANISM: Artificial
<220> FEATURE:
<223> OTHER INFORMATION: primer sequence

<400> SEQUENCE: 117
ttacctggac gcctcctcac tc                                             22

<210> SEQ ID NO 118
<211> LENGTH: 21
<212> TYPE: DNA
<213> ORGANISM: Artificial
<220> FEATURE:
<223> OTHER INFORMATION: primer sequence

<400> SEQUENCE: 118
caccatgtgc ggcgaccagt c                                              21

<210> SEQ ID NO 119
<211> LENGTH: 21
<212> TYPE: DNA
<213> ORGANISM: Artificial
<220> FEATURE:
<223> OTHER INFORMATION: primer sequence

<400> SEQUENCE: 119
```

```
ttaatacaac aatcgcgccg g                                              21

<210> SEQ ID NO 120
<211> LENGTH: 25
<212> TYPE: DNA
<213> ORGANISM: Artificial
<220> FEATURE:
<223> OTHER INFORMATION: primer sequence

<400> SEQUENCE: 120
caccatgatt cccacgatga catcg                                          25

<210> SEQ ID NO 121
<211> LENGTH: 17
<212> TYPE: DNA
<213> ORGANISM: Artificial
<220> FEATURE:
<223> OTHER INFORMATION: primer sequence

<400> SEQUENCE: 121
ttagcgccga cggaacg                                                   17

<210> SEQ ID NO 122
<211> LENGTH: 49
<212> TYPE: DNA
<213> ORGANISM: Artificial
<220> FEATURE:
<223> OTHER INFORMATION: primer sequence

<400> SEQUENCE: 122
ggggacaagt ttgtacaaaa aagcaggctt aatcacaaac ctccgacgc                49

<210> SEQ ID NO 123
<211> LENGTH: 51
<212> TYPE: DNA
<213> ORGANISM: Artificial
<220> FEATURE:
<223> OTHER INFORMATION: primer sequence

<400> SEQUENCE: 123
ggggaccact ttgtacaaga aagctgggtc ctagttgcac gcccagttga c             51

<210> SEQ ID NO 124
<211> LENGTH: 24
<212> TYPE: DNA
<213> ORGANISM: Artificial
<220> FEATURE:
<223> OTHER INFORMATION: primer sequence

<400> SEQUENCE: 124
caccttgtcg gcgtcagtgt ctgc                                           24

<210> SEQ ID NO 125
<211> LENGTH: 17
<212> TYPE: DNA
<213> ORGANISM: Artificial
<220> FEATURE:
<223> OTHER INFORMATION: primer sequence

<400> SEQUENCE: 125
ttatggcggt tgcgccc                                                   17

<210> SEQ ID NO 126
<211> LENGTH: 29
<212> TYPE: DNA
<213> ORGANISM: Artificial
```

```
<220> FEATURE:
<223> OTHER INFORMATION: primer sequence

<400> SEQUENCE: 126
caccatgagt ttccacgatc ttcatcacc                               29

<210> SEQ ID NO 127
<211> LENGTH: 24
<212> TYPE: DNA
<213> ORGANISM: Artificial
<220> FEATURE:
<223> OTHER INFORMATION: primer sequence

<400> SEQUENCE: 127
ttacgttgta ctcgtgcggt tctc                                    24

<210> SEQ ID NO 128
<211> LENGTH: 22
<212> TYPE: DNA
<213> ORGANISM: Artificial
<220> FEATURE:
<223> OTHER INFORMATION: primer sequence

<400> SEQUENCE: 128
caccgtggtc aagcgctctc gg                                      22

<210> SEQ ID NO 129
<211> LENGTH: 22
<212> TYPE: DNA
<213> ORGANISM: Artificial
<220> FEATURE:
<223> OTHER INFORMATION: primer sequence

<400> SEQUENCE: 129
ttattccgac tcgagtgggt ga                                      22

<210> SEQ ID NO 130
<211> LENGTH: 24
<212> TYPE: DNA
<213> ORGANISM: Artificial
<220> FEATURE:
<223> OTHER INFORMATION: primer sequence

<400> SEQUENCE: 130
caccatgtct aaaccccgca agca                                    24

<210> SEQ ID NO 131
<211> LENGTH: 19
<212> TYPE: DNA
<213> ORGANISM: Artificial
<220> FEATURE:
<223> OTHER INFORMATION: primer sequence

<400> SEQUENCE: 131
ttacgactgc cgtgccacg                                          19

<210> SEQ ID NO 132
<211> LENGTH: 30
<212> TYPE: DNA
<213> ORGANISM: Artificial
<220> FEATURE:
<223> OTHER INFORMATION: primer sequence

<400> SEQUENCE: 132
caccgtgacc tatgtgatcg gtagtgagtg                              30
```

```
<210> SEQ ID NO 133
<211> LENGTH: 20
<212> TYPE: DNA
<213> ORGANISM: Artificial
<220> FEATURE:
<223> OTHER INFORMATION: primer sequence

<400> SEQUENCE: 133
ttaagggcac tccaccggga                                               20

<210> SEQ ID NO 134
<211> LENGTH: 26
<212> TYPE: DNA
<213> ORGANISM: Artificial
<220> FEATURE:
<223> OTHER INFORMATION: primer sequence

<400> SEQUENCE: 134
caccatgaac caatcacaca aacccc                                        26

<210> SEQ ID NO 135
<211> LENGTH: 25
<212> TYPE: DNA
<213> ORGANISM: Artificial
<220> FEATURE:
<223> OTHER INFORMATION: primer sequence

<400> SEQUENCE: 135
ttacagatac tgctgaccga cgacc                                         25

<210> SEQ ID NO 136
<211> LENGTH: 20
<212> TYPE: DNA
<213> ORGANISM: Artificial
<220> FEATURE:
<223> OTHER INFORMATION: primer sequence

<400> SEQUENCE: 136
caccatgacg gagccagcgg                                               20

<210> SEQ ID NO 137
<211> LENGTH: 18
<212> TYPE: DNA
<213> ORGANISM: Artificial
<220> FEATURE:
<223> OTHER INFORMATION: primer sequence

<400> SEQUENCE: 137
ttatggcgag gcttccgg                                                 18

<210> SEQ ID NO 138
<211> LENGTH: 49
<212> TYPE: DNA
<213> ORGANISM: Artificial
<220> FEATURE:
<223> OTHER INFORMATION: primer sequence

<400> SEQUENCE: 138
ggggacaagt ttgtacaaaa aagcaggctt actgatgacc gcagcggct               49

<210> SEQ ID NO 139
<211> LENGTH: 53
<212> TYPE: DNA
<213> ORGANISM: Artificial
<220> FEATURE:
<223> OTHER INFORMATION: primer sequence

<400> SEQUENCE: 139
```

```
gggggaccact ttgtacaaga aagctgggtc ctacagaccg gtcgggtagg ttt          53
```

<210> SEQ ID NO 140
<211> LENGTH: 48
<212> TYPE: DNA
<213> ORGANISM: Artificial
<220> FEATURE:
<223> OTHER INFORMATION: primer sequence

<400> SEQUENCE: 140

```
ggggacaagt ttgtacaaaa aagcaggctt agccaccacc cttcccgt               48
```

<210> SEQ ID NO 141
<211> LENGTH: 54
<212> TYPE: DNA
<213> ORGANISM: Artificial
<220> FEATURE:
<223> OTHER INFORMATION: primer sequence

<400> SEQUENCE: 141

```
ggggaccact ttgtacaaga aagctgggtc ctagttggtg gaccggatct gaat         54
```

<210> SEQ ID NO 142
<211> LENGTH: 22
<212> TYPE: DNA
<213> ORGANISM: Artificial
<220> FEATURE:
<223> OTHER INFORMATION: primer sequence

<400> SEQUENCE: 142

```
caccatgccg gacaccatgg tg                                           22
```

<210> SEQ ID NO 143
<211> LENGTH: 24
<212> TYPE: DNA
<213> ORGANISM: Artificial
<220> FEATURE:
<223> OTHER INFORMATION: primer sequence

<400> SEQUENCE: 143

```
ttagtgatcc ttagcccgaa cgtg                                         24
```

<210> SEQ ID NO 144
<211> LENGTH: 52
<212> TYPE: DNA
<213> ORGANISM: Artificial
<220> FEATURE:
<223> OTHER INFORMATION: primer sequence

<400> SEQUENCE: 144

```
ggggacaagt ttgtacaaaa aagcaggctt aatgccactg ctaaccattg gc          52
```

<210> SEQ ID NO 145
<211> LENGTH: 52
<212> TYPE: DNA
<213> ORGANISM: Artificial
<220> FEATURE:
<223> OTHER INFORMATION: primer sequence

<400> SEQUENCE: 145

```
ggggaccact ttgtacaaga aagctgggtc ctaggccgaa gccttgagga gt          52
```

<210> SEQ ID NO 146
<211> LENGTH: 25
<212> TYPE: DNA
<213> ORGANISM: Artificial

```
<220> FEATURE:
<223> OTHER INFORMATION: primer sequence

<400> SEQUENCE: 146
caccatgtct gggagaggag agccg                                              25

<210> SEQ ID NO 147
<211> LENGTH: 21
<212> TYPE: DNA
<213> ORGANISM: Artificial
<220> FEATURE:
<223> OTHER INFORMATION: primer sequence

<400> SEQUENCE: 147
ttagcgaacg acaagcaccg a                                                  21

<210> SEQ ID NO 148
<211> LENGTH: 48
<212> TYPE: DNA
<213> ORGANISM: Artificial
<220> FEATURE:
<223> OTHER INFORMATION: primer sequence

<400> SEQUENCE: 148
ggggacaagt ttgtacaaaa aagcaggctt acgtgatgcg atcccgct                     48

<210> SEQ ID NO 149
<211> LENGTH: 50
<212> TYPE: DNA
<213> ORGANISM: Artificial
<220> FEATURE:
<223> OTHER INFORMATION: primer sequence

<400> SEQUENCE: 149
ggggaccact ttgtacaaga aagctgggtc ctaccccgca tcggaaaacc                   50

<210> SEQ ID NO 150
<211> LENGTH: 51
<212> TYPE: DNA
<213> ORGANISM: Artificial
<220> FEATURE:
<223> OTHER INFORMATION: primer sequence

<400> SEQUENCE: 150
ggggacaagt ttgtacaaaa aagcaggctt aatggcaagt tctgcgagcg a                 51

<210> SEQ ID NO 151
<211> LENGTH: 51
<212> TYPE: DNA
<213> ORGANISM: Artificial
<220> FEATURE:
<223> OTHER INFORMATION: primer sequence

<400> SEQUENCE: 151
ggggaccact ttgtacaaga aagctgggtc ctaggaacgg tcgcgctgtg t                 51

<210> SEQ ID NO 152
<211> LENGTH: 22
<212> TYPE: DNA
<213> ORGANISM: Artificial
<220> FEATURE:
<223> OTHER INFORMATION: primer sequence

<400> SEQUENCE: 152
caccatgtcc acgcaacgac cg                                                 22
```

```
<210> SEQ ID NO 153
<211> LENGTH: 21
<212> TYPE: DNA
<213> ORGANISM: Artificial
<220> FEATURE:
<223> OTHER INFORMATION: primer sequence

<400> SEQUENCE: 153
ttaaccgcaa cggcaatctc a                                            21

<210> SEQ ID NO 154
<211> LENGTH: 24
<212> TYPE: DNA
<213> ORGANISM: Artificial
<220> FEATURE:
<223> OTHER INFORMATION: primer sequence

<400> SEQUENCE: 154
caccatgcga tcagaacgtc tccg                                         24

<210> SEQ ID NO 155
<211> LENGTH: 23
<212> TYPE: DNA
<213> ORGANISM: Artificial
<220> FEATURE:
<223> OTHER INFORMATION: primer sequence

<400> SEQUENCE: 155
ttaggatcta tggctgccga gtc                                          23

<210> SEQ ID NO 156
<211> LENGTH: 21
<212> TYPE: DNA
<213> ORGANISM: Artificial
<220> FEATURE:
<223> OTHER INFORMATION: primer sequence

<400> SEQUENCE: 156
caccatgctg caccgcgacg a                                            21

<210> SEQ ID NO 157
<211> LENGTH: 23
<212> TYPE: DNA
<213> ORGANISM: Artificial
<220> FEATURE:
<223> OTHER INFORMATION: primer sequence

<400> SEQUENCE: 157
ttacacatcg agcgttaccg cac                                          23

<210> SEQ ID NO 158
<211> LENGTH: 48
<212> TYPE: DNA
<213> ORGANISM: Artificial
<220> FEATURE:
<223> OTHER INFORMATION: primer sequence

<400> SEQUENCE: 158
ggggacaagt ttgtacaaaa aagcaggctt agtgacgcaa accggcaa               48

<210> SEQ ID NO 159
<211> LENGTH: 52
<212> TYPE: DNA
<213> ORGANISM: Artificial
<220> FEATURE:
<223> OTHER INFORMATION: primer sequence

<400> SEQUENCE: 159
```

```
gggggaccact ttgtacaaga aagctgggtc ctacatctcc tggttctcgg cc          52

<210> SEQ ID NO 160
<211> LENGTH: 49
<212> TYPE: DNA
<213> ORGANISM: Artificial
<220> FEATURE:
<223> OTHER INFORMATION: primer sequence

<400> SEQUENCE: 160
ggggacaagt ttgtacaaaa aagcaggctt acgcgtcggt attccgacc             49

<210> SEQ ID NO 161
<211> LENGTH: 48
<212> TYPE: DNA
<213> ORGANISM: Artificial
<220> FEATURE:
<223> OTHER INFORMATION: primer sequence

<400> SEQUENCE: 161
ggggaccact ttgtacaaga aagctgggtc ctacacgctg gcgggctc              48

<210> SEQ ID NO 162
<211> LENGTH: 28
<212> TYPE: DNA
<213> ORGANISM: Artificial
<220> FEATURE:
<223> OTHER INFORMATION: primer sequence

<400> SEQUENCE: 162
caccatggtc atccggtttg atcaaata                                    28

<210> SEQ ID NO 163
<211> LENGTH: 24
<212> TYPE: DNA
<213> ORGANISM: Artificial
<220> FEATURE:
<223> OTHER INFORMATION: primer sequence

<400> SEQUENCE: 163
ttatggattg tcaatgacag ccca                                        24

<210> SEQ ID NO 164
<211> LENGTH: 26
<212> TYPE: DNA
<213> ORGANISM: Artificial
<220> FEATURE:
<223> OTHER INFORMATION: primer sequence

<400> SEQUENCE: 164
caccgtgctc aagaacgcag tcttgc                                      26

<210> SEQ ID NO 165
<211> LENGTH: 21
<212> TYPE: DNA
<213> ORGANISM: Artificial
<220> FEATURE:
<223> OTHER INFORMATION: primer sequence

<400> SEQUENCE: 165
ttaaggcggg ctgaaccaac c                                           21

<210> SEQ ID NO 166
<211> LENGTH: 20
<212> TYPE: DNA
<213> ORGANISM: Artificial
```

```
<220> FEATURE:
<223> OTHER INFORMATION: primer sequence

<400> SEQUENCE: 166
caccgtgtgg tccgcctcgg                                               20

<210> SEQ ID NO 167
<211> LENGTH: 20
<212> TYPE: DNA
<213> ORGANISM: Artificial
<220> FEATURE:
<223> OTHER INFORMATION: primer sequence

<400> SEQUENCE: 167
ttagcccgcc ttgatcagga                                               20

<210> SEQ ID NO 168
<211> LENGTH: 20
<212> TYPE: DNA
<213> ORGANISM: Artificial
<220> FEATURE:
<223> OTHER INFORMATION: primer sequence

<400> SEQUENCE: 168
caccgtggtg caaggccgca                                               20

<210> SEQ ID NO 169
<211> LENGTH: 22
<212> TYPE: DNA
<213> ORGANISM: Artificial
<220> FEATURE:
<223> OTHER INFORMATION: primer sequence

<400> SEQUENCE: 169
ttatcgctgg ttgtgtgacg ag                                            22

<210> SEQ ID NO 170
<211> LENGTH: 29
<212> TYPE: DNA
<213> ORGANISM: Artificial
<220> FEATURE:
<223> OTHER INFORMATION: primer sequence

<400> SEQUENCE: 170
caccatgaat cacctaacga cacttgacg                                     29

<210> SEQ ID NO 171
<211> LENGTH: 23
<212> TYPE: DNA
<213> ORGANISM: Artificial
<220> FEATURE:
<223> OTHER INFORMATION: primer sequence

<400> SEQUENCE: 171
ttacacaacc agcgatagcg ctc                                           23

<210> SEQ ID NO 172
<211> LENGTH: 23
<212> TYPE: DNA
<213> ORGANISM: Artificial
<220> FEATURE:
<223> OTHER INFORMATION: primer sequence

<400> SEQUENCE: 172
caccatgaac acccatttcc cgg                                           23
```

```
<210> SEQ ID NO 173
<211> LENGTH: 23
<212> TYPE: DNA
<213> ORGANISM: Artificial
<220> FEATURE:
<223> OTHER INFORMATION: primer sequence

<400> SEQUENCE: 173
ttagcaccgt tgtcgcagta gct                                            23

<210> SEQ ID NO 174
<211> LENGTH: 23
<212> TYPE: DNA
<213> ORGANISM: Artificial
<220> FEATURE:
<223> OTHER INFORMATION: primer sequence

<400> SEQUENCE: 174
caccatgaca acaggggggcc tcg                                           23

<210> SEQ ID NO 175
<211> LENGTH: 22
<212> TYPE: DNA
<213> ORGANISM: Artificial
<220> FEATURE:
<223> OTHER INFORMATION: primer sequence

<400> SEQUENCE: 175
ttactgcgac aacggtgctg ac                                             22

<210> SEQ ID NO 176
<211> LENGTH: 22
<212> TYPE: DNA
<213> ORGANISM: Artificial
<220> FEATURE:
<223> OTHER INFORMATION: primer sequence

<400> SEQUENCE: 176
caccatgagc gatcctcggc ca                                             22

<210> SEQ ID NO 177
<211> LENGTH: 23
<212> TYPE: DNA
<213> ORGANISM: Artificial
<220> FEATURE:
<223> OTHER INFORMATION: primer sequence

<400> SEQUENCE: 177
ttacaagttg gcactgcgta ccg                                            23

<210> SEQ ID NO 178
<211> LENGTH: 32
<212> TYPE: DNA
<213> ORGANISM: Artificial
<220> FEATURE:
<223> OTHER INFORMATION: primer sequence

<400> SEQUENCE: 178
ccggctgaga tctatgacag aatacgaagg gc                                  32

<210> SEQ ID NO 179
<211> LENGTH: 24
<212> TYPE: DNA
<213> ORGANISM: Artificial
<220> FEATURE:
<223> OTHER INFORMATION: primer sequence

<400> SEQUENCE: 179
```

```
ccccgccagg gaactagagg cggc                                          24

<210> SEQ ID NO 180
<211> LENGTH: 22
<212> TYPE: DNA
<213> ORGANISM: Artificial
<220> FEATURE:
<223> OTHER INFORMATION: primer sequence

<400> SEQUENCE: 180
caccatgaca tgggccgacg ag                                            22

<210> SEQ ID NO 181
<211> LENGTH: 20
<212> TYPE: DNA
<213> ORGANISM: Artificial
<220> FEATURE:
<223> OTHER INFORMATION: primer sequence

<400> SEQUENCE: 181
ttagcgagtg gtcccgttcg                                               20

<210> SEQ ID NO 182
<211> LENGTH: 22
<212> TYPE: DNA
<213> ORGANISM: Artificial
<220> FEATURE:
<223> OTHER INFORMATION: primer sequence

<400> SEQUENCE: 182
caccgtgtcc gacggcgaac aa                                            22

<210> SEQ ID NO 183
<211> LENGTH: 15
<212> TYPE: DNA
<213> ORGANISM: Artificial
<220> FEATURE:
<223> OTHER INFORMATION: primer sequence

<400> SEQUENCE: 183
ttacggcccc ggccc                                                    15

<210> SEQ ID NO 184
<211> LENGTH: 8
<212> TYPE: DNA
<213> ORGANISM: Artificial
<220> FEATURE:
<223> OTHER INFORMATION: reference sequence

<400> SEQUENCE: 184 agtcagtc                                                             8

<210> SEQ ID NO 185
<211> LENGTH: 8
<212> TYPE: DNA
<213> ORGANISM: Artificial
<220> FEATURE:
<223> OTHER INFORMATION: reference sequence

<400> SEQUENCE: 185 aatcaatc                                                             8

<210> SEQ ID NO 186
<211> LENGTH: 6
<212> TYPE: DNA
<213> ORGANISM: Artificial
```

```
<220> FEATURE:
<223> OTHER INFORMATION: reference sequence

<400> SEQUENCE: 186 agtgtc                                                                  6

<210> SEQ ID NO 187
<211> LENGTH: 8
<212> TYPE: DNA
<213> ORGANISM: Artificial
<220> FEATURE:
<223> OTHER INFORMATION: reference sequence

<400> SEQUENCE: 187 agtcagtc                                                                8
```